United States Patent
Bearne et al.

(10) Patent No.: US 12,251,518 B2
(45) Date of Patent: *Mar. 18, 2025

(54) HEADGEAR FOR BREATHING MASK

(71) Applicant: FISHER & PAYKEL HEALTHCARE LIMITED, Auckland (NZ)

(72) Inventors: Peter David Alexander Bearne, Auckland (NZ); Roheet Patel, Auckland (NZ); Kirstin Elizabeth Middelkoop, Auckland (NZ); Fadi Karim Moh'd Mashal, Auckland (NZ); Michael John Henri Cox, Auckland (NZ); Blair Raymund Dadson Murphy, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 18/341,623

(22) Filed: Jun. 26, 2023

(65) Prior Publication Data
US 2024/0017033 A1  Jan. 18, 2024

Related U.S. Application Data

(63) Continuation of application No. 16/888,539, filed on May 29, 2020, now abandoned, which is a
(Continued)

(51) Int. Cl.
*A61M 16/06* (2006.01)
*A61M 16/08* (2006.01)
*A62B 18/08* (2006.01)

(52) U.S. Cl.
CPC ........ *A61M 16/0683* (2013.01); *A61M 16/06* (2013.01); *A61M 16/0605* (2014.02);
(Continued)

(58) Field of Classification Search
CPC .............. A61M 16/06; A61M 16/0605; A61M 16/0616; A61M 16/0633; A61M 16/0683;
(Continued)

(56) References Cited

U.S. PATENT DOCUMENTS 235,643 A  12/1880  Nolen
443,191 A  12/1890  Illing
(Continued)

FOREIGN PATENT DOCUMENTS

AU  2005/100738  11/2005
AU  2016/238904 A1  10/2016
(Continued)

OTHER PUBLICATIONS

Definition of "lock", defined by Merriamwebster.com, captured on Jan. 23, 2024.*
(Continued)

*Primary Examiner* — Tu A Vo
(74) *Attorney, Agent, or Firm* — VIA LLP

(57) ABSTRACT

An interface assembly includes an interface, such as a mask, that is secured to a head using a headgear assembly. The headgear assembly can include at least one halo portion and a plurality of straps. The headgear assembly can include both a front halo portion and a rear halo portion. In some arrangements, the headgear and mask define an adjustable closed loop. In some arrangements, the headgear can include one or more rigid portions that contact the user's face to at least partially isolate a seal of the mask from tightening forces applied to the headgear. In some arrangements, the mask is an oral-nasal mask and the headgear applies a force to the mask comprising an upward force component. In some arrangements, the headgear can be contoured to the user's head.

20 Claims, 65 Drawing Sheets

Related U.S. Application Data continuation of application No. 14/786,957, filed as application No. PCT/NZ2014/000075 on Apr. 28, 2014, now Pat. No. 10,668,242.

(60) Provisional application No. 61/816,602, filed on Apr. 26, 2013.

(52) U.S. Cl.
CPC ....... *A61M 16/0616* (2014.02); *A62B 18/084* (2013.01); *A61M 16/0666* (2013.01); *A61M 2210/0618* (2013.01); *A61M 2210/0625* (2013.01)

(58) Field of Classification Search
CPC .......... A61M 16/0688; A61M 16/0694; A61M 2210/06; A42B 1/00; A62B 18/00; A62B 18/02; A62B 18/04; A62B 18/08; A62B 18/084; A61F 5/56; A61F 9/02; A61F 9/027
See application file for complete search history.

(56) References Cited

U.S. PATENT DOCUMENTS

| | | |
|---|---|---|
| 2,317,608 A | 4/1943 | Heidbrink |
| 2,353,643 A | 7/1944 | Bulbulian |
| 2,403,046 A | 7/1946 | Bulbulian |
| 2,414,405 A | 1/1947 | Bierman et al. |
| 2,415,846 A | 2/1947 | Eugene |
| 2,444,417 A | 7/1948 | Bierman |
| 2,540,567 A | 2/1951 | Ray |
| 2,742,039 A | 4/1956 | Aaron |
| 2,867,812 A | 1/1959 | Roth et al. |
| 2,875,757 A | 3/1959 | Galleher, Jr. |
| 2,931,356 A | 4/1960 | Hermann |
| 3,040,741 A | 6/1962 | Carolan |
| 3,117,574 A | 1/1964 | Replogle |
| 3,234,939 A | 2/1966 | Morton, Jr. |
| 3,234,940 A | 2/1966 | Morton, Jr. |
| 3,292,618 A | 12/1966 | Davis et al. |
| 3,315,674 A | 4/1967 | Aaron et al. |
| 3,330,274 A | 7/1967 | Ray |
| 3,599,635 A | 8/1971 | Ansite |
| 3,752,157 A | 8/1973 | Malmin |
| 4,231,137 A | 11/1980 | Fujimoto |
| 4,263,908 A | 4/1981 | Mizerak |
| 4,603,692 A | 8/1986 | Montesi |
| 4,960,121 A | 10/1990 | Nelson et al. |
| 5,181,507 A | 1/1993 | Michel et al. |
| 5,441,046 A | 8/1995 | Starr |
| 5,517,986 A | 5/1996 | Starr et al. |
| 5,542,128 A | 8/1996 | Lomas |
| 5,570,684 A | 11/1996 | Behr |
| D383,204 S | 9/1997 | Lomas |
| 5,664,298 A | 9/1997 | Nessar-Ivanovic |
| 5,724,965 A | 3/1998 | Handke |
| 5,832,918 A | 11/1998 | Pantino |
| 5,934,276 A | 8/1999 | Fabro et al. |
| 6,119,694 A | 9/2000 | Correa et al. |
| 6,292,985 B1 | 9/2001 | Grunberger |
| 6,338,342 B1 | 1/2002 | Fecteau |
| 6,341,382 B1 | 1/2002 | Ryvin et al. |
| 6,371,110 B1 | 4/2002 | Peterson et al. |
| 6,374,826 B1 | 4/2002 | Gunaratnam et al. |
| 6,418,928 B1 | 7/2002 | Bordewick et al. |
| 6,422,238 B1 | 7/2002 | Lithgow |
| 6,470,886 B1 | 10/2002 | Jestrabek-Hart |
| 6,497,232 B2 | 12/2002 | Fecteau |
| 6,536,435 B1 | 3/2003 | Fecteau et al. |
| 6,598,272 B2 | 7/2003 | Nire |
| 6,615,834 B2 | 9/2003 | Gradon |
| 6,789,541 B2 | 9/2004 | Olsen |
| 6,823,869 B2 | 11/2004 | Raje et al. |
| 6,907,882 B2 | 6/2005 | Ging et al. |
| 6,990,691 B2 | 1/2006 | Klotz et al. |
| 7,063,088 B1 | 6/2006 | Christopher |
| 7,096,867 B2 | 8/2006 | Smith |
| 7,152,602 B2 | 12/2006 | Bateman et al. |
| 7,210,481 B1 | 5/2007 | Lovell et al. |
| 7,296,575 B1 | 11/2007 | Radney |
| 7,318,437 B2 | 1/2008 | Gunaratnam et al. |
| 7,353,826 B2 | 4/2008 | Sleeper et al. |
| 7,455,063 B2 | 11/2008 | Geiselhart |
| 7,509,958 B2 | 3/2009 | Amarasinghe et al. |
| 7,556,043 B2 | 7/2009 | Ho et al. |
| 7,658,189 B2 | 2/2010 | Davidson et al. |
| 7,708,017 B2 | 5/2010 | Davidson et al. |
| 7,721,737 B2 | 5/2010 | Radney |
| 7,849,855 B2 | 12/2010 | Woodard |
| 7,861,718 B2 | 1/2011 | Janbakhsh et al. |
| 7,905,232 B2 | 3/2011 | Olsen |
| 7,942,148 B2 | 5/2011 | Davidson et al. |
| 7,975,694 B2 | 7/2011 | Ho |
| 7,992,560 B2 | 8/2011 | Burton et al. |
| 8,028,699 B2 | 10/2011 | Ho et al. |
| 8,042,538 B2 | 10/2011 | Ging et al. |
| 8,136,523 B2 | 3/2012 | Rudolph |
| 8,196,583 B2 | 6/2012 | Radney |
| 8,230,559 B2 | 7/2012 | Fildan et al. |
| 8,286,636 B2 | 10/2012 | Gunaratnam et al. |
| 8,490,624 B2 | 7/2013 | Ho et al. |
| 8,522,784 B2 * | 9/2013 | Ng .................... A61M 16/0694 128/206.28 |
| 8,550,084 B2 | 10/2013 | Ng et al. |
| 8,596,271 B2 | 12/2013 | Matula, Jr. et al. |
| 8,636,007 B2 | 1/2014 | Rummery et al. |
| 8,733,358 B2 | 5/2014 | Lithgow et al. |
| 8,757,157 B2 | 6/2014 | Price et al. |
| 8,800,563 B2 | 8/2014 | Doherty et al. |
| 8,931,484 B2 | 1/2015 | Melidis |
| 8,950,404 B2 | 2/2015 | Formica et al. |
| 8,985,117 B2 | 3/2015 | Gunaratnam et al. |
| 8,997,742 B2 | 4/2015 | Moore |
| 8,997,743 B2 | 4/2015 | Huddart |
| 9,032,955 B2 | 5/2015 | Lubke et al. |
| 9,044,564 B2 | 6/2015 | Dravitzki et al. |
| 9,149,593 B2 | 10/2015 | Dravitzki et al. |
| 9,211,388 B2 | 12/2015 | Swift et al. |
| 9,220,860 B2 | 12/2015 | Davidson et al. |
| 9,387,302 B2 | 7/2016 | Dravitzki et al. |
| 9,480,809 B2 | 11/2016 | Guney et al. |
| 9,539,403 B2 | 1/2017 | Eves et al. |
| 9,764,107 B2 | 9/2017 | Grashow et al. |
| 10,130,785 B2 | 11/2018 | Dravitzki et al. |
| 10,201,678 B2 | 2/2019 | Guney et al. |
| 10,668,242 B2 * | 6/2020 | Bearne .................. A62B 18/084 |
| 2002/0088466 A1 | 7/2002 | Brostrom et al. |
| 2002/0174868 A1 | 11/2002 | Kwok |
| 2003/0111080 A1 | 6/2003 | Olsen |
| 2003/0154984 A1 | 8/2003 | Fernandes |
| 2003/0196655 A1 | 10/2003 | Ging et al. |
| 2003/0196657 A1 | 10/2003 | Ging |
| 2004/0025882 A1 | 2/2004 | Madaus |
| 2004/0067333 A1 | 4/2004 | Amarasinghe |
| 2004/0083534 A1 | 5/2004 | Ruiz |
| 2004/0107547 A1 | 6/2004 | Chung |
| 2004/0112377 A1 | 6/2004 | Amarasinghe |
| 2005/0028822 A1 | 2/2005 | Sleeper et al. |
| 2005/0056286 A1 | 3/2005 | Huddart et al. |
| 2005/0121030 A1 | 6/2005 | Bateman et al. |
| 2006/0042629 A1 | 3/2006 | Geist |
| 2006/0090760 A1 | 5/2006 | Gradon |
| 2006/0124131 A1 | 6/2006 | Chandran et al. |
| 2006/0150304 A1 | 7/2006 | Bentz |
| 2006/0174887 A1 | 8/2006 | Chandran et al. |
| 2006/0174892 A1 | 8/2006 | Leksutin et al. |
| 2006/0272646 A1 * | 12/2006 | Ho .................... A61M 16/0633 128/207.17 |
| 2006/0283461 A1 | 12/2006 | Lubke et al. |
| 2007/0006879 A1 | 1/2007 | Thornton |
| 2007/0125385 A1 * | 6/2007 | Ho .................... A61M 16/0683 128/206.26 |

(56) References Cited

U.S. PATENT DOCUMENTS

| | | |
|---|---|---|
| 2007/0130663 A1 | 6/2007 | Lang |
| 2007/0144525 A1 | 6/2007 | Davidson et al. |
| 2007/0175480 A1 | 8/2007 | Gradon |
| 2007/0209663 A1 | 9/2007 | Marque |
| 2007/0246043 A1 | 10/2007 | Kwok et al. |
| 2008/0092906 A1 | 4/2008 | Gunaratnam |
| 2008/0178875 A1 | 7/2008 | Henry |
| 2008/0190432 A1 | 8/2008 | Blochlinger |
| 2008/0230068 A1 | 9/2008 | Rudolph |
| 2009/0038619 A1 | 2/2009 | Ho et al. |
| 2009/0044808 A1 | 2/2009 | Guney et al. |
| 2009/0101141 A1 | 4/2009 | Ging et al. |
| 2009/0126739 A1 | 5/2009 | Ng |
| 2009/0173349 A1 | 7/2009 | Hernandez |
| 2009/0178680 A1 | 7/2009 | Chang |
| 2009/0241961 A1 | 10/2009 | Mcauley |
| 2009/0277452 A1 | 11/2009 | Lubke et al. |
| 2010/0000543 A1 | 1/2010 | Berthon-Jones |
| 2010/0037897 A1 | 2/2010 | Wood |
| 2010/0083961 A1 | 4/2010 | McAulet et al. |
| 2010/0218768 A1 | 9/2010 | Radney |
| 2010/0258136 A1 | 10/2010 | Doherty et al. |
| 2010/0313891 A1 | 12/2010 | Veliss et al. |
| 2010/0325844 A1 | 12/2010 | Fiedler |
| 2011/0000492 A1 | 1/2011 | Veliss |
| 2011/0072553 A1 | 3/2011 | Ho |
| 2011/0197341 A1 | 8/2011 | Formica et al. |
| 2011/0253143 A1 | 10/2011 | Ho et al. |
| 2011/0265796 A1 | 11/2011 | Amarasinghe et al. |
| 2012/0041331 A1 | 2/2012 | Burton et al. |
| 2012/0067349 A1 | 3/2012 | Barlow et al. |
| 2012/0067351 A1 | 3/2012 | Macmillan |
| 2012/0080035 A1 | 4/2012 | Guney et al. |
| 2012/0138061 A1* | 6/2012 | Dravitzki .......... A61M 16/0616 128/205.25 |
| 2012/0138063 A1 | 6/2012 | Eves et al. |
| 2012/0190998 A1 | 7/2012 | Armitstead |
| 2012/0216819 A1 | 8/2012 | Raje et al. |
| 2012/0304999 A1 | 12/2012 | Swift et al. |
| 2012/0325219 A1 | 12/2012 | Smith |
| 2013/0008446 A1 | 1/2013 | Carroll et al. |
| 2013/0092174 A1 | 4/2013 | Jackman |
| 2013/0152937 A1 | 6/2013 | Jablonski et al. |
| 2013/0152938 A1 | 6/2013 | Jablonski |
| 2013/0199537 A1* | 8/2013 | Formica ............ A61M 16/0683 128/205.25 |
| 2013/0213400 A1 | 8/2013 | Barlow et al. |
| 2013/0220327 A1 | 8/2013 | Barlow et al. |
| 2013/0228173 A1 | 9/2013 | Busch |
| 2013/0263859 A1 | 10/2013 | Ho |
| 2013/0298912 A1 | 11/2013 | Gulliver |
| 2013/0306077 A1 | 11/2013 | Greenberg |
| 2013/0319422 A1 | 12/2013 | Ho et al. |
| 2014/0034057 A1 | 2/2014 | Todd et al. |
| 2014/0053844 A1 | 2/2014 | Rummery et al. |
| 2014/0069433 A1 | 3/2014 | Walker et al. |
| 2014/0083427 A1 | 3/2014 | Andrews |
| 2014/0094669 A1 | 4/2014 | Jaffe et al. |
| 2014/0166018 A1 | 6/2014 | Dravitzki et al. |
| 2014/0166019 A1 | 6/2014 | Ho et al. |
| 2014/0174447 A1 | 6/2014 | Ho |
| 2014/0190486 A1 | 7/2014 | Dunn |
| 2014/0209098 A1 | 7/2014 | Dunn et al. |
| 2014/0224253 A1 | 8/2014 | Law et al. |
| 2014/0261412 A1 | 9/2014 | Guney et al. |
| 2014/0261434 A1 | 9/2014 | Ng et al. |
| 2014/0261440 A1 | 9/2014 | Chodkowski |
| 2014/0283826 A1* | 9/2014 | Murray ............ A61M 16/0683 128/202.27 |
| 2014/0283841 A1 | 9/2014 | Chodkowski |
| 2014/0283843 A1 | 9/2014 | Eves et al. |
| 2014/0305439 A1* | 10/2014 | Chodkowski ..... A61M 16/0605 128/207.11 |
| 2014/0311494 A1 | 10/2014 | Gibson et al. |
| 2015/0028519 A1 | 1/2015 | Lang et al. |
| 2015/0059759 A1 | 3/2015 | Frater et al. |
| 2015/0083124 A1* | 3/2015 | Chodkowski ..... A61M 16/0816 128/202.27 |
| 2015/0128952 A1 | 5/2015 | Matula, Jr. et al. |
| 2015/0128953 A1 | 5/2015 | Formica et al. |
| 2015/0196726 A1 | 7/2015 | Skipper et al. |
| 2015/0217074 A1 | 8/2015 | Wells et al. |
| 2015/0246199 A1 | 9/2015 | Matula, Jr. et al. |
| 2015/0246200 A1 | 9/2015 | Neff, Jr. |
| 2015/0290415 A1 | 10/2015 | Dunn |
| 2016/0022944 A1 | 1/2016 | Chodkowski et al. |
| 2016/0067441 A1 | 3/2016 | Bearne et al. |
| 2016/0074613 A1 | 3/2016 | Davidson et al. |
| 2017/0000964 A1 | 1/2017 | Shafer |
| 2017/0056611 A1 | 3/2017 | Frater et al. |
| 2017/0361048 A1 | 12/2017 | Moiler et al. |
| 2018/0001044 A1 | 1/2018 | Stephens et al. |
| 2018/0250486 A1 | 9/2018 | Amarasinghe et al. |
| 2020/0289777 A1 | 9/2020 | Bearne |

FOREIGN PATENT DOCUMENTS

| | | |
|---|---|---|
| AU | 2017 238904 A1 | 10/2016 |
| CN | 1623609 A | 6/2005 |
| CN | 101237902 A | 8/2008 |
| CN | 101378810 A | 3/2009 |
| CN | 101455871 A | 6/2009 |
| CN | 102014999 A | 4/2011 |
| CN | 102245250 | 11/2011 |
| CN | 102458548 | 5/2012 |
| CN | 102596299 A | 7/2012 |
| CN | 102753230 A | 10/2012 |
| EP | 1020201 A2 | 7/2000 |
| EP | 1163923 B1 | 11/2005 |
| EP | 2042209 A1 | 4/2009 |
| EP | 2060294 B1 | 7/2013 |
| EP | 2054114 B1 | 3/2015 |
| EP | 2950864 A9 | 12/2015 |
| EP | 2996752 A1 | 3/2016 |
| GB | 472897 A | 9/1937 |
| GB | 521282 A | 5/1940 |
| GB | 2385533 A | 8/2003 |
| JP | 2003-525715 A | 9/2003 |
| JP | 2006505373 | 2/2006 |
| JP | 2006-507858 A | 3/2006 |
| JP | 2008-501438 A | 1/2008 |
| JP | 2008-532659 A | 8/2008 |
| JP | 2009-039528 | 2/2009 |
| JP | 2010-536407 A | 12/2010 |
| JP | 2011-512967 | 4/2011 |
| JP | 2012-511341 A | 5/2012 |
| JP | 2012-513231 A | 6/2012 |
| JP | 2012530561 | 12/2012 |
| NZ | 547748 A | 7/2010 |
| WO | WO 1999/006116 A1 | 2/1999 |
| WO | WO 2001/062326 A1 | 8/2001 |
| WO | WO 2002/007806 A1 | 1/2002 |
| WO | WO 2002/047749 A1 | 6/2002 |
| WO | WO 2003/013657 A1 | 2/2003 |
| WO | WO 2003/039637 A1 | 5/2003 |
| WO | WO 2003/076020 A2 | 9/2003 |
| WO | WO 2004/041325 A2 | 5/2004 |
| WO | WO 2004/073778 A1 | 9/2004 |
| WO | WO 2005/032634 A1 | 4/2005 |
| WO | WO 2005/118042 A2 | 12/2005 |
| WO | WO 2006/130903 A1 | 12/2006 |
| WO | WO 2008/030831 A2 | 3/2008 |
| WO | WO 2008/063923 A2 | 5/2008 |
| WO | WO 2010/073142 A1 | 7/2010 |
| WO | 2011077254 A2 | 6/2011 |
| WO | WO 2012/040791 A1 | 4/2012 |
| WO | WO 2012/040792 A1 | 4/2012 |
| WO | WO 2012/069951 A1 | 5/2012 |
| WO | WO 2012/140514 A1 | 10/2012 |
| WO | WO 2012/177152 A1 | 12/2012 |
| WO | WO 2013/066195 A1 | 5/2013 |
| WO | WO 2013/175409 A1 | 11/2013 |
| WO | WO 2014/025267 A1 | 2/2014 |
| WO | WO 2014/062070 A1 | 4/2014 |

(56) References Cited

FOREIGN PATENT DOCUMENTS

| WO | WO 2014/141029 A1 | 9/2014 |
|---|---|---|
| WO | WO 2014/165906 A9 | 12/2014 |
| WO | WO 2015/006826 A1 | 1/2015 |
| WO | WO 2015/020535 A1 | 2/2015 |
| WO | WO 2015/068067 A1 | 5/2015 |
| WO | WO 2015/070289 A1 | 5/2015 |
| WO | WO 2015/092621 A1 | 6/2015 |
| WO | WO 2017/120643 A1 | 7/2017 |
| WO | WO 2017/124152 A1 | 7/2017 |
| WO | WO 2018/177794 A1 | 10/2018 |

OTHER PUBLICATIONS

Chinese First Official Action, CN 201480036408.2, dated Nov. 1, 2016, in 10 pages.
European Patent Office, Examination Report, Application No. 14 787 540.5-1122, dated Jun. 12, 2018, in 5 pages.
Examination Report for Australian Patent Application No. 2019275639 dated Jan. 29, 2021, 5 pages.
Examination Report for Brazilian Patent Application No. BR112015026821-8 dated Dec. 31, 2019, 5 pages.
Examination Report for Canadian Patent Application No. 2909993 dated Jul. 20, 2020, 5 pages.
Examination Report for Chinese Patent Application No. 201811001050.6 dated Jun. 8, 2020, 10 pages.
Examination Report for Japanese Patent Application No. 2018-088678 dated Jan. 14, 2020, 5 pages.
Examination Report, Australian Patent Application No. 2014258012, dated Sep. 7, 2018, in 5 pages.
Examination Report in Great Britain Patent Application No. GB1518497.1 dated Nov. 13, 2019, 4 pages.
First Official Japanese Office Action, Application No. JP 2016-510642, dated Sep. 11, 2017, in 4 pages.
International Search Report; PCT/NZ2014/000075, dated Aug. 1, 2014; 11 pages.
State Intellectual Property Office of the People's Republic of China, Second Office Action, Application No. 201480036408.2, dated Aug. 1, 2017, in 9 pages.
Third Official Japanese Office Action, Application No. JP 2018-088678, dated Oct. 1, 2020, in 5 pages.

* cited by examiner

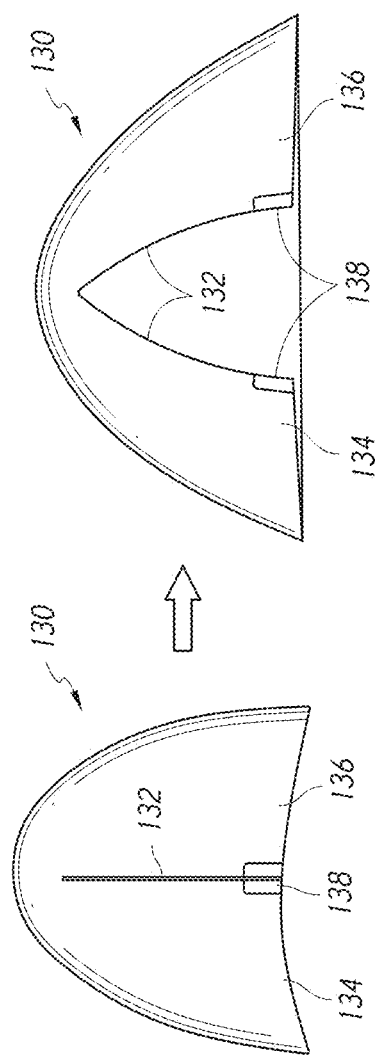

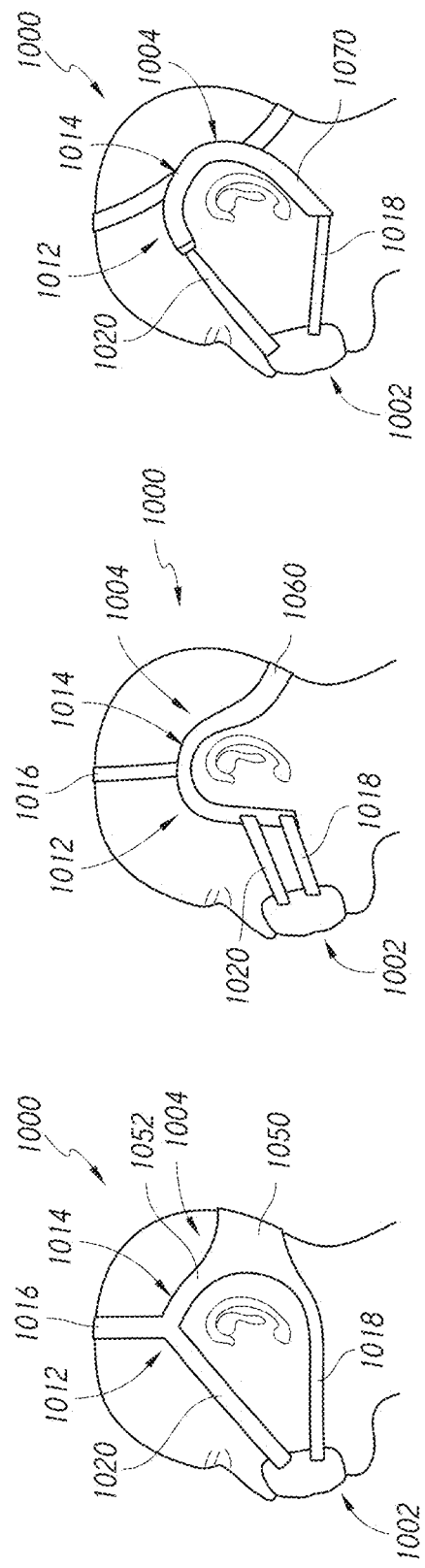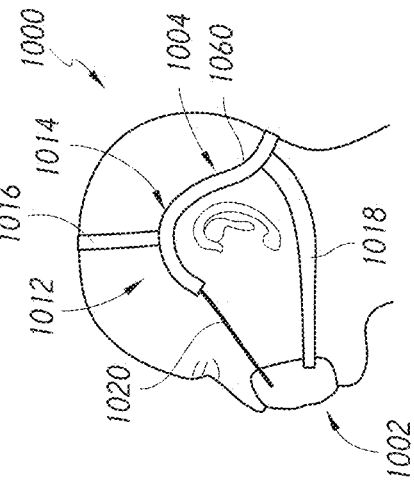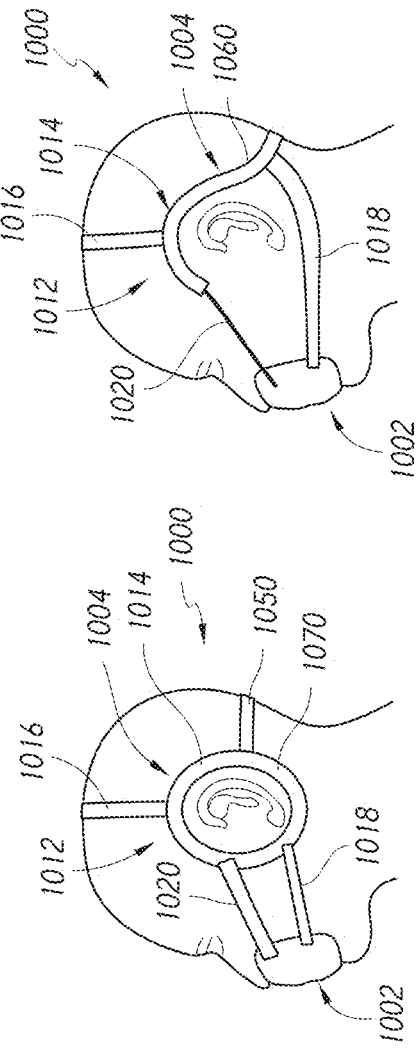

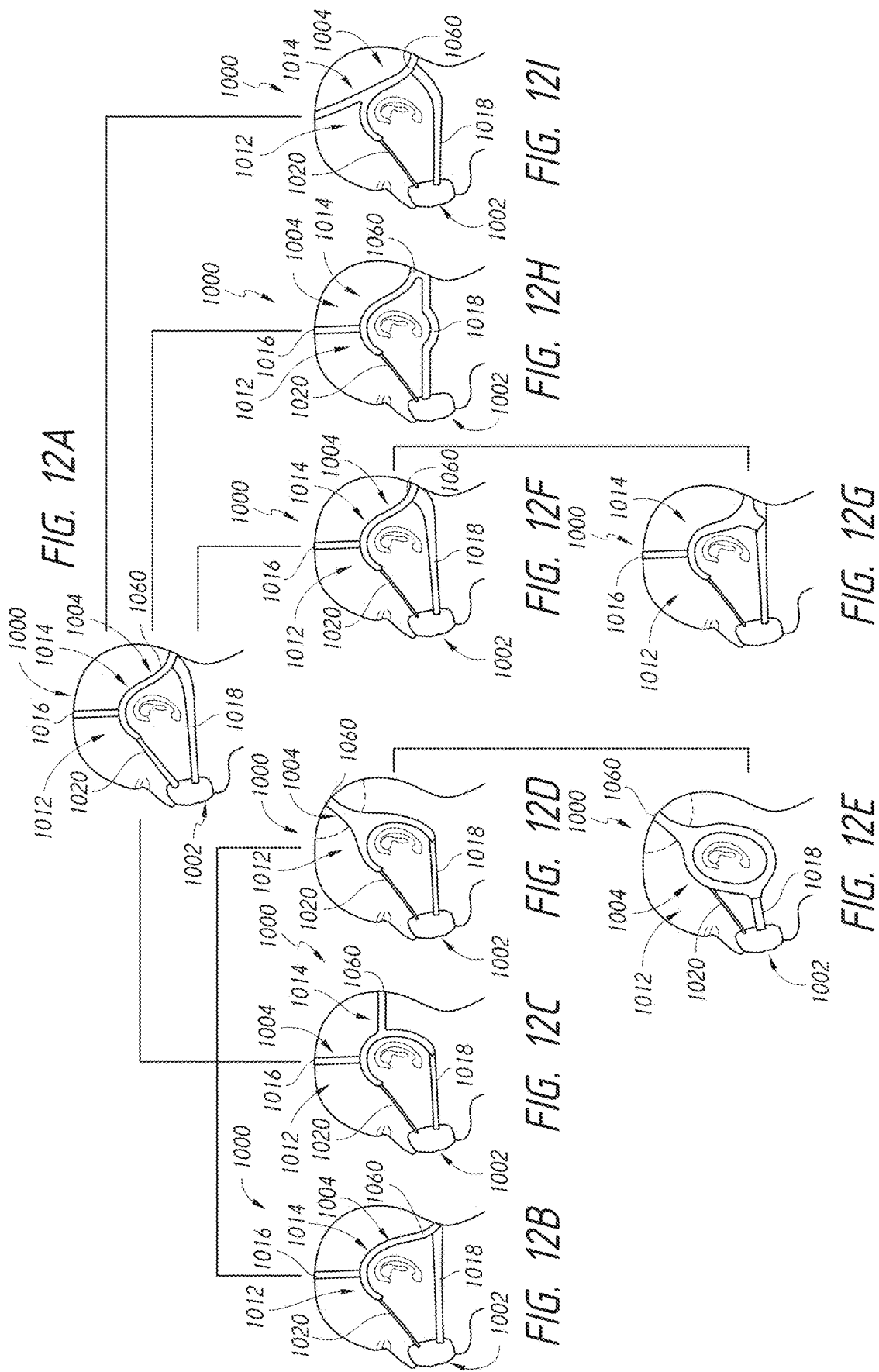

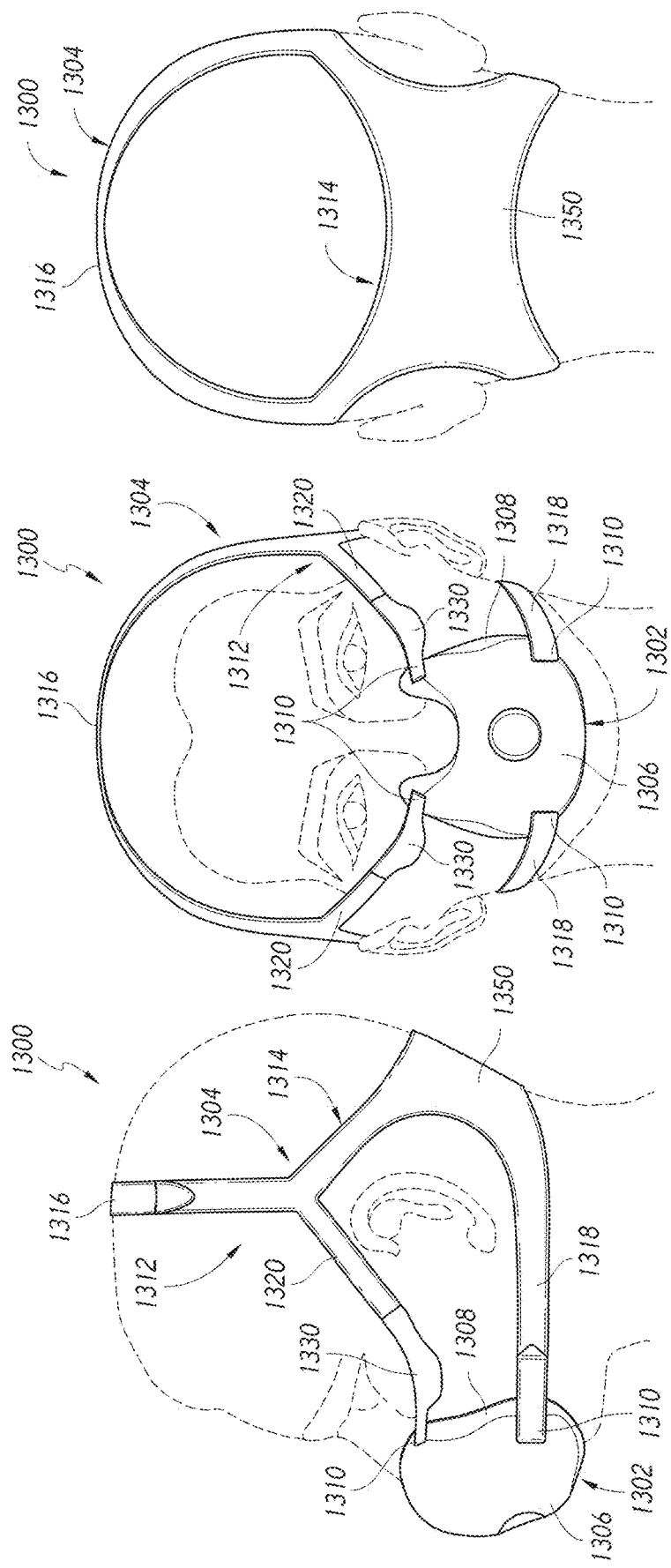

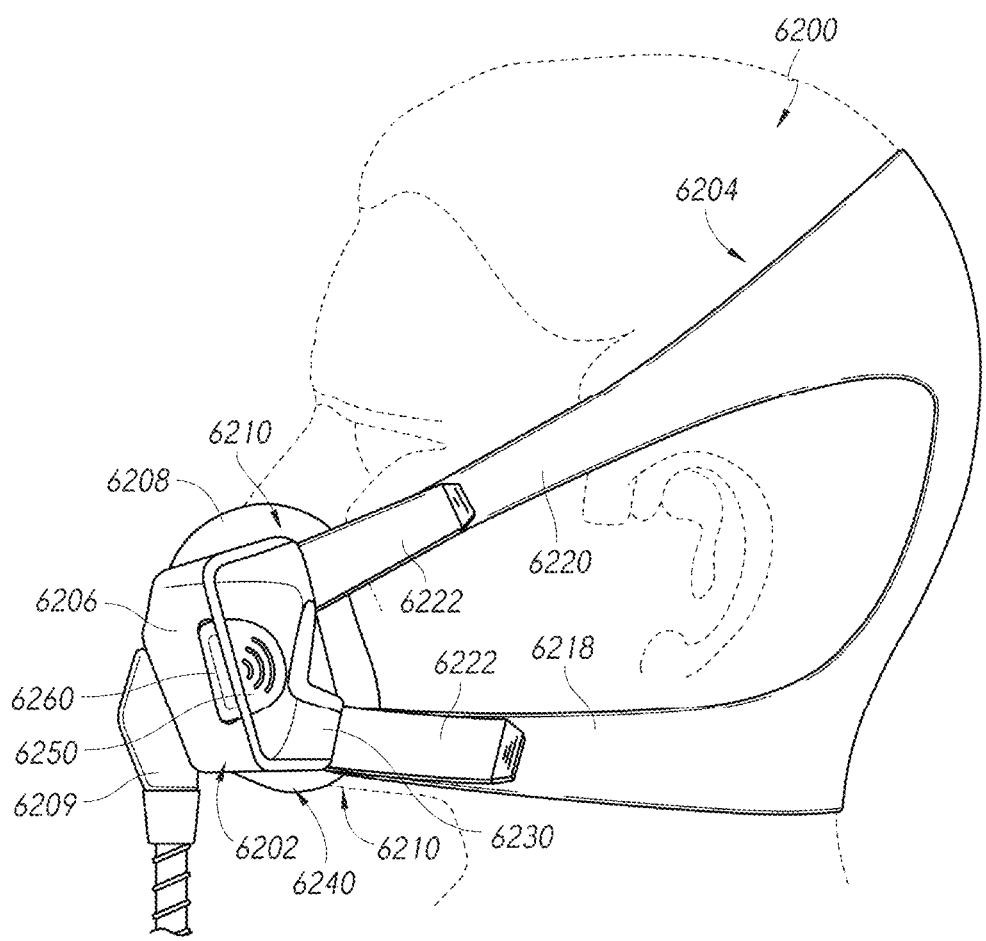
FIG. 62
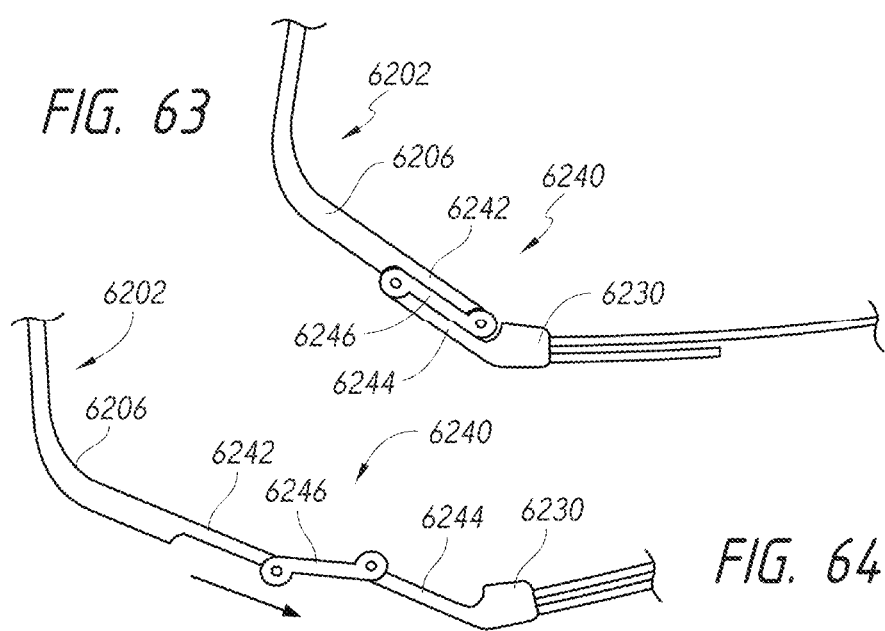
FIG. 63
FIG. 64

HEADGEAR FOR BREATHING MASK

INCORPORATION BY REFERENCE TO ANY PRIORITY APPLICATIONS

Any and all applications for which a foreign or domestic priority claim is identified in the Application Data Sheet as filed with the present application are hereby incorporated by reference and made a part of the present disclosure.

BACKGROUND

Field

The present invention generally relates to headgear of breathing masks. More particularly, certain aspects of the present invention relate to headgear used with breathing masks that seal under the nose and around the mouth.

Description of the Related Art

Breathing masks come in many different configurations. To secure the breathing masks to the user, headgear can be attached to the masks. While different styles of headgear are available, the headgear and the breathing masks ideally cooperate to provide a desired interface assembly.

SUMMARY

In some configurations, masks can be provided that seal around a mouth of a user and on an underside of a nose of the user. Such a mask can provide pressurized air flow to both the nose and the mouth of the user. In some configurations, the mask may omit a forehead support, which is different from many of the nasal masks and many of the oral-nasal masks available in the market.

With such masks, the headgear has to overcome one or more of a number of challenges. For instance, the nasal sealing surface should be secured up against the lower surface of the user's nose. Securing the nasal sealing surface against the nose helps achieve an effective seal without applying excessive force to the nose. To achieve this, the headgear can provide a force to the mask that is at least partially perpendicular to the underside of the nose.

In some configurations, the lack of a forehead support means that the mask may be prone to rocking on the face. In such configurations, the headgear can hold the seal against the face evenly in such a manner that the likelihood is reduced of significant rocking of the top away from the nose or movement of the bottom of the mask away from the chin.

An aspect involves an interface assembly including a mask and a headgear. The mask includes a seal that surrounds and delivers a flow of breathing gas to a mouth of a user. The headgear secures the mask to the face of the user. The headgear includes relatively rigid portions that contact the cheeks of the user and support the mask relative to the face of the user. The relatively rigid portions have sufficient rigidity to maintain a position of the mask and limit compression of the seal in response to tightening of the headgear.

In some configurations, a cheek pad positioned on at least a skin-contacting side of each of the relatively rigid portions. The cheek pad can be contoured. The cheek pad can surround the relatively rigid portion.

In some configurations, the headgear further comprises an upper arm or strap extending rearwardly from each of the relatively rigid portions toward a location generally above the user's ear.

In some configurations, the headgear includes a rear halo portion surrounding a parietal region of the user's head and coupled to the upper arms or straps. A portion of the rear halo portion, the upper arms or straps, and the mask can cooperate to form a front halo portion.

In some configurations, the headgear comprises a crown strap, which forms a part of each of the front halo portion and the rear halo portion, and a rear strap, which forms a part of the rear halo portion.

In some configurations, at least portions of the upper arm, the crown strap and the rear strap are constructed from a relatively rigid material or a relatively non-stretch material.

In some configurations, the headgear includes a pair of rigid sections, each rigid section comprising an upper arm, a portion of the crown strap and a portion of the rear strap, wherein each of the crown strap and the rear strap comprises adjustment arrangements that connect the rigid sections to one another and permit adjustment of the front halo portion and the rear halo portion. The adjustment arrangements can comprise flexible straps.

In some configurations, each of the rigid sections is covered by a soft material padding. The soft material padding can be overmolded onto the rigid sections.

In some configurations, the mask is supported relative to the headgear by a rotational coupling. The mask can be secured in a rotational position relative to the headgear. The mask can be secured in the rotational position by a lock or detent mechanism incorporated into the rotational coupling. In some configurations, the mask is secured in the rotational position by a strap of the headgear.

In some configurations, at least one quick-release mechanism permits separation of two portions of the interface assembly to open or increase a circumference of the interface assembly. The quick-release mechanism can include a tether between the two portions of the interface assembly. The tether can be elastic. In some configurations, the quick-release mechanism comprises a clip that connects the headgear to the mask. The clip can define at least two spaced engagement points with the mask. In some configurations, a magnetic coupling guides the clip into position relative to the mask. The quick-release mechanism can include a clip that connects the headgear to the mask, and the tether can be hidden between the clip and the mask when the clip is secured to the mask. In some configurations, the quick-release mechanism comprises a release buckle.

In some configurations, a position of the seal is adjustable relative to a frame or support structure of the mask to which the relatively rigid portions are connected. A dial adjuster can be provided that adjusts the position of the seal.

An aspect involves an interface assembly including a mask and a headgear. The mask includes a seal that surrounds and delivers a flow of breathing gas to a mouth of a user. The headgear secures the mask to the user's face. A closed loop adjustment mechanism couples a first portion of the interface assembly to a second portion of the interface assembly and is movable between a contracted orientation and an elongated orientation to vary an overall circumference of the interface assembly while maintaining a closed loop. In the contracted orientation, the mask is supported against the face of the user and, in the elongated orientation, the interface assembly can be applied to or removed from the head of the user. At least a portion of the closed loop adjustment mechanism is located on the mask.

In some configurations, the closed loop adjustment mechanism comprises a loop that forms a portion of the circumference of the interface assembly, wherein the loop can be secured to the mask at first and second spaced locations to define a first section length, and wherein the loop can be disconnected from the second location to define a second section length that is greater than the first section length to increase the circumference of the interface assembly. In some configurations, the second location can be a retention cleat that the loop can be looped around. In some configurations, the second location can be an opening or bar that is engaged by a clip connected to the loop. The first location can be a friction guide through which the loop passes, wherein the friction guide frictionally engages the loop to maintain a desired relative position between the loop and the mask in response to normal operational forces.

In some configurations, the closed loop adjustment mechanism comprises a clip that connects the headgear to the mask. The clip can define at least two spaced engagement points with the mask. In some configurations, a magnetic coupling that guides the clip into position relative to the mask. The closed loop adjustment mechanism can include a tether between the clip and the mask. In some configurations, the tether is elastic. The closed loop adjustment can include a clip on each side of the mask and the tether can extend between the two clips. In some configurations, the tether is hidden between the clip and the mask when the clip is secured to the mask.

In some configurations, the closed loop adjustment mechanism comprises a folding clasp having multiple segments movable between an open position and a closed position. In some configurations, at least two segments of the folding clasp are nested in the closed position of the folding clasp. In some configurations, one of the segments defines a generally U-shape and a second one of the segments is positioned within a central space of the U-shaped segment in a closed position of the folding clasp. In some configurations, one of the segments is carried by the mask and a second one of the segments is carried by the headgear. A locking adjuster can be provided between the second one of the segments and the headgear to permit adjustment of a relative position of the folding clasp and the headgear. In some configurations, the folding clasp locks in the closed position.

An aspect involves an interface assembly including a mask and a headgear. The mask includes a seal that surrounds and delivers a flow of breathing gas to a mouth of a user. The headgear secures the mask to the user's face and includes at least one adjustment loop. A sliding buckle receives a portion of the headgear within a tortuous pathway and is coupled to a portion of the adjustment loop, wherein movement of the sliding buckle along the portion of the headgear alters a size of the adjustment loop to alter an overall size of the headgear.

In some configurations, a pull tab is coupled to the sliding buckle to facilitate movement of the sliding buckle. In some configurations, a coupler secures the pull tab relative to the sliding buckle when not in use. The coupler can be a magnetic coupler.

In some configurations, the pull tab is slidably mounted to the sliding buckle such that the pull tab can move relative to the sliding buckle in a direction of movement of the sliding buckle.

In some configurations, at least one clip that couples the headgear to the mask. The clip can be tethered to the mask.

In some configurations, clip defines at least two spaced engagement points with the mask.

An aspect involves an interface assembly including a mask and a headgear. The mask includes a seal that surrounds and delivers a flow of breathing gas to a mouth of a user. The headgear secures the mask to the user's face. The headgear is constructed from at least two flat portions of material that are connected along sew lines to form a seam, wherein the sew lines of the portions of material do not have the same shape, such that, when connected, tension and/or compression is introduced into the material to provide the headgear with a contoured shape.

In some configurations, the sew lines are defined by edges of the portions of material.

In some configurations, the connection between the portions extends in a vertical direction along a rear portion of the headgear.

An aspect involves an interface assembly including a mask and a headgear. The mask includes a seal that surrounds and delivers a flow of breathing gas to a mouth of a user. The headgear secures the mask to the face of the user. The headgear includes a rear halo portion surrounding a parietal region of the user's head and the headgear cooperates with the mask to form a front halo portion surrounding a frontal region of the user's head. The headgear includes a relatively stretchable portion and a relatively non-stretchable portion, wherein the relatively non-stretchable portion surrounds at least one of the front halo portion and the rear halo portion.

In some configurations, the relatively non-stretchable portion surrounds each of the front halo portion and the rear halo portion.

In some configurations, one or both of the front halo portion and the rear halo portion are adjustable in circumference.

In some configurations, a break-fit assembly permits the headgear to move between a normal configuration and an enlarged configuration. The break-fit assembly can include a separation between a first portion of the headgear and a second portion of the headgear, wherein the first and second portions are held together in the normal configuration and are moved apart in the enlarged configuration. The first and second portions can be held together by a magnetic closure.

In some configurations, the first and second portions comprise first and second flaps, respectively. In some configurations, the first and second flaps are joined by a pleat.

In some configurations, the front halo portion connects to each side of the mask at a first location, wherein the headgear further comprises straps on each side of the headgear that each connect to a respective side of the mask at a second location spaced from the first location. The first and second locations can be upper and lower locations, respectively.

In some configurations, strengthening features are formed into or otherwise secured to the relatively stretchable portion of the headgear.

An aspect involves an interface assembly including a mask and a headgear. The mask includes a seal that surrounds and delivers a flow of breathing gas to a mouth of a user, the mask comprising a support structure having an elongated slot. The headgear secures the mask to the face of the user, wherein the headgear comprises an end portion that passes through the elongated slot of the mask and is folded to form a loop, the loop having a fold that supports the mask, wherein the end portion can be adjusted in an upward or downward direction to adjust an angle of the mask relative to the headgear.

In some configurations, the end portion defines a tapered shape.

In some configurations, the end portion can be coupled to the headgear to secure the mask in a desired angular position.

In some configurations, the elongated slot is linear in shape.

In another aspect, the invention involves the headgear of any of the above-described interface assemblies configured for use with any of the above-described interfaces or any other compatible interface.

In a further aspect, the invention consists in components as herein described with reference to any one or more of the drawings.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

This invention may also be said broadly to consist in the parts, elements and features referred to or indicated in the specification of the application and/or statements of invention, individually or collectively, and any or all combinations of any two or more said parts, elements features or statements of invention, and where specific integers are mentioned herein which have known equivalents in the art to which this invention relates, such known equivalents are deemed to be incorporated herein as if individually set forth.

The invention consists in the foregoing and also envisages constructions of which the following gives examples only.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

Further aspects and advantages of the present invention will become apparent from the ensuing description which is given by way of example only.

BRIEF DESCRIPTION OF THE DRAWINGS

These and other features, aspects and advantages of the present disclosure are described with reference to the drawings of preferred embodiments, which embodiments are intended to illustrate and not to limit the disclosure.

FIGS. 5A and 5B illustrate a break-fit arrangement of the interface assembly of FIG. 1.

FIGS. 10A-10E are side views of several interface assemblies, each having an interface, such as a mask, and a headgear.

FIGS. 12A-12I are side views of several interface assemblies, each having an interface, such as a mask, and a headgear.

FIG. 13 is a side view of an interface assembly having an interface, such as a mask, and a headgear.

FIG. 14 is a front view of the interface assembly of FIG. 13.

FIG. 15 is a rear view of the interface assembly of FIG. 13.

FIG. 58 is a perspective view of an interface assembly having a quick-release mechanism, which includes an elasticated tether that couples the clip to a remainder of the mask.

FIG. 62 is a side view of an interface assembly having an interface, such as a mask, and a headgear. The interface assembly includes a folding clasp quick-release mechanism between the mask and the headgear.

FIG. 63 is a top view of the folding clasp quick-release mechanism of FIG. 62 in a closed state.

FIG. 64 is a top view of the folding clasp quick-release mechanism of FIG. 62 in an open state.

DETAILED DESCRIPTION

Figure 3:
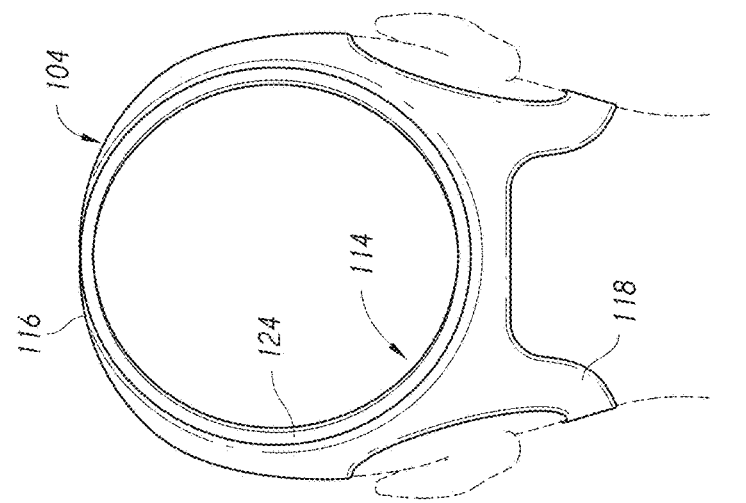
FIG. 3 is a rear view of the interface assembly of FIG. 1.
Figure 2:
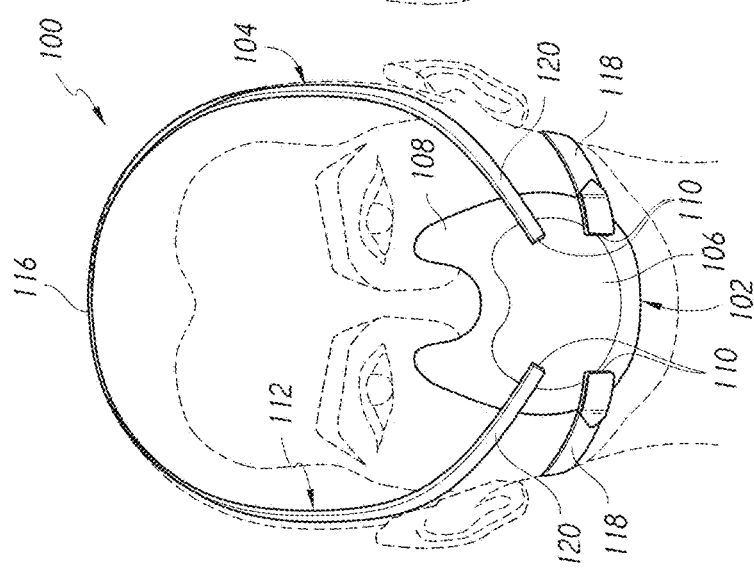
FIG. 2 is a front view of the interface assembly of FIG. 1.
Figure 1:
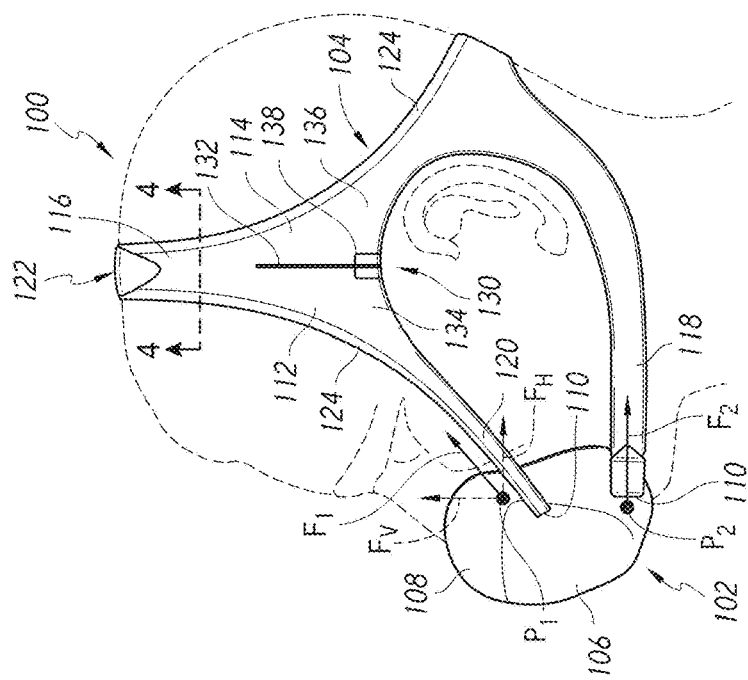
FIG. 1 is a side view of an interface assembly having an interface, such as a mask, and a headgear.

With reference to FIGS. 1-3, an interface assembly 100 is illustrated. The interface assembly 100 can have any suitable configuration. The illustrated interface assembly 100 includes an interface portion, or interface 102, and a headgear portion, or headgear 104. The illustrated interface 102 is a nasal-oral mask but, in some configurations, certain features, aspects and advantages of the disclosed embodiments can be used with any type of interface, including but not limited to full face masks, nasal masks, nasal pillows, oral masks and cannulas. Accordingly, the interface 102 is also referred to herein as a "mask" for convenience. The use of the term "mask" is intended to cover interfaces generally, and can be replaced with the term "interface" unless indicated otherwise, either explicitly or by the context of the disclosure. Examples of nasal-oral masks are provided in PCT Patent Publication No. WO2013/066195, the entirety of which is incorporated by reference herein.

The illustrated mask 102 generally comprises a support structure, such as a frame 106, which supports a seal 108. The mask 102 (e.g., the frame 106 and/or the seal 108) can be connected to a supply conduit (not shown), which in some configurations can be connected to the frame by an elbow. The supply conduit can be used to supply breathing gases to a user through the seal 108. The seal 108 or a combination of the seal 108 and the frame 106 can define a chamber that receives the breathing gases from the supply conduit.

As described above, in some configurations, the mask 102 can seal around a mouth of a user and on an underside of a nose of the user. Such a mask 102 can provide pressurized air flow to both the nose and the mouth of the user. With such masks 102, the headgear 104 preferably secures the nasal sealing surface up against the lower surface of the user's nose. Securing the nasal sealing surface against the nose helps achieve an effective seal without applying excessive force to the nose. As the air pressure within the chamber of the mask 102 increases, the force applied by the headgear 104 attempts to restrain the mask 102 from lifting from the face. As a result of the mask 102 being sealed against the underside of the user's nose, the force applied to the mask 102 as a result of the air pressure has a downwardly-directed component. However, in general, the largest component of the force is directed away from the user's face. To address the forces acting on the mask as a result of the air pressure, the headgear 104 preferably provides a force to the mask 102 that has at least a small upwardly-directed component. In some configurations, the headgear 104 can provide a force to the mask 102 that is directed generally or substantially perpendicular to the underside of the user's nose.

Preferably, the mask 102 comprises mounting locations or mounting points 110. The mounting points 110 can be formed on at least one of the frame 106, the seal 108, the conduit and the elbow. Any suitable mounting points 110 can be used to facilitate connection between the mask 102 and the headgear 104, which will be described below. Often, the mounting points 110 are located on a relatively rigid portion of the mask 102, such as the frame 106 or another support structure for the seal 108. Therefore, references to the frame 106, in the context of the headgear 104 being coupled at the mounting points 110 on the frame 106, can refer to any support structure of the mask 102 to which the headgear 104 is coupled, such as a seal housing, for example.

In some configurations, the mounting points 110 facilitate easy connection and disconnection of the headgear 104 and the mask 102. In some configurations, the headgear 104 and the mask 102 can be joined together such that the headgear 104 is not generally removable from one or more component of the mask 102. In some configurations, the headgear 104 and the mask 102 can be integrally formed. In some configurations, two mounting points 110 are provided on each side of the mask 102 and are spaced from one another in a vertical direction or height direction of the mask 102.

In some configurations, the headgear 104 can comprise a front halo portion 112 and a rear halo portion 114. Preferably, the headgear 104 comprises at least the rear halo portion 114. The front halo portion 112 can be configured to generally encircle the frontal region or upper half of the face of the user and resist rearward and downward directed forces. The rear halo portion 114 can be configured to generally encircle the parietal region of the head and resist forward and downward directed forces. In some configurations, the rear halo portion 114, when coupled to the mask 102, can resist a substantial portion or an entirety of the magnitude and/or direction of forces applied to the mask 102 during use. Thus, in some configurations, the rear halo portion 114 can be utilized without the front halo portion 112. However, the front halo portion 112 can assist in inhibiting or preventing rotation of the interface assembly 100 on the user's head. The front halo portion 112 can also resist downward forces to support the weight of the mask 102 and other generally downward forces, such as hose pull forces, for example. Thus, in many applications, the use of a front halo portion 112 can be desirable. In some configurations, the front halo structure 112 and the rear halo structure 114 are generally adjacent to each other. In some such configurations, the front halo structure 112 and the rear halo structure 114 can share a common crown strap 116.

In some configurations, under-ear straps or ear straps 118 can extend from lower portions of the rear halo portion 114 on each side of the headgear 104. As shown in the illustrated configurations, lower or forward strap portions 120 of the front halo structure 112 can be attached to the upper section of the mask 102 at mounting points 110 on each side of the mask 102. The forward strap portions 120 of the front halo structure 112 can be angled such that the force applied by the forward strap portions 120 will have an upwardly-directed component. As described above, in some configurations, the force can be approximately or largely perpendicular to the underside of the user's nose. Such an arrangement can assist in creating a seal between the mask 102 and the underside of the user's nose. The attachment location and the angle will help to address both of the challenges mention above.

The ear straps 118 can be attached to the lower portion of the mask 102 at mounting points 110 on each side of the mask 102. By attaching the ear straps 118 to the lower portion of the mask 102, forces applied by the ear straps 118 can cooperate with forces applied by the forward strap portions 120 of the front halo portion 112 to influence an angular position of the mask 102, as described below. The forward strap portions 120 of the front halo portion 112 can be referred to as "upper straps" relative to the ear straps 118, which are the relative "lower straps" and can be referred to as such herein. The balancing of forces can reduce the likelihood of mask rocking.

With reference to FIG. 1, the mask 102 can be viewed as having an upper point P1 and a lower point P2 at which the mask 102 contacts the user's face. The upper point P1 can be generally or substantially at an intersection between the underside of the user's nose and upper lip. The lower point P2 can be located on the user's chin. Adjustment of the forward strap portions 120 tends to rotate the mask 102 about the lower point P2. Adjustment of the ear straps 118 tends to rotate the mask 102 about the upper point P1. Thus, the existence of both of the straps 118, 120 tends to inhibit or prevent undesired rotation about either point P1, P2 when the headgear 104 is properly adjusted.

The headgear 104 can apply a force F1 to the mask 102 through the upper straps 120 and a force F2 to the mask 102 through the lower straps 118. The force F1 can be at least be oriented upward relative to horizontal or relative to a line that is perpendicular to a line passing through the points P1 and P2 (or a line defined by upper and lower points on the mask seal 108). The force F2 can be generally rearward, horizontal or along a line that is perpendicular to a line passing through the points P1 and P2 (or a line defined by upper and lower points on the mask seal 108). The force F1 can be between about 0 degrees and about 90 degrees. However, because the force applied to the headgear 104 by the mask 102 as a result of air pressure is primarily away from the user's face, preferably, a horizontal component FH of the force F1 is at least as large as or larger than a vertical component FV of the force F1. Thus, the angle of the force F1 can be about 45 degrees or less. However, if a greater vertical component FV is desired, such as to increase sealing force on the underside of the user's nose, the angle of the force F1 can be adjusted.

In some configurations, one or more of the upper straps 120 and the lower straps 118 used to attach to the mask 102 may be adjustable in length. In some configurations, both of the upper straps 120 and the lower straps 118 can be adjustable in length. However, in the illustrated arrangement, the length of the upper straps 120 is fixed and the overall circumference of the front halo portion 112 is adjusted by the central adjustment feature 122, which also adjusts the circumference of the rear halo portion 114. The lower straps 118 are adjustable to permit a rotational position of the mask 102 (relative to the upper mounting points 110 of the upper straps 120) to be adjusted.

In some configurations, the crown strap 116 can have a central adjustment feature 122. The central adjustment feature 122 can allow the size of the headgear 104 to be modified. The central adjustment feature 122 can have any suitable configuration. In some configurations, the central adjustment feature 122 can include a buckle component and portions of the crown strap 116 can pass through the buckle and double over another portion of the crown strap 116. In some configurations, the central adjustment feature 122 can be as simple as providing a hook and loop connection between two portions the crown strap 116.

The headgear 104 can be formed of any suitable materials. In some configurations, at least a portion of the headgear 104 will be made of a material with some stretch. In some configurations, the headgear 104 is formed of a stretchable material, such as Breath-o-Prene®, for example but without limitation. Breath-o-Prene® is a heat laminated material made of polyurethane foam with an outer layer of nylon and spandex. In some configurations, the headgear 104 may be thermoformed to provide structure and support.

The headgear 104 also may comprise non-stretch sections 124. In some configurations, the non-stretch sections 124 can extend around the perimeters of one or both of the halo portions 112, 114. In the illustrated arrangement, non-stretch sections 124 extend around an entire perimeter of the front halo portion 112 (with the exception of the mask 102) and an entire perimeter of the rear halo portion 114. In some configurations, non-stretch sections can also be incorporated in the lower strap 118. The non-stretch sections 124 can reduce the likelihood of the front halo portion 112 and/or rear halo portion 114 stretching over the head relative to a similar arrangement of stretchable material. Stretching of the rear halo portion 114 can cause the mask 102 to move away from or slip off the face. Stretching of the front halo portion 112 can allow rotation of the headgear 104 on the user's head. As used herein, the term "non-stretch" in the context of the non-stretch sections 124 refers to sections that are less stretchable than the stretchable or other portions of the headgear 104. In some configurations, the non-stretch sections 124 can resist substantial stretching or elongation in response to normal or expected forces applied to the mask 102 or headgear 104 to retain the halo portion(s) 112, 114 in place on the user's head, but may still be somewhat stretchable. The non-stretch sections 124 can reduce the likelihood of the upper sealing surface of the seal 108 being pulled away from the nose. In some configurations, the non-stretch sections 124 may be included in other regions of the headgear 104. Stretchable material can refer to materials typically used in headgear assemblies or can refer to materials that exhibit greater stretch than materials typically used in headgear assemblies.

FIGS. 4A-4F illustrates some possible strap cross-sections but any suitable strap configuration or combination of configurations can be used. In FIGS. 4A-4F, the hashed regions 124 can represent a material that is largely or relatively non-stretch or semi-rigid. The non-hashed regions 126 can represent a softer and/or more stretch/less rigid/more elastic material, such as Breath-o-Prene®, for example. In the illustrations shown in FIGS. 4A-4F, it is intended that the lower edge of each cross-section represents the surface that would be in contact with the patient's head. In most configurations, at least part of the surface that comes into contact with the patients head can be formed from or of a softer material.

Figure 4A:
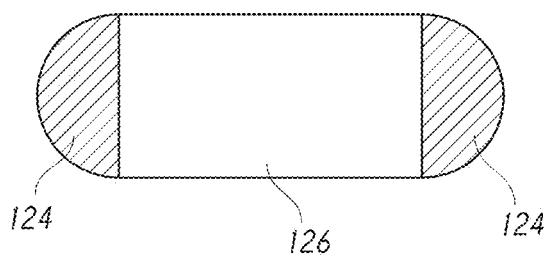
FIGS. 4A-4F illustrate various possible cross-sections of a headgear of the interface assembly of FIG. 1.
Figure 4B:
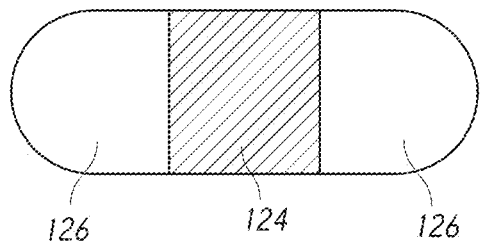
Figure 4C:
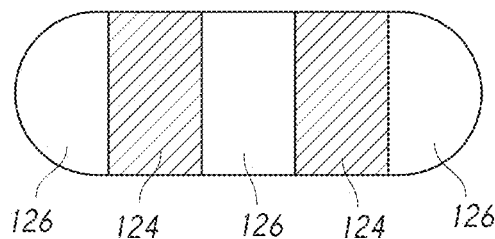
Figure 4D:
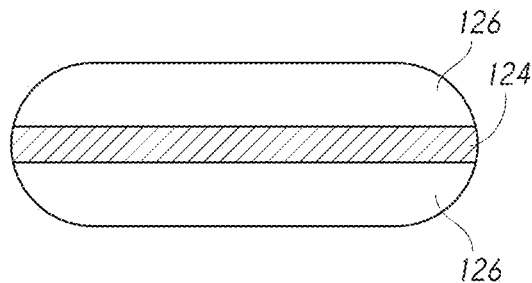
Figure 4E:
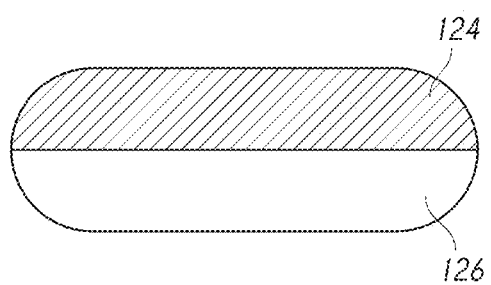
Figure 4F:
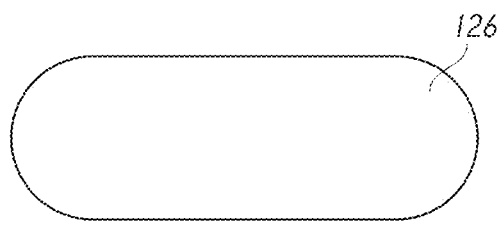

In FIG. 4A, the strap cross-section includes a non-stretch region 124 at at least one lateral edge and, preferably, at each lateral edge of the strap. A stretch region 126 extends between the laterally-spaced non-stretch regions 124. In FIG. 4B, the strap cross-section includes a central non-stretch region 124 with stretch regions 126 on each side of the non-stretch region 124. In FIG. 4C, the strap cross-section includes a plurality of spaced non-stretch regions 124 alternating with stretch regions 126. In the illustrated arrangement, the stretch regions 126 are positioned on each lateral edge and in the center with non-stretch regions 124 between the center and edge stretch regions 126. In FIG. 4D, a non-stretch region 124 extends in a width direction of the strap cross-section. In the illustrated arrangement, the regions are layered with a stretch region 126 on at least one side and, preferably, on each side of the non-stretch region 124. In FIG. 4E, a non-stretch region 124 and a stretch region 126 extend in a width direction of the strap and each occupies one-half of the strap thickness. In the illustrated arrangement, the stretch region 126 is positioned closest to the user's head. In FIG. 4F, the entire strap cross-section is a stretch region 126.

With reference to FIGS. 1, 5A and 5B, in some configurations, the headgear 104 can include a so-called break-fit assembly 130, which can be utilized to move the headgear 104 between a fitted or operating condition, in which the headgear 104 holds the mask 102 in contact with the user's face, and a fitment or removal condition, in which application or removal of the headgear 104 is facilitated. Preferably, the operating condition is a properly adjusted condition for an individual user and the break-fit assembly 130 permits quick and easy transition between the operating condition and the fitment/removal condition. That is, in contrast to designs that readjustment with each application of the interface assembly 100, the break-fit assembly 130 allows the headgear 104 to remain in a properly adjusted state, but be enlarged or opened to a certain extent to facilitate application or removal. Preferably, adjustment features separate from the break-fit assembly 130 are provided to permit adjustment of the headgear 104 to fit an individual user. Break-fit assemblies could be provided in other locations of the headgear 104, such as any strap portion of the headgear 104 or any of the other locations disclosed herein, such as in connection with FIG. 89, for example and without limitation.

The break-fit assembly 130 can resist elongation/expansion under some conditions and permits elongation/expansion under other conditions. For example, the break-fit assembly 130 can be automatic, in which elongation/expansion of the headgear 104 is resisted or prevented until a predetermined or desired yield force is exceeded, at which point the headgear can elongate/expand. In some configurations, the break-fit assembly 130 can be manually operated to move the headgear 104 between the operating condition and the fitment/removal condition.

The illustrated break-fit assembly 130 comprises a separation 132 between a first flap 134 and a second flap 136 of material. As illustrated in FIGS. 5A and 5B, the first flap 134 and the second flap 136 can be joined or their respective edges brought close to one another to define a fitted or operating condition or the flaps 134, 136 can be separated to define a fitment/removal condition. Optionally, a retention mechanism, fastener or closure 138, such as a magnetic closure, can be utilized to secure the flaps 134, 136 in a fitted or operation condition. In some configurations, the flaps 134, 136 can be connected to one another by material extending between the edges defining the separation 132, such as by a pleat. Other suitable arrangements to facilitate fitment of the headgear 102 and/or interface assembly 100 can also be used. For example, the break-fit assembly can include any of those described in U.S. Provisional Patent Application No. 61/681,024, filed on Aug. 8, 2012, for example but without limitation, which is hereby incorporated by reference in its entirety.

Figure 6:
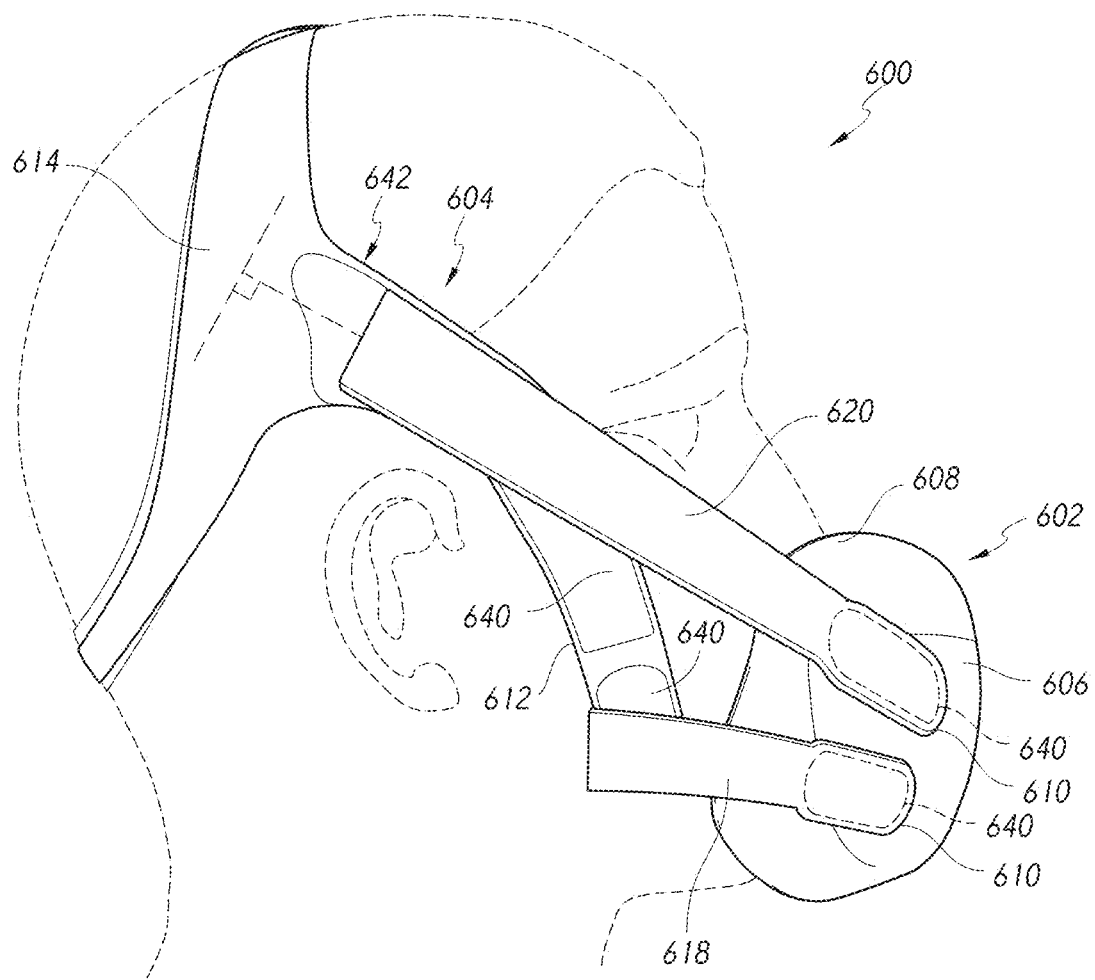
FIG. 6 is a side view of an interface assembly having an interface, such as a mask, and a headgear.

With reference to FIG. 6, another interface assembly 600 is arranged and configured in accordance with certain features, aspects and advantages of the present disclosure. The illustrated interface assembly 600 includes an interface 602 and a headgear 604. The illustrated interface 602 is a nasal-oral mask but, as described herein, other types of interfaces can be used with the disclosed headgear 604. The illustrated mask 602 generally comprises a frame 606 that supports a seal 608. The mask 602 can be connected to a supply conduit (not shown), which can be used to supply breathing gases to a user. As described above, in some configurations, the mask 602 can seal around a mouth of a user and on an underside of a nose of the user. Such a mask 602 can provide pressurized air flow to both the nose and the mouth of the user. The headgear 604 can be coupled to the mask 602 at one or more mounting locations or mounting points 610, as described below. Unless indicated otherwise, features of the interface assembly 600 or portions thereof can be the same as or similar to other interfaces or portions thereof described herein, or can be of another suitable arrangement.

In some configurations, the headgear 604 can comprise a generally non-stretch/semi-rigid halo shaped portion 614 (referred to herein as the "halo portion"). In some such configurations, the halo portion 614 can generally encircle the parietal region of a user's head. In some such configurations, the headgear 604 can have a mounting portion in the form of rigid hook-shaped extensions or hook portions 612 that extend forward from the halo portion 614 on each side of the user's face. Preferably, the hook portions 612 sit over and in front of the user's ears and provide a mounting location for coupling the mask 602 to the halo portion 614.

Preferably, the headgear 604 comprises two or more straps that couple the mask 602 to the halo portion 614. In the illustrated configuration, a first or lower strap 618 and a second or upper strap 620 are provided on each side of the headgear 604 to connect the mask 602 to the halo portion 614 and permit rotational adjustment of the mask 602. The illustrated straps 618, 620 indirectly couple the mask 602 to the halo portion 614. The straps 618, 620 are coupled directly to the hook portions 612, which transfer force from the straps 618, 620 to the halo portion 614. In some configurations, the one or more of the straps 618, 620 can have an adjustable length or an adjustable effective length. In the illustrated arrangement, the actual length of each strap 618 and 620 is fixed; however, the positioning of the straps 618, 620 on the hook portions 612 can be varied to adjust a length of each of the straps 618, 620 that extends forward from the hook portions 612. The straps 618, 620 can be secured to hook portions 612 and mask 602 by any suitable arrangement, such as cooperating hook-and-loop fastener portions 640. A substantial portion of the hook portions 612 can be covered by the hook-and-loop fastener portions 640 to provide a substantial amount of length adjustment of the straps 618, 620. In some configurations, an entirety or substantial entirety of an inward-facing surface of the straps 618, 620 can comprise hook-and-loop fastener portions 640.

In some configurations, the halo portion 614 is generally semi-rigid. In some such configurations, the semi-rigid halo portion 614 can help the headgear 604 remain open to facilitate the application or fitment process. In some such configurations, the semi-rigid halo portion 614 can reduce the likelihood of the headgear 604 (especially the halo portion 614) collapsing as a result of its own weight. In some such configurations, the semi-rigid nature of the halo portion 614 makes fitting easy while not being so rigid that the halo portion 614 is uncomfortable to wear.

In some configurations, the hook portions 612 of the headgear 604 can be more rigid than the halo portion 614. In some configurations, the hook portions 612 are rigid enough to reduce the likelihood of bending above the ear in response to normal or expected forces during use. Undesired movement of the mask 602 can result from substantial bending of the hook portions 612.

In some configurations, an initial extension 642 of the hook portions 612 from the halo portion 614 may be substantially perpendicular. In some configurations, the substantially perpendicular extension 642 can help apply a desired force angle to the mask 602. In some such configurations, the desired force angle helps to seal the mask 602 along the bottom of the user's nose.

The upper strap 620 can be attached to the hook portions 612 at an angle. In some such configurations, the angle can be approximately perpendicular to the underside of the user's nose. The lower strap 618 can be attached to the bottom of the mask 602. In some such configurations, the lower strap 618 can reduce the likelihood of the mask 602 lifting upwards away from the user's chin. In some configurations, one or more of the lower and upper straps 618, 620 can be formed of or from a material such as Breath-o-Prene®, for example but without limitation. The straps 618, 620 can be formed of or from a material that provides flexibility for easy adjustment and to minimize excessive force being applied to the user's face. Preferably, the straps 618, 620 at least substantially limit extension along an axial direction of the straps 618, 620 in response to normal or expected forces in use to maintain the mask 602 in position on the user's face. As used herein, an "axial" direction can be a direction aligned with a geometric axis of the strap (or other component) in a lengthwise direction or a direction along which the relevant force is applied. An axis of a strap or other component can be non-linear (e.g., curved). In some instances, such as in connection with straps or components having a complex shape, an "axial" direction may not be aligned with a geometric axis, but may be defined by end or connection points of the strap or may be generally aligned with a resistance force provided by the strap or other component.

Figure 9:
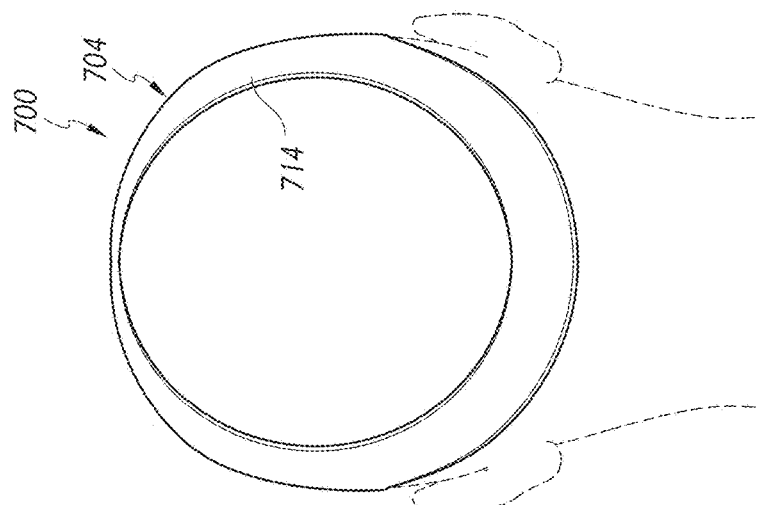
FIG. 9 is a rear view of the interface assembly of FIG. 7.
Figure 8:
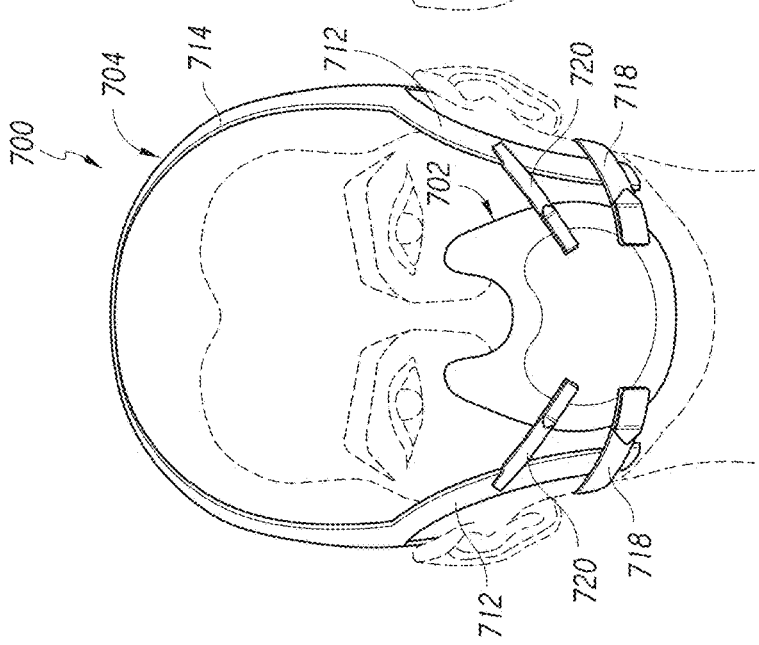
FIG. 8 is a front view of the interface assembly of FIG. 7.
Figure 7:
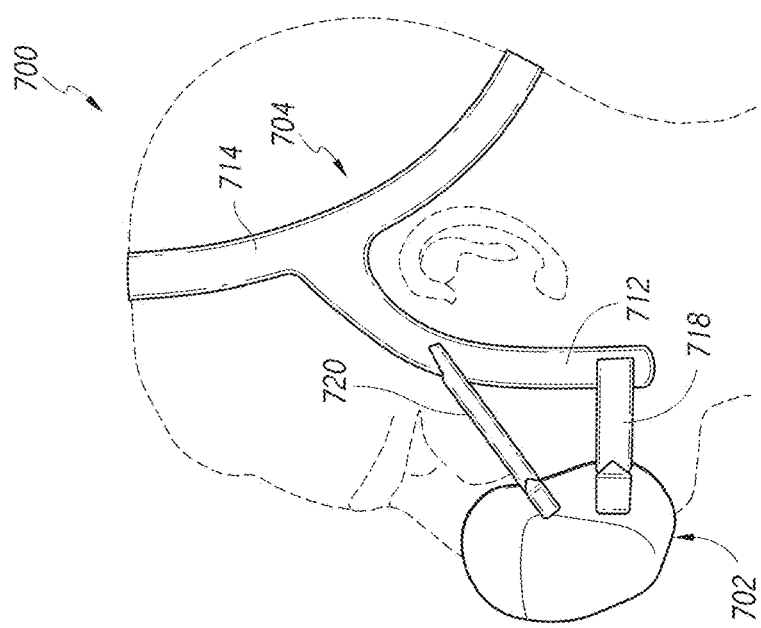
FIG. 7 is a side view of an interface assembly having an interface, such as a mask, and a headgear.

With reference to FIGS. 7-9, another interface assembly 700 is arranged and configured in accordance with certain features, aspects and advantages of the present disclosure. The illustrated interface assembly 700 is substantially similar to the interface assembly 600 in that the interface assembly 700 includes a mask 702 and a headgear 704. The illustrated mask 702 is a nasal-oral mask, but could be any other type of interface. The headgear 704 includes a halo portion 714 and a pair of hook portions 712 on each side of the headgear 704. A lower strap 718 and an upper strap 720 connect the mask 702 to the hook portions 712 on each side of the headgear 704. Unlike the interface assembly 600, the straps 718, 720 of the interface assembly 700 preferably are adjustable in length by varying a portion of the strap 718, 720 that is doubled over on itself. In the illustrated arrangement, mounting points 710 of the mask 702 include a ring, bar or similar structure that permits the strap 718, 720 to be connected to the mask 702 in a loop, with a free end of the strap 718, 720 doubled back on itself and secured, such as with a hook-and-loop fastener. In other respects, the interface assembly 700 can be the same as or substantially similar to the interface assembly 600, including any of the features described with respect thereto, or can be of any other suitable arrangement.

With reference to FIGS. 10A-10E, several variations of interface assemblies 1000 are shown, each of which can be substantially similar to the interface assemblies 600 and 700 and to one another. Accordingly, the same reference numbers are utilized throughout FIGS. 10A-10E for the same or corresponding components or features. Each interface assembly 1000 includes a mask 1002 and a headgear 1004. Each headgear 1004 also includes at least a rear halo portion 1014 or a similar effective arrangement. Preferably, each headgear 1004 also includes a front halo portion 1012 or similar effective arrangement. As described previously, the mask 1002 can cooperate with the headgear 1004 to form a portion of the front halo portion 1012. A lower strap 1018 and an upper strap 1020 are provided on each side of the headgear 1004 to connect the mask 1002 to the headgear 1004. Preferably, the upper strap 1020 applies a force to the mask 1002 in a direction that facilitates or assists in sealing the mask 1002 against a bottom surface of the user's nose and the lower strap 1018 facilitates or assists in rotational adjustment of the mask 1002. A crown strap 1016, a rear strap 1050 and/or a rigid backbone 1060, among other portions of the interface assemblies 1000, can be adjustable to fit an individual user. In some configurations, multiple sizes of headgear 1004 can be provided. The unique features and arrangements of the interface assemblies 1000 will now be described.

The interface assembly 1000 of FIG. 10A includes a relatively wide rear strap portion 1050 that rests at least partially on the occipital bone and spreads the load over a larger area of the user's head as compared to a thin strap. The lower strap 1018 passes below the user's ear and connects to the rear portion 1050. The upper strap 1020 passes above the user's ear and connects to a forward extension 1052 of the rear portion 1050 at a junction with the crown strap 1016. The crown strap 1016 and rear portion 1050 cooperate to form a halo portion 1014. The entire headgear 1004 can be constructed of a flexible material, such as Breath-o-Prene®, for example.

The interface assembly of FIG. 10B includes a rigid backbone portion 1060, which extends along the back of the user's head near the base of the skull and up and over the ears on each side. The rigid backbone 1060 can be more rigid than other portions of the headgear 1004 and can be formed from a semi-rigid or rigid material. Preferably, the ends of the rigid backbone 1060 extend forward of the user's ears. In the interface assembly 1000 of FIG. 10B, the ends of the rigid backbone 1060 extend downwardly in front of the user's ears to form a shape similar to the hook portions 612 or 712. The upper strap 1020 and lower strap 1018 can extend between the mask 1002 and the ends of the rigid backbone 1060. A crown strap 1016 can pass over the crown of the user's head and connect to each side of the rigid backbone 1060. The crown strap 1016 and rear portion of the rigid backbone 1060 cooperate to form a halo portion 1014. Preferably, at least the end portions of the rigid backbone 1060 are constructed from a relatively rigid material, similar to the hook portions 612 or 712, to resist bending. In some configurations, the entire rigid backbone 1060 can be constructed from a relatively rigid material. The lower, upper and crown straps 1018, 1020 and 1016 can be constructed from a softer, less rigid, more flexible or more stretchable material.

The interface assembly 1000 of FIG. 10C includes rigid ear loop portions 1070 on each side, which extend in an arcuate manner behind the user's ear from below to above the ear. A halo portion 1014 can couple the ear loop portions 1070 to one another. The upper straps 1020 extend from respective upper ends of the ear loop portions 1070 and the lower straps 1018 extend from respective lower ends of the ear loop portions 1070. Preferably, at least the ear loop portions 1070 are constructed from a relatively rigid material. The other portions can be constructed from a softer, less rigid, more flexible or more stretchable material.

The interface assembly 1000 of FIG. 10D includes rigid ear loops 1070 that completely encircle the user's ears. A crown strap 1016 passes over the crown of the user's head and connects the ear loops 1070 and a rear strap 1050 passes across the rear of the user's head and also connects the ear loops 1070. Each of the crown strap 1016 and the rear strap 1050 extend in a generally radial direction from the ear loop 1070 and are oriented generally perpendicular to one another. The crown strap 1016, rear strap 1050 and portions of the ear loops 1070 between the crown strap 1016 and the rear strap 1050 cooperate to define a halo portion 1014. As described above, preferably, the crown strap 1016 and rear strap 1050 are capable of adjustment such that the ear loops 1070 can be properly positioned relative to the user's ears. Preferably, at least the ear loop portions 1070 are constructed from a relatively rigid material. The other portions can be constructed from a softer, less rigid, more flexible or more stretchable material.

The interface assembly 1000 of FIG. 10E includes a rigid backbone portion 1060 similar to the headgear 1004 of FIG. 10B; however, the ends of the rigid backbone 1060 in FIG. 10E do not extend downwardly in front of the user's ear, or at least to any significant extent or as compared to the rigid backbone 1060 of FIG. 10B. The lower straps 1018 extend from the rigid backbone 1060, below the user's ears, and connect to the mask 1002. The upper straps 1020 extend from the ends of the rigid backbone from a location above the user's ear and connect to the mask 1002 at a location above the lower straps 1018. The upper straps 1020 can be of a thin construction, such as a line or cable-type construction, to minimize height and interference with vision, while providing suitable tensile properties. Preferably, at least the rigid backbone 1060 is constructed from a relatively rigid material. The other portions can be constructed from a softer, less rigid, more flexible or more stretchable material. In other respects, the interface assemblies 1000 can be the same as or substantially similar to the interface assemblies 600 or 700, including any of the features described with respect thereto, or can be of any other suitable arrangement. Features of the various interface assemblies 600, 700, 1000 can be combined with one another as desired, such as to the extent that the features are not mutually exclusive.

Figure 11A:
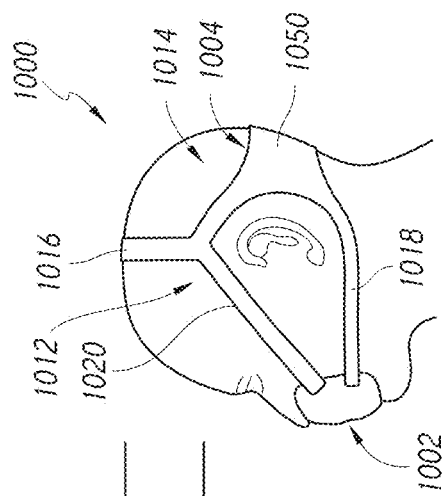
FIGS. 11A-11C are side views of several interface assemblies, each having an interface, such as a mask, and a headgear.
Figure 11C:
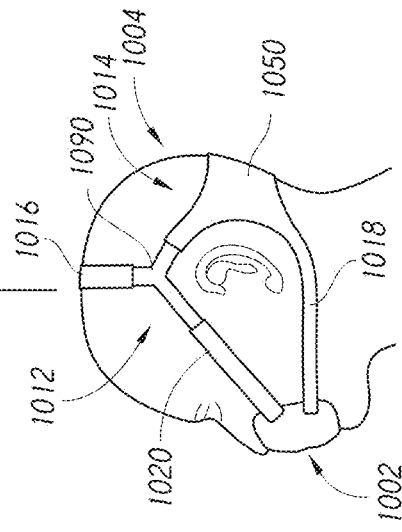
Figure 11B:
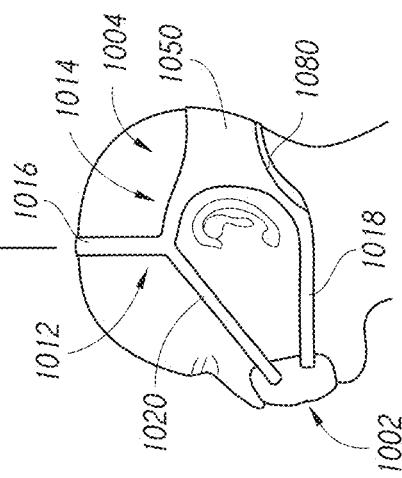

FIGS. 11A-11C illustrate several variations of interface assemblies 1000, each of which can be substantially similar to the interface assemblies 1000 of FIGS. 10A-Accordingly, the same reference numbers are utilized throughout FIGS. 11A-11C for the same or corresponding components or features. The interface assembly 1000 of FIG. 11A preferably is identical to the interface assembly 1000 of FIG. 10A. The interface assemblies 1000 of FIGS. 11B and 11C are described with respect the differences relative to the interface assembly 1000 of FIG. 11A. The interface assembly 1000 of FIG. 11B includes a relatively more rigid or semi-rigid portion 1080 positioned within the rear portion 1050. Preferably, the semi-rigid portion 1080 extends along a lower edge of the rear portion 1050, such as along an entirety or at least a substantial entirety of the rear portion 1050. The semi-rigid portion 1080 can reduce pressure on the back of the user's neck and/or reduce or prevent slipping of the headgear 1004 on the user as a result of the increased rigidity at least relative to the interface assembly 1000 of FIG. 11A.

The interface assembly 1000 of FIG. 11C includes a relatively more rigid or semi-rigid connector 1090 that couples the upper strap 1020, the crown strap 1016 and an upper portion of the rear strap or rear portion 1050. The semi-rigid connector 1090 can reduce or prevent rotation of the crown strap 1016 by stabilizing or fixing the relative positions of the crown strap 1016, the upper strap 1020 and the upper portion of the rear strap or rear portion 1050. In other respects, the interface assemblies 1000 can be the same as or substantially similar to the interface assemblies 600 or 700, or the interfaces 1000 of FIGS. 10A-10E, including any of the features described with respect thereto, or can be of any other suitable arrangement. Features of the various interface assemblies 600, 700, 1000 can be combined with one another as desired, such as to the extent that the features are not mutually exclusive.

FIGS. 12A-12I illustrate several variations of interface assemblies 1000, each of which can be substantially similar to the interface assemblies 1000 of FIGS. 10A-10E or 11A-11C. Accordingly, the same reference numbers are utilized throughout FIGS. 12A-12I for the same or corresponding components or features. The interface assembly 1000 of FIG. 12A preferably is substantially similar to the interface assembly 1000 of FIGS. 10E, except the illustrated upper straps 1020 are wider or have a greater height dimension in the orientation as worn. The upper straps 1020 of the interface assemblies 1000 of FIGS. 12B-12I can be of a thin construction, such as a line or cable-type construction, similar to the interface assembly 1000 of FIG. 10E. The interface assemblies 1000 of FIGS. 12B-12I are described with respect the differences relative to the interface assembly 1000 of FIG. 12A.

In the interface assembly 1000 of FIG. 12B, the rear section of the rigid backbone 1060 sits lower on the user's head compared to the interface assembly 1000 of FIG. 12A. Preferably, the rear portion of the rigid backbone 1060 sits at or near a junction between the skull and the neck muscles of the user. In some configurations, the rear portion can sit on the neck muscles of the user. In addition, the lower straps 1018 can be straight and arranged in a generally horizontal manner from the rear portion of the rigid backbone 1060 to the mask 1002.

In the interface assembly 1000 of FIG. 12C, the rear portion of the rigid backbone 1060 is higher than the interface assembly 1000 of FIG. 12A and, preferably, sits on the occipital bone of the user. Such an arrangement reduces the likelihood of the headgear 1004 rotating on the user's head. The rigid backbone 1060 can extend downwardly from the rear portion and partially around the ear of the user in a manner similar to the ear loops 1070 of FIG. 10C. The crown strap 1016 and the rear portion of the rigid backbone 1060 can be oriented approximately perpendicular to one another.

In the interface assembly 1000 of FIG. 12D, the rigid backbone 1060 includes ear portions similar to the ear loops 1070 of FIGS. 10C and 12C. However, preferably, the rear portion of the rigid backbone 1060 passes across the top of the head, such as across the parietal bone. In some configurations, the rear portion of the rigid backbone 1060 passes across an intermediate portion of the parietal bone and can be positioned generally between the crown strap 1016 and the rear portion of the rigid backbone 1060 of the headgear 1004 of FIG. 12C. Accordingly, the crown strap 1016 can be omitted in the headgear 1004 of FIG. 12D.

The interface assembly 1000 of FIG. 12E is similar to the interface assembly 1000 of FIG. 12D except that the rigid backbone 1060 includes full ear loops similar to the ear loops 1070 of FIG. 10D. The lower straps 1018 can extend from a lower portion of the ear loops of the rigid backbone 1060 to a lower portion of the mask 1002. In the illustrated arrangement, the lower straps 1018 extend from a position above a lowermost portion of the ear loop. However, in other arrangements, the lower straps 1018 could extend from a lowermost portion of the ear loops and/or could be generally horizontal.

In the interface assembly 1000 of FIG. 12F, the lower strap 1018 includes additional material at least in the rear portion to increase the height of the strap 1018 and the overall height of the combination of the strap 1018 and the rear portion of the rigid backbone 1060. A lower edge of the rear portion of the strap 1018 can be positioned at or near a junction between the skull and the neck muscles of the user. In some configurations, the lower edge can be on the neck muscles of the user. In some configurations, the entire rear portion can be defined by the rigid backbone 1060.

Relative to the interface assembly 1000 of FIG. 12F, the interface assembly 1000 of FIG. 12G includes relatively rigid extensions 1062 provided on lateral sides of the rear portion of the rigid backbone 1060. Preferably, the extensions 1062 extend downwardly and/or forwardly from the rear portion of the rigid backbone 1060 and provide an anchor point or support for the lower straps 1018. Such an arrangement can guide the lower straps 1018 and, in some configurations, permit the lower straps 1018 to have a generally horizontal orientation.

In the interface assembly 1000 of FIG. 12H, the rigid backbone 1060 is shaped substantially similar to the rigid backbone 1060 of FIG. 12A. Preferably, the rear portion of the rigid backbone 1060 extends across a lower portion of the bottom of the user's skull, such as across the occipital bone and, in some configurations, above the user's neck muscles. The lower straps 1018 preferably extend in a generally horizontal manner and can connect at a higher point on the mask 1002 relative to the interface assembly 1000 of FIG. 12. In some configurations, the lower straps 1018 are still vertically-spaced from the upper straps 1020 at the mask 1002. The lower straps 1018 can include a downwardly-curved or U-shaped section that defines a cut-out or space to accommodate the user's ears.

In the interface assembly 1000 of FIG. 12I, the rigid backbone 1060 defines a halo portion 1014 including a rear portion and a portion equivalent to the crown strap. The entire halo portion 1014 can be constructed from a relatively rigid material, such as a semi-rigid or rigid material, or certain portions can be constructed from a relatively rigid material (e.g., the hook portions) and other portions can be constructed from a relatively less rigid material (e.g., the upper crown portion).

FIGS. 13-15 illustrate an interface assembly 1300 that is arranged and configured in accordance with certain features, aspects and advantages of the present disclosure. The illustrated interface assembly 1300 includes an interface 1302 and a headgear 1304. The illustrated interface 1302 is a nasal-oral mask but, as described herein, other types of interfaces can be used with the disclosed headgear 1304. The illustrated mask 1302 generally comprises a frame 1306 that supports a seal 1308. The mask 1302 can be connected to a supply conduit (not shown), which can be used to supply breathing gases to a user. As described above, in some configurations, the mask 1302 can seal around a mouth of a user and on an underside of a nose of the user. Such a mask 1302 can provide pressurized air flow to both the nose and the mouth of the user.

The headgear 1304 can be coupled to the mask 1302 at one or more mounting locations or mounting points 1310, as described below. The headgear 1304 can include a crown strap 1316 that extends across the top of the user's head. Preferably, a lower strap 1318 and an upper strap 1320 are provided on each side of the headgear 1304 to connect the mask 1302 to the rear halo portion 1314 or a rear portion of the headgear 1304. Preferably, the headgear 1304 can also define a front halo portion 1312. Unless indicated otherwise, features of the interface assembly 1300 or portions thereof can be the same as or similar to other interfaces or portions thereof described herein, or can be of another suitable arrangement.

The headgear 1304 can incorporate one or more support portions or support members 1330 that can engage the head of the user to help secure the headgear 1304 in place, guide portions of the headgear 1304 in a desired path, or improve user comfort or user experience. In some configurations, the support members 1330 can contact an anatomical feature of the user's head. In the illustrated configuration, the upper straps 1320 include cheek supports 1330 that contact the cheeks of the user. In particular, the cheek supports 1330 can contact the cheeks at or near a location of the zygomatic and/or maxilla bones of the user. The cheek supports 1330 can be utilized to guide the upper straps 1320 into a non-linear path. The cheek supports 1330 can allow the upper straps 1320 to extend from the mask 1302 initially in a generally lateral direction and then upwardly to a connection point with the halo portion 1314 or a junction between the crown strap 1316 and a rear strap portion 1350 of the headgear 1304. The non-linear path can position the upper straps 1320 further from the user's eyes for improved vision and/or comfort.

In some configurations, the cheek supports 1330 can be relatively rigid and can anchor against the user's cheeks to reduce compression of the seal 1308 of the mask 1002 in response to tightening of the headgear 1304. That is, the cheek supports 1330 inhibit the retention force of the headgear 1304 from being fully transferred to the seal 1308. The cheek supports 1330 can be provided with a soft covering or skin-contact material for comfort and/or to increase grip on the user's skin to assist with redirection of the upper straps 1320. In some configurations, the cheek supports 1330 can be a portion of the mask frame 1306. In some configurations, the cheek supports 1330 can be a separate member that is coupled to the mask frame 1306. The cheek supports 1330 can have an upwardly curved shape (in the illustrated orientation) to be positioned out of or further away from the user's line of sight for a less intrusive experience when worn.

Figure 16:
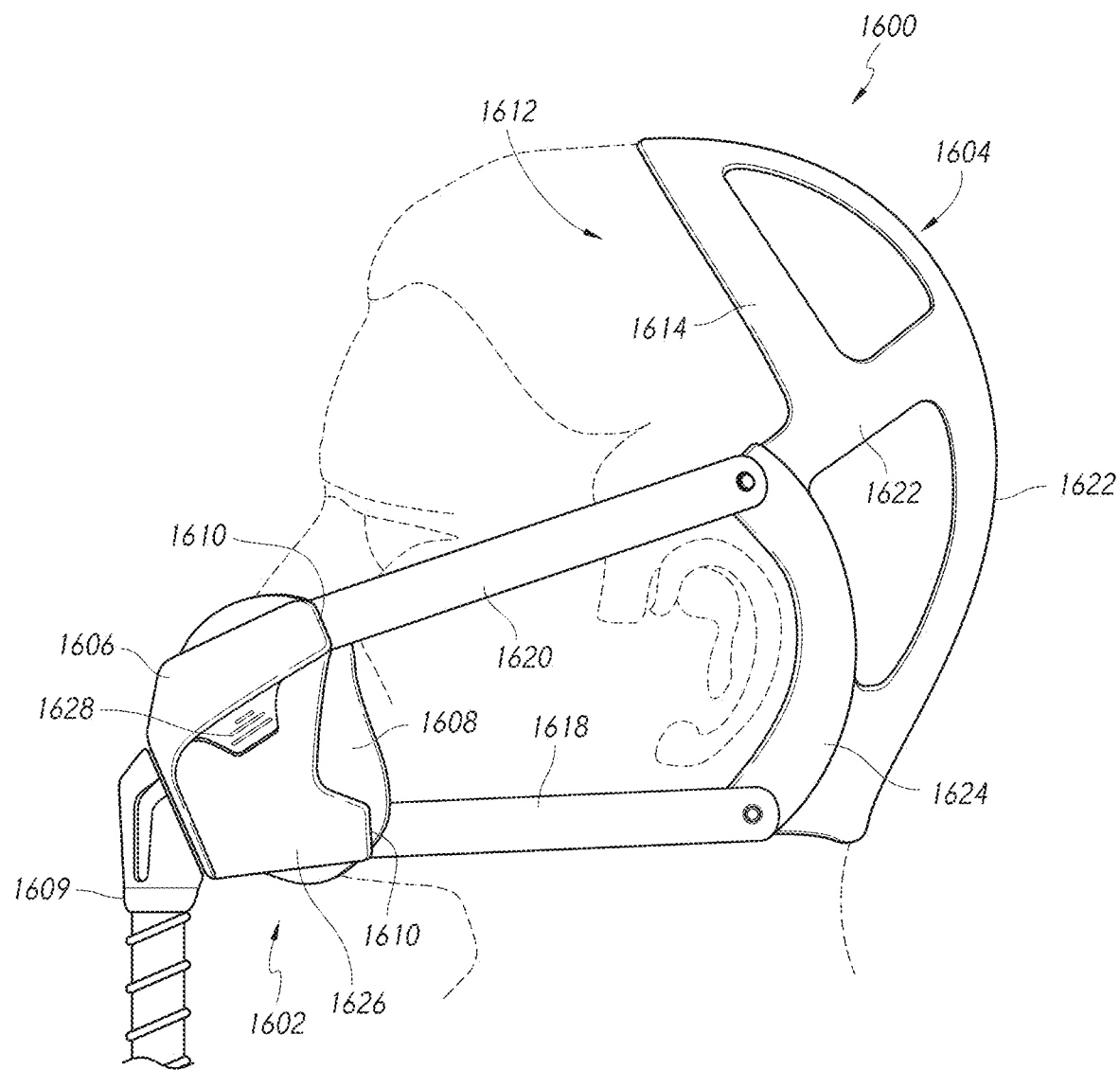
FIG. 16 is a side view of an interface assembly having an interface, such as a mask, and a headgear.

FIG. 16 illustrates an interface assembly 1600 that is arranged and configured in accordance with certain features, aspects and advantages of the present disclosure. The illustrated interface assembly 1600 includes an interface 1602 and a headgear 1604. The illustrated interface 1602 is a nasal-oral mask but, as described herein, other types of interfaces can be used with the disclosed headgear 1604. The illustrated mask 1602 generally comprises a frame 1606 that supports a seal 1608. The mask 1602 can be connected to a supply conduit 1609, which can be used to supply breathing gases to a user. As described above, in some configurations, the mask 1602 can seal around a mouth of a user and on an underside of a nose of the user. Such a mask 1602 can provide pressurized air flow to both the nose and the mouth of the user.

The headgear 1604 can be coupled to the mask 1602 at one or more mounting locations or mounting points 1610. Preferably, a lower strap 1618 and an upper strap 1620 are provided on each side of the headgear 1604 to connect the mask 1602 to a rear portion of the headgear 1604. Unless indicated otherwise, features of the interface assembly 1600 or portions thereof can be the same as or similar to other interfaces or portions thereof described herein, or can be of another suitable arrangement.

The illustrated headgear 1604 is of a pocket-like arrangement that receives and cups the back of the user's head. In the illustrated configuration, the headgear 1604 is of a skeleton or web-like configuration that includes interior open spaces within the headgear 1604. In some configurations, an outer perimeter 1614 of the headgear 1604 generally defines a rear halo portion. Interior strap portions 1622 extend between different points of the perimeter 1614 in generally vertical and/or generally horizontal directions and can help maintain the shape of the outer perimeter 1614. The upper strap 1620 and the rear portion of the headgear 1604 can cooperate to define a front halo portion 1612.

The headgear 1604 can include one or more relatively rigid portions 1624, which can be more rigid than other portions of the headgear 1604 and can be semi-rigid or rigid. The rigid portions 1624 can define mounting locations between the rear portion of the headgear 1604 and one or both of the lower strap 1618 and the upper strap 1620. In some configurations, the rigid portions 1624 can be located behind each ear of the user and can be curved to generally follow the shape of the ear. The rigid portions 1624 can provide anchor points for the lower strap 1618 and upper strap 1620 below and above the ear, respectively.

The rigid portions 1624 can transfer the load of the straps 1618, 1620 to a larger portion of the rear portion of the headgear 1604 and help maintain the shape of the outer perimeter 1614 of the headgear 1604 in response to forces applied by the straps 1618, 1620. The interior straps 1614 and portions of the outer perimeter 1614 other than the rigid portions 1624 can be constructed from a flexible, less rigid material, such as a textile material, for example. Such an arrangement can provide even load distribution over a significant area of the user's head without excessive heat retention.

The lower strap 1618 and upper strap 1620 can be constructed from an elastic material to have some amount of stretch. The stretch inherent in the straps 1618, 1620 can be selected to provide an appropriate mounting force for the mask 1602. However, the straps 1618, 1620 could, in addition or in the alternative, be capable of length adjustment. In some configurations, a portion 1626 of the mask 1602 to which the straps 1618, 1620 are coupled can be removable to loosen the straps and facilitate fitment or removal of the interface assembly 1610. For example, the removable portion 1626 can have a snap-fit arrangement with a remainder of the mask 1602. The removable portion 1626 can be selectively disengaged from the remainder of the mask 1602. The removable portion 1626 can be completely separated from the remainder of the mask 1602 such that the interface assembly 1600 defines an open loop or the removable portion 1626 can remain tethered to the remainder of the mask 1602 to create an increased-circumference to facilitate fitment or removal of the interface assembly 1600. A push button release 1628 can be provided to facilitate disengagement of the removable portion 1626. The removable portion 1626 can be coupled to the remainder of the mask 1602 by any suitable coupling arrangement, including those disclosed herein, for example but without limitation. A removable portion 1626 can be provided on each side of the mask 1602, if desired.

Figure 17:
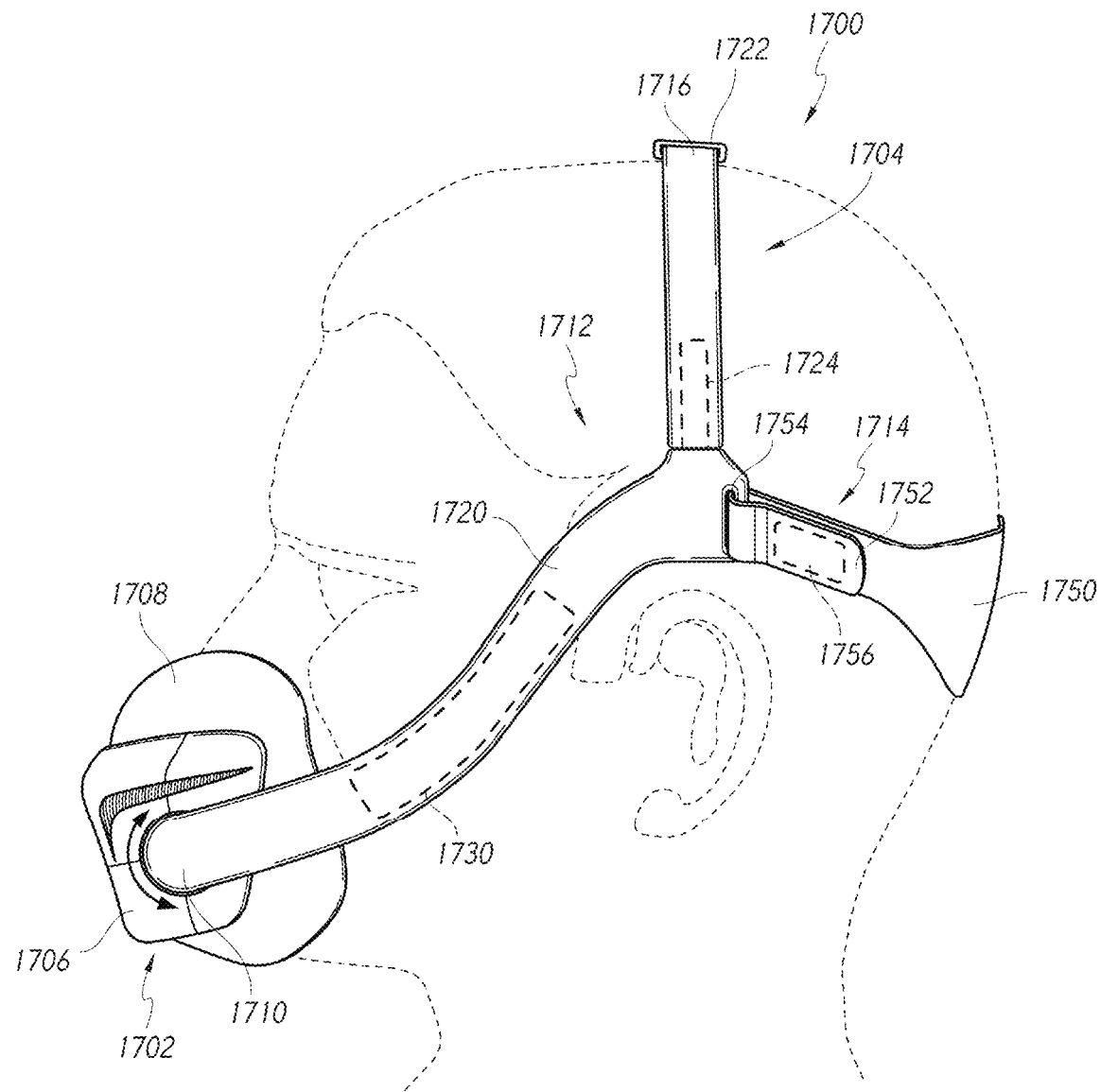
FIG. 17 is a side view of an interface assembly having an interface, such as a mask, and a headgear.

FIG. 17 illustrates an interface assembly 1700 that is arranged and configured in accordance with certain features, aspects and advantages of the present disclosure. The illustrated interface assembly 1700 includes an interface 1702 and a headgear 1704. The illustrated interface 1702 is a nasal-oral mask but, as described herein, other types of interfaces can be used with the disclosed headgear 1704. The illustrated mask 1702 generally comprises a frame 1706 that supports a seal 1708. The mask 1702 can be connected to a supply conduit (not shown), which can be used to supply breathing gases to a user. As described above, in some configurations, the mask 1702 can seal around a mouth of a user and on an underside of a nose of the user. Such a mask 1702 can provide pressurized air flow to both the nose and the mouth of the user.

The headgear 1704 can be coupled to the mask 1702 at one or more mounting locations or mounting points 1710. Preferably, the mask 1702 is capable of rotational adjustment relative to the headgear 1704 to permit angular adjustment of the mask 1702 to fit different facial geometries. Unlike the prior interfaces that rely on a pair of straps to permit angular adjustment of the mask, the interface assembly 1700 utilizes relative rotational movement between the mask 1702 and the headgear 1704, as described below. Unless indicated otherwise, features of the interface assembly 1700 or portions thereof can be the same as or similar to other interfaces or portions thereof described herein, or can be of another suitable arrangement.

The headgear 1704 can comprise a single side arm or side strap 1720 on each side of the interface assembly 1700. The side strap 1720 can be relatively rigid such that it substantially retains its shape in response to normal or expected forces in use. The side strap 1720 can extend from the mask 1702 to a location above the user's ear. In some configurations, the side strap 1720 can be curved along its length. The side strap 1720 can connect to the mask 1702 at a mounting point 1710 that is located in a generally intermediate vertical position of the mask 1702, as illustrated. However, in other configurations, the mounting point 1710 can be located elsewhere, such as generally at a pivot point of the mask 1702 at a junction between the underside of the user's nose and the user's upper lip (see, for example, FIGS. 1 and 84). The side strap 1720 can curve upwardly in a direction from front to rear to be positioned at a desirable location on the user's face, which can be away from the user's eyes. In some configurations, the side strap 1720 can include padding that rests against the user's skin, such as a cheek pad 1730 on an inside surface of the side strap 1720. In other configurations, a greater portion or a substantial entirety of the side strap 1720 can be provided with padding. As described above, the mask 1702 can be rotatable relative to the side strap 1720 and, preferably, can be secured in a desired rotational position.

The headgear 1704 can include a crown strap 1716. In some configurations, the crown strap 1716 can be integrated or formed as a single piece with the side straps 1720. For example, the crown strap 1716 can be constructed from a less rigid material, such as a semi-rigid material, and can be removably or permanently coupled to the side straps 1720. The crown strap 1716 can be a member that is overmolded onto the side straps 1720. Each side strap 1720 can include an extension or mounting portion 1724 that provides a mechanical interface for the overmolded crown strap 1716. In some configurations, the crown strap 1716 can be formed from a thermoplastic elastomer or silicone material, for example.

The headgear 1704 can also include a rear strap 1750 that extends along the back of the user's head between rear portions of the side straps 1720. The rear strap 1750 can be relatively less rigid than the side straps 1720. In some configurations, the rear strap 1750 is a flexible and/or somewhat stretchable material, such as a textile material. The rear strap 1750 can have one or more adjustment portions 1752, such as an adjustment portion 1752 on each end of the rear strap 1750. The adjustment portion 1752 can be an adjustable loop that is passed through an opening or slot 1754 of the side strap 1720. The loop can be secured to the rear strap 1750 by a suitable connector 1756, such as a hook-and-loop fastener, for example. In some configurations, one or more additional adjustment points can be provided, such as an adjustment feature 1722 within the crown strap 1716, which permits a length of the crown strap 1716 to be adjusted. In the illustrated configurations, three adjustment points are provided, thereby permitting adjustment of a circumference of a front halo portion 1712 (via the adjustment feature 1722) and a circumference of a rear halo portion 1714 (via the adjustment feature 1722 and the adjustment portions 1752).

Figure 18:
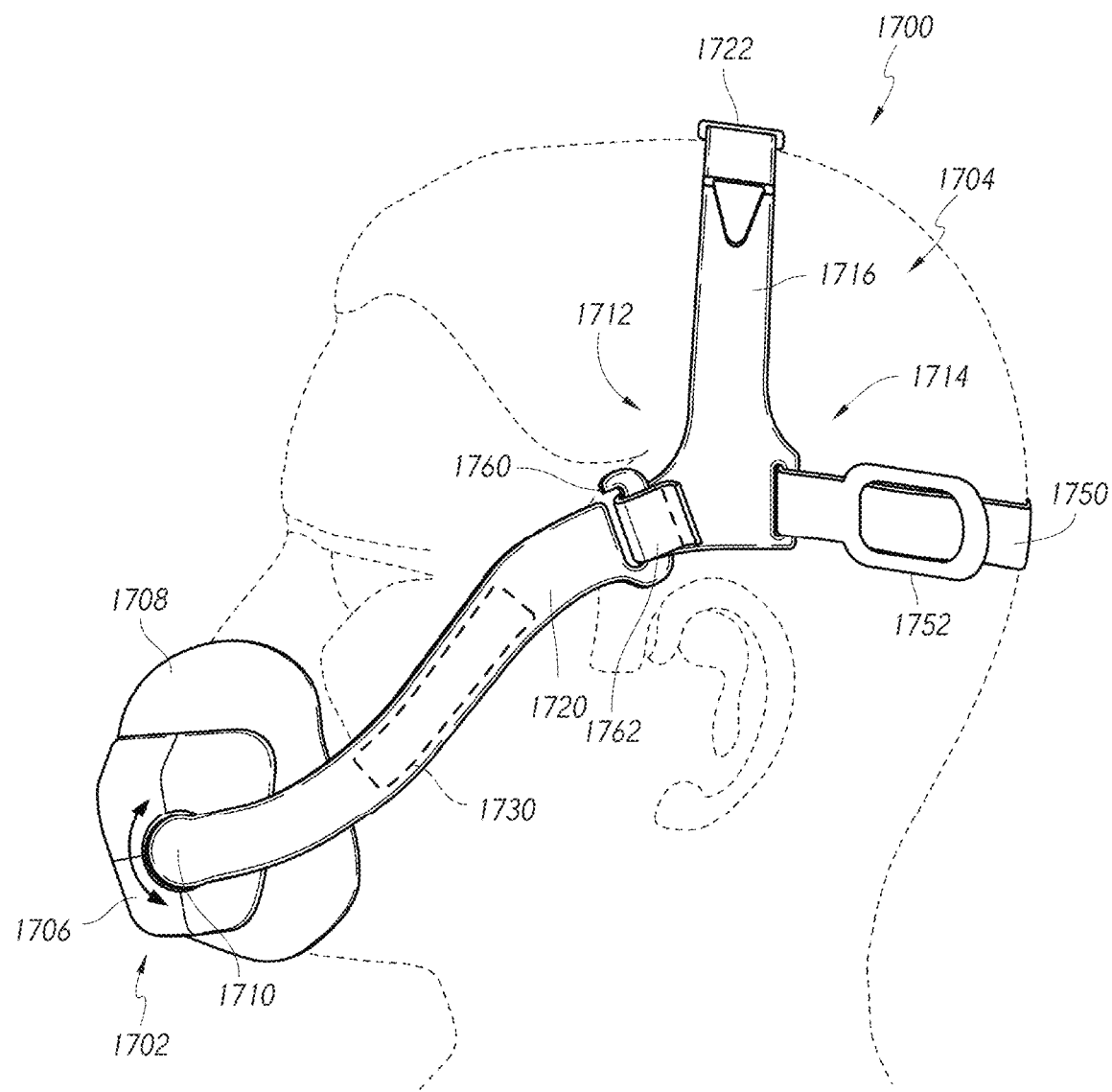
FIG. 18 is a side view of an interface assembly having an interface, such as a mask, and a headgear.

FIG. 18 illustrates an interface assembly 1700 preferably that is substantially similar to the interface assembly 1700 of FIG. 17. Accordingly, the same reference numbers are utilized for the same or corresponding components or features. The interface assembly 1700 of FIG. 18 is described with respect the differences relative to the interface assembly 1700 of FIG. 17. Unless indicated otherwise, features of the interface assembly 1700 or portions thereof can be the same as or similar to other interfaces or portions thereof of the interface assembly 1700 of FIG. 17, other interface assemblies described herein, or can be of another suitable arrangement.

The side strap 1720 of the interface assembly 1700 of FIG. 18 can have a rearward end positioned at or near a forward, upper portion of the user's ear. The side strap 1720 and the rear strap 1750 can connect to a base of the crown strap 1716, which can be a separate component from the side strap 120 and/or rear strap 1750. The rearward end of the side strap 1720 can include a hook 1760 that engages a loop 1762 of the crown strap 1716. The loop 1762 can be a portion of the crown strap 1716 material that is folded over onto itself and sewn in place. Other suitable arrangements can also be used, such as a ring member coupled to the crown strap 1716, for example. The adjustment portion 1752 of the rear strap 1750 can be a sliding buckle adjuster, for example.

Figure 19:
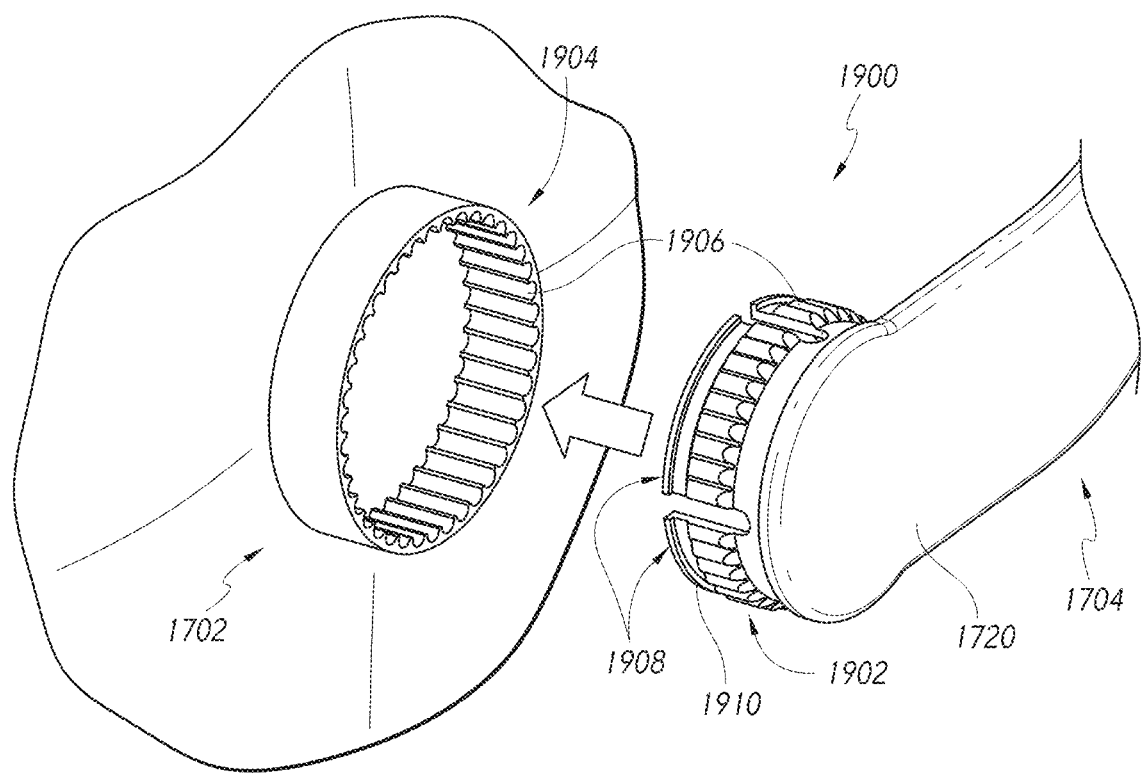
FIG. 19 is an exploded view of the rotational adjuster of the interface assembly of FIG. 18.

FIG. 19 illustrates a rotational adjustment arrangement or rotational adjuster 1900 that can provide rotational adjustment between two components of an interface assembly, such as between the mask and the headgear. The rotational adjuster 1900 can be utilized in the interface assemblies 1700 of FIGS. 17 and 18, for example, as well as other interface assemblies, including those disclosed herein. For convenience, the rotational adjuster 1900 is described in the context of the interface assemblies 1700.

Preferably, the rotational adjuster 1900 includes a first portion 1902 that is capable of engagement with a second portion 1904 in a plurality of rotational positions in order to adjust the fit to different facial geometries. In the illustrated arrangement, the first portion 1902 is a male portion and the second portion 1904 is a female portion. The first portion 1902 is formed by, carried by or otherwise coupled to the headgear 1704 (e.g., the side strap 1720) and the second portion 1904 is formed by, carried by or otherwise coupled to the mask 1702. However, this arrangement could be reversed. The illustrated first portion 1902 is an axle and the illustrated second portion 1904 is a sleeve or hub. The axle 1902 is received within the sleeve 1904 in one of a plurality of optional rotational positions. The axle 1902 and the sleeve 1904 can comprise cooperating interference or detent surfaces 1906, which permit rotational adjustment between a plurality of relative rotational positions. The detent surfaces 1906 can be of any suitable arrangement, such as protrusions and recesses, for example.

In some configurations, the axle 1902 comprises two or more flexible or deflectable tabs 1908 to permit the axle 1902 to be assembled into engagement with the sleeve 1904. Preferably, the tabs 1908 are stiff enough to inhibit undesired rotational movement of the mask 1702 in response to normal or expected forces in use. A rim or flange 1910 can be provided at a free end of the axle 1902 to secure the axle 1902 within the sleeve 1904 in an axial direction. However, other rotational adjustment arrangements can be used with the interface assembly 1700 or any other interface assembly disclosed herein. Any suitable arrangement for providing rotational adjustment between two components can be used. In some configurations, the rotational adjustment arrangement can be fixed in the desired rotational position instead of relying on another fixing component, such as another mask strap, for example. For example, a nut-and-bolt arrangement, ratchet-type arrangement or other types of detent arrangements could be used, among other suitable arrangements.

Figure 20:
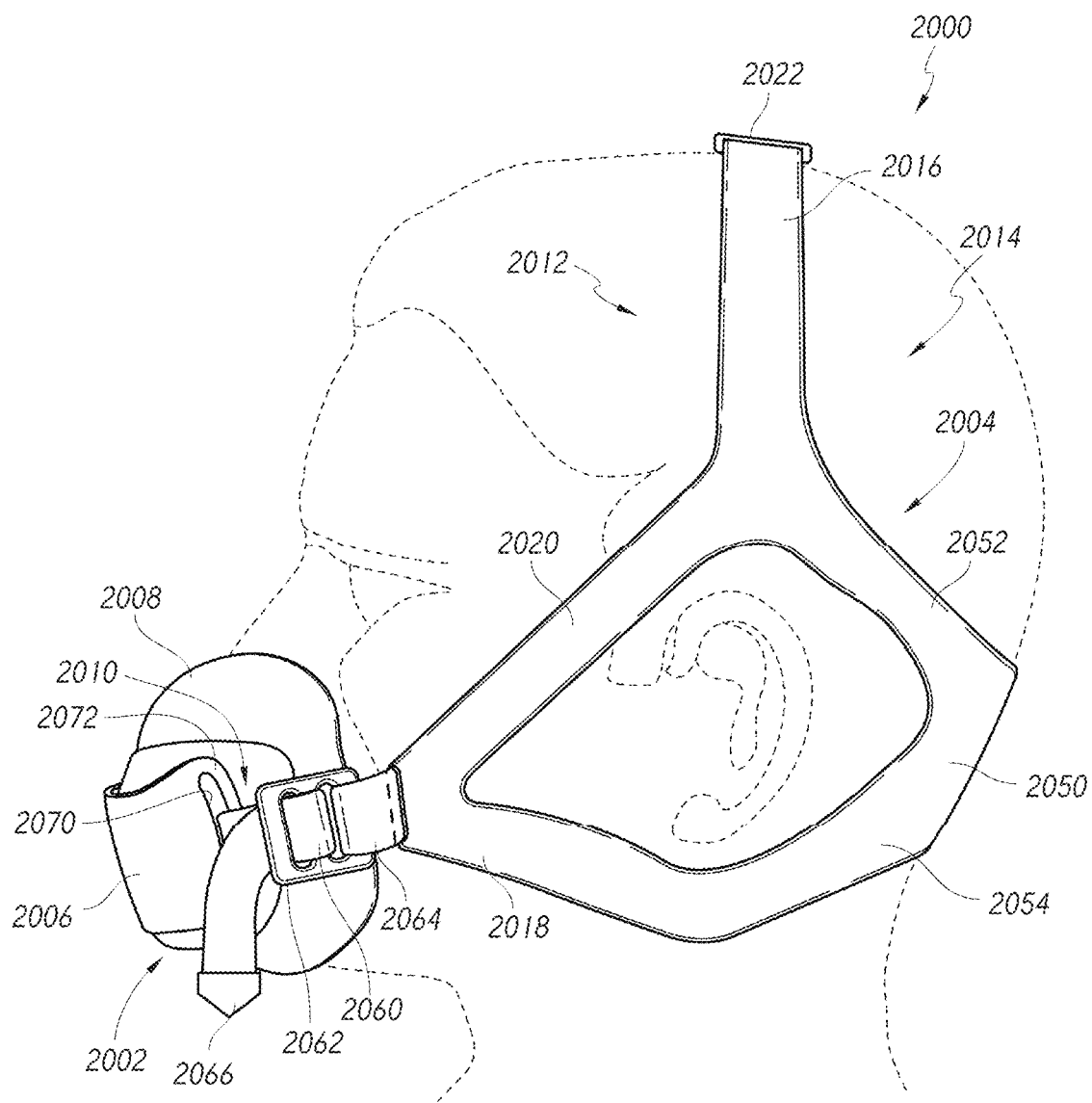
FIG. 20 is a side view of an interface assembly having an interface, such as a mask, and a headgear.

FIG. 20 illustrates an interface assembly 2000 that is arranged and configured in accordance with certain features, aspects and advantages of the present disclosure. The illustrated interface assembly 2000 includes an interface 2002 and a headgear 2004. The illustrated interface 2002 is a nasal-oral mask but, as described herein, other types of interfaces can be used with the disclosed headgear 2004. The illustrated mask 2002 generally comprises a frame 2006 that supports a seal 2008. The mask 2002 can be connected to a supply conduit (not shown), which can be used to supply breathing gases to a user. As described above, in some configurations, the mask 2002 can seal around a mouth of a user and on an underside of a nose of the user. Such a mask 2002 can provide pressurized air flow to both the nose and the mouth of the user.

The headgear 2004 can be coupled to the mask 2002 at one or more mounting locations or mounting points 2010. Preferably, a lower strap 2018 and an upper strap 2020 are provided on each side of the headgear 2004 to connect the mask 2002 to a rear portion of the headgear 2004. Unless indicated otherwise, features of the interface assembly 2000 or portions thereof can be the same as or similar to other interfaces or portions thereof described herein, or can be of another suitable arrangement.

In the illustrated arrangement, forward ends of the lower strap 2018 and the upper strap 2020 can join one another and be coupled to the mask 2002 at a single mounting location or mounting point 2010 on each side of the mask 2002. The rear strap portion 2050 can have bifurcated end portions, each having an upper end portion 2052 and a lower end portion 2054. The upper end portion 2052 can connect to the upper strap 2020 and, in some configurations, with a crown strap 2016. The lower end portion 2054 can connect to the lower strap 2018. In some configurations, the lower strap 2018, upper strap 2020, crown strap 2016 and rear strap portion 2050 can be constructed as a single piece or single structure of any suitable material, such as a relatively flexible material. The crown strap 2016 can include an adjustment feature 2022 to permit adjustment of a front halo portion 2012 and a rear halo portion 2014 and/or other adjustment mechanisms for the headgear 2004 can be provided.

An adjustment strap 2060 can be provided on each side of the interface assembly 2000 to couple the mask 2002 to a main portion of the headgear 2004. The adjustment strap 2060 can engage a buckle 2062, which can be connected to the main portion of the headgear 2004 (e.g., the combined forward ends of the straps 2018, 2020) by any suitable arrangement, including a loop 2064 of material, for example. The adjustment strap 2060 can be movable within the buckle to adjust an effective length of the strap 2060 and thereby adjust a position of the mask 2002 relative to the headgear 2004. To tighten the strap 2060, a user can pull on a free end 2066 of the strap 2060. Such an arrangement can be quieter to adjust and/or easier to fine tune the adjustment compared to a hook-and-loop fastener adjustment, for example.

The mask 2002 can include an elongate slot 2070 near an edge of the mask frame 2006 such that the mask frame 2006 defines an elongate bar 2072. The strap 2060 can be secured to the bar 2062 to couple the strap 2060 to the mask 2002. In some configurations, the slot 2070 and/or bar 2072 define a length (or height in the illustrated orientation) that is greater than a width (or height in the illustrated orientation) of the strap 2060 such that the strap 2060 is movable within the slot 2070 or along the bar 2072. Preferably, the slot 2070 and/or bar 2072 are arcuate or curved in shape such that moving the mask 2002 relative to the strap 2060 changes an angle or rotational position of the mask 2002 relative to the headgear 2004 and the user. In use, the user can position the mask 2002 and headgear 2004 and then tighten the strap(s) 2060 to secure the mask 2002 in place. The strap(s) 2060 can automatically settle into a desired location within the slot 2070 or along the bar 2072. The user could also manually adjust an angle or rotational position of the mask 2002 relative to the strap(s) 2060 and/or headgear 2004 after the interface assembly 2000 has been fitted.

Figure 21:
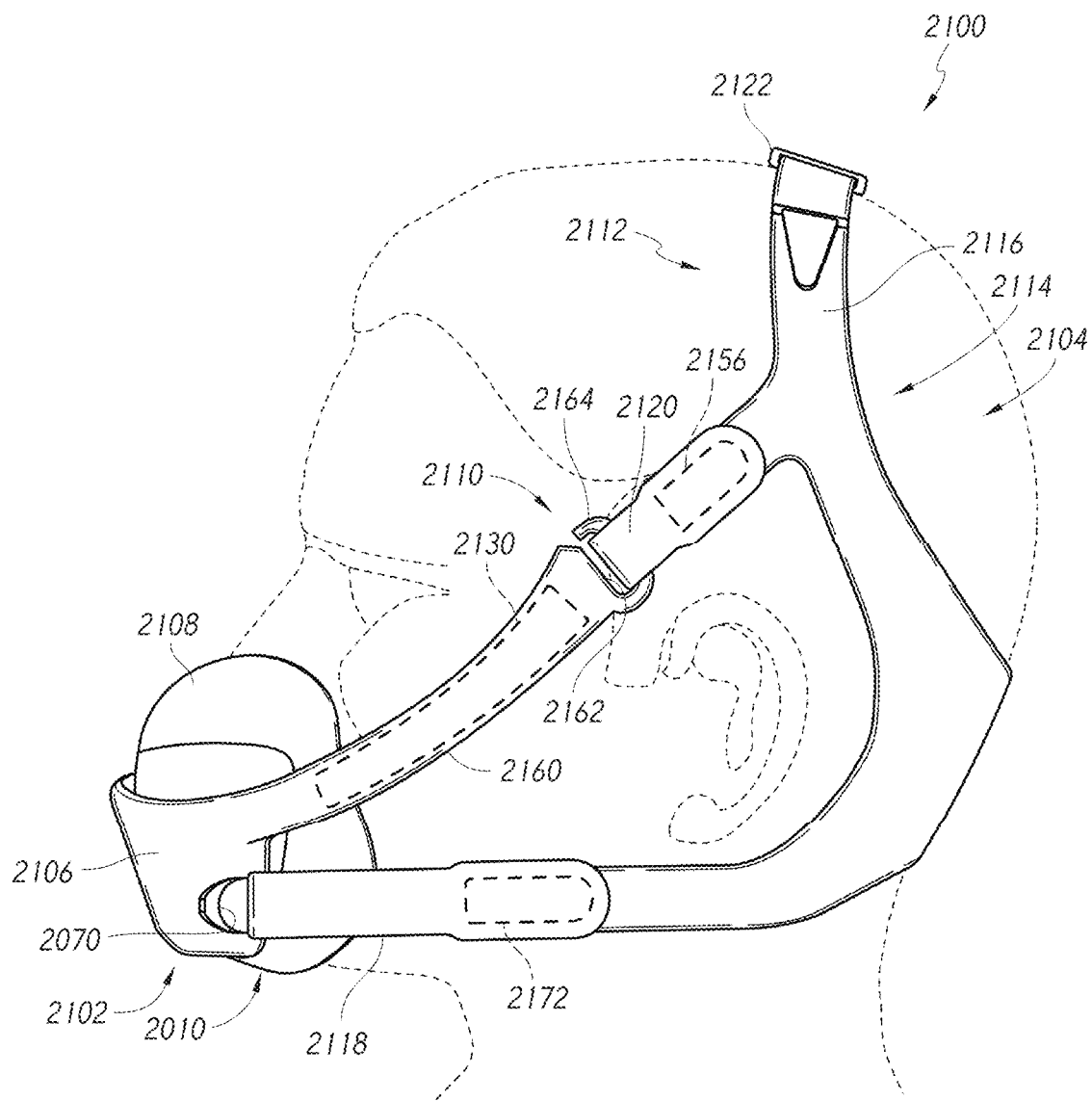
FIG. 21 is a side view of an interface assembly having an interface, such as a mask, and a headgear.

FIG. 21 illustrates an interface assembly 2100 that is arranged and configured in accordance with certain features, aspects and advantages of the present disclosure. The illustrated interface assembly 2100 includes an interface 2102 and a headgear 2104. The illustrated interface 2102 is a nasal-oral mask but, as described herein, other types of interfaces can be used with the disclosed headgear 2104. The illustrated mask 2102 generally comprises a frame 2106 that supports a seal 2108. The mask 2102 can be connected to a supply conduit (not shown), which can be used to supply breathing gases to a user. As described above, in some configurations, the mask 2102 can seal around a mouth of a user and on an underside of a nose of the user. Such a mask 2102 can provide pressurized air flow to both the nose and the mouth of the user.

The headgear 2104 can be coupled to the mask 2102 at one or more mounting locations or mounting points 2110. Preferably, a lower strap 2118 and an upper strap 2120 are provided on each side of the headgear 2104 to connect the mask 2102 to a rear portion of the headgear 2104. Unless indicated otherwise, features of the interface assembly 2100 or portions thereof can be the same as or similar to other interfaces or portions thereof described herein, or can be of another suitable arrangement.

In the illustrated arrangement, the mask 2102 includes an elongate, rearwardly-extending rigid arm 2160 on each side of the mask 2102 that is coupled to a respective one of the upper straps 2120 of the headgear 2104. In some configurations, the rigid arm 2160 can be a portion of the mask frame 2106. In some configurations, the rigid arm 2160 can be a separate member that is coupled to the mask frame 2006. The rigid arm 2160 can have an upwardly curved shape (in the illustrated orientation) to be positioned out of or further away from the user's line of sight for a less intrusive experience when worn. In some configurations, the rigid arm 2160 can include padding, such as a cheek pad 2130 that contacts the skin of the user for comfort and/or grip on the skin.

The rigid arm 2160 can be coupled to the upper strap 2120 by any suitable arrangement. In some configurations, the rigid arm 2160 includes an opening 2162 through which the upper strap 2120 can be passed and doubled over on itself to form a loop. The loop of the upper strap 2120 can be secured by a connector 2156, such as a hook-and-loop fastener, for example. In some configurations, the opening 2162 of the rigid arm 2160 is defined by a hook 2164, which defines an entry into the opening 2162 to facilitate quick separation of the upper strap 2120 from the rigid arm 2160.

The lower strap 2118 can be coupled to the mask 2102 by any suitable arrangement, such as passed through an opening 2170 in the mask 2102 and doubled over on itself to form a loop. The loop of the lower strap 2118 can be secured by a connector 2172, such as a hook-and-loop fastener, for example. As in other interface assemblies described herein, the upper strap 2120 and lower strap 2118 can be adjusted to place the mask 2102 in a desirable rotational position. In some configurations, the crown strap 2116 can include an adjustment feature 2122. Other suitable arrangements can also be used to permit adjustment of the headgear 2104 (e.g., the front halo portion 2112 and/or rear halo portion 2114), including one or more of the lower strap 2118, upper strap 2120 and crown strap 2116, for example and without limitation.

Figure 22A:
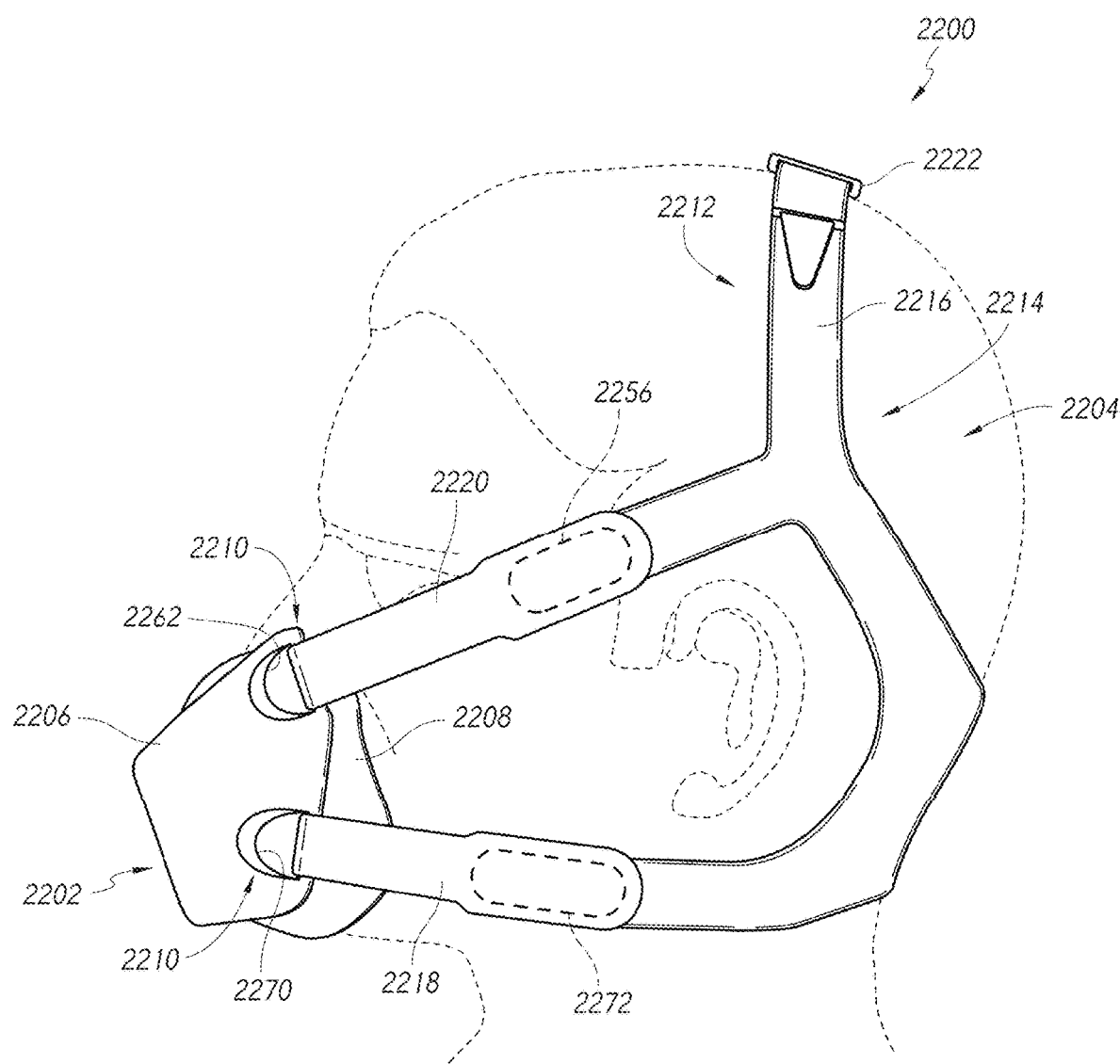
FIG. 22A is a side view of an interface assembly having an interface, such as a mask, and a headgear.
Figure 22B:
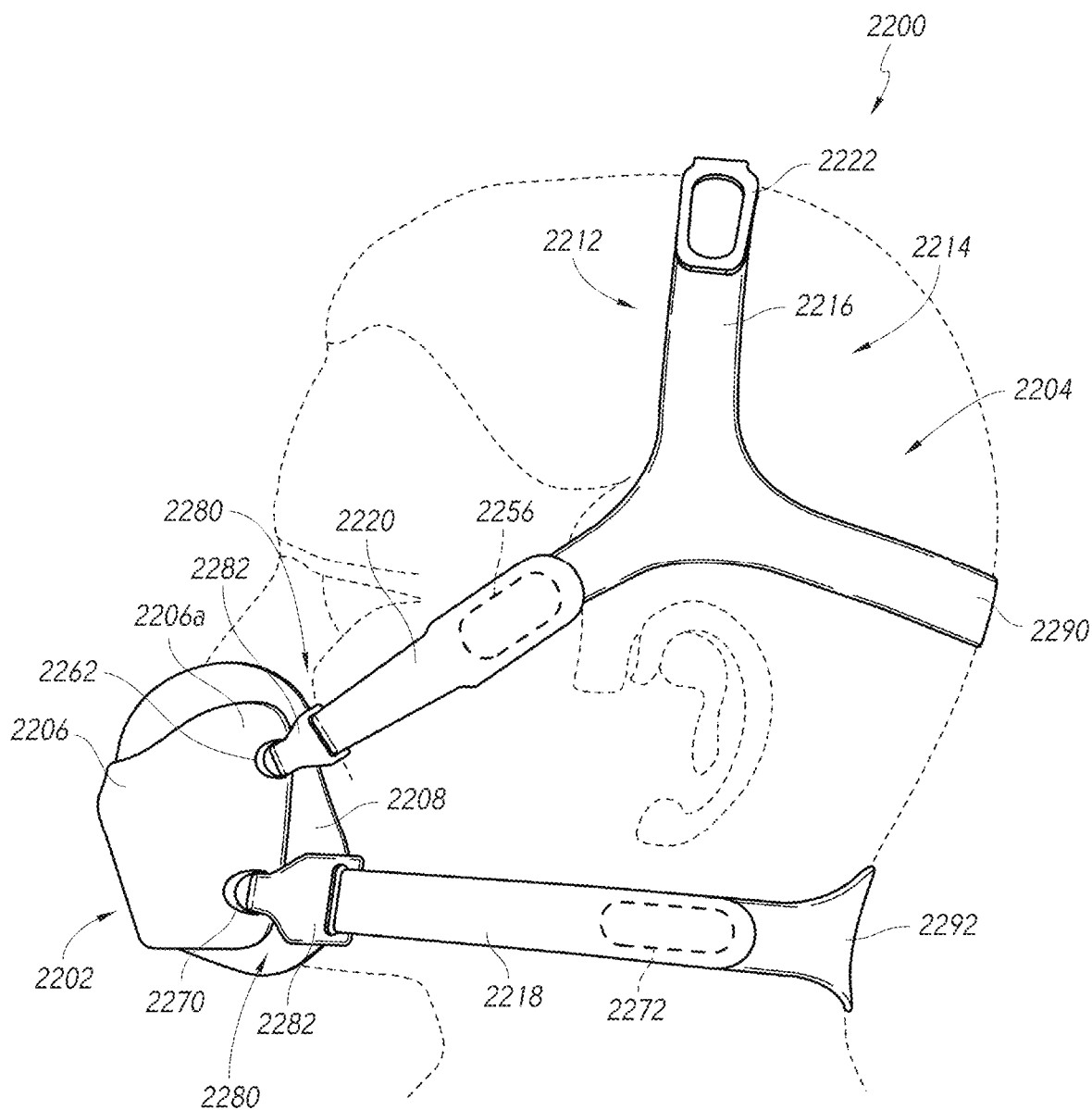
FIG. 22B is a side view of an interface assembly having an interface, such as a mask, and a headgear.

FIGS. 22A and 22B illustrate interface assemblies 2200 that are arranged and configured in accordance with certain features, aspects and advantages of the present disclosure. The illustrated interface assemblies 2200 include an interface 2202 and a headgear 2204. The illustrated interface 2202 is a nasal-oral mask but, as described herein, other types of interfaces can be used with the disclosed headgear 2204. The illustrated mask 2202 generally comprises a frame 2206 that supports a seal 2208. The mask 2202 can be connected to a supply conduit (not shown), which can be used to supply breathing gases to a user. As described above, in some configurations, the mask 2202 can seal around a mouth of a user and on an underside of a nose of the user. Such a mask 2202 can provide pressurized air flow to both the nose and the mouth of the user. The frame 2206 can comprise rigid, upwardly-extending paddle portions 2206a positioned on each side of the nose portion of the seal 2208 to resist expansion of the nose portion of the seal 2208 in response to pressurized air within the mask 2202.

The headgear 2204 can be coupled to the mask 2202 at one or more mounting locations or mounting points 2210. Preferably, a lower strap 2218 and an upper strap 2220 are provided on each side of the headgear 2204 to connect the mask 2202 to a rear portion of the headgear 2204. Unless indicated otherwise, features of the interface assemblies 2200 or portions thereof can be the same as or similar to other interfaces or portions thereof described herein, or can be of another suitable arrangement. In particular, the interface assemblies 2200 are similar to the interface assembly 2100 of FIG. 21 and, for the sake of convenience, will be described in the context of the differences relative to that interface assembly 2100.

In the illustrated arrangement of FIG. 22A, the upper strap 2220 is coupled to the mask 2202 at a mounting point 2210 that is located at or near the seal 2208 of the mask 2202. In particular, the mounting point 2210 of the upper strap 2220 preferably is located between a forward edge and a rearward edge of the seal 2208 when viewed from the side. In some configurations, the mounting point 2210 is located at or near the upper end of the seal 2208 and/or at or near the user's nose. Such an arrangement can provide a suitable force vector to facilitate the creation of a seal between the mask seal 2208 and the underside of the user's nose. The upper strap 2220 can be coupled to the mask 2202 by any suitable arrangement, such as passed through an opening 2262 in the mask 2202 and doubled over on itself to form a loop. The loop of the upper strap 2220 can be secured by a connector 2256, such as a hook-and-loop fastener, for example.

The lower strap 2218 can be coupled to the mask 2202 at a mounting point 2210 that is located toward a bottom portion of the seal 2208, such as at or near the user's mount or chin. In a fore-aft direction, the mounting point 2210 can be generally aligned with the mounting point 2210 of the upper strap 2220. The lower strap 2218 can be coupled to the mask 2202 by any suitable arrangement, such as passed through an opening 2270 in the mask 2202 and doubled over on itself to form a loop. The loop of the lower strap 2218 can be secured by a connector 2272, such as a hook-and-loop fastener, for example.

As in other interface assemblies described herein, the upper strap 2220 and lower strap 2218 can be adjusted to place the mask 2202 in a desirable rotational position. The substantial vertical separation between the mounting points 2210 of the upper strap 2220 and the lower strap 2218 permits fine control of the angular adjustment of the mask 2202.

In some configurations, a crown strap 2216 of the headgear 2204 can include an adjustment feature 2222. Other suitable arrangements can also be used to permit adjustment of the headgear 2204 (e.g., the front halo portion 2212 and/or rear halo portion 2214), including one or more of the lower strap 2218, upper strap 2220 and crown strap 2216, for example and without limitation.

The interface assembly 2200 of FIG. 22B provides quick-release couplings 2280 between the mask 2202 and the headgear 2204. In particular, each strap 2218, 2220 is coupled to the mask by a clip 2282, which preferably includes a hook-shaped end portion or other suitable arrangement to engage the respective openings 2262, 2270 of the mask 2202. The straps 2218, 2220 can be adjusted relative to the clips 2282. In addition, the headgear 2204 includes separate upper and lower portions. The upper strap 2220 is coupled to the upper portion of the headgear 2204, which preferably includes the crown strap 2216 and a first or upper rear head strap 2290. The upper strap 2220, the crown strap 2216 and the upper rear head strap 2290 cooperate to form the front halo portion 2212 and the rear halo portion 2214. The upper rear head strap 2290 can extend around the back of the user's head at, near or above a level of an upper portion of the user's ears, such as on or near a transition between the parietal bone and the occipital bone. The lower strap 2218 is coupled to a second or lower rear head strap 2292, which can extend around the back of the user's head at, near or blow a level of a lower portion of the user's ears. In some configurations, the lower rear head strap 2292 sits on the user's occipital bone and/or on the user's upper neck muscles. A rear portion of the lower rear head strap 2292 can be enlarged in a vertical direction to spread the load on the user's neck and/or head area. The provision of separate straps 2290, 2292 can facilitate fitting and removal.

Figure 23:
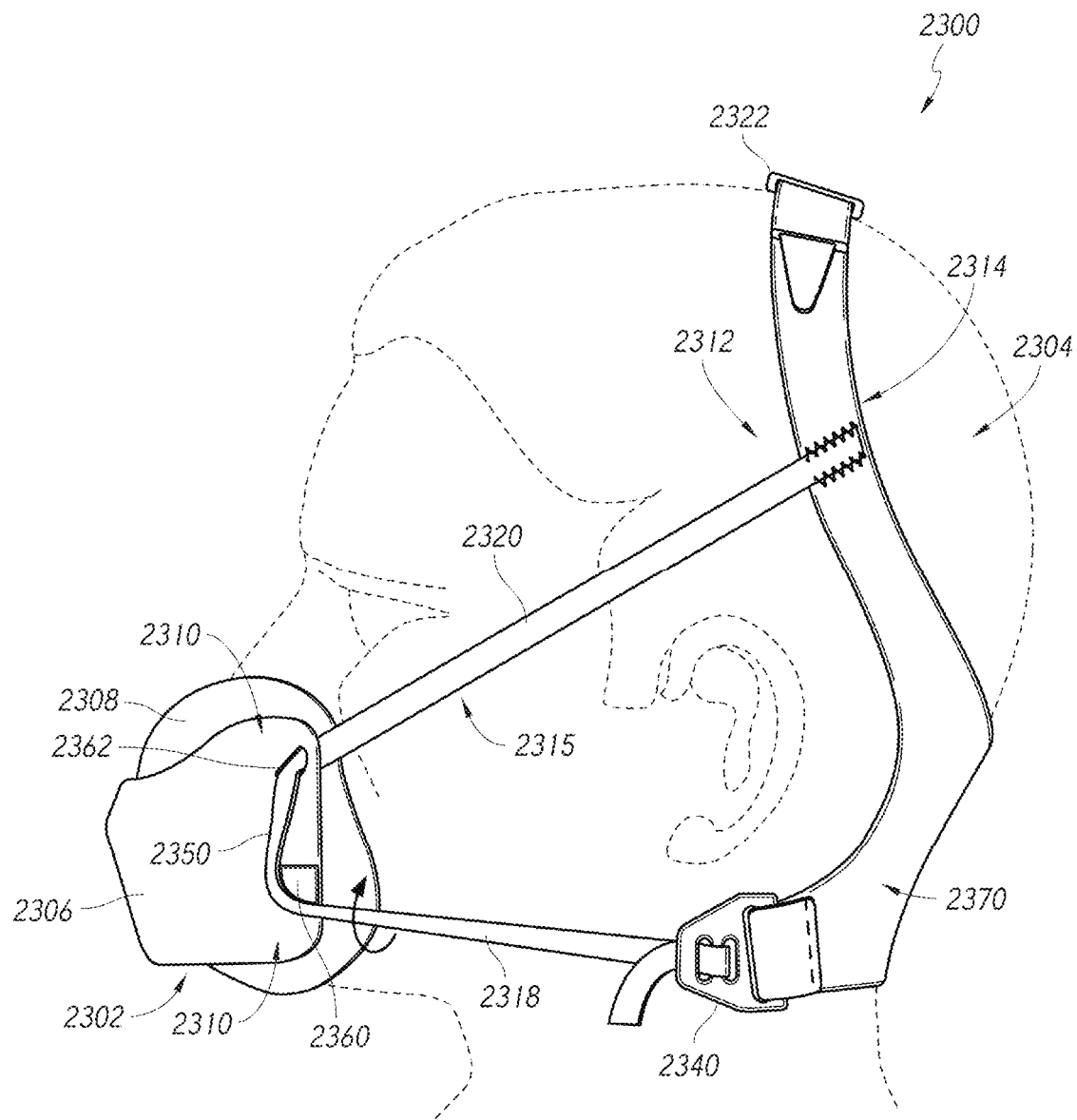
FIG. 23 is a side view of an interface assembly having an interface, such as a mask, and a headgear.
Figure 24:
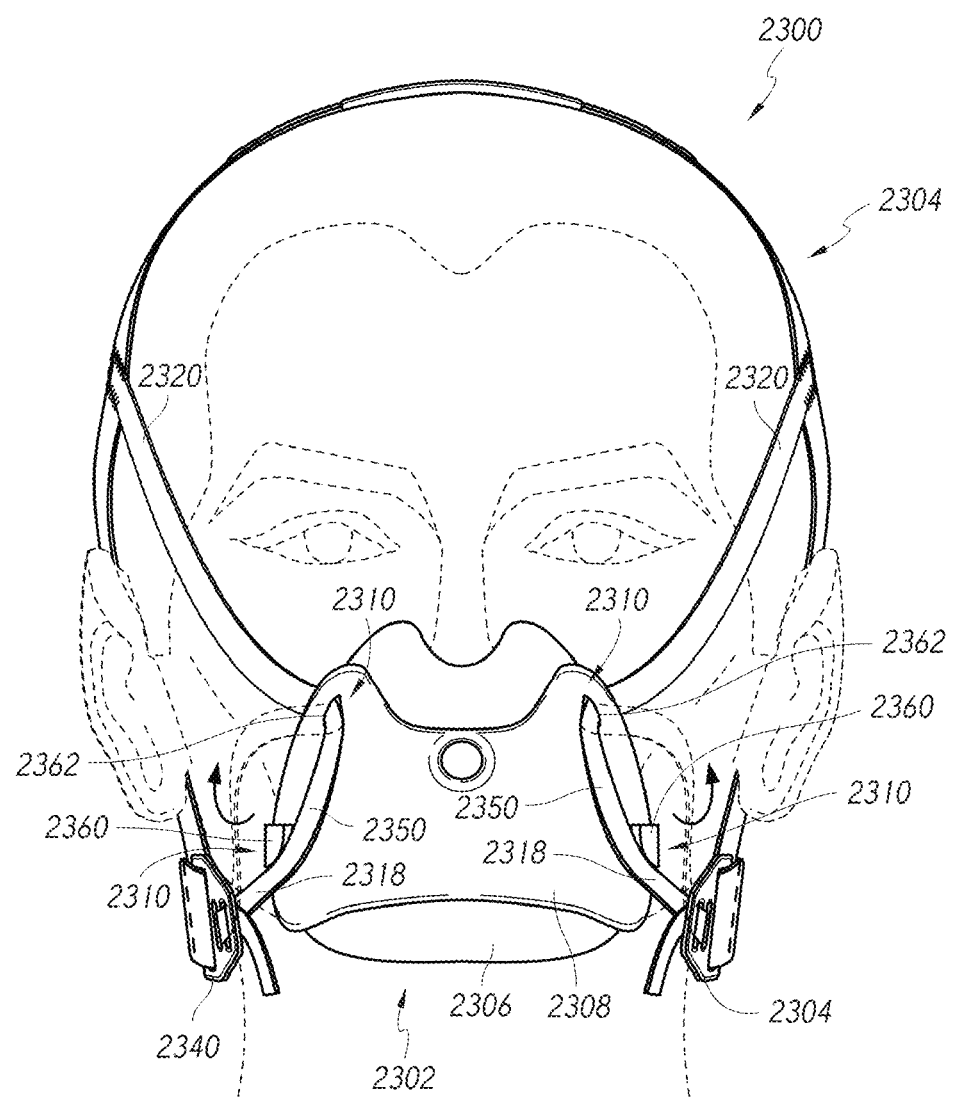
FIG. 24 is a front view of the interface assembly of FIG. 23.

FIGS. 23 and 24 illustrate an interface assembly 2300 that is arranged and configured in accordance with certain features, aspects and advantages of the present disclosure. The illustrated interface assembly 2300 includes an interface 2302 and a headgear 2304. The illustrated interface 2302 is a nasal-oral mask but, as described herein, other types of interfaces can be used with the disclosed headgear 2304. The illustrated mask 2302 generally comprises a frame 2306 that supports a seal 2308. The mask 2302 can be connected to a supply conduit (not shown), which can be used to supply breathing gases to a user. As described above, in some configurations, the mask 2302 can seal around a mouth of a user and on an underside of a nose of the user. Such a mask 2302 can provide pressurized air flow to both the nose and the mouth of the user.

The headgear 2304 can be coupled to the mask 2302 at one or more mounting locations or mounting points 2310. Preferably, a strap 2315 including a lower strap portion 2318 and an upper strap portion 2320 is provided on one or both sides of the headgear 2304 to connect the mask 2302 to a rear portion of the headgear 2304. In some configurations, the strap 2315 can be substantially non-stretchable. The strap 2315 can be constructed from a thin textile webbing. Unless indicated otherwise, features of the interface assembly 2300 or portions thereof can be the same as or similar to other interfaces or portions thereof described herein, or can be of another suitable arrangement.

In the illustrated configuration, each strap 2315 on each side of the interface assembly 2300 is a single strap comprising an upper strap portion 2320 and a lower strap portion 2318. One or both of the upper strap portion 2320 and the lower strap portion 2318 can be adjustably secured to the headgear 2304. In the illustrated arrangement, the upper strap portion 2320 is fixedly secured to the headgear 2304 and the lower strap portion 2318 is adjustably secured to the headgear 2304. However, this arrangement could be reversed. The lower strap portion 2318 can be coupled to the headgear 2304 by a suitable adjustment mechanism, such as a buckle 2340, for example and without limitation.

The strap 2315 can include an intermediate strap portion 2350 that engages the mask 2302 at the mounting points 2310. The mask 2302 can include a pair of spaced-apart mounting points 2310 on the same side of the mask 2302. In some configurations, the mounting points 2310 comprise an upper mounting point and a lower mounting point. One of the upper and lower mounting points 2310 can permit the intermediate strap portion 2350 to be conveniently disengaged from the mounting point 2310 to provide slack in the strap 2315, which can facilitate fitment or removal of the interface assembly 2300. If such straps 2315 are provided on each side of the interface assembly 2300, the amount of slack provided can be doubled.

In the illustrated arrangement, the mask 2302 comprises a retention structure 2360, such as a cleat or a block, around which the intermediate strap portion 2350 can be passed and retained and which defines a mounting point 2310. However, other suitable structures or arrangements could also be used. Preferably, the mask 2302 also comprises a guide 2362 for the intermediate strap portion 2350 that defines another mounting point 2310. The guide 2362 can be an opening or slot that preferably frictionally engages the intermediate strap portion 2350 to inhibit or prevent movement in response to normal or expected forces on the strap 2315 during use to retain the mask 2302 in a desired orientation (e.g., angular orientation) relative to the headgear 2304. However, preferably, the guide 2362 allows movement of the strap 2315 when desired to permit adjustment of the mask 2302 relative to the headgear 2304. In the illustrated arrangement, the guide 2362 defines an upper mounting point 2310 and the retention structure 2360 defines a lower mounting point 2310. However, this arrangement could be reversed or the mounting points 2310 could be otherwise spaced.

The headgear 2304 preferably comprises a front halo portion 2312 and a rear halo portion 2314. The headgear 2304 preferably also comprises a rear strap portion 2370 that is coupled to the rear halo portion 2314. Adjustment of the rear halo portion 2314 can be provided by, for example, an adjustment feature 2322. The lower strap portion 2318 can be coupled to the rear strap portion 2370 and the upper strap portion 2320 can be coupled to the rear strap portion 2370 such that the upper strap portion 2320 is passes above an ear of the user and the lower strap portion 2318 passes below the ear of the user.

In use, the intermediate strap portion 2350 can be disengaged from the retention structure 2360 to introduce slack into the strap 2315 as illustrated by the dashed lines of FIG. 24. The interface assembly 2300 can be fitted to the user with the mask 2302 placed over the user's mouth and against the underside of the user's nose. The headgear 2304 can be placed on the back of the user's head. Then, the intermediate strap portion 2350 can be engaged with the retention structure 2360 to take up the slack in the strap 2315. If necessary or desired, the rotational position of the mask 2302 relative to the headgear 2304 can be adjusted by moving the intermediate strap portion 2350 through the guide 2362. Preferably, the guide 2362 then holds the intermediate strap portion 2350 in place to maintain the desired rotational position of the mask 2302. In some cases, such as if the interface assembly 2300 has been previously fitted, the rotational position of the mask 2302 may already be set. To remove the interface assembly 2300, the process is reversed and the intermediate strap portion 2350 is disengaged from the retention structure 2360 to provide slack in the strap 2315. As discussed, such a strap 2315 can be provided on one or both sides of the interface assembly 2300. Even if two such straps 2315 are provided, disengagement of one strap 2315 may provide sufficient slack to permit removal of the interface assembly 2300.

Figure 25:
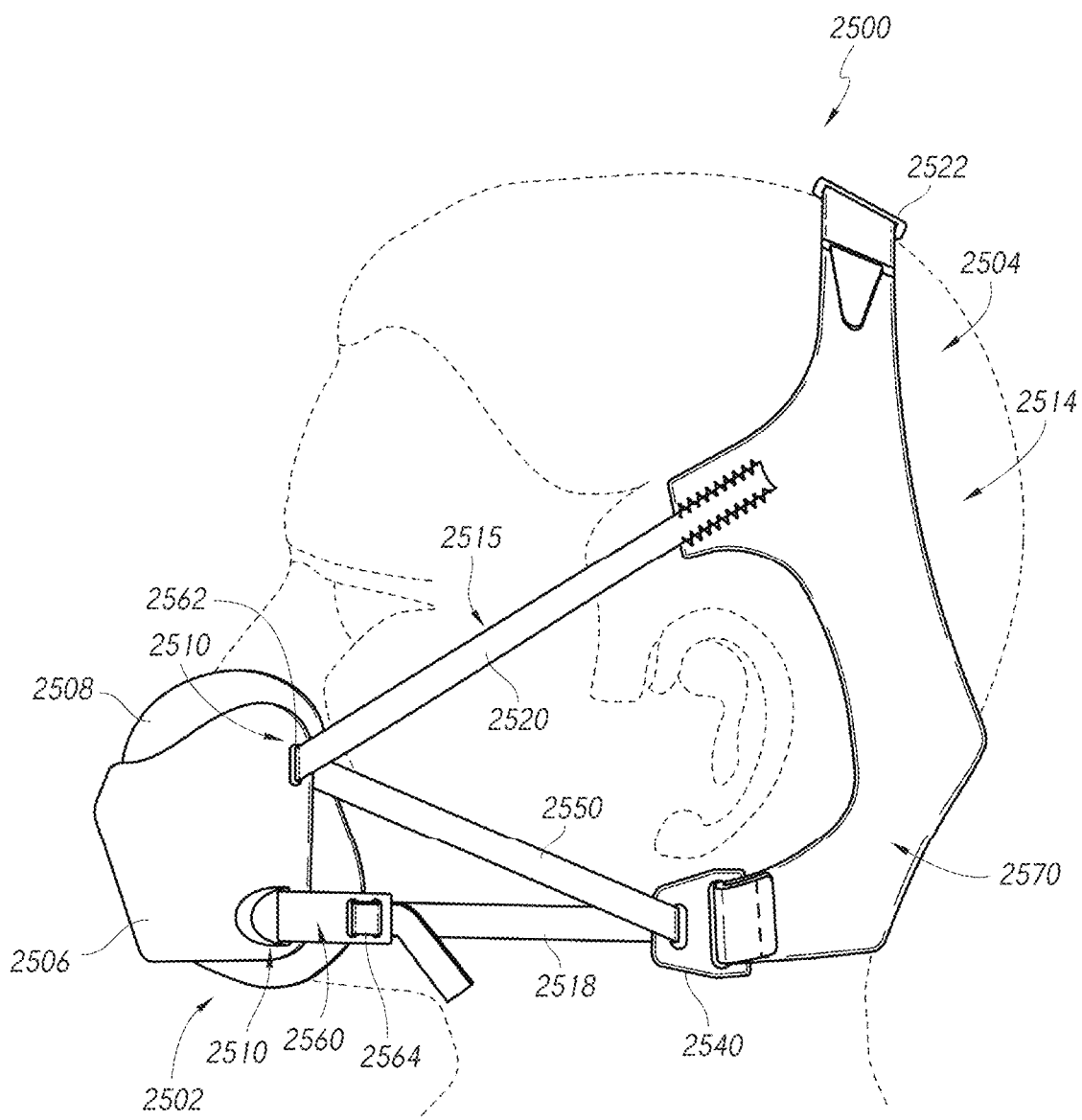
FIG. 25 is a side view of an interface assembly having an interface, such as a mask, and a headgear.

FIG. 25 illustrates an interface assembly 2500 that is arranged and configured in accordance with certain features, aspects and advantages of the present disclosure. The illustrated interface assembly 2500 includes an interface 2502 and a headgear 2504. The illustrated interface 2502 is a nasal-oral mask but, as described herein, other types of interfaces can be used with the disclosed headgear 2504. The illustrated mask 2502 generally comprises a frame 2506 that supports a seal 2508. The mask 2502 can be connected to a supply conduit (not shown), which can be used to supply breathing gases to a user. As described above, in some configurations, the mask 2502 can seal around a mouth of a user and on an underside of a nose of the user. Such a mask 2502 can provide pressurized air flow to both the nose and the mouth of the user.

The headgear 2504 can be coupled to the mask 2502 at one or more mounting locations or mounting points 2510. Preferably, a strap 2515 that includes a lower strap portion 2518 and an upper strap portion 2520 is provided on each side of the headgear 2504 to connect the mask 2502 to a rear portion of the headgear 2504. Unless indicated otherwise, features of the interface assembly 2500 or portions thereof can be the same as or similar to other interfaces or portions thereof described herein, or can be of another suitable arrangement. In particular, the interface assembly 2500 is similar to the interface assembly 2300 of FIGS. 23 and 24 and, for the sake of convenience, will be described in the context of the differences relative to that interface assembly 2300.

The headgear 2504 preferably comprises a front halo portion 2512, a rear halo portion 2514 and a rear strap portion 2570 that is coupled to the rear halo portion 2314. Adjustment of the rear halo portion 2514 can be provided by, for example, an adjustment feature 2522. The upper strap portion 2320 can be coupled to rear halo portion 2514 of the headgear 2504.

An intermediate strap portion 2550 of the strap 2515 extends from a friction guide 2562 of the mask 2502 to the rear strap portion 2570 of the headgear 2504. Preferably, a low friction guide or ring 2540 is coupled to the rear strap portion 2570 of the headgear 2504. The strap 2515 passes through an opening of the low friction guide 2540 and a lower strap portion 2518 of the strap 2515 extends toward a lower end of the mask 2502. Preferably, the lower strap portion 2518 is connected to the mask 2502 by a clip 2360. The clip 2360 can releasably engage the mask 2502, such as with a hook and bar arrangement, for example. The clip 2360 can include a buckle portion 2564 through which the lower strap portion 2518 can be passed. The lower strap portion 2518 can be adjusted relative to the buckle portion 2564 to permit an effective length of the lower strap portion 2518 to be adjusted.

Similar to the interface assembly 2300, the strap 2515 can be adjusted relative to the friction guide 2562 to adjust an effective length of the upper strap portion 2520. The lower strap portion 2518 can be adjusted relative to the clip 2360 to adjust an angular or rotational position of the mask 2502. Adjustment of the lower strap portion 2518 can also adjust the tension of the strap 2515 when the interface assembly 2500 is fitted to a user.

To fit or remove the interface assembly 2500, the clip 2560 can be disengaged from the mask 2502, which can free the lower portion of the mask 2502. With the clip 2360 disengaged, the low friction guide 2540 also permits an effective length of the intermediate strap portion 2550 to be increased to thereby increase a distance between the rear strap portion 2570 and the mask 2502, which may permit the interface assembly 2500 to be fitted or removed from the user. In necessary or desired, the strap 2515 can also be adjusted relative to the friction guide 2562 to increase an effective length of the upper strap portion 2520 to facilitate fitment of removal of the interface assembly 2500.

Figure 26:
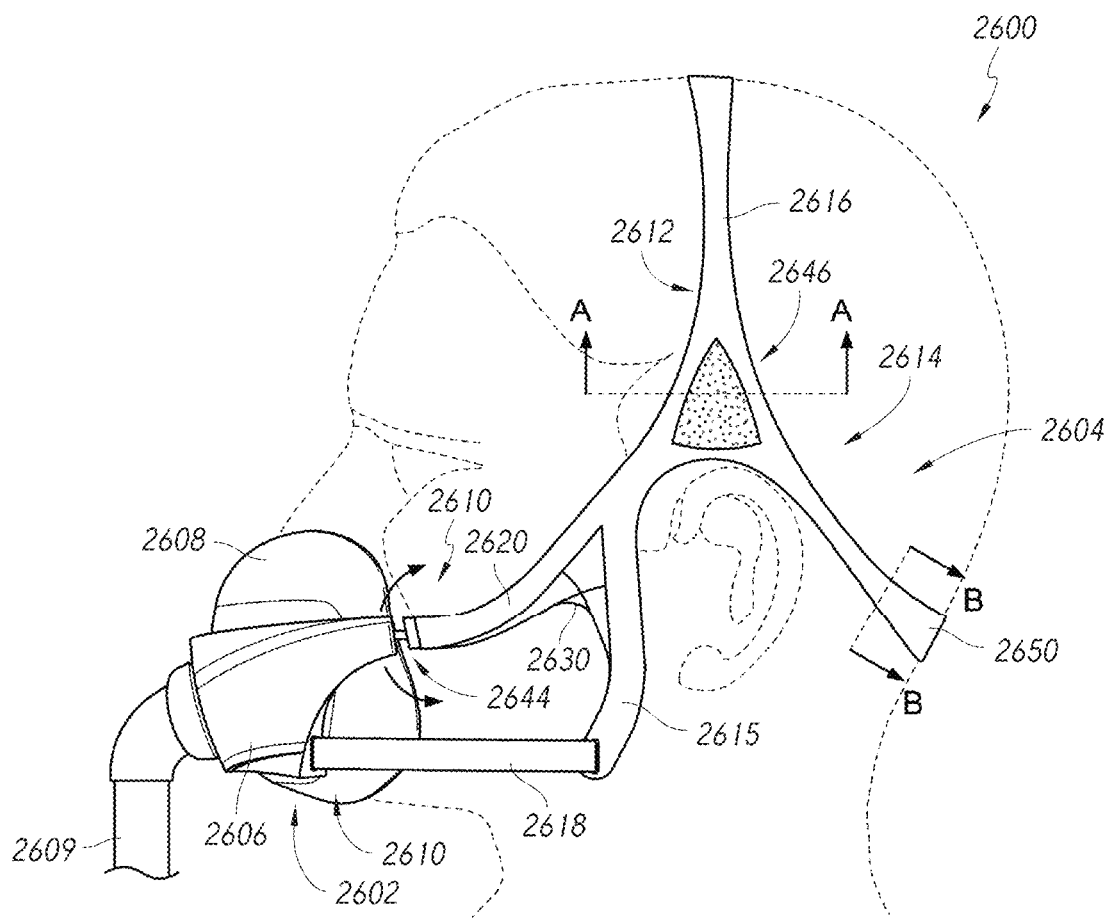
FIG. 26 is a side view of an interface assembly having an interface, such as a mask, and a headgear.
Figure 27:
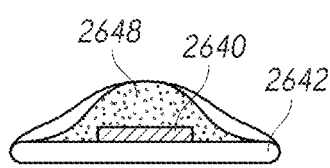
FIG. 27 is a cross-sectional view of a first portion of the headgear of the interface assembly of FIG. 26.

FIGS. 26-28 illustrate an interface assembly 2600 that is arranged and configured in accordance with certain features, aspects and advantages of the present disclosure. The illustrated interface assembly 2600 includes an interface 2602 and a headgear 2604. The illustrated interface 2602 is a nasal-oral mask but, as described herein, other types of interfaces can be used with the disclosed headgear 2604. The illustrated mask 2602 generally comprises a frame 2606 that supports a seal 2608. The mask 2602 can be connected to a supply conduit 2609, which can be used to supply breathing gases to a user. As described above, in some configurations, the mask 2602 can seal around a mouth of a user and on an underside of a nose of the user. Such a mask 2602 can provide pressurized air flow to both the nose and the mouth of the user. The headgear 2604 can be coupled to the mask 2602 at one or more mounting locations or mounting points 2610. Unless indicated otherwise, features of the interface assembly 2600 or portions thereof can be the same as or similar to other interfaces or portions thereof described herein, or can be of another suitable arrangement.

In the illustrated arrangement, a lower strap 2618 and an upper arm 2620 are provided on each side of the headgear 2604 to connect the mask 2602 to a rear portion of the headgear 2604. Preferably, similar to the interface assembly 600 of FIG. 6, the headgear 2604 of the interface assembly 2600 includes a hook portion 2615 extending downwardly in front of the user's ear that supports the lower strap 2618. The upper arm 2620 and the hook portion 2615 can be an integral or single-piece construction. In some configurations, a gusset 2630 or other support structure can be provided between the upper arm 2620 and the hook portion 2615.

The headgear 2604 can also include a crown strap 2616 portion and a rear strap 2650 portion. The upper arm 2620 and crown strap 2616 can cooperate to form a front halo portion 2612 and the rear strap 2650 can cooperate to form a rear halo portion 2614. Some or all of the upper arm 2620, hook portion 2615, crown strap 2616 and rear strap 2650 portions of the headgear 2604 can be an integrated or single-piece construction. In some configurations, some or all of the upper arm 2620, hook portion 2615, crown strap 2616 and rear strap 2650 portions of the headgear 2604 can comprise a relatively rigid frame 2640 that can be partially or completely covered by a softer and/or less rigid material exterior or cover 2642. Any materials suitable for the rigid frame 2640 and soft cover 2642 can be used. For example and without limitation, the rigid frame 2640 can be constructed from polycarbonate, nylon, ABS, polypropylene or other materials having similar mechanical properties, especially with respect to rigidity. The soft cover 2642, for example and without limitation, can be constructed from silicone, thermoplastic elastomer, thermoplastic polyurethane, other materials with similar mechanical properties, cloth-type materials (cloth covered foam), rubber/foam materials or other suitable soft materials. In some configurations, an adjustment mechanism, stretchable component or less rigid portion can be provided within the crown strap 2616 and/or rear strap 2650 to facilitate size adjustment or fitting. Thus, the headgear 2604 could be constructed from multiple sections or portions (e.g., two halves), each of which could comprise an integrated or single-piece construction of some or all of the upper arm 2620, hook portion 2615, crown strap 2616 or rear strap 2650.

Preferably, a coupler 2644 allows for rotational or pivotal movement of the mask 2602 relative to the upper arm 2620. Any suitable arrangement of the coupler 2644 to achieve rotational or pivotal movement of the mask 2602 can be used. For example, the mask 2602 can be coupled to the upper arm 2620 by a flexible shaft or cable or by a pivotal joint. In addition, preferably, the lower strap 2618 is capable of length adjustment, such as by any of the adjustment arrangements disclosed herein or any other suitable arrangement. Accordingly, rotational adjustment and fixation of the mask 2602 can be achieved. The coupler 2644 can allow the mask to freely rotate with fixation provided by the lower strap 2618. In other configurations, other rotational adjustment arrangements could be used that allow adjustment and fixation of the mask 2602, such as the arrangement disclosed in connection with FIG. 19, for example and without limitation.

In some configurations, one or more portions of the headgear 2604 can comprise a padded portion 2646. For example, a junction between the upper arm 2620/hook portion 2615, the crown strap 2616 and the rear strap 2650, which can be located generally above the user's ear, can comprise a padded portion 2646. Any suitable type of padding can be used. For example, with reference to FIG. 27, a padding material 2648, such as a gel or other highly compressible material can be utilized, such as between the rigid frame 2640 and soft cover 2642. A bottom surface of the section of the headgear 2604 in FIG. 27 represents a surface that would contact the user's head.

Figure 28B:
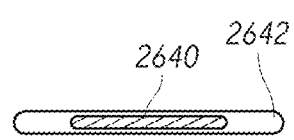
FIGS. 28A-28C illustrate several possible cross-sections of a second portion of the headgear of the interface assembly of FIG. 26.
Figure 28A:
Figure 28C:
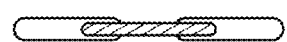

FIGS. 28A-28C illustrate possible constructions for other (e.g., non-padded) portions of the headgear 2604. For example, portions of some or all of the upper arm 2620, hook portion 2615, crown strap 2616 or rear strap 2650 could be constructed in a manner similar to any of the arrangements of FIGS. 28A-28C. A bottom surface of the section of the headgear 2604 in FIGS. 28A-28C represents a surface that would contact the user's head. The arrangement of FIG. 28A comprises a variable thickness cover 2642. For example, the thickness is greater in a center portion of the cross-section compared to the edge portions, which results in a non-linear surface adjacent the user's head and/or facing away from the user's head. FIG. 28B illustrates an arrangement with consistent thickness of the cover 2642 and the overall cross-section of the portion of the headgear 2604. FIG. 28C illustrates a version in which the cover 2642 does not cover an entirety of the rigid frame 2640. For example, a center portion of the rigid frame 2640 is left exposed and the cover 2642 is provided on each edge portion of the rigid frame 2640. Any suitable manner of coupling the cover 2642 and/or padding 2648 to the rigid frame 2640 can be utilized, such as overmolding, for example. Arrangements to provide mechanical interlocking of the rigid frame 2640 and the cover 2642 and/or padding 2648 can be utilized for increased durability.

Figure 29:
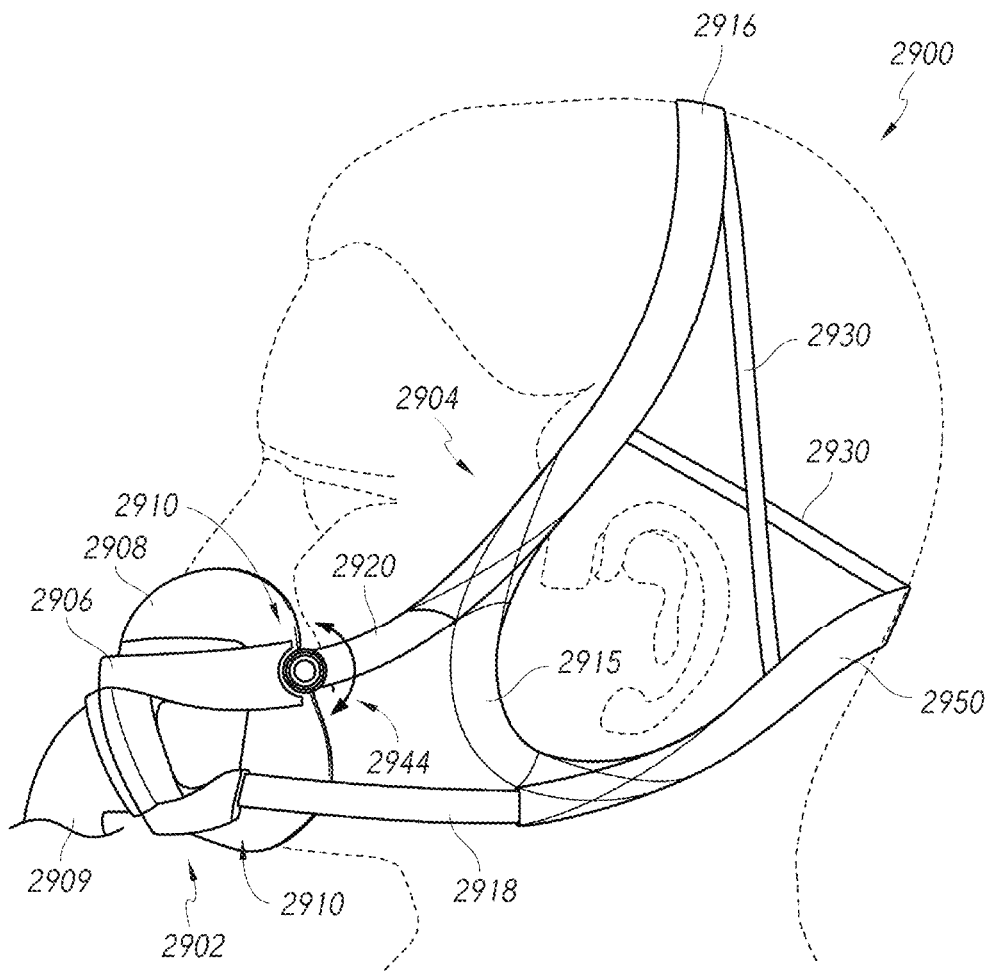
FIG. 29 is a side view of an interface assembly having an interface, such as a mask, and a headgear. The interface assembly has a rotational coupling between the mask and the headgear.

FIG. 29 illustrates an interface assembly 2900 that is arranged and configured in accordance with certain features, aspects and advantages of the present disclosure. The illustrated interface assembly 2900 includes an interface 2902 and a headgear 2904. The illustrated interface 2902 is a nasal-oral mask but, as described herein, other types of interfaces can be used with the disclosed headgear 2904. The illustrated mask 2902 generally comprises a frame 2906 that supports a seal 2908. The mask 2902 can be connected to a supply conduit 2909, which can be used to supply breathing gases to a user. As described above, in some configurations, the mask 2902 can seal around a mouth of a user and on an underside of a nose of the user. Such a mask 2902 can provide pressurized air flow to both the nose and the mouth of the user.

The headgear 2904 can be coupled to the mask 2902 at one or more mounting locations or mounting points 2910. Preferably, a lower strap portion 2918 and an upper arm 2920 are provided on each side of the headgear 2904 to connect the mask 2902 to a rear portion of the headgear 2904. Unless indicated otherwise, features of the interface assembly 2900 or portions thereof can be the same as or similar to other interfaces or portions thereof described herein, or can be of another suitable arrangement. In particular, the interface assembly 2900 is similar to the interface assembly 2600 of FIGS. 26-28 and, for the sake of convenience, will be described in the context of the differences relative to that interface assembly 2600.

The headgear 2904 utilizes a rear strap 2950 portion that couples to the hook portion 2915 at a lower end thereof, such that the rear strap 2950 extends below the user's ear toward the hook portion 2915. Thus, a crown strap 2916, the hook portion 2915 and the rear strap 2950 of the headgear 2904 cooperate to form a generally U-shaped or C-shaped profile. One or more supports, such as elasticated or semi-rigid straps 2930, can provide support between different portions of the headgear 2904. For example, one or more (e.g., a pair) of straps 2930 can extend between the crown strap 2916 and the rear strap 2950 to support the "ends" of the U-shaped or C-shaped profile and inhibit those portions from moving apart from one another. In some configurations, the straps 2930 cross one another.

In the illustrated configuration, an upper portion of the mask 2902 is rotationally or pivotally coupled to the upper arm 2920 by a rotational coupling 2944. The lower strap 2918 can permit adjustment of a rotational position of the mask 2902. For example, a length of the lower strap 2918 could be adjustable. In some configurations, the lower strap 2918 can be constructed from an elasticated material that automatically adjusts a rotational position of the mask 2902.

Figure 30:
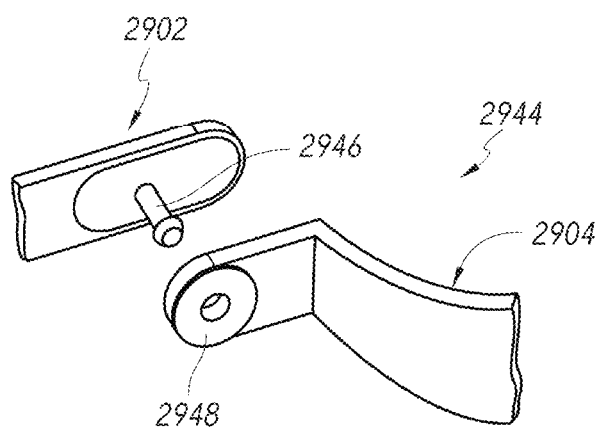
FIG. 30 is an exploded view of the rotational coupling of the interface assembly of FIG. 29.

FIG. 30 illustrates one possible construction of the rotational coupling 2944. In some configurations, one of the mask 2902 and the headgear 2904 supports a shaft or axle 2946 and the other of the mask 2902 and the headgear 2904 supports a hub 2948. The hub 2948 is rotatable about the axle 2946 to permit rotational adjustment of the mask 2902 relative to the headgear 2904. In the illustrated arrangement, the axle 2946 is carried by the mask 2902 and the hub 2948 is carried by the headgear 2904. However, this arrangement could be reversed. If desired, a detent assembly could be utilized to maintain a desired rotational position of the mask 2902. In some configurations, the lower strap 2918 is utilized to maintain a desired rotational position of the mask 2902.

Figure 31:
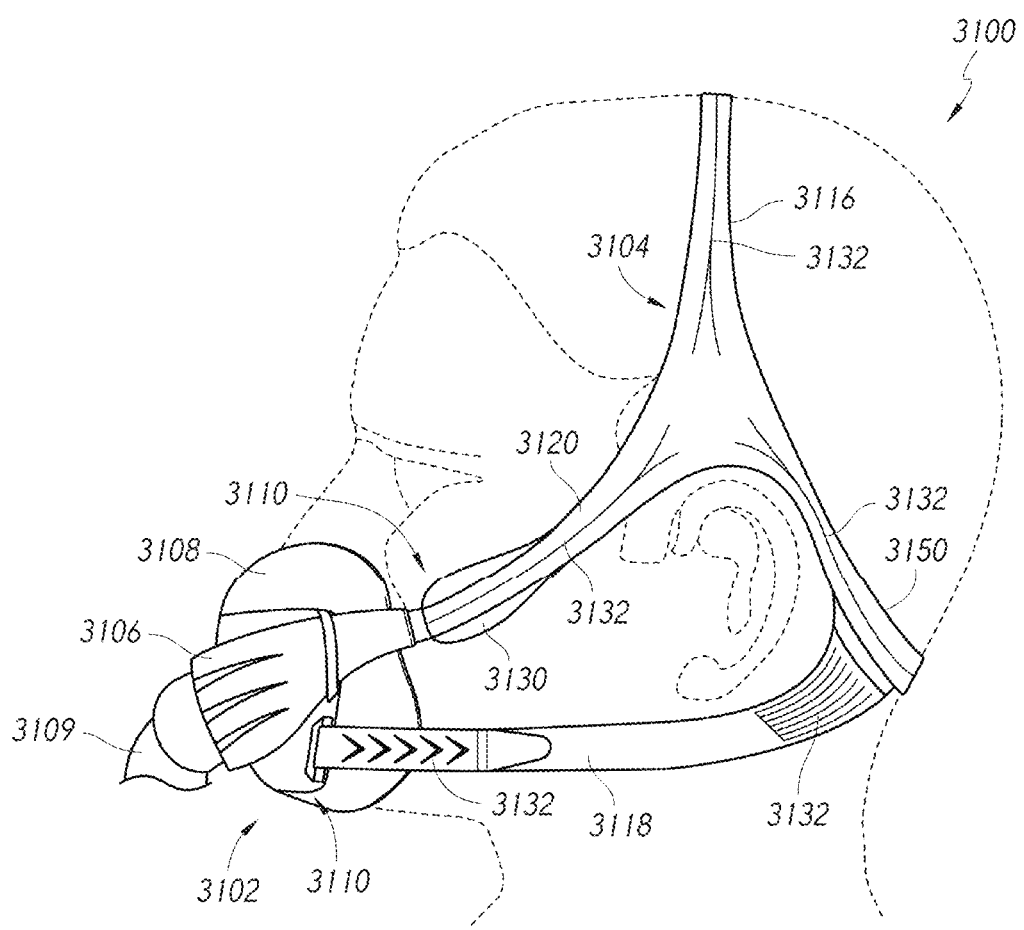
FIG. 31 is a side view of an interface assembly having an interface, such as a mask, and a headgear. The headgear includes a cheek pad.
Figure 32:
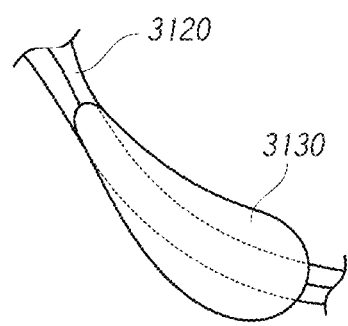
FIG. 32 is a perspective view of a cheek pad portion of the headgear of the interface assembly of FIG. 31.

FIGS. 31 and 32 illustrate an interface assembly 3100 that is arranged and configured in accordance with certain features, aspects and advantages of the present disclosure. The illustrated interface assembly 3100 includes an interface 3102 and a headgear 3104. The illustrated interface 3102 is a nasal-oral mask but, as described herein, other types of interfaces can be used with the disclosed headgear 3104. The illustrated mask 3102 generally comprises a frame 3106 that supports a seal 3108. The mask 3102 can be connected to a supply conduit 3109, which can be used to supply breathing gases to a user. As described above, in some configurations, the mask 3102 can seal around a mouth of a user and on an underside of a nose of the user. Such a mask 3102 can provide pressurized air flow to both the nose and the mouth of the user.

The headgear 3104 can be coupled to the mask 3102 at one or more mounting locations or mounting points 3110. Preferably, a lower strap portion 3118 and an upper strap portion 3120 are provided on each side of the headgear 3104 to connect the mask 3102 to a rear portion of the headgear 3104. Unless indicated otherwise, features of the interface assembly 3100 or portions thereof can be the same as or similar to other interfaces or portions thereof described herein, or can be of another suitable arrangement. In particular, the interface assembly 3100 is similar to the interface assembly 1300 of FIGS. 13-15 and, for the sake of convenience, will be described in the context of the differences relative to that interface assembly 1300.

The upper strap portion 3120 of the headgear 3104 incorporates a cheek pad 3130, which preferably is constructed from a relatively or highly compressible material for user comfort. FIG. 32 is an enlarged view of the cheek pad 3130 and upper strap portion 3120 of the opposite side of the headgear 3104 from that shown in FIG. 31. As illustrated, the cheek pad 3130 can have a contoured shape, with a wider portion being positioned closer toward the mask 3102 or centerline of the user's head than the narrower portion. For example, the cheek pad 3130 could have a generally teardrop shape, among other possible tapered or non-tapered shapes. The cheek pad 3130 can be secured to the upper strap 3120 by any suitable arrangement, such as by overmolding, for example. In some configurations, the cheek pad 3130 can include an interior passage and the cheek pad 3130 can be slid onto the upper strap 3120. If desired, the cheek pad 3130 can be rigid to provide a hard stop in response to tightening of the headgear 3104 to at least partially isolate compression of the mask seal 3108 from tightening forces applied to the headgear 3104, such as described in connection with FIGS. 13-15 and 75-79, for example.

The headgear 3104 can include various features configured to influence the flexibility, strength or rigidity. For example, if the headgear 3104 is constructed primarily from a flexible material, the features can alter the inherent or base properties (e.g., flexibility, strength or rigidity) of the material of the headgear 3104. In some configurations, the features can comprise one or more types of strips or ribs 3132 formed into or applied to the headgear 3104 in a manner to provide desirable properties to the headgear 3104. For example, elongate ribs 3132 can be provided on one or more of the upper strap 3120, a crown strap 3116 or a rear strap 3150 of the headgear 3104. Each or any one of the elongate ribs 3132 can define an end portion that diverges or splits, such as an end nearest a convergence of the upper strap 3120, crown strap 3116 or rear strap 3150. For example, the ribs 3132 of the upper strap 3120, crown strap 3116 or rear strap 3150 can increase the tensile or bending strength of the straps.

A rear portion of the bottom strap 3118 near a junction between a rearward end of the bottom strap 3118 and the rear strap 3150 can comprise a rib or ribs 3132. For example, a series of ribs 3132 can be vertically-stacked or stacked in a width direction of the strap 3118. The ribs 3132 can follow a curvature (e.g., an upward curvature) of the rear portion of the rear strap 3150. The ribs 3132 of the rear strap 3150 can increase the bending strength of the rear strap 3150 and can help the curved rearward portion of the rear strap 3150 maintain its shape in response to loading.

The lower strap 3118 can include a series of ribs 3132 spaced from one another in a lengthwise direction of the strap 3132. In the illustrated arrangement, the ribs 3132 are or comprise chevrons. Such an arrangement can inhibit folding of the strap 3118 along a lengthwise axis and/or can increase bending strength, but can maintain the inherent axial properties (e.g., tensile strength or flexibility in an axial direction).

The ribs 3132 can be of any suitable arrangement. For example, the ribs 3132 could be formed into the material of the headgear 3104 (e.g., thermoformed). The ribs 3132 could protrude outwardly from an adjacent or base surface of the headgear 3104 or could extend inwardly from an adjacent or base surface of the headgear 3104. In some configurations, the ribs 3132 could be additional structures that are attached (e.g., adhesive, RF welding, ultrasonic welding, thermoforming, stitching, chemical bonding, mechanical bonding or otherwise adhered) to the base headgear 3104 structure. The features of the headgear 3104 can be applied to any of the other headgear arrangements described herein.

Figure 33:
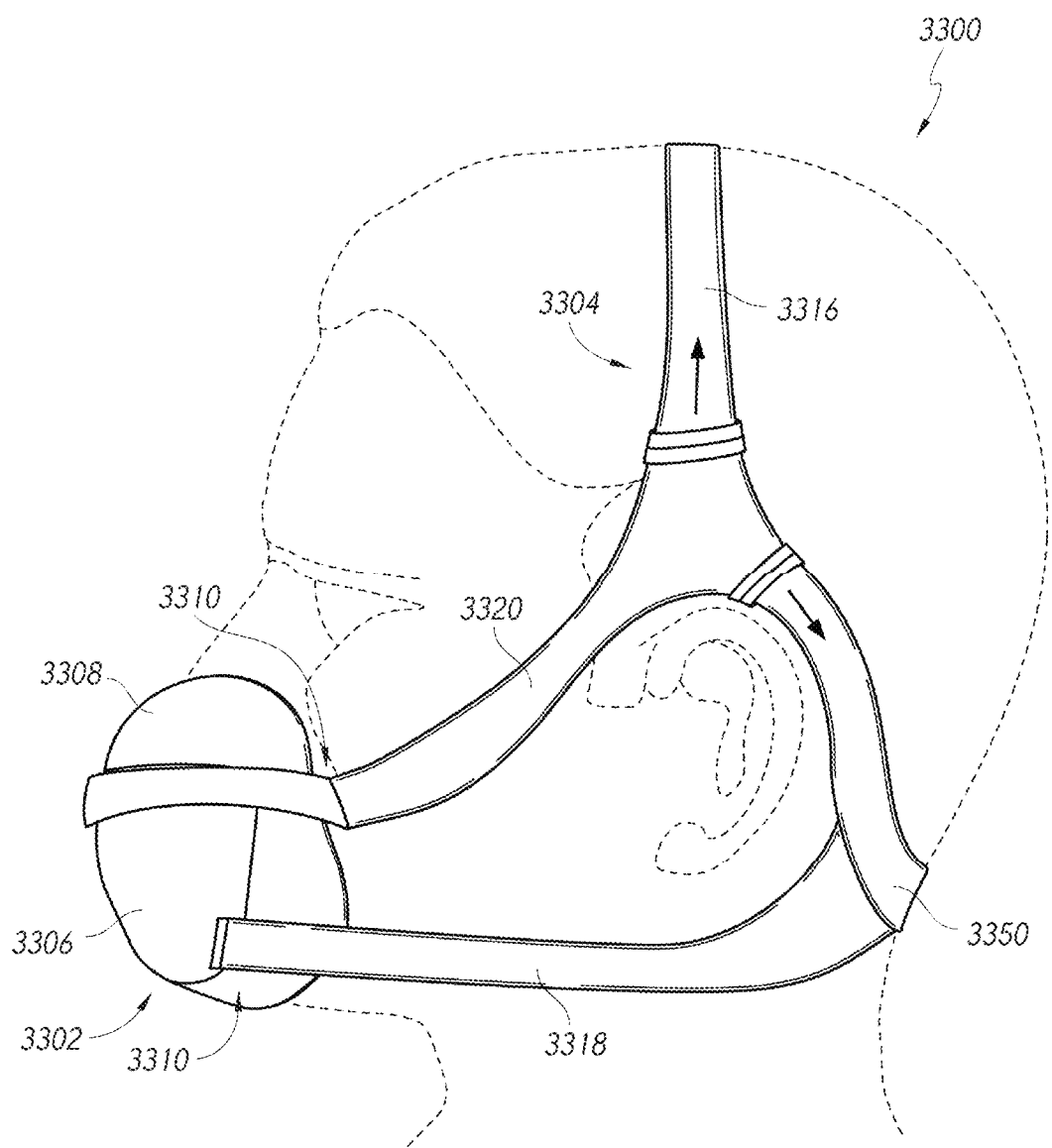
FIG. 33 is a side view of an interface assembly having an interface, such as a mask, and a headgear.

FIG. 33 illustrates an interface assembly 3300 that is arranged and configured in accordance with certain features, aspects and advantages of the present disclosure. The illustrated interface assembly 3300 includes an interface 3302 and a headgear 3304. The illustrated interface 3302 is a nasal-oral mask but, as described herein, other types of interfaces can be used with the disclosed headgear 3304. The illustrated mask 3302 generally comprises a frame 3306 that supports a seal 3308. The mask 3302 can be connected to a supply conduit (not shown), which can be used to supply breathing gases to a user. As described above, in some configurations, the mask 3302 can seal around a mouth of a user and on an underside of a nose of the user. Such a mask 3302 can provide pressurized air flow to both the nose and the mouth of the user.

The headgear 3304 can be coupled to the mask 3302 at one or more mounting locations or mounting points 3310. Preferably, a lower strap portion 3318 and an upper strap portion 3320 are provided on each side of the headgear 3304 to connect the mask 3302 to a rear portion of the headgear 3304. Unless indicated otherwise, features of the interface assembly 3300 or portions thereof can be the same as or similar to other interfaces or portions thereof described herein, or can be of another suitable arrangement.

The headgear 3304 can comprise a rigid portion or portions and a less rigid portion or portions. In the illustrated arrangement, the upper arm 3320 is constructed from a relatively rigid or rigid material. Other portions of the headgear 3304 can be constructed from a relatively less rigid material, such as flexible material. For example, a crown strap 3316 can be coupled to the rigid upper arm 3320 and can be constructed from a less rigid material. In some configurations, the headgear 3304 can include a rear strap 3350 that is coupled to the rigid upper arm 3320 and can be constructed from a less rigid material. In the illustrated arrangement, the less rigid portions (e.g., the crown strap 3316, the rear strap 3350 or the lower arm 3318) of the headgear 3304 can be coupled to the rigid upper arm 3320 such that forces applied to the less rigid portions are substantially or primarily axial. That is, preferably, the forces applied to the less rigid portion are generally aligned with a lengthwise direction of the portions, in a direction aligned with a geometric axis of the portions or otherwise aligned with a direction in which the portions are configured to resist elongation. In some configurations, an axial direction can include a direction passing through end points or end portions of a strap or other component or a direction along which forces are applied to the strap or other component. In some cases, the axial direction may not coincide with the shape of the strap or other component, but may define a virtual axis.

Figure 34:
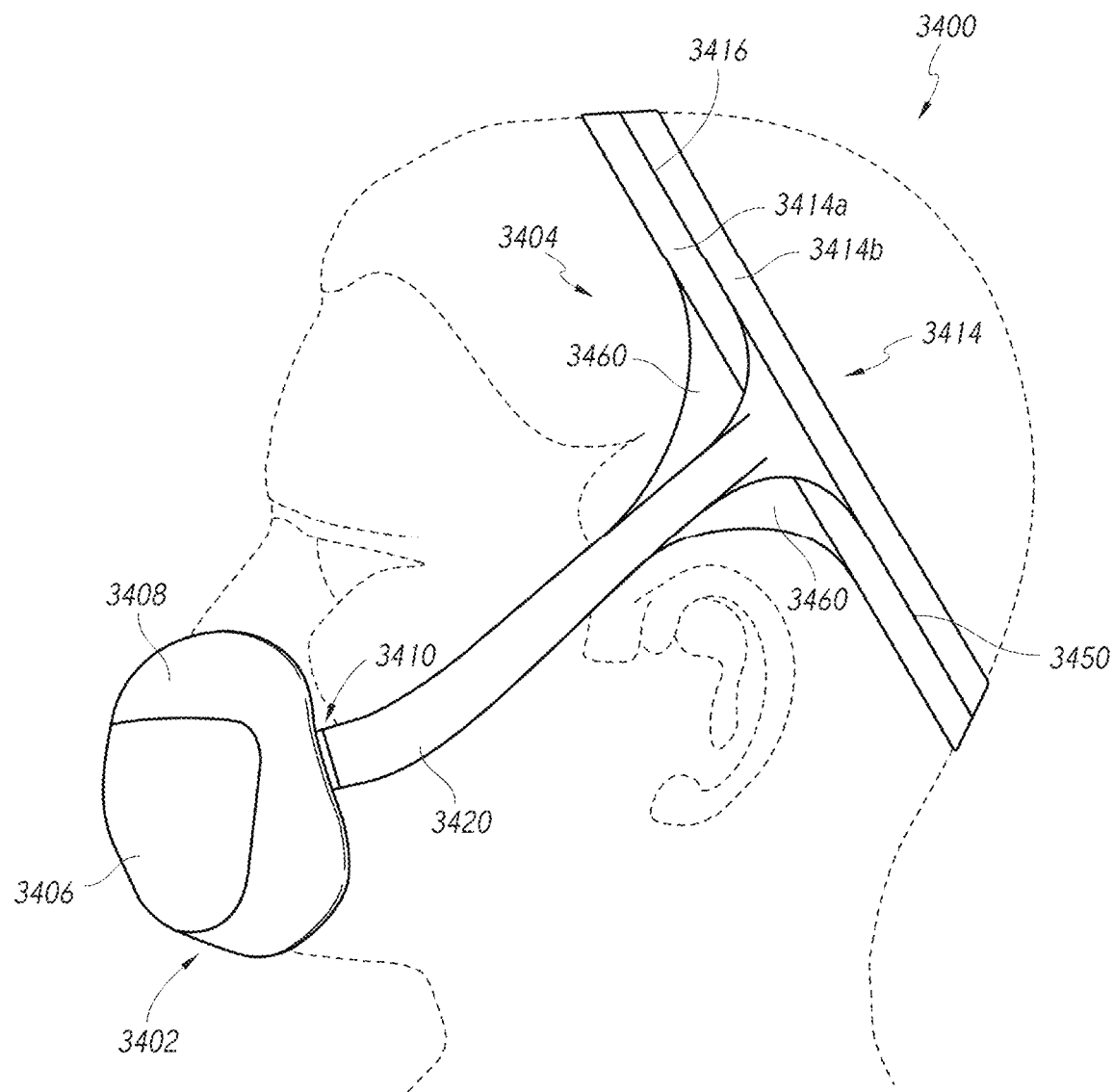
FIG. 34 is a side view of an interface assembly having an interface, such as a mask, and a headgear.

FIG. 34 illustrates an interface assembly 3400 that is arranged and configured in accordance with certain features, aspects and advantages of the present disclosure. The illustrated interface assembly 3400 includes an interface 3402 and a headgear 3404. The illustrated interface 3402 is a nasal-oral mask but, as described herein, other types of interfaces can be used with the disclosed headgear 3404. The illustrated mask 3402 generally comprises a frame 3406 that supports a seal 3408. The mask 3402 can be connected to a supply conduit (not shown), which can be used to supply breathing gases to a user. As described above, in some configurations, the mask 3402 can seal around a mouth of a user and on an underside of a nose of the user. Such a mask 3402 can provide pressurized air flow to both the nose and the mouth of the user.

The headgear 3404 can be coupled to the mask 3402 at one or more mounting locations or mounting points 3410. Preferably, a strap portion 3420 is provided on each side of the headgear 3404 to connect the mask 3402 to a rear portion of the headgear 3404. In the illustrated arrangement, the strap portion 3420 is positioned in a manner similar to the upper straps/arms in other arrangements disclosed herein and the lower strap can be omitted. Thus, the strap 3420 on each side can be the only connection between the mask 3402 and a rear portion of the headgear 3404. The strap 3420 can be oriented generally perpendicular with respect to a halo portion 3414 of the headgear 3404, which can be defined by a combination of a crown strap portion 3416 and a rear strap portion 3450. Preferably, the crown strap portion 3416 and the rear strap portion 3450 are aligned with one another such that the halo portion 3414 is generally flat or planar. The strap 3420 can extend upwardly from the mask 3402 and above the user's ear to the halo portion 3414 and can be generally straight or only slightly curved in comparison to many upper strap portions disclosed herein.

The halo portion 3414 can have a forward portion 3414a and a rearward portion 3414b. The strap 3420 can be coupled to the rearward portion 3414b and gussets 3460 can extend between the strap 3420 and the forward portion 3414a of the halo portion 3414 on one or both sides of the strap 3420. The strap 3420 and the halo portion 3414 can be constructed from a relatively rigid material or a relatively less-rigid material or any combination thereof. In some configurations, the strap 3420 can be constructed from a relatively rigid material and the halo portion 3414 can be constructed from a relatively less rigid material. Otherwise, features of the interface assembly 3400 or portions thereof can be the same as or similar to other interfaces or portions thereof described herein, or can be of another suitable arrangement.

Figure 35:
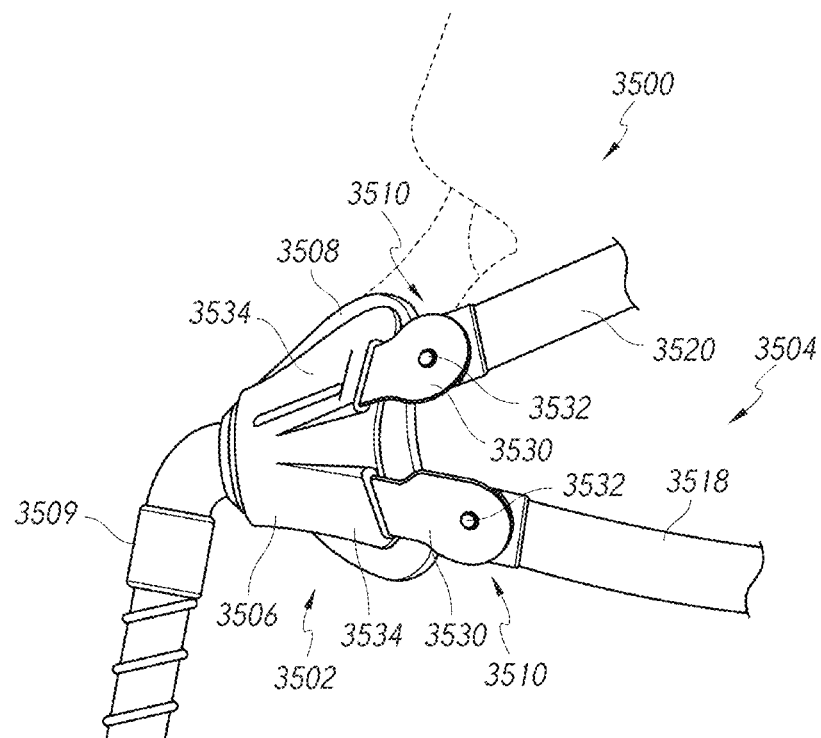
FIG. 35 is a side view of an interface assembly having an interface, such as a mask, and a headgear. The interface assembly includes quick-release mechanisms between the headgear and the mask.

FIG. 35 illustrates a portion of an interface assembly 3500 that is arranged and configured in accordance with certain features, aspects and advantages of the present disclosure. The illustrated interface assembly 3500 includes an interface 3502 and a headgear 3504. The illustrated interface 3502 is a nasal-oral mask but, as described herein, other types of interfaces can be used with the disclosed headgear 3504. The illustrated mask 3502 generally comprises a frame 3506 that supports a seal 3508. The mask 3502 can be connected to a supply conduit 3509, which can be used to supply breathing gases to a user. As described above, in some configurations, the mask 3502 can seal around a mouth of a user and on an underside of a nose of the user. Such a mask 3502 can provide pressurized air flow to both the nose and the mouth of the user.

The headgear 3504 can be coupled to the mask 3502 at one or more mounting locations or mounting points 3510. Preferably, a lower strap portion 3518 and an upper strap portion 3520 are provided on each side of the headgear 3504 to connect the mask 3502 to a rear portion of the headgear 3504. Unless indicated otherwise, features of the interface assembly 3500 or portions thereof can be the same as or similar to other interfaces or portions thereof described herein, or can be of another suitable arrangement.

The lower strap 3518 and the upper strap 3520 can be coupled to the mask 3502 by quick-release mechanisms, such as snap-locks or clips (e.g., hook-and-bar arrangement) 3530. The lower strap 3518 and upper strap 3520 can be rotatable relative to the clips 3530 to permit angular adjustment of the straps 3518, 3520. For example, the ends of the straps 3518, 3520 can carry pins 3532 that engage openings of the clips 3530. The portions of the mask 3502 that receive the clips 3530 can define one or more elongate protrusions 3534, surfaces of which extend outwardly beyond adjacent surfaces of the mask 3402. In some configurations, a surface between the portions of the mask 3502 that receive the clips 3530 is recessed such that a pair of protrusions 3534 is provided. Such an arrangement can provide tactile indications of the proper locations for engaging the clips 3530 with the mask in addition to providing a unique appearance.

Figure 36:
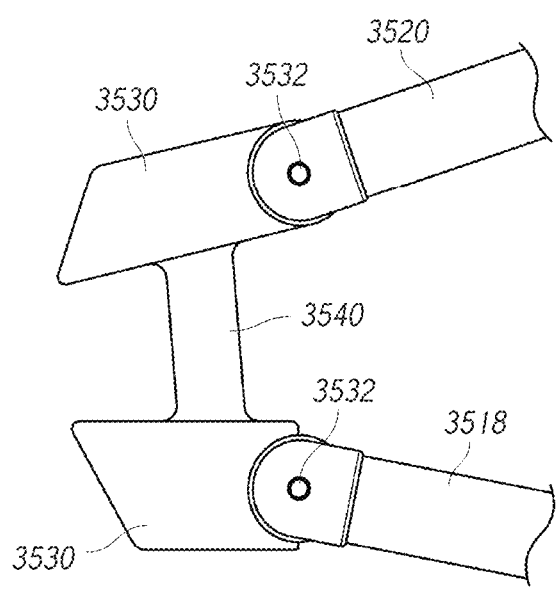
FIG. 36 is a side view of an alternative quick-release mechanism.

FIG. 36 illustrates an arrangement in which the clips 3530 are coupled to one another such that both clips 3530 and both straps 3518, 3520 can be coupled to the mask 3502 in a single action. For example, a bridge or strut portion 3540 can extend in a vertical direction between the clips 3530, which could be angled relative to one another. The clips 3530 and strut 3540 can be formed from a single piece of material, if desired. In addition, in the arrangement of FIG.

36, the pins 3532 are carried by the clips 3530 and corresponding openings are provided in the ends of the straps 3518, 3520.

Figure 37:
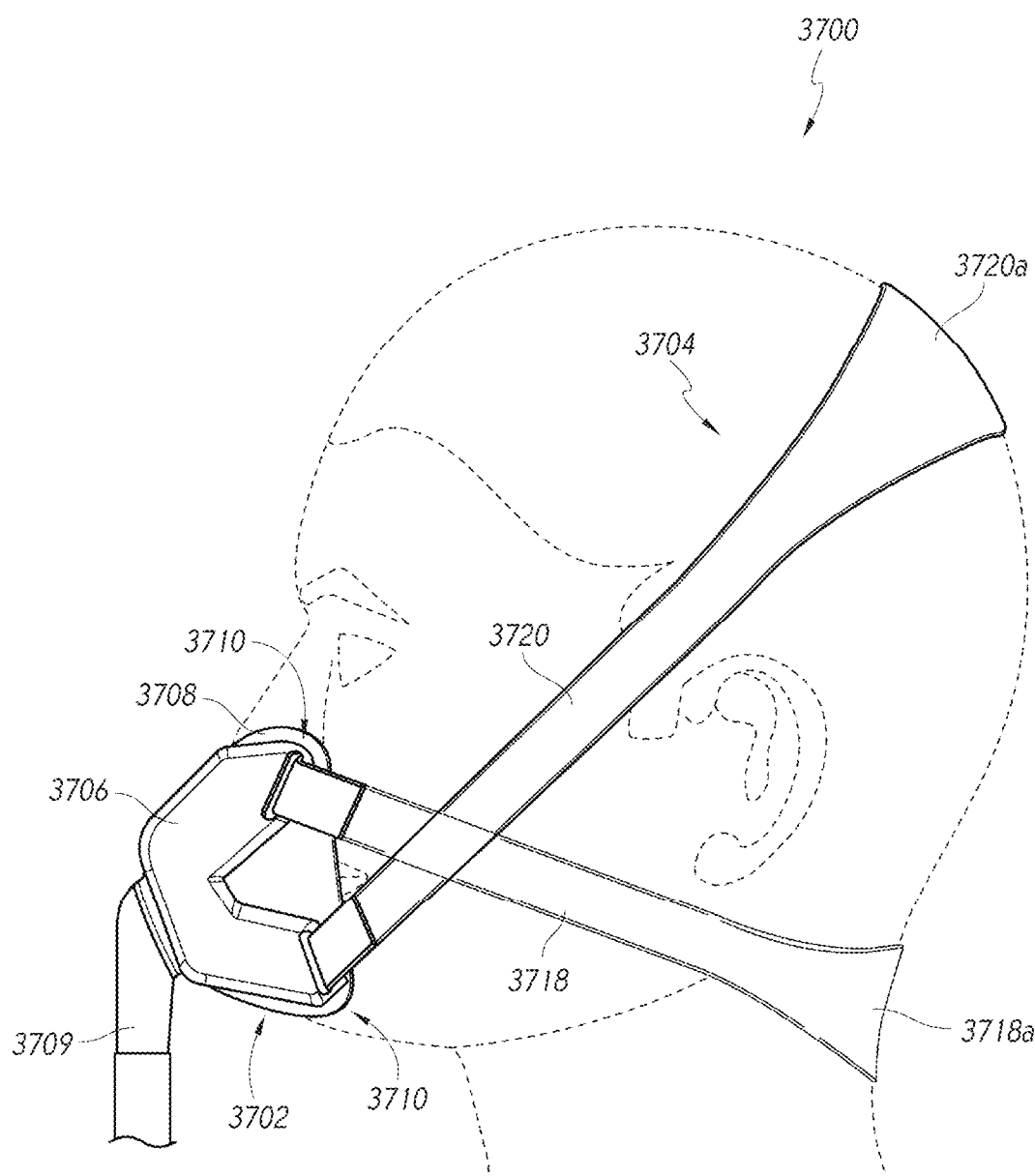
FIG. 37 is a side view of an interface assembly having an interface, such as a mask, and a headgear.

FIG. 37 illustrates an interface assembly 3700 that is arranged and configured in accordance with certain features, aspects and advantages of the present disclosure. The illustrated interface assembly 3700 includes an interface 3702 and a headgear 3704. The illustrated interface 3702 is a nasal-oral mask but, as described herein, other types of interfaces can be used with the disclosed headgear 3704. The illustrated mask 3702 generally comprises a frame 3706 that supports a seal 3708. The mask 3702 can be connected to a supply conduit 3709, which can be used to supply breathing gases to a user. As described above, in some configurations, the mask 3702 can seal around a mouth of a user and on an underside of a nose of the user. Such a mask 3702 can provide pressurized air flow to both the nose and the mouth of the user.

The headgear 3704 can be coupled to the mask 3702 at one or more mounting locations or mounting points 3710. Preferably, a lower strap portion 3718 and an upper strap portion 3720 are provided on each side of the headgear 3704 and connect to the mask 3702 by any suitable arrangement, such as by a quick-release mechanism (e.g., snap-lock or clips). In the illustrated arrangement, the straps 3718, 3720 extend from one side of the mask 3702 to the other and central portions of the straps 3718, 3720 form a rear portion of the headgear 3704. In addition, the lower strap 3718 connects to the mask 3702 at an upper mounting point 3710 and the upper strap 3720 connects to the mask 3702 at a lower mounting point 3710 such that the straps 3718, 3720 cross one another rearwardly of the mask 3702, preferably between the mask 3702 and the user's ear. The straps 3718, 3720 can be coupled to one another at the location in which they cross, if desired. The straps 3718, 3720 can be constructed of a flexible material, which may be elasticated, and can included enlarged width rear portions 3718a, 3720a to spread load for user comfort. In other arrangements, the straps 3718, 3720 could connect to a separate rear portion of a headgear 3704. Unless indicated otherwise, features of the interface assembly 3700 or portions thereof can be the same as or similar to other interfaces or portions thereof described herein, or can be of another suitable arrangement.

Figure 38:
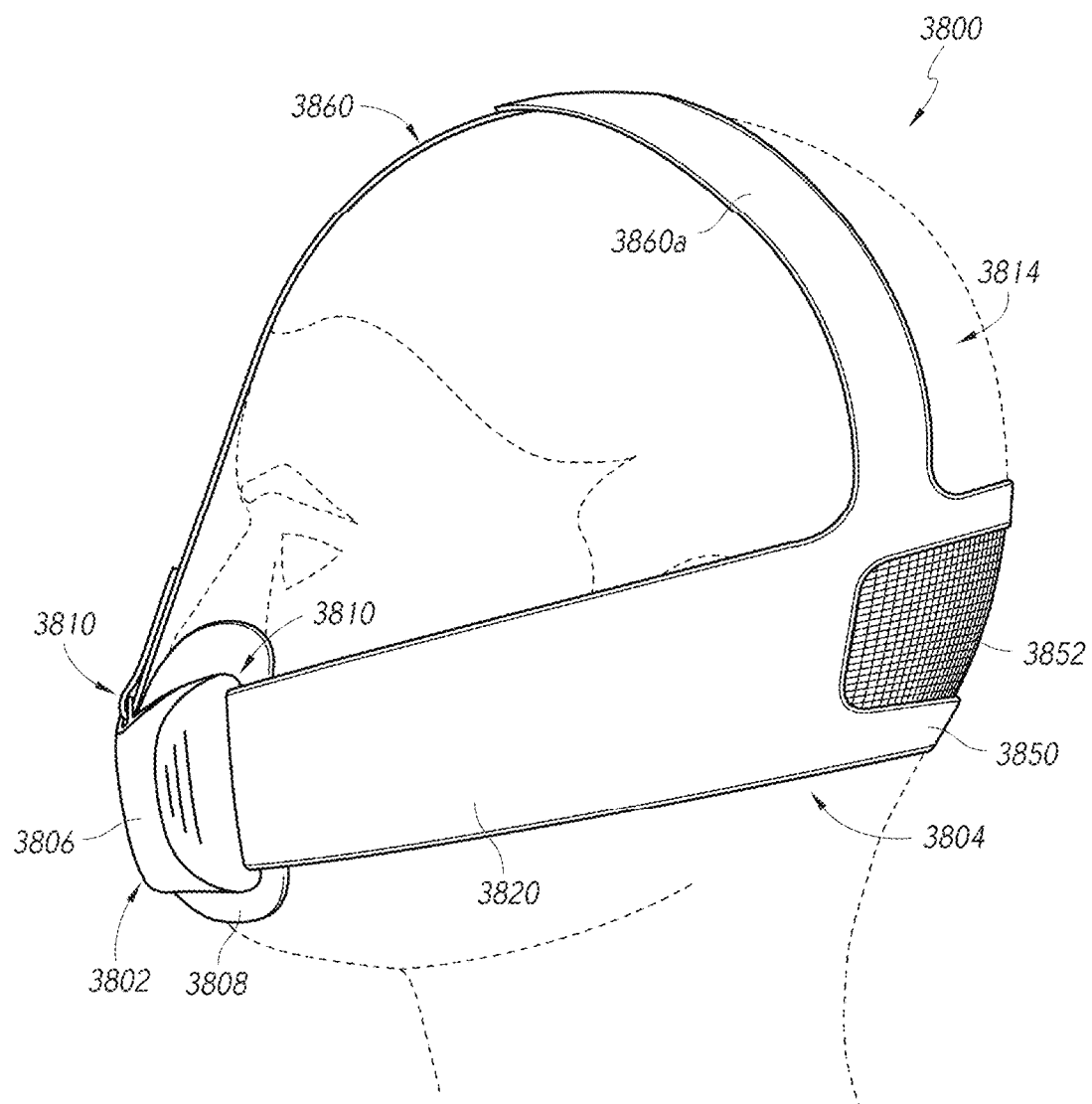
FIG. 38 is a side view of an interface assembly having an interface, such as a mask, and a headgear.
Figure 39:
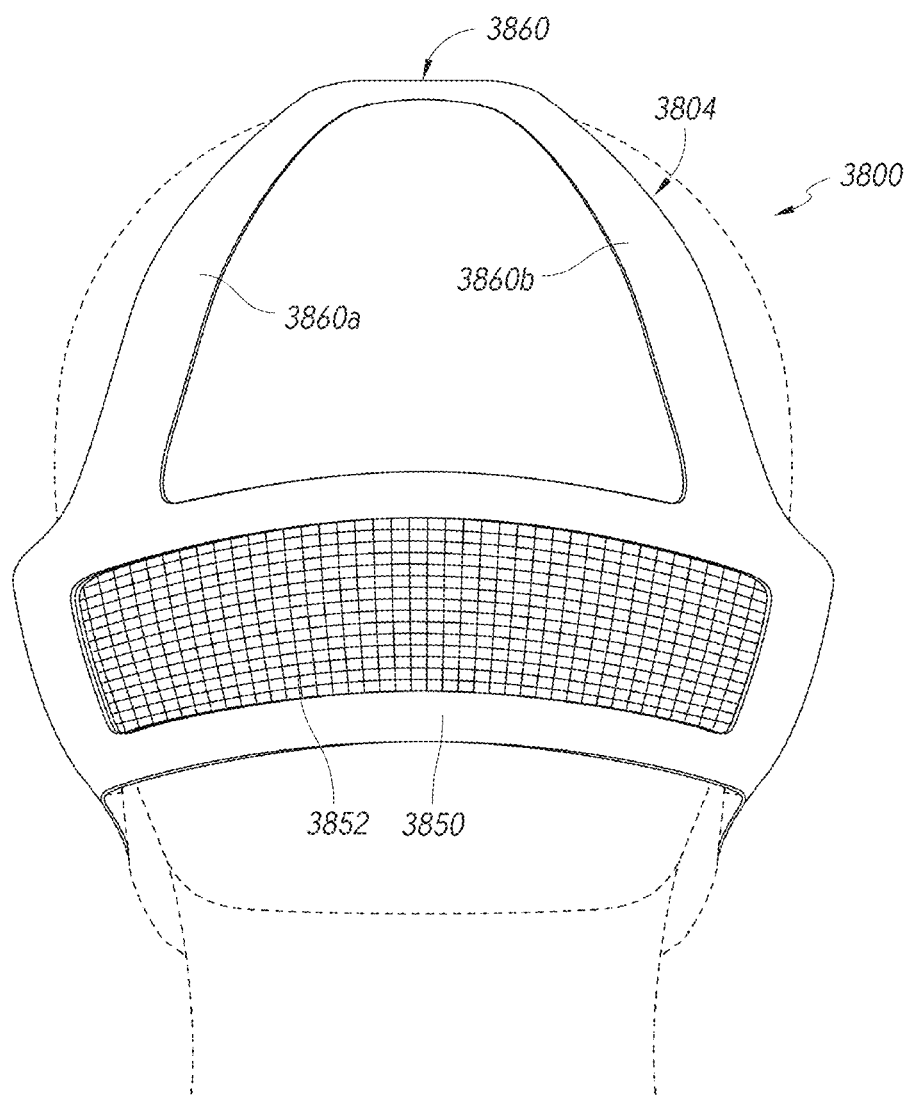
FIG. 39 is a rear view of the interface assembly of FIG. 38.

FIGS. 38 and 39 illustrate an interface assembly 3800 that is arranged and configured in accordance with certain features, aspects and advantages of the present disclosure. The illustrated interface assembly 3800 includes an interface 3802 and a headgear 3804. The illustrated interface 3802 is a nasal-oral mask but, as described herein, other types of interfaces can be used with the disclosed headgear 3804. The illustrated mask 3802 generally comprises a frame 3806 that supports a seal 3808. The mask 3802 can be connected to a supply conduit (not shown), which can be used to supply breathing gases to a user. As described above, in some configurations, the mask 3802 can seal around a mouth of a user and on an underside of a nose of the user. Such a mask 3802 can provide pressurized air flow to both the nose and the mouth of the user.

The headgear 3804 can be coupled to the mask 3802 at one or more mounting locations or mounting points 3810 by any suitable coupling, such as a quick-release mechanism, for example. Preferably, a strap portion 3820 is provided on each side of the headgear 3804 to connect the mask 3802 to a rear portion of the headgear 3804. In the illustrated arrangement, the headgear 3804 includes a single strap portion 3820 that is coupled to the mask 3802 at a single, vertically-elongated mounting point 3810 on each side of the interface assembly 3800. The strap portion 3820 can pass directly over the user's ear and, in some configurations, is wide enough to cover most, substantially all or the user's entire ear. The strap 3820 can extend all the way from one side of the mask 3802 to the other side and a central portion of the strap 3820 can define a rear strap portion 3850, which can include a vent 3852 to reduce heat build-up under the strap portion 3850. The vent 3852 can be constructed of a mesh or other breathable material and can extend along a substantial entirety of a length of the rear strap portion 3850. The vent 3852 can also extend along a substantial portion of the height of the rear strap portion 3850 such that the vent 3852 occupies a substantial portion of an overall area of the rear strap portion 3850, such as at least about 50, 60, 70 or 80% of an overall area. Preferably, the vent 3852 is of a sufficient size to significantly reduce heat build-up under the rear strap portion 3850 relative to a similarly sized strap without a vent. In some configurations, the vent 3852 is sized to maximize vented area while not compromising the structure of the strap portion 3850 or creating pressure points on the user's head.

The headgear 3804 can include a top strap 3860 that can extend upwardly from a center of the mask 3802 over top of the user's head and connect to the rear strap portion 3850. The top strap 3860 can extend along the user's nose, between the eyes and can bifurcate into two strap portions 3860a, 3860b to form a triangulated arrangement with the rear strap portion 3850 and form a halo portion 3814. The top strap 3860 can apply an upwardly-directed force to the mask 3802 to assist in creating a seal against the underside of the user's nose. In some configurations, a length of the top strap 3860 is adjustable to allow for adjustment of a position of and/or upward force applied to the mask 3802. In other respects, features of the interface assembly 3800 or portions thereof can be the same as or similar to other interfaces or portions thereof described herein, or can be of another suitable arrangement.

Figure 40:
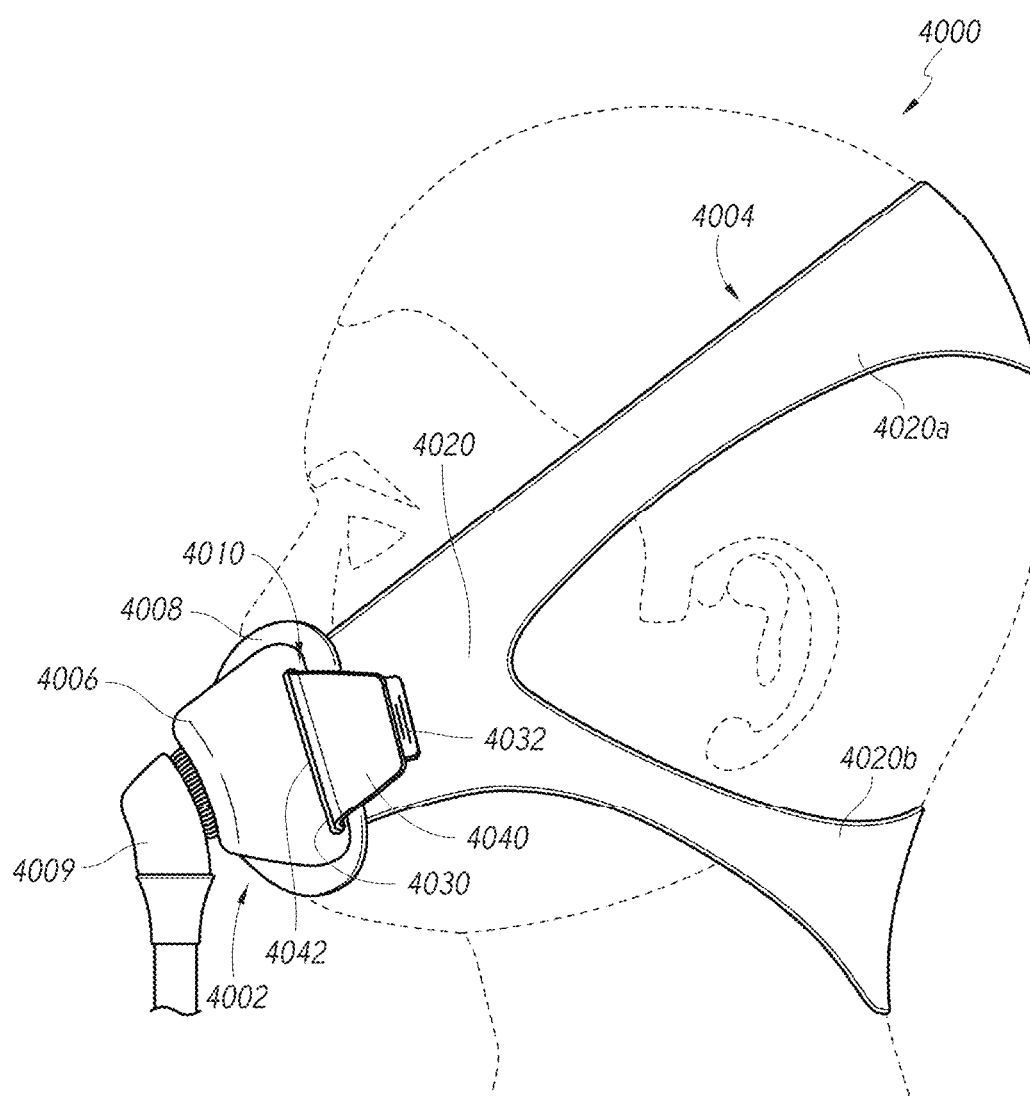
FIG. 40 is a side view of an interface assembly having an interface, such as a mask, and a headgear.

FIG. 40 illustrates an interface assembly 4000 that is arranged and configured in accordance with certain features, aspects and advantages of the present disclosure. The illustrated interface assembly 4000 includes an interface 4002 and a headgear 4004. The illustrated interface 4002 is a nasal-oral mask but, as described herein, other types of interfaces can be used with the disclosed headgear 4004. The illustrated mask 4002 generally comprises a frame 4006 that supports a seal 4008. The mask 4002 can be connected to a supply conduit 4009, which can be used to supply breathing gases to a user. As described above, in some configurations, the mask 4002 can seal around a mouth of a user and on an underside of a nose of the user. Such a mask 4002 can provide pressurized air flow to both the nose and the mouth of the user.

The headgear 4004 can be coupled to the mask 4002 at one or more mounting locations or mounting points 4010 by any suitable coupling arrangement. In the illustrated arrangement, the headgear 4004 includes a single strap portion 4020 that is coupled to the mask 4002 at a single, vertically-elongated mounting point 4010 on each side of the interface assembly 4000. The strap 4020 can extend all the way from one side of the mask 4002 to the other side. Preferably, the strap 4020 is bifurcated rearwardly of the mask 4002 to define an upper strap 4020a and a lower strap 4020b that pass above and below the user's ear, respectively. Central portions of the upper strap 4020a and the lower strap 4020b can be enlarged in a width or vertical direction to spread a load applied to the user's head over a relatively large area for comfort.

Each side of the mask 4002 can include an elongate slot 4030 through which the strap 4020 can pass. End portions 4040 of the strap 4020 can fold over to form a loop and can be secured to a portion of the strap 4020 rearward of the mask 4002 by a suitable fastener, such as a hook-and-loop fastener, for example. The end portions 4040 of the strap 4020 can include a finger tab 4032, which can provide a finger grip area to facilitate assembly and adjustment of the strap 4020 relative to the mask 4002. The slot 4030 can be generally or substantially straight and, in some configurations, can be generally or substantially aligned with a rearward surface of the mask 4002 (e.g., rearward surface of the frame 4006 and/or seal 4008). An overall size or circumference of the interface assembly 4000 can be adjusted by altering a length of the end portions 4040 of the strap 4020 that are pulled through the slot 4030 to vary a size of the loop. Angular adjustment of the mask 4002 can be accomplished by moving the end portions 4040 in a generally vertical direction to alter a vertical orientation of a forward end or fold 4042 of the end portions 4040 of the strap 4020. That is, the end portion 4040 can be moved or angled upwardly to pull in the bottom of the mask 4002 relative to the top of the mask 4002. Conversely, the end portion 4040 can be moved or angled downwardly to pull in the top of the mask 4002 relative to the bottom of the mask 4002. Thus, preferably, the straps 4020 increase in height (in the illustrated orientation or in a width direction of the strap 4020, itself) in a direction from each of the end portions 4040 toward the center of the strap 4020 to provide surface area of the strap 4020 for upward and downward adjustment of the end portions 4040 of the strap 4020. In other respects, features of the interface assembly 4000 or portions thereof can be the same as or similar to other interfaces or portions thereof described herein, or can be of another suitable arrangement.

Figure 41:
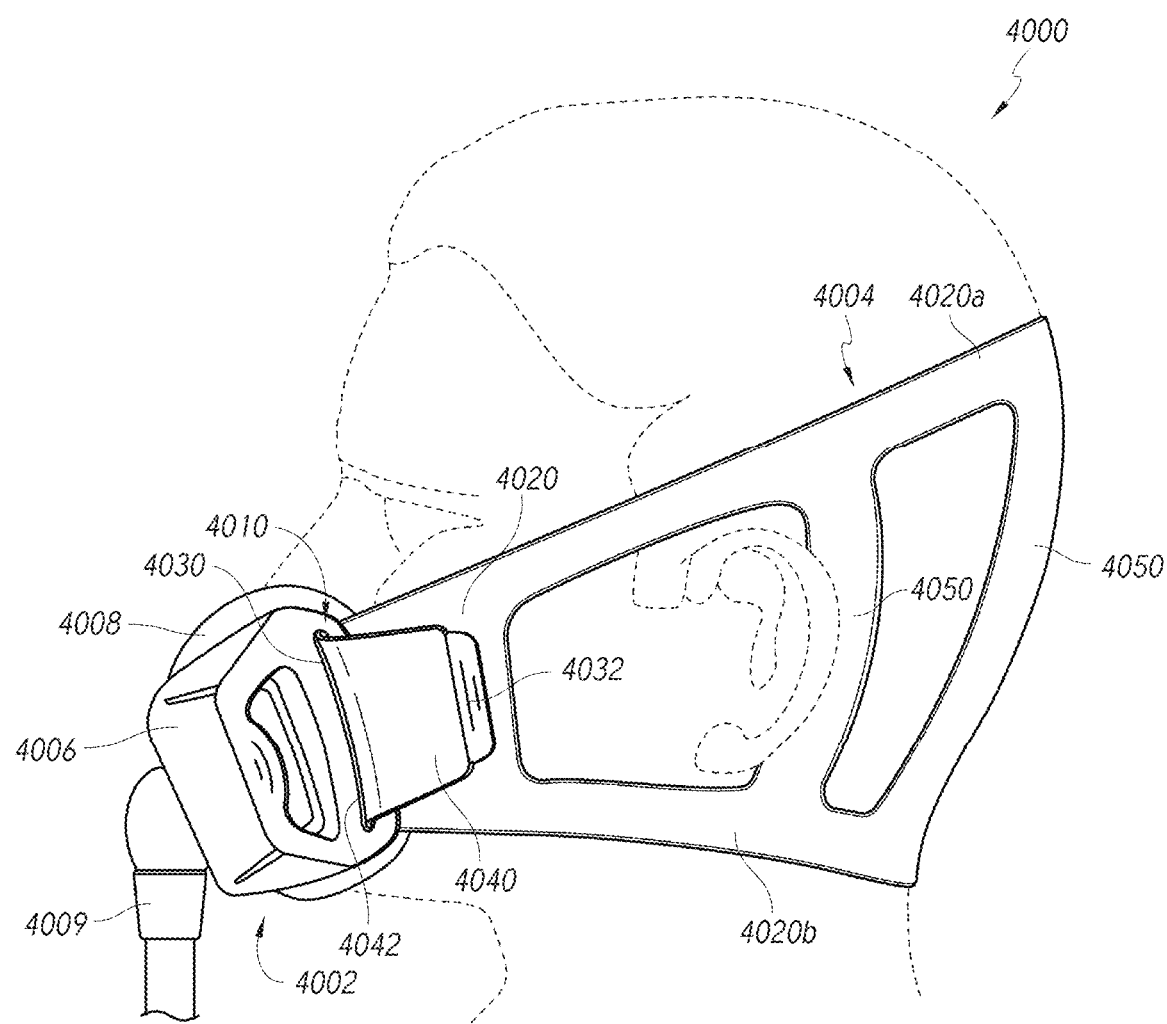
FIG. 41 is a side view of an interface assembly having an interface, such as a mask, and a headgear.
Figure 42:
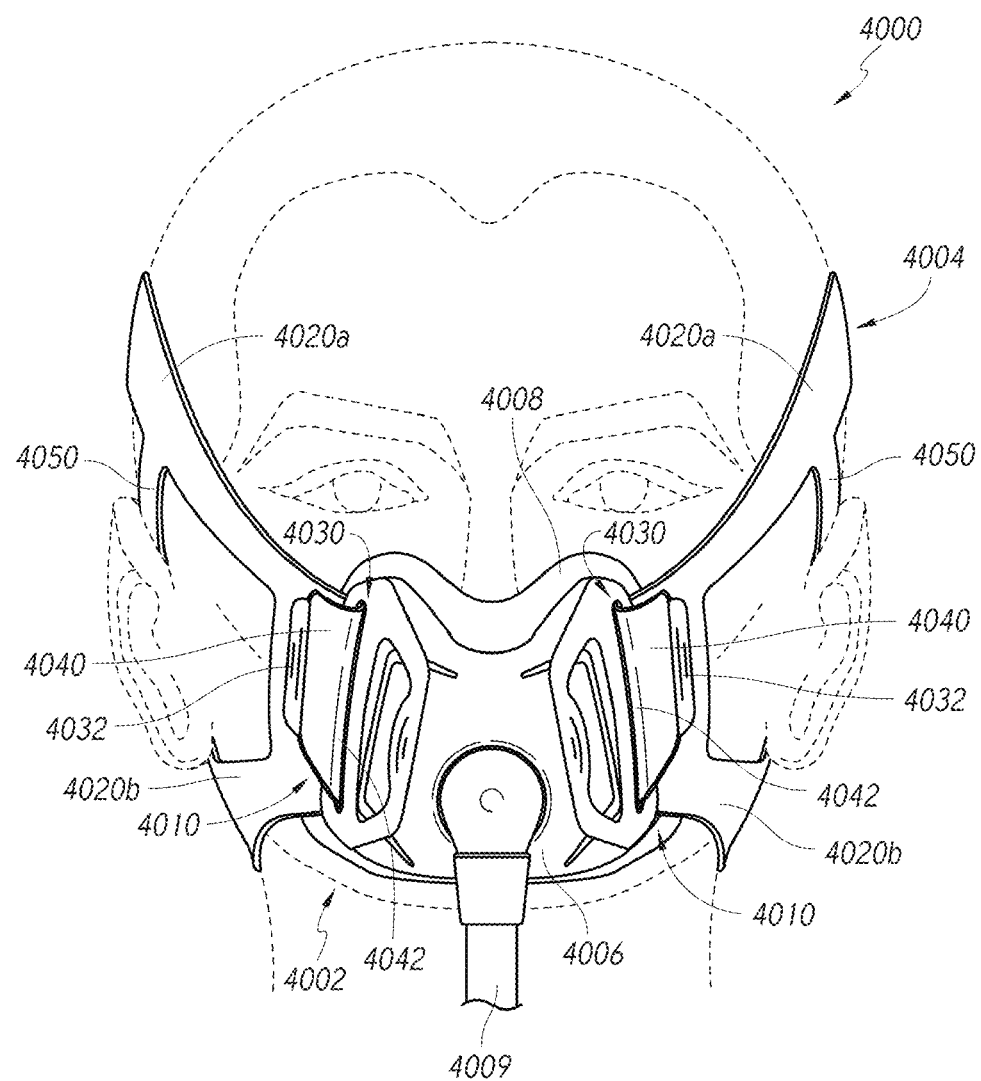
FIG. 42 is a front view of the interface assembly of FIG. 41.

FIGS. 41 and 42 illustrate an interface assembly 4000 that is similar in many respects to the interface assembly 4000 of FIG. 40. Therefore, the same reference numbers are used to refer to the same or corresponding components or features. In addition, the interface assembly 4000 of FIGS. 41 and 42 is described in the context of the differences relative to the interface assembly 4000 of FIG. 40. Features of the interface assembly 4000 or portions thereof not specifically described can be assumed to be the same as or similar to features of the interface assembly 4000 of FIG. 40, other interfaces or portions thereof described herein, or can be of another suitable arrangement.

In the arrangement of FIGS. 41 and 42, the upper strap 4020a and the lower strap 4020b can be positioned closer to one another than in the arrangement of FIG. 40. For example, the upper strap 4020a can be positioned lower on the user's head (e.g., at or near an upper edge of the occipital bone) and can pass just above the user's ear. The lower strap 4020b can be positioned higher on the user's head, such as above the user's neck muscled and/or on the occipital bone. In addition, the upper strap 4020a and the lower strap 4020b can be connected by one or more vertical connecting portions 4050. For example, on each side of the interface assembly 4000, a first vertical connecting portion 4050 can be positioned behind the user's ear and a second vertical connecting portion 4050 can be positioned further rearward of the first vertical connecting portion 4050. The vertical connecting portions 4050 can secure the upper strap 4020a and the lower strap 4020b in desired positioned relative to one another and inhibit or prevent migration of the straps 4020a, 4020b apart from one another.

Figure 43:
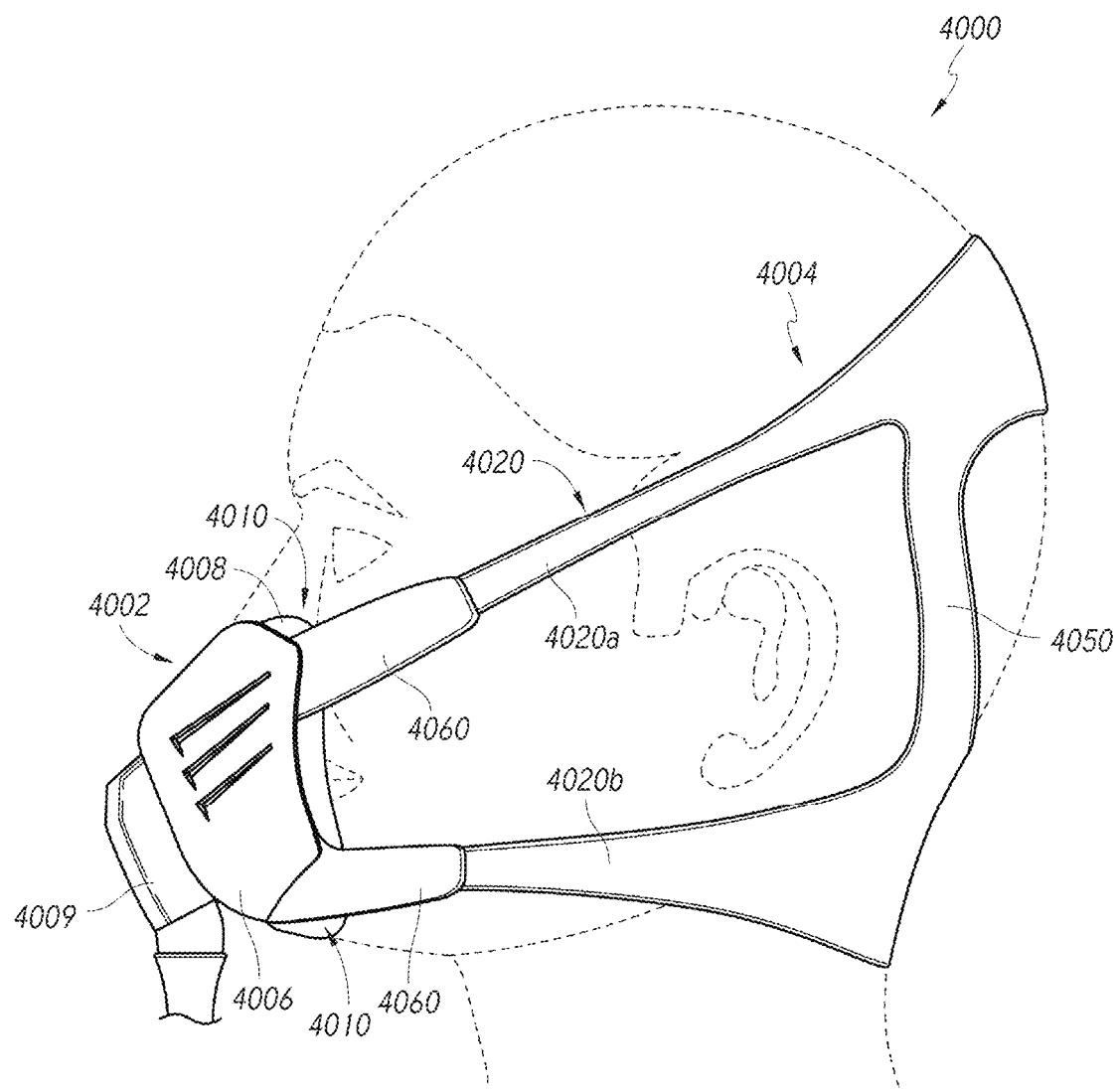
FIG. 43 is a side view of an interface assembly having an interface, such as a mask, and a headgear.

FIG. 43 illustrates an interface assembly 4000 that is similar in many respects to the interface assemblies 4000 of FIGS. 40-42. Therefore, the same reference numbers are used to refer to the same or corresponding components or features. In addition, the interface assembly 4000 of FIG. 43 is described in the context of the differences relative to the interface assemblies 4000 of FIGS. 40-42. Features of the interface assembly 4000 or portions thereof not specifically described can be assumed to be the same as or similar to features of the interface assembly 4000 of FIGS. 40-42, other interfaces or portions thereof described herein, or can be of another suitable arrangement.

The positioning of the upper strap 4020a and the lower strap 4020b of the headgear 4004 of FIG. 43 relative to the user's head can be similar to the straps in the headgear 4004 of FIG. 40. However, preferably, one or more connecting straps 4050 are provided that extend between and connect the upper strap 4020a and the lower strap 4020b, similar to the headgear 4004 of FIGS. 41 and 42.

In addition, the strap 4020 can be connected to the mask 4002 in a different manner. For example, the upper strap 4020a and the lower strap 4020b can be coupled to the mask 4002 at separate mounting points 4010. In some configurations, the straps 4020a, 4020b can be coupled to the mask 4002 by connectors having some amount of elasticity. In some configurations, the elasticity is relatively low. For example, the connectors can be silicone tension straps 4060. Such silicon tension straps 4060 can provide for rotational adjustment and tensioning of the mask 4002 against the user's face. However, other adjusters for the mask 4002 and/or headgear 4004 could also be provided. In addition, other materials with properties (e.g., elasticity, flexibility) similar to silicone could also be used.

Figure 44:
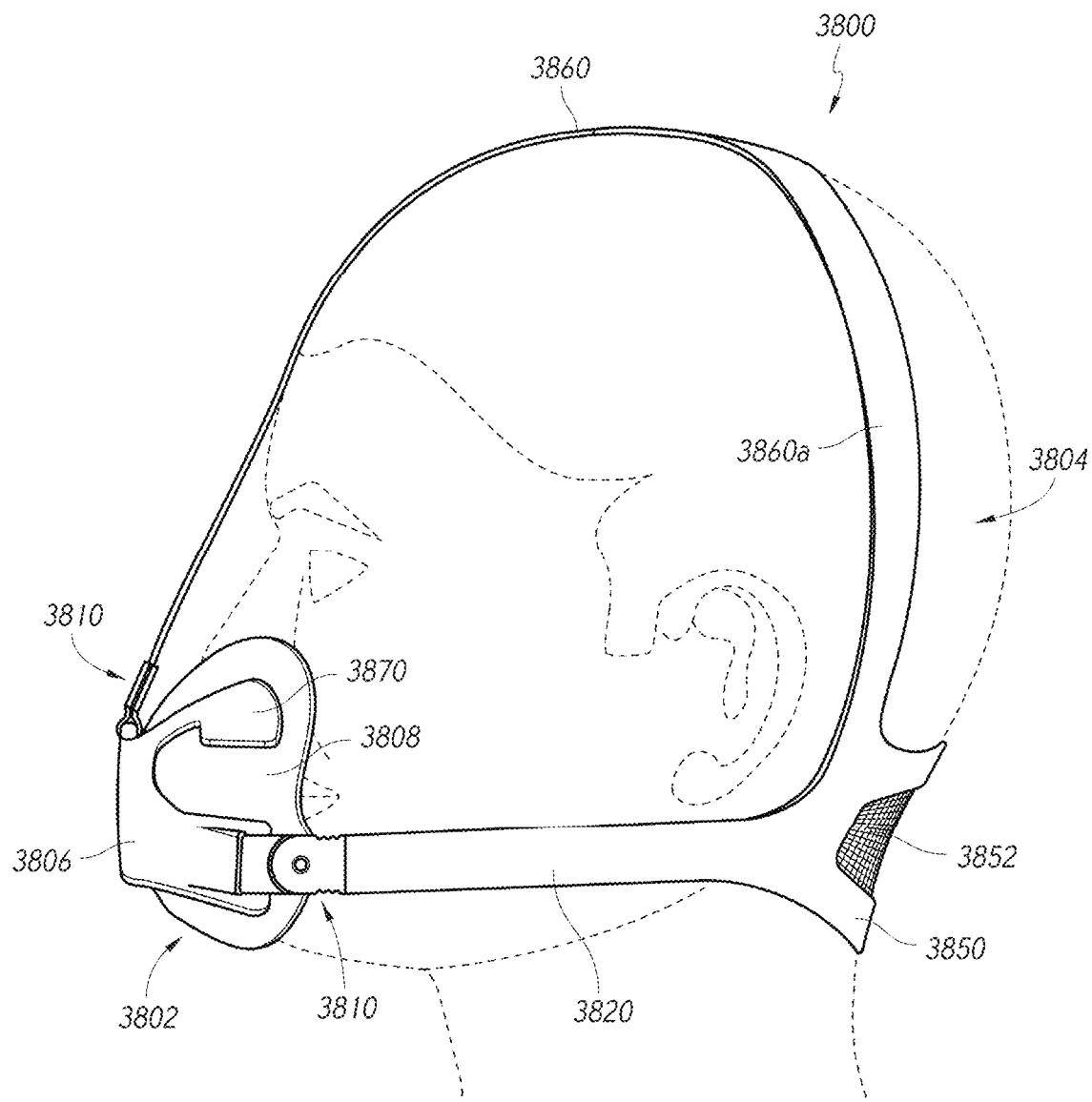
FIG. 44 is a side view of an interface assembly having an interface, such as a mask, and a headgear.
Figure 45:
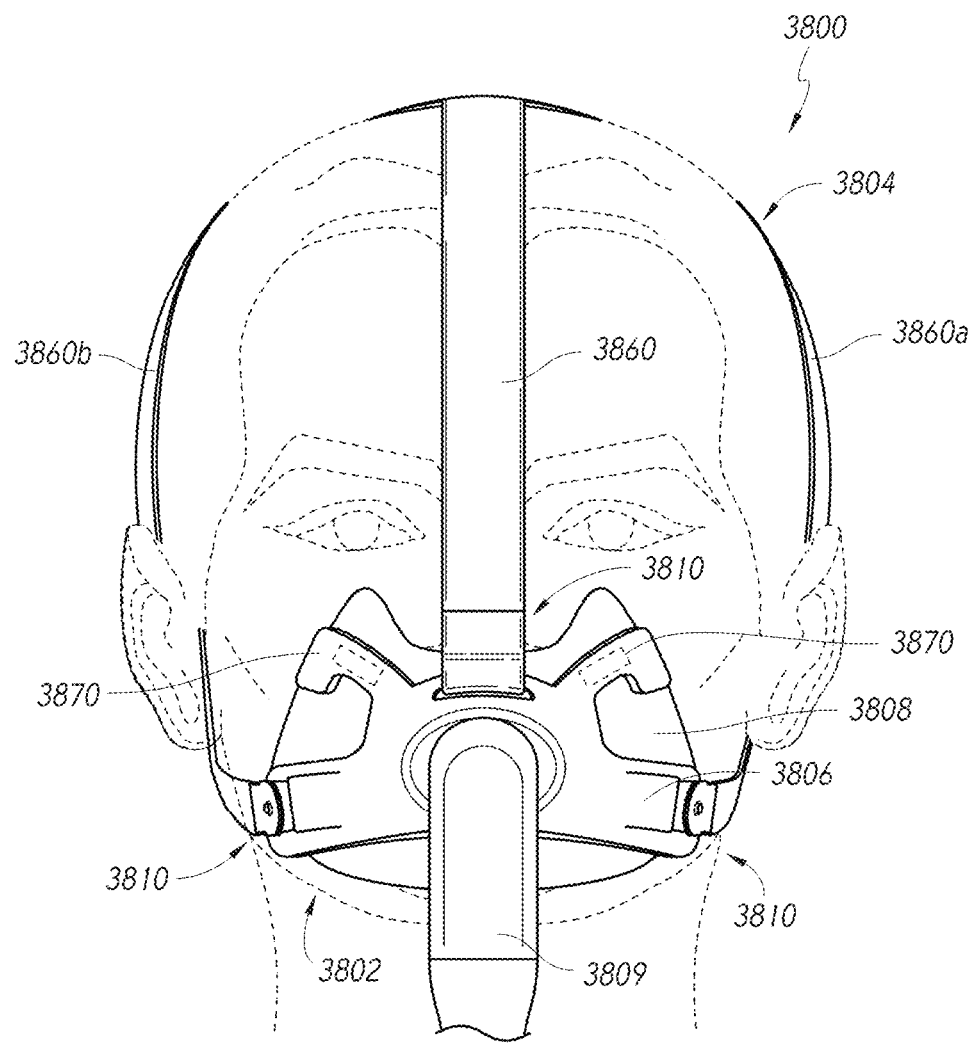
FIG. 45 is a front view of the interface assembly of FIG. 44.

FIGS. 44 and 45 illustrate an interface assembly 3800 that is similar in many respects to the interface assembly 3800 of FIGS. 38 and 39. Therefore, the same reference numbers are used to refer to the same or corresponding components or features. In addition, the interface assembly 3800 of FIGS. 44 and 45 is described in the context of the differences relative to the interface assembly 3800 of FIGS. 38 and 39. Features of the interface assembly 3800 or portions thereof not specifically described can be assumed to be the same as or similar to features of the interface assembly 3800 of FIGS. 38 and 39, other interfaces or portions thereof described herein, or can be of another suitable arrangement.

Unlike the strap portion 3820 of the headgear 3804 of FIGS. 38 and 39, the strap portion 3820 of FIGS. 44 and 45 preferably does not cover the user's ear. Rather, the strap portion 3820 preferably passes below the user's ear. The rear portion 3850 of the strap 3820 can be smaller in height (or width of the strap 3820, itself) compared to the rear portion 3850 of FIGS. 38 and 30. In some configurations, the strap 3820 is coupled to the mask 3802 by a rotatable coupling, such as those described in connection with FIGS. 35 and 36 or elsewhere herein.

In addition, the mask 3802 can include support portions, such as paddles 3870 that support the upper portion of the seal 3808. For example, the paddles 3870 can be a portion of or can be connected to the mask frame 3806 and can be positioned on lateral sides of the upper portion of the seal 3808 to provide support to the seal 3808 and maintain the seal 3808 in contact with the user's nose when the seal 3808 is pressurized. In some configurations, the paddles 3870 are constructed from silicone, or a similar material. In addition, FIG. 45 illustrates the supply conduit 3809.

Figure 46:
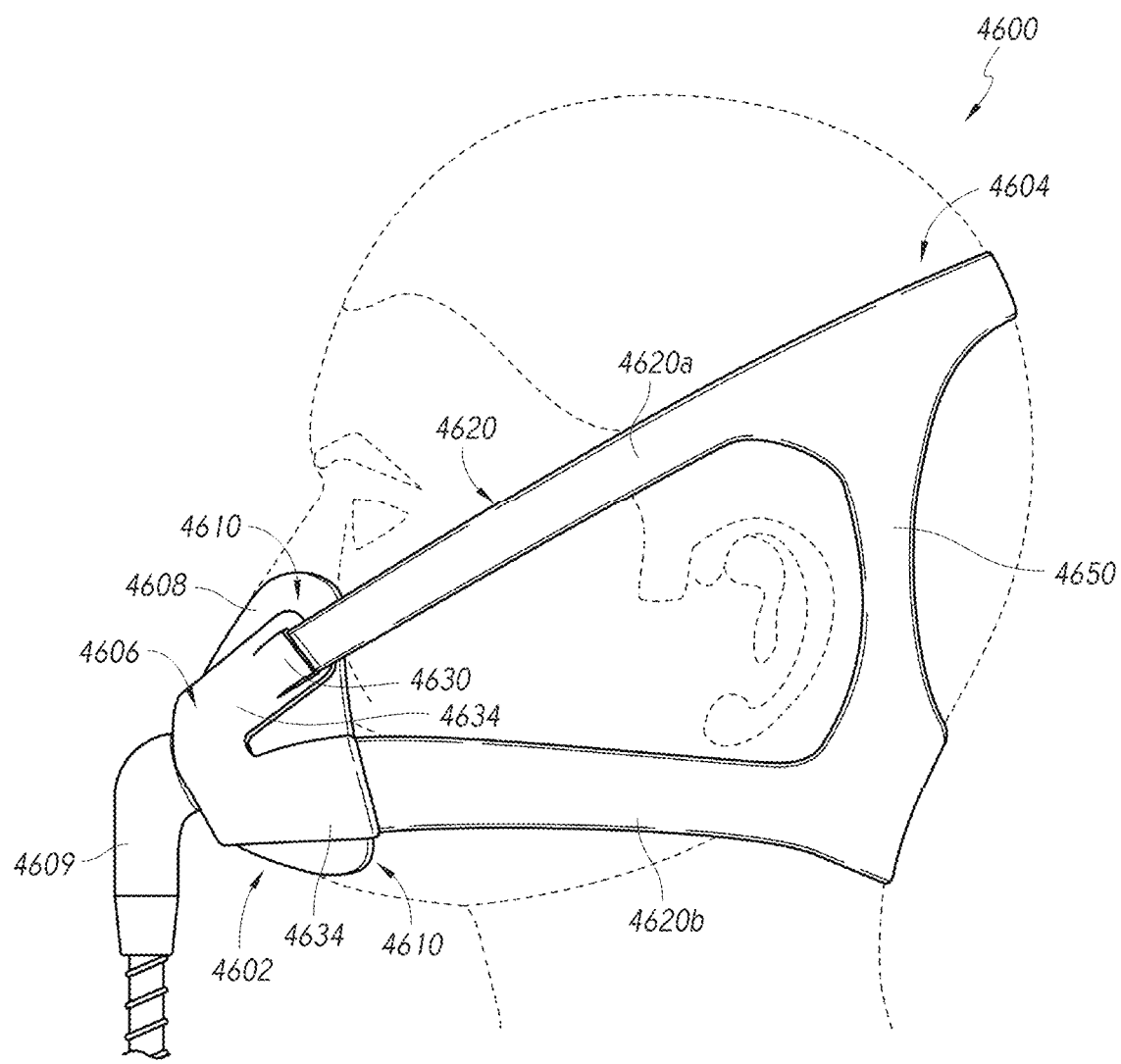
FIG. 46 is a side view of an interface assembly having an interface, such as a mask, and a headgear.

FIG. 46 illustrates an interface assembly 4600 that is similar in many respects to the interface assembly 3500 of FIGS. 35 and 36 and the interface assembly 4000 of FIG. 43. The interface assembly 4600 is described primarily in the context of the differences relative to the interface assemblies 3500 and 4000. Features of the interface assembly 3500 or portions thereof not specifically described can be assumed to be the same as or similar to features of the interface assemblies 3500 or 4000, other interfaces or portions thereof described herein, or can be of another suitable arrangement.

The interface assembly 4600 utilizes an interface or mask 4602 that is substantially similar to the mask 3502 of FIG. 35 and a headgear 4604 that is substantially similar to the headgear 4004 of FIG. 43. In particular, the mask 4602 preferably includes a frame 4606 and a seal 4608. A supply conduit 4609 delivers breathing gases to a user. As described above, in some configurations, the mask 4602 can seal around a mouth of a user and on an underside of a nose of the user. Such a mask 4602 can provide pressurized air flow to both the nose and the mouth of the user.

The headgear 4604 can be coupled to the mask 4602 at one or more mounting locations or mounting points 4610 by any suitable coupling arrangement. For example, the headgear can comprise a strap 4620 having an upper strap portion 4620a and a lower strap portion 4620b coupled to each side of the mask 4602 at separate mounting points 4610. A connecting strap portion 4650 couples the upper strap portion 4620a and the lower strap portion 4620b. The connecting strap portion 4650 can be provided on each side of the headgear 4604 behind the user's ear.

One or both of the upper strap 4620a and the lower strap 4620b can be coupled to the mask 4602 by any suitable arrangement. In some configurations, the straps 4620a, 4620b are coupled to the mask 4602 by quick-release mechanisms, such as snap-locks or clips (e.g., hook-and-bar arrangement) 4630. In some configurations, the straps 4620a, 4620b can be rotatable relative to the clips 4630 to permit angular adjustment of the straps 4620a, 4620b. The portions of the mask 4602 that receive the clips 4630 can define one or more elongate protrusions 4634, surfaces of which extend outwardly beyond adjacent surfaces of the mask 4602. In some configurations, a surface between the portions of the mask 4602 that receive the clips 4630 or straps 4620a, 4620b is recessed such that a pair of protrusions 4634 is provided. Such an arrangement can provide tactile indications of the proper locations for engaging the clips 4630 with the mask in addition to providing a unique appearance. Unless indicated otherwise, features of the interface assembly 4600 or portions thereof can be the same as or similar to other interfaces or portions thereof described herein, or can be of another suitable arrangement.

Figure 47:
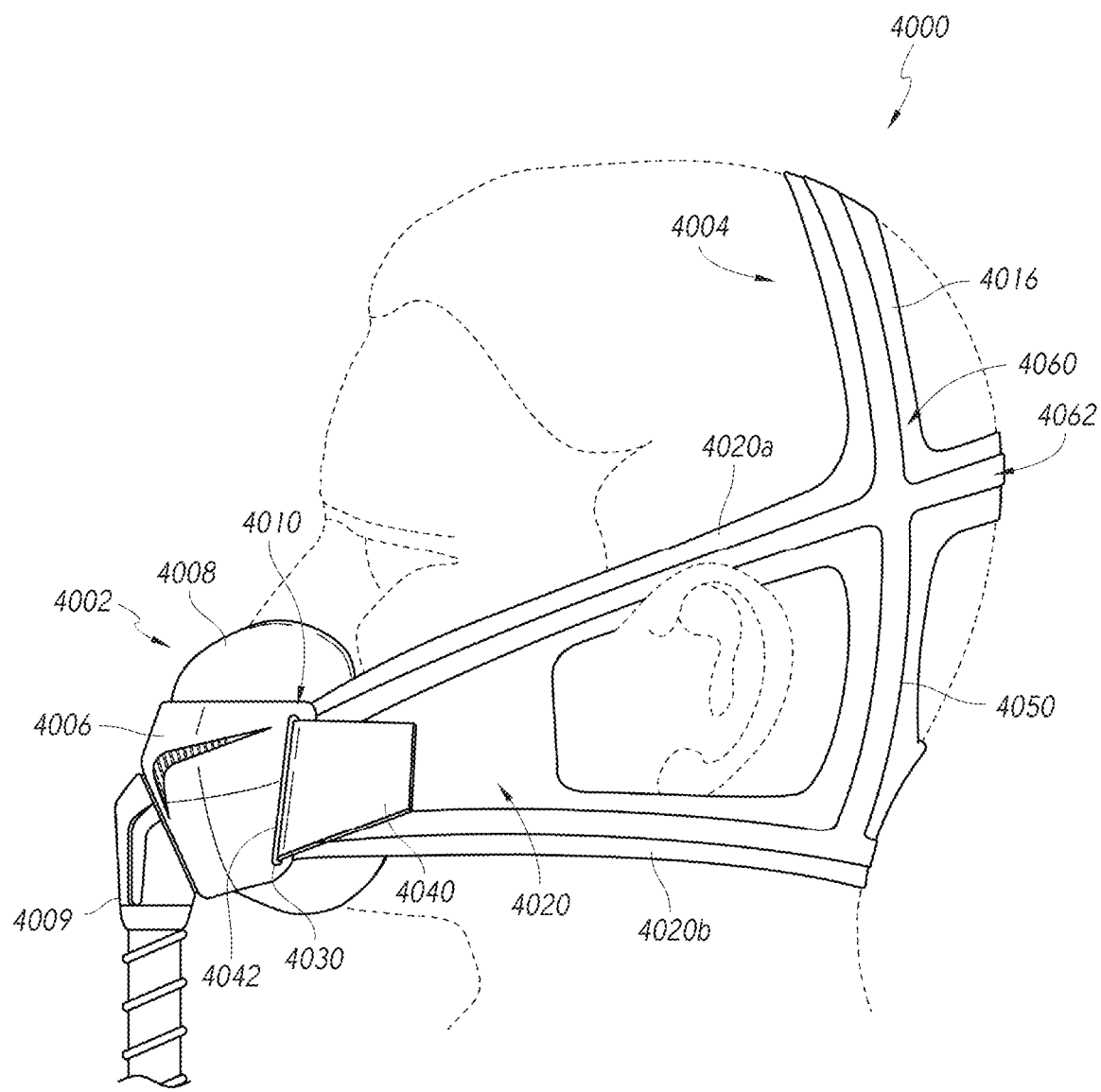
FIG. 47 is a side view of an interface assembly having an interface, such as a mask, and a headgear. The headgear includes a low profile adjustment mechanism.

FIG. 47 illustrates an interface assembly 4000 that is similar in many respects to the interface assembly 4000 of FIG. 40 and the interface assembly 4000 of FIGS. 41 and 42. Therefore, the same reference numbers are used to refer to the same or corresponding components or features. In addition, the interface assembly 4000 of FIG. 47 is described in the context of the differences relative to the interface assemblies 4000 of FIGS. 40-42. Features of the interface assembly 4000 or portions thereof not specifically described can be assumed to be the same as or similar to features of the interface assemblies 4000 of FIGS. 40-42, other interfaces or portions thereof described herein, or can be of another suitable arrangement.

In the arrangement of FIG. 47, the upper strap 4020a and the lower strap 4020b can be positioned relative to one another in a manner similar to the arrangement of FIGS. 44 and 42. In addition, the upper strap 4020a and the lower strap 4020b are similarly connected by one or more vertical connecting portions 4050. In the illustrated arrangement, a vertical connecting portion 4050 can be positioned behind the user's ear on each side of the interface assembly 4000. A crown strap 4016 can extend over the top of the user's head from one side of the upper strap 4020a to the other side of the upper strap 4020a. In some configurations, the crown strap 4016 can be aligned with the connecting portions 4050.

The headgear 4004 can be constructed as a composite structure of a relatively rigid material and a relatively less rigid material. For example, a flexible material, such as a textile material, can be utilized to construct a base 4060 of the headgear. A semi-rigid or rigid material can be applied to the base 4060 to form a support structure 4062. One example of a semi-rigid material is polypropylene sheet material having a thickness of about millimeters, for example. The support structure 4062 can be bonded to an outer surface of the base 4060, such as with an adhesive, RF welding, ultrasonic welding, thermoforming, stitching, chemical bonding, mechanical bonding or any other suitable method. In the illustrated arrangement, the base 4060 has a greater width than the support structure 4062. The support structure 4062 can be provided on some portions or a substantial entirety of the headgear 4004. For example, preferably, the support structure 4062 extends along at least a substantial length of the upper strap 4020a, lower strap 4020b, the crown strap 4016 and the connecting straps 4050. In some configurations, the support structure can be constructed from a single piece of material.

Figure 48:
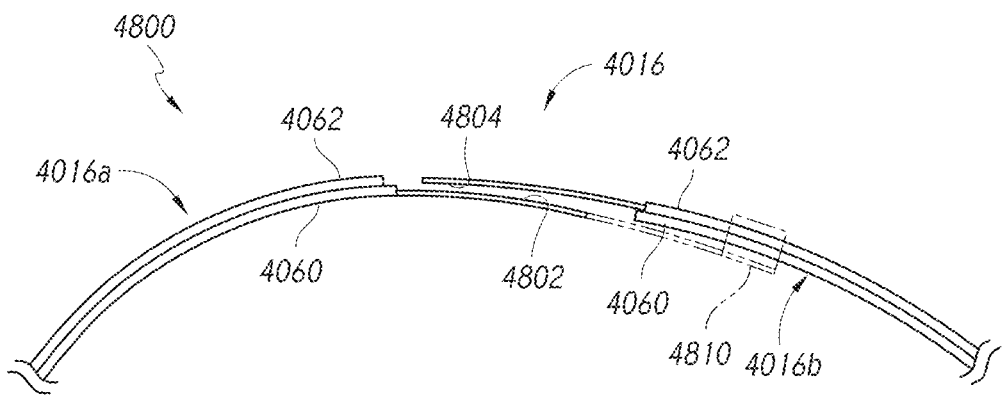
FIG. 48 is an enlarged view of the low profile adjustment mechanism of FIG. 47.

FIG. 48 illustrates a low-profile adjustment arrangement 4800 that can be used to adjust a length of a headgear strap, such as any of the straps of the headgear 4004 of FIG. 47. In one arrangement, the low-profile adjustment arrangement 4800 is utilized in the crown strap 4016 of the headgear 4004 of FIG. 47. In the illustrated arrangement, the crown strap 4016 is split along its length into a first crown strap portion 4016a and a second crown strap portion 4016b. The first crown strap portion 4016a comprises a first component 4802 of a fastener, such as a hook-and-loop fastener, and the second crown strap portion 4016b comprises a second component 4804 of the fastener. The first component 4802 can be selectively engaged at a desired position with the second component 4804 to adjust a length of the crown strap 4016.

In some configurations, the first component 4802 is carried by or secured to one of the base 4060 and the support structure 4062 of the crown strap 4016 and the second component 4804 is carried by or secured to the other of the base 4060 and the support structure 4062 of the crown strap 4016. Such an arrangement takes advantage of the dual layer construction of the crown strap 4016 to provide adjustment without doubling the thickness of the crown strap 4016. In some configurations, an end of at least one of the first crown strap portion 4016a and the second crown strap portion 4016b comprises a loop 4810 that surrounds the other of the first crown strap portion 4016a and the second crown strap portion 4016b to facilitate maintaining axial alignment of the first crown strap portion 4016a and the second crown strap portion 4016b.

Figure 49:
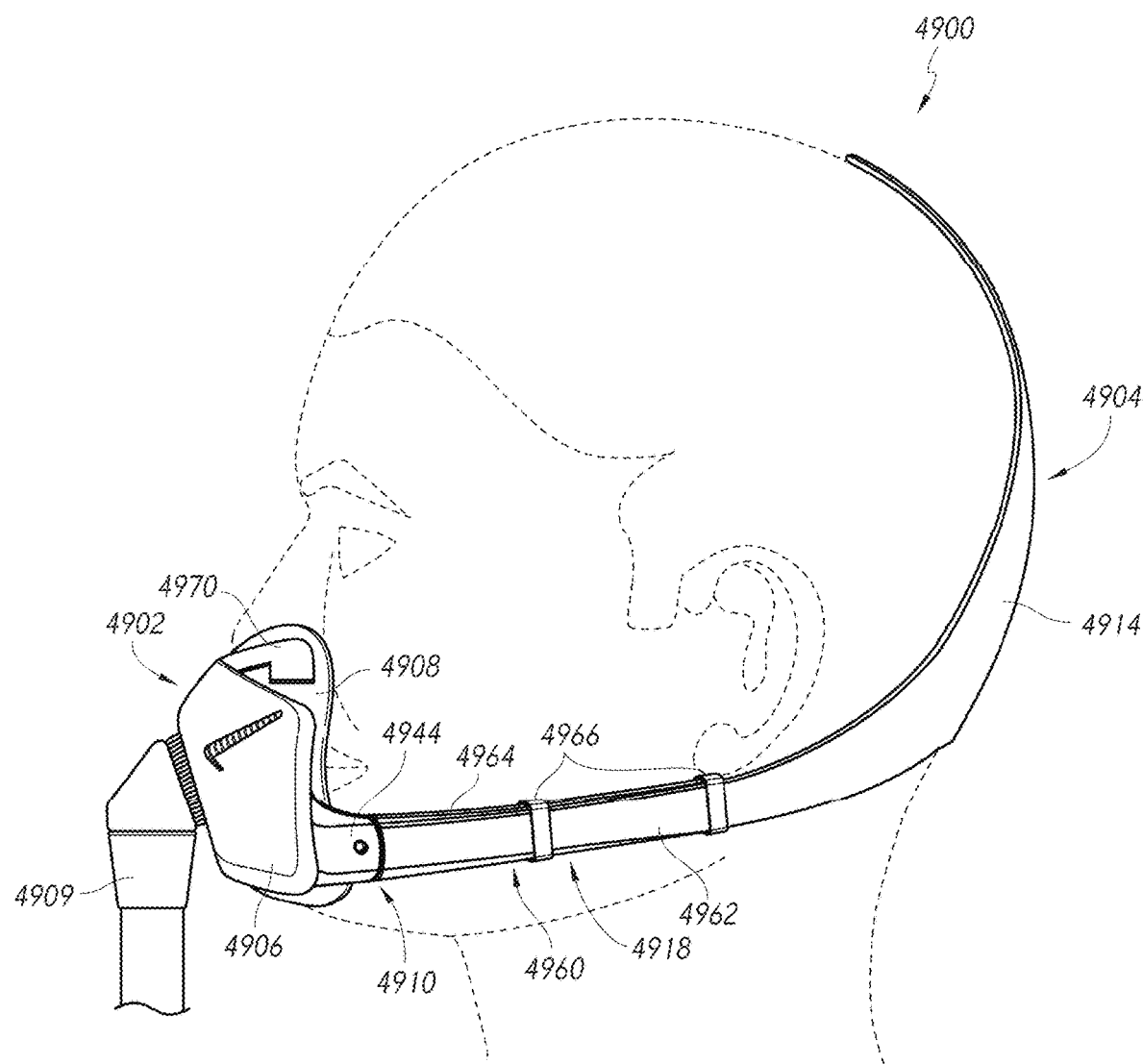
FIG. 49 is a side view of an interface assembly having an interface, such as a mask, and a headgear.

FIG. 49 illustrates an interface assembly 4900 that is arranged and configured in accordance with certain features, aspects and advantages of the present disclosure. The illustrated interface assembly 4900 includes an interface 4902 and a headgear 4904. The illustrated interface 4902 is a nasal-oral mask but, as described herein, other types of interfaces can be used with the disclosed headgear 4904. The illustrated mask 4902 generally comprises a frame 4906 that supports a seal 4908. The mask 4902 can be connected to a supply conduit 4909, which can be used to supply breathing gases to a user. As described above, in some configurations, the mask 4902 can seal around a mouth of a user and on an underside of a nose of the user. Such a mask 4902 can provide pressurized air flow to both the nose and the mouth of the user. The mask frame 4906 can include or carry support structures 4970 for providing lateral support to an upper portion of the mask seal 4908. The support structures 4970 can be the same as or similar to the paddles 3870 of FIGS. 44 and 45.

The headgear 4904 can be coupled to the mask 4902 at one or more mounting locations or mounting points 4910. In some configurations, the mask 4902 can be rotatably coupled to the headgear 4904 by a rotational coupling 4944, which can be substantially similar to the rotational couplings of FIG. 29, 35 or 36, for example. In addition, the headgear 4904 can include a lower strap or lower arm 4918 on each side of the interface assembly 4900 that pass below the user's ears and can omit upper straps. Thus, in some configurations, the lower arms 4918 are the only connections between the mask 4902 and the headgear 4904. The headgear 4904 can include a rear portion 4914, which can be a rear halo portion or can be of a similar arrangement. In some configurations, the rear portion 4914 is not annular in shape. The rear portion 4914 can comprise a cradle structure that extends in a vertical direction along the back of the user's head and, in some configurations, from a location at or near a lower end of the user's head to a location at or near a crown of the user's head. The cradle structure of the rear portion 4914 can be curved in a vertical and/or horizontal direction to generally conform to the shape of the user's head.

The lower arm 4918 can comprise an adjustment arrangement 4960 that permits a distance between the mask 4902 and the rear portion 4914 of the headgear 4904 to be adjusted. In the illustrated interface 4900, the adjustment arrangement 4960 comprises a sliding arrangement. In particular, the adjustment arrangement 4960 comprises a first arm portion 4962 that is fixed for movement with the rear portion 4914 in at least a fore-aft direction and a second arm portion 4964 that is fixed for movement with the mask 4902 in at least a fore-aft direction. In some configurations, the second arm portion 4964 can be integral or unitary with a portion of the mask 4902 (e.g., the mask frame 4906).

The first arm portion 4962 and the second arm portion 4964 are slidably or telescopically engaged with one another, for example by one or more loops 4966 coupled to one of the first arm portion 4962 and the second arm portion 4964, which surround the other of the first arm portion 4962 and the second arm portion 4964. Thus, movement of the second arm portion 4964 relative to the first arm portion 4962 can adjust a retention force applied to the mask 4902. Preferably, the adjustment arrangement 4960 secures the arm portions 4962, 4964 and, thus, the mask 4902 and headgear 4904 in a desired position once adjusted. For example, the loops 4966 can frictionally engage the arm portion 4962 or 4964. In other configurations, a lock arrangement can be provided to secure the arm portions 4962 or 4964 in a desired position. Other suitable arrangements could also be used. In other respects, features of the interface assembly 4900 or portions thereof can be the same as or similar to other interfaces or portions thereof described herein, or can be of another suitable arrangement.

Figure 50:
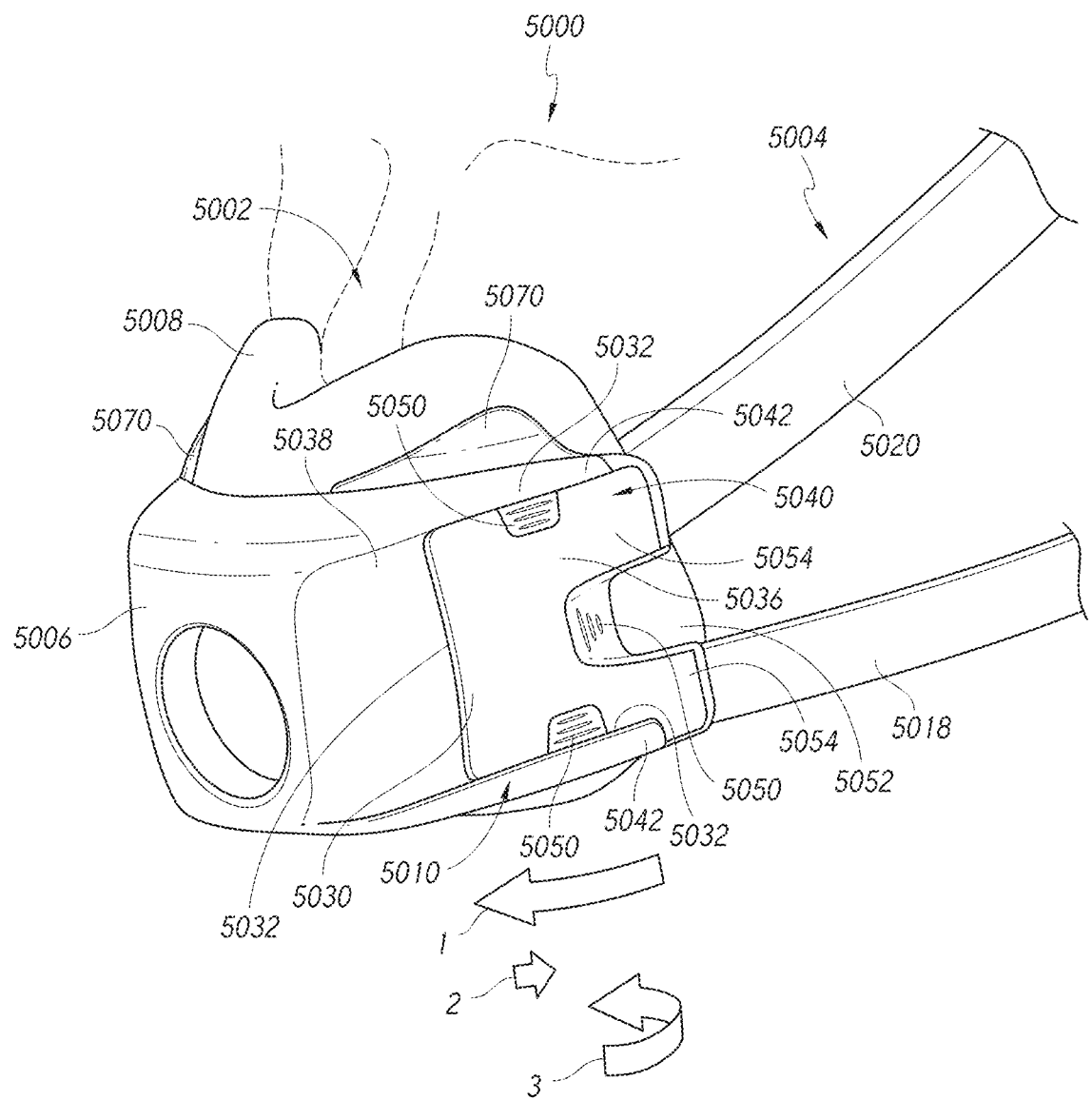
FIG. 50 is a perspective view of an interface assembly having an interface, such as a mask, and a headgear. The interface assembly includes a quick-release mechanism between the mask and the headgear.

FIG. 50 illustrates an interface assembly 5000 that is arranged and configured in accordance with certain features, aspects and advantages of the present disclosure. Unless indicated otherwise, features of the interface assembly 5000 or portions thereof can be the same as or similar to other interfaces or portions thereof described herein, or can be of another suitable arrangement. The illustrated interface assembly 5000 includes an interface 5002 and a headgear 5004. The illustrated interface 5002 is a nasal-oral mask but, as described herein, other types of interfaces can be used with the disclosed headgear 5004. The illustrated mask 5002 generally comprises a frame 5006 that supports a seal 5008. The mask 5002 can be connected to a supply conduit (not shown), which can be used to supply breathing gases to a user.

As described above, in some configurations, the mask 5002 can seal around a mouth of a user and on an underside of a nose of the user. Such a mask 5002 can provide pressurized air flow to both the nose and the mouth of the user. The mask 5002 can include supports or paddles 5070 that extend upwardly from the mask frame 5006 along the sides of the nose portion of the seal 5008 to provide lateral support to the nose portions of the mask seal 5008. The supports 5070 can be permanently or removably coupled to the mask 5002. In the illustrated configuration, the supports 5070 are removably coupled to the mask frame 5006 and can be provided in several sizes or shapes to allow a user to fine tune the amount of support provided to the sides of the nose portion of the seal 5008.

The headgear 5004 can be coupled to the mask 5002 at one or more mounting locations or mounting points 5010. Preferably, a lower strap portion 5018 and an upper strap portion 5020 are provided on each side of the headgear 5004 to connect the mask 5002 to a rear portion of the headgear 5004. In the illustrated arrangement, the lower strap 5018 and the upper strap 5020 on at least one side of the mask 5002 are coupled to the mask 5002 by a single clip 5030, which can be the same as or similar to the arrangement described in connection with FIGS. 35 and 36. In some configurations, a clip 5030 is provided on only one side of the mask 5002. The straps 5018, 5020 can be permanently coupled to the mask 5002 on the other side or coupled in a manner that is not as convenient to connect and remove as the clip 5030 (e.g., coupled via an adjustment mechanism).

The clip 5030 and the mask frame 5006 can be configured in a complementary manner to facilitate location of the proper position of the clip 5030 for engagement with the mask 5002 and/or to inhibit undesired disengagement of the clip 5030 from the mask 5002. For example, the mask frame 5006 can comprise one or more edges 5032 that cooperate to define a recess for receiving the clip 5030. In the illustrated arrangement, the edges 5032 define a rearwardly-opening recess and the clip 5030 passes through the rearward opening 5034. In some configurations, the clip 5030 is configured to occupy an entirety or a substantial entirety of the recess defined by the edges 5032. Thus, an outwardly-facing surface 5036 of the clip 5030 can be flush with an outwardly-facing surface 5038 of adjacent portions of the mask frame 5006, at least at locations in which the clip 5030 and the mask frame 5006 meet. With such an arrangement, the edges 5032 of the recess inhibit the clip 5030 from moving in a direction (e.g., forwardly) that would permit undesired or unintentional disengagement of the clip 5030 from the mask 5002. However, a user could intentionally move the clip 5030, for example, in a lateral direction away from the mask frame 5006 and out of engagement with the mask 5002.

As illustrated by the arrows in FIG. 50, the clip 5030 can be brought adjacent to the mask frame 5002 and, preferably, at least slightly forward of the recess defined by the edges 5032. The edges 5032 can provide tactile feedback to the user to facilitate identification of the proper location for the clip 5030. The clip 5030 can be moved or allowed to move rearwardly and into engagement with the recess defined by the edges 5032. In some configurations, a forward end of the clip 5030 can be first engaged with the recess and then a rear portion of the clip 5030 can be moved inwardly into engagement with the recess. In some such configurations, a rear portion 5040 of the clip 5030 can abut against a rear edge 5042 of the mask frame 5006 to inhibit undesired forward movement and/or undesired or unintentional disengagement of the clip 5030 from the mask frame 5006.

In some configurations, the clip 5030 defines one or more finger access or finger grip portions 5050, which can provide a convenient location for the user to grasp the clip 5030. In some configurations, the finger grip portion 5050 provides tactile feedback to the user to facilitate non-visual location of the clip 5030. In the illustrated arrangement, a finger grip portion 5050 is provided between and at a forward end of a space 5052 defined by rearward protruding portions 5054 of the clip 5030. Finger grip portions 5050 are also provided on upper and lower edges of the clip 5030. Any combination or all of the illustrated locations can be used. The protruding portions 5054 can be generally aligned with a length or axial direction of the straps 5018, 5020.

FIGS. 51-57 illustrate interface assemblies 5000 that are similar in many respects to the interface assembly 5000 of FIG. 50. Therefore, the same reference numbers are used to refer to the same or corresponding components or features. In addition, the interface assemblies 5000 of FIG. 51-57 are described in the context of the differences relative to the interface assembly 5000 of FIG. 50 and/or the differences relative to each other. Features of the interface assemblies 5000 or portions thereof not specifically described can be assumed to be the same as or similar to features of the interface assembly 5000 of FIG. 50, other interfaces or portions thereof described herein, or can be of another suitable arrangement.

Figures 51, 52, 53:
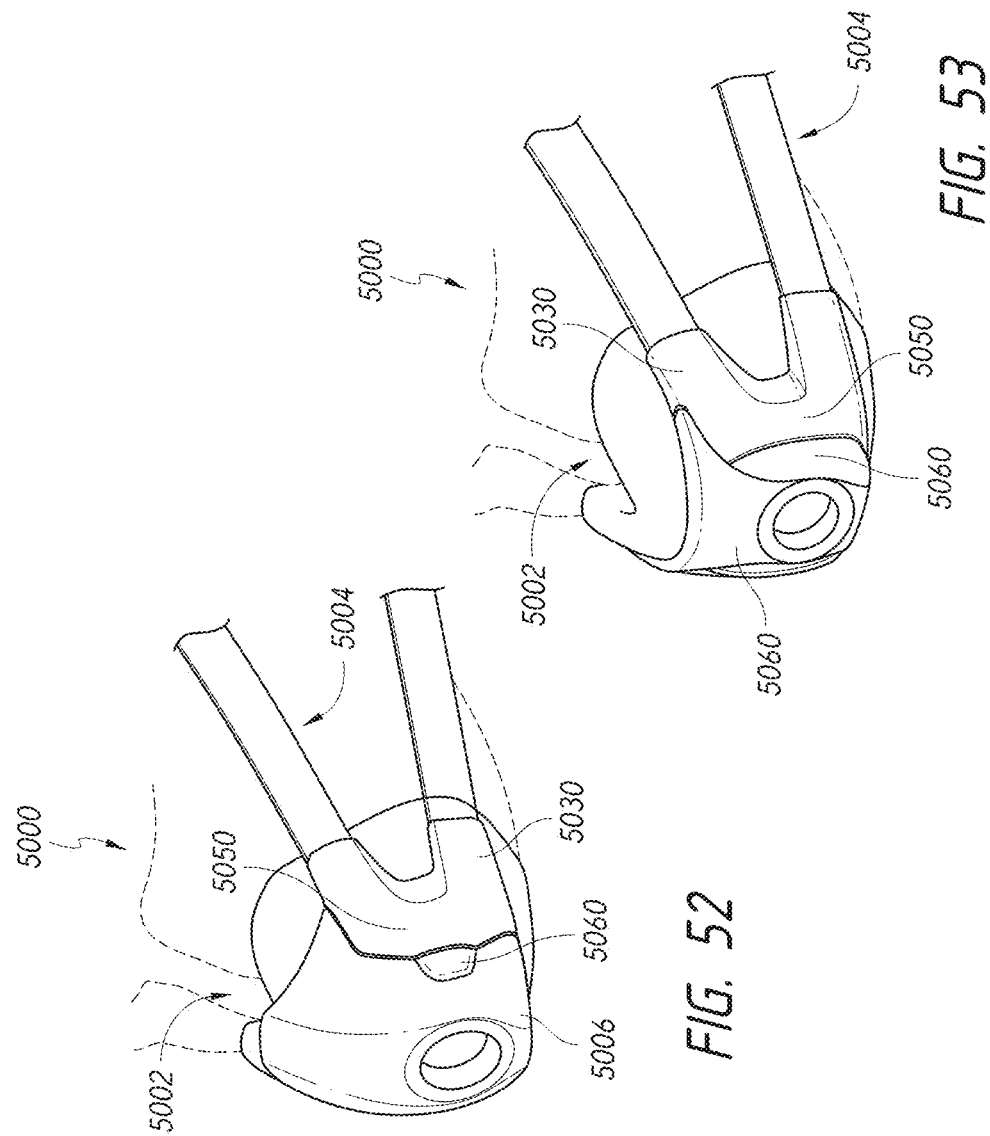
FIG. 51 is a perspective view of an interface assembly having an alternative quick-release mechanism.
FIG. 52 is a perspective view of an interface assembly having another alternative quick-release mechanism.
FIG. 53 is a perspective view of an interface assembly having yet another alternative quick-release mechanism.

The interface assembly 5000 of FIG. 51 places the finger grip portion 5050 on a forward portion of the clip 5030. In particular, the finger grip portion 5050 is defined by a raised or outwardly offset portion on a forward edge of the clip 5030. The finger grip portion 5050 can be generally centered in a vertical direction of the clip 5030. The mask frame 5006 can define a recessed portion 5060 that is positioned adjacent the finger grip portion 5050 and facilitates the user accessing the inward-facing surface of the finger grip portion 5050. In the interface assembly 5000 of FIG. 52, the finger grip portion 5050 is not raised relative to a surrounding portion of the clip 5030. Instead, the recessed portion 5060 of the mask frame 5006 can be configured (e.g., enlarged relative to the portion 5060 of FIG. 51) to facilitate access to the finger grip portion 5050.

The interface assembly 5000 of FIG. 53 is similar to FIG. 52 in that the finger grip portion 5050 is not raised or outwardly offset relative to surrounding portions of the clip 5030. However, the recessed portion 5060 of the mask frame 5006 can extend along a substantial portion or a substantial entirety of a front edge of the clip 5030. In some configurations, the recessed portion 5060 has a length that is a substantial portion of the overall height of the mask frame 5006, such as at least about one-half or at least about two-thirds of a height of the mask frame 5006.

Figure 54:
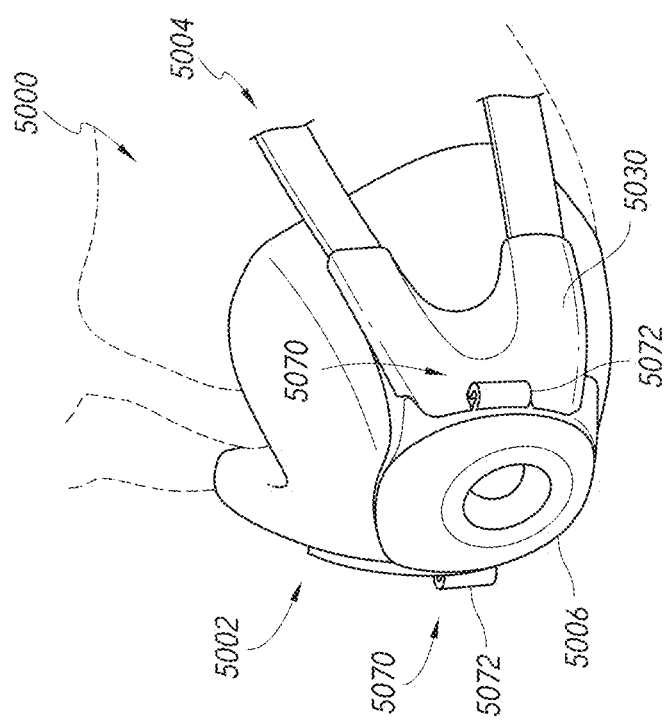
FIG. 54 is a perspective view of an interface assembly having still another alternative quick-release mechanism.

The interface assembly 5000 of FIG. 54 incorporates a lock arrangement 5070 to secure the clip 5030 to the mask frame 5006. The lock arrangement 5070 can be in addition to or in alternative to other engagement features of the clip 5030 (e.g., hook-and-bar arrangement). The lock arrangement 5070 can comprise a snap-lock feature, such as a resilient locking clip 5072, for example and without limitation. The resilient locking clip 5072 can be placed on either the mask frame 5006 or the clip 5030 and can be located in a manner similar to the finger grip portions 5050 or recessed portions 5060 described herein. When placed on the clip 5030, the resilient locking clip 5072 can also function as a finger grip portion 5050.

Figure 55:
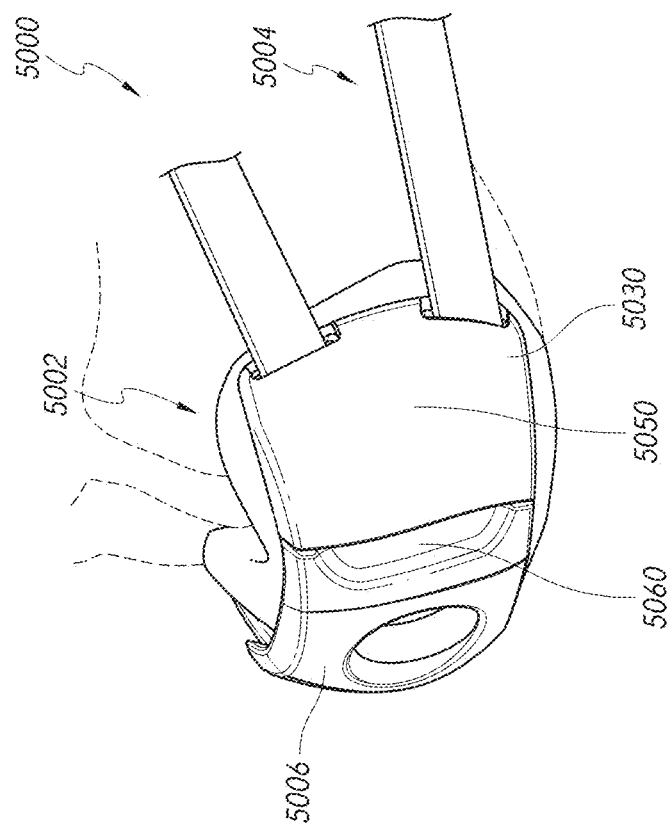
FIG. 55 is a perspective view of an interface assembly having another alternative quick-release mechanism including a clip.
Figure 56:
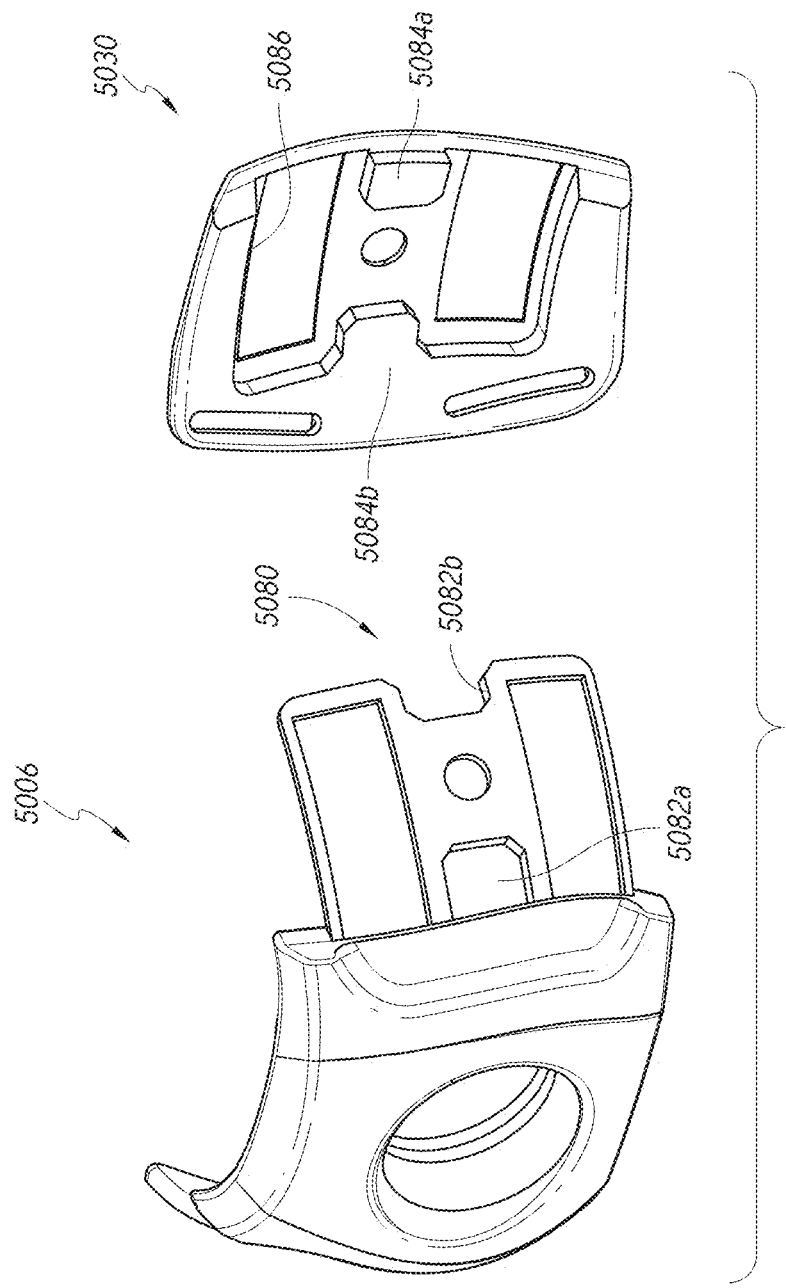
FIG. 56 is a perspective view of the mask of the interface assembly of FIG. 55.

The interface assembly 5000 of FIGS. 55-56 is similar to the assemblies 5000 of FIGS. 52 and 53. In particular, the finger grip portion 5050 of the clip 5030 of FIGS. 55-56 is not raised or outwardly offset relative to adjacent portions of the clip 5030 and the recessed portion 5060 of the mask frame 5006 is configured to facilitate access to the finger grip portion 5050. The recessed portion 5060 is a relatively discrete structure with a relatively sharp transition from surrounding surfaces of the clip 5030 similar to the portion 5060 of FIG. 52, but extends along a greater vertical distance similar to the portion 5060 of FIG. 53.

FIG. 56 illustrates an example of interference or interlocking features 5080 of the mask frame 5006 and the clip 5030. In the illustrated arrangement, the mask frame 5006 comprises at least one opening and, preferably, a pair of openings 5082a, 5082b. The forward opening 5082a is completely surrounded by the mask frame 5006, while the rear opening 5082b is only partially surrounded by the mask frame 5006. The clip 5030 comprises at least one engagement member or engagement block and, preferably, a pair of engagement blocks 5084a, 5084b configured to engage a respective one of the openings 5082a, 5082b. The openings 5082a, 5082b and engagement blocks 5084a, 5084b are axially-spaced (e.g., generally aligned with a direction of a force vector acting on the clip 5030) to inhibit rotation of the clip 5030 relative to the mask frame 5006. In the illustrated arrangement, the openings 5082a, 5082b and engagement blocks 5084a, 5084b are aligned in a vertical direction; however, the openings 5082a, 5082b and engagement blocks 5084a, 5084b could be offset in the vertical direction. In some configurations, the clip 5030 defines a recess 5086 that is shaped complementary to and receives an overlapping portion of the mask frame 5006 when the clip 5030 is engaged with the mask frame 5006.

When engaged with the mask frame 5006, the clip 5030 exerts a generally rearward force on the mask frame 5006 via engagement of the openings 5082a, 5082b and engagement blocks 5084a, 5084b. As a result of the laterally-curved shape of the mask frame 5006 and/or the complete perimeter engagement of the engagement block 5084a with the surfaces of the mask frame 5006 defining the opening 5082a, the force acting on the clip 5030 (which can be generated by the headgear) tends to pull the engagement block 5084b into engagement with the opening 5082b thereby enhancing engagement of the clip 5030 with the mask frame 5006.

Figure 57:
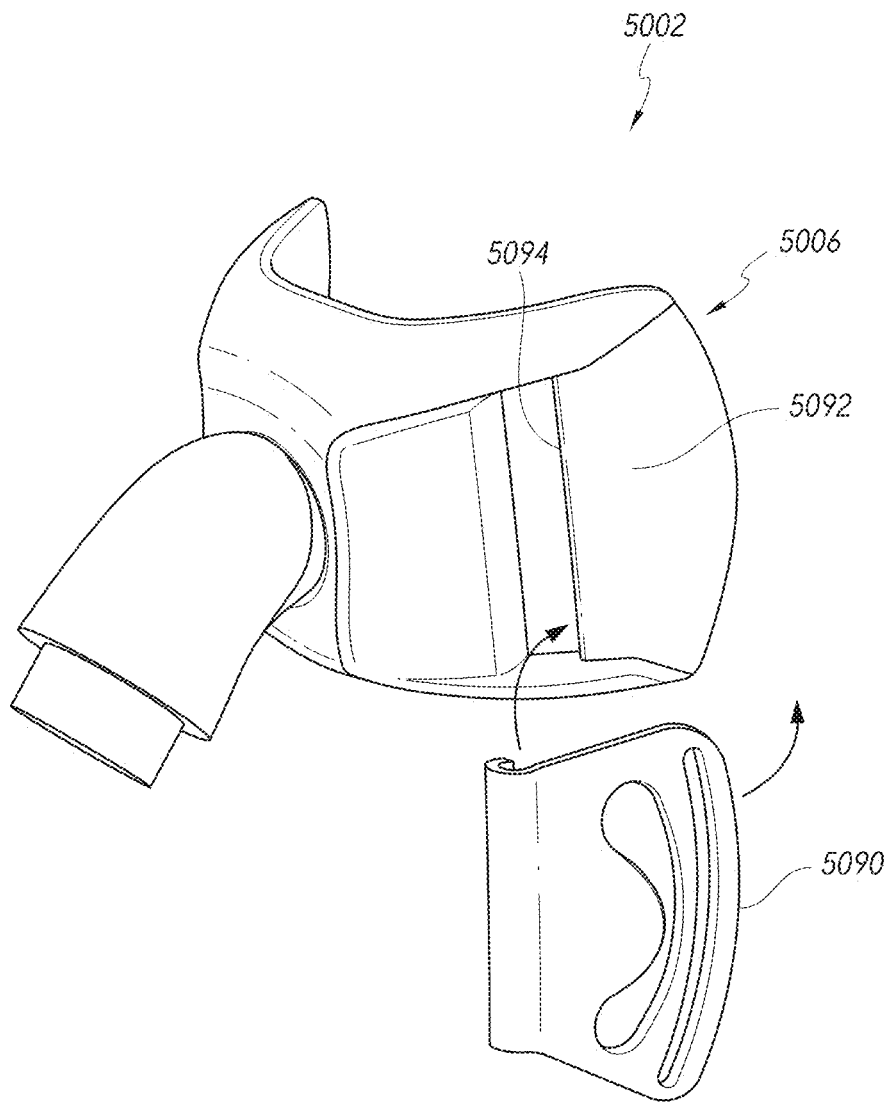
FIG. 57 is a perspective view of an interior surface of the clip of the quick-release mechanism of the interface assembly of FIG. 55.

FIG. 57 illustrates another example of an interlocking feature 5080 between a mask frame 5006 and a clip 5030. The illustrated arrangement comprises a hook-and-bar type interaction between the clip 5030 and the frame 5006. Preferably, the clip 5030 includes a hook 5090 that engages an engagement surface or bar 5092 of the mask frame 5006. In some configurations, this arrangement could be reversed. The mask frame 5006 includes an opening 5094 that accommodates the hook 5090 of the clip 5030 when the clip 5030 is engaged with the mask 5002. In some configurations, a surface that defines a portion of the opening 5094 also defines the bar 5092. The bar 5092 can be any structure or portion of a structure configured to interact with the hook 5090 and retain the clip 5030 to the mask 5002. To couple the clip 5030 to the mask 5002, a portion of the hook 5090 can be passed through the opening 5094 to engage the hook 5090 with the bar 5092 and the body of the clip 5030 can be rotated into a resting position adjacent or against the mask 5002 (e.g., mask frame 5006). To remove the clip 5030, this process can be reversed.

FIGS. 50-57 (among others herein) disclose interface assemblies 5000 that permit a circumferential loop of the interface assembly 5000 to be opened to facilitate application and removal of the interface assembly 5000. In such configurations, the headgear 5004 can be completely separated from the mask 5002 at at least one location to define an open loop. While such an open loop configuration can facilitate application or removal of the interface assembly 5000, it has been discovered by the present inventors that it can sometimes be difficult or annoying for a user to locate the loose clip 5030 or other portion of the headgear 5004 for attachment to the mask 5002. Even if only one clip 5030 is disengaged from the mask 5002, depending on the configuration of the headgear 5004, the loose clip 5030 could move a significant distance from the mask 5002, such as fall behind the head of the user, for example. If clips 5030 on both sides of the mask 5002 are disengaged, complete separation of the headgear 5004 from the mask 5002 can occur. Accordingly, in some applications or uses, it can be desirable to tether the clip 5030 to the mask 5002 to facilitate location of the clip 5030, especially when visual location is difficult or not possible. The interface assemblies 5800 of FIGS. 58-61 are closed loop configurations, which move between an expanded orientation, which facilitates application or removal of the interface assembly 5800, and a contracted orientation. Preferably, the interface assemblies 5800 are elasticated closed loop configurations, in which an elasticated tethering arrangement maintains a closed loop, but permits expansion or enlargement of the circumference of the interface assembly 5800 to facilitate application or removal.

The interface assemblies 5800 of FIGS. 58-61 generally include an interface 5802 and a headgear 5804. The illustrated interface 5802 is a nasal-oral mask but, as described herein, other types of interfaces can be used with the disclosed headgear 5804.

The illustrated mask 5802 generally comprises a frame 5806 that supports a seal 5808. The mask 5802 can be connected to a supply conduit (not shown), which can be used to supply breathing gases to a user. As described above, in some configurations, the mask 5802 can seal around a mouth of a user and on an underside of a nose of the user. Such a mask 5802 can provide pressurized air flow to both the nose and the mouth of the user.

The headgear 5804 can be coupled to the mask 5802 at one or more mounting locations or mounting points by any suitable arrangement, including the clips 5830 that are the same as or similar to the clips 5030 of FIGS. 50-57, for example and without limitation. In some configurations, a lower strap 5818 and an upper strap 5820 are provided on each side of the headgear 5804 to connect the mask 5802 to a rear portion of the headgear 5804. Unless indicated otherwise, features of the interface assembly 5800 or portions thereof can be the same as or similar to other interfaces or portions thereof described herein, or can be of another suitable arrangement.

Figure 58:
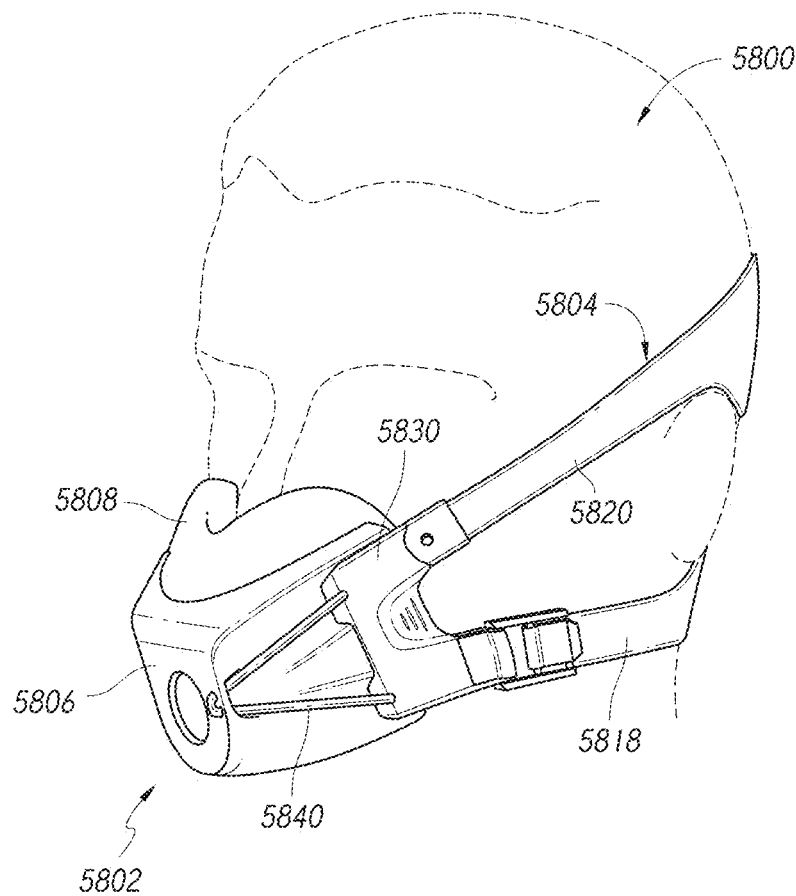
FIG. 58 is an exploded perspective view of an interface assembly having a quick-release mechanism.

The interface assembly 5800 of FIG. 58 includes an elasticated tether 5840 that couples the clip 5830 to the mask 5802. The illustrated elastic tether 5840 is a cable or cord-like member that is coupled between the clip 5830 and the mask 5802 in a triangulated manner. In particular, a center portion of the elastic tether 5840 is coupled to the mask 5802 and end portions of the elastic tether 5840 are coupled to the clip 5830. Preferably, the elastic tether 5840 is configured to not only retain the clip 5830 near the mask 5802 when the clip 5830 is disengaged from the mask 5802, but also tends to locate the clip 5830 properly relative to the mask 5802. For example, a tension on the upper and lower or the two end portions of the elastic tether 5840 can be generally even when the clip 5830 is properly located relative to the mask 5802. Thus, the elastic tether 5840 tends to pull the clip 5830 into the proper position for engagement with the mask 5802.

Figure 59:
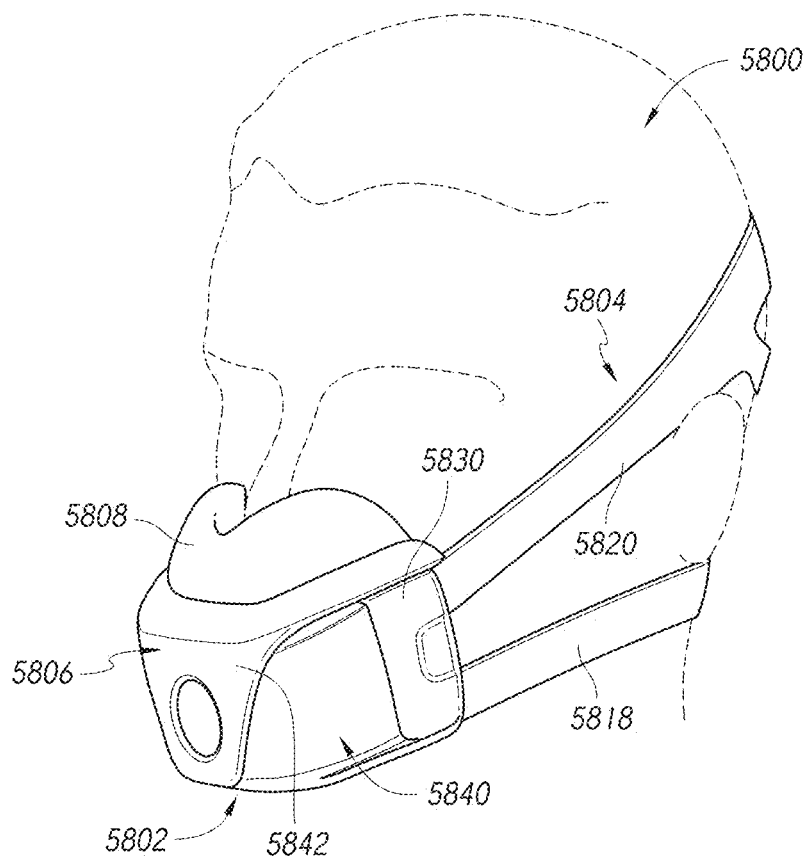
FIG. 59 is a perspective view of an interface assembly having an alternative quick-release mechanism with an elasticated tether.
Figure 60:
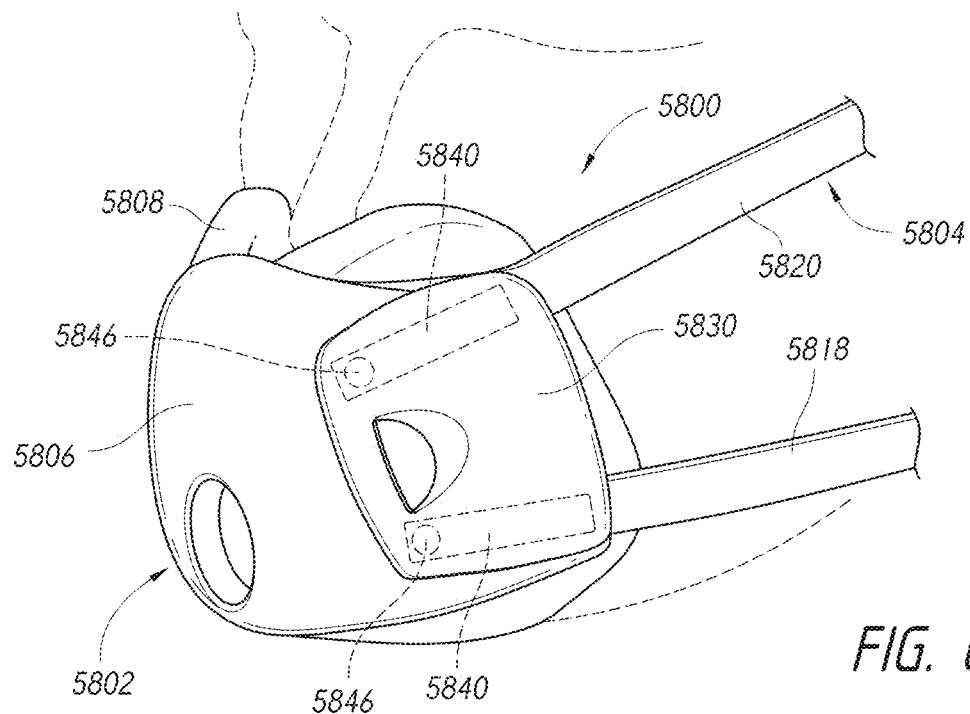
FIG. 60 is a perspective view of an interface assembly having another alternative quick-release mechanism with an elasticated tether.

The interface assembly 5800 of FIG. 59 includes an elasticated tether 5840 in the form of a wide elastic strap. The elastic strap 5840 can extend from one side of the mask 5802 to the other. Each end of the elastic strap 5840 can connect to a clip 5830. An intermediate portion of the elastic strap 5840 can be secured to the mask 5802. For example, the mask frame 5802 can comprise a loop portion 5842 that forms a passage through which the elastic strap 5840 can pass. In some configurations, the elastic strap 5840 is loosely received in the passage and is movable relative to the mask 5802. The clips 5830 can prevent the elastic strap 5840 from being disengaged from the mask 5802.

In the interface assemblies 5800 of FIGS. 58 and 59, the elastic tethers 5840 are exposed. In some applications or uses, it may be desirable for the elastic tether 5840 to be covered or concealed, at least when the clip 5830 is engaged with the mask 5802. The interface assembly 5800 of FIGS. 60 and 61 conceals the elastic tether 5840 when the clip 5830 is engaged with the mask 5802. In the illustrated configuration, the elastic tether 5840 includes at least one and preferably a pair of elastic elements. The elastic elements can be in the form of elastic straps 5840, which can be spaced vertically from one another and extend generally in a fore-aft direction. In some configurations, the elastic straps 5840 can be generally or substantially aligned with a respective one of the lower strap 5818 and the upper strap 5820 of the headgear 5804.

The clip 5830 can capture the elastic straps 5840 between the clip 5830 and the mask frame 5806 when the clip 5830 is engaged with the mask 5802. In the illustrated arrangement, a first end of each elastic strap 5840 is secured to a rearward end portion of the mask frame 5806 and a second end of each elastic strap 5840 is secured to a forward end of the clip 5830. Such an arrangement permits the elastic straps 5840 to lay relatively flat between the mask frame 5806 and the clip 5830 and also maximizes the growth in the circumference of the interface assembly 5800 permitted by the elastic straps 5840. The mask frame 5806 and/or the clip 5830 can include recesses 5844 that receive and at least partially accommodate a thickness of the elastic straps 5840 when the clip 5830 is engaged with the mask 5802.

Figure 61:
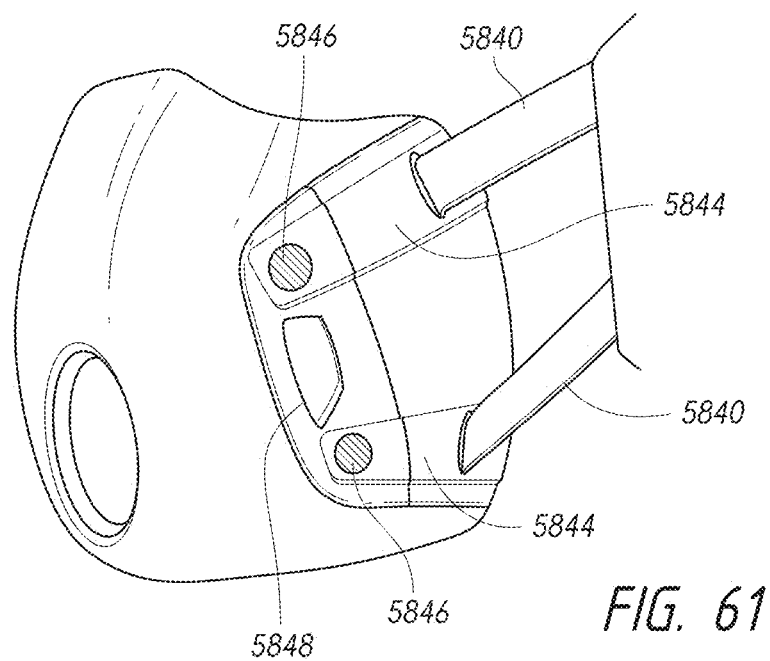
FIG. 61 is a perspective view of the interface assembly of FIG. 60 with the quick-release mechanism in a disconnected state.
Figure 65:
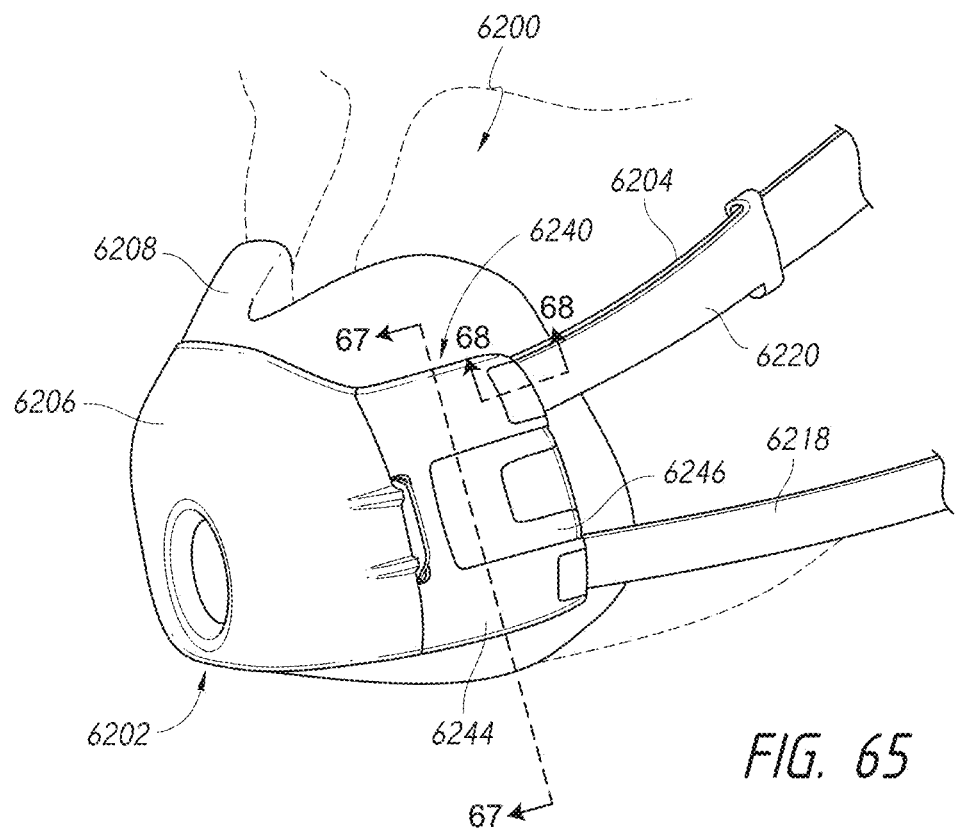
FIG. 65 is a perspective view of an interface assembly with an alternative folding clasp quick-release mechanism connecting the headgear and the mask. The folding clasp quick-release mechanism is shown in a closed state.
Figure 66:
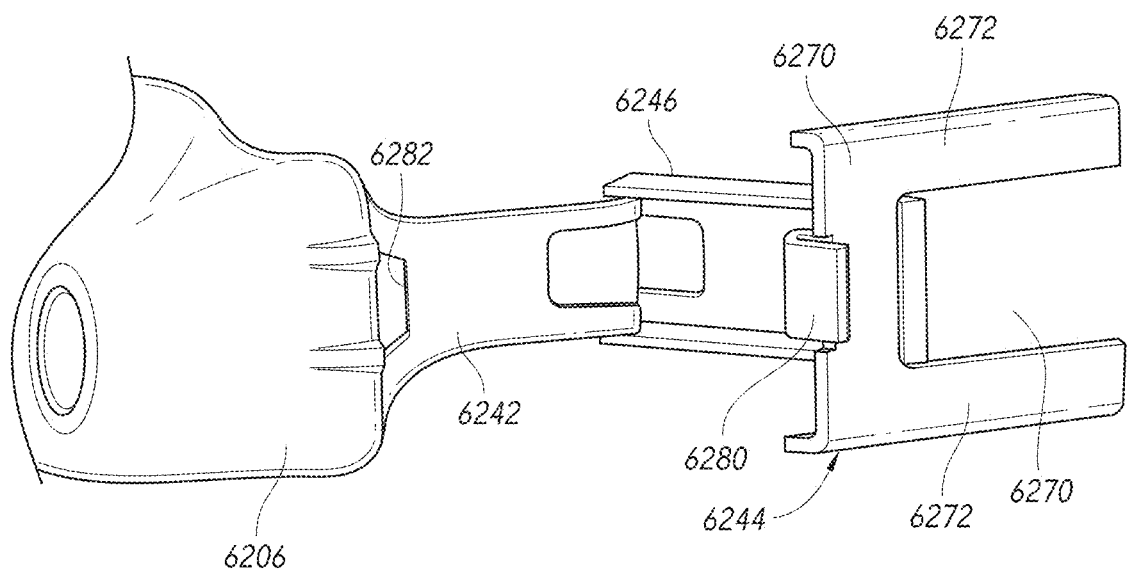
FIG. 66 is a perspective view of the interface assembly of FIG. 65 with the folding clasp quick-release mechanism in an open state.

As described above, the elastic tethers 5840 can be configured to help guide the clip 5830 to a proper location for engagement with the mask 5802. However, in the configuration of FIGS. 60 and 61, the elastic straps 5840 may not pull the clip 5830 all the way to the proper position for engagement with the mask 5802. That is, the clip 5830 can be moved away from the engagement location by a distance generally equivalent to an un-stretched length of the elastic straps 5840. In such a configuration, or if desirable in any other configuration, the interface assembly 5800 can include additional features to assist in location of the clip 5830 relative to the mask 5802. For example, one or more magnets 5846 can be provided on the mask 5802, the clip 5830 or both to facilitate location of the clip 5830 relative to the mask 5802. A single magnet arrangement can be used, but the other component typically will have a magnetically attractive material. In the illustrated arrangement, a magnet 5846 is provided at the forward ends of the recesses 5844 on the mask 5802 and clip 5830 (magnets 5846 not shown on the clip 5830). In addition, FIG. 61 illustrates an opening 5848, which can be engaged by a suitable structure of the clip 5830, such as a hook or block (not shown).

FIGS. 62-64 illustrates an interface assembly 6200 that is of an elongating closed loop configuration, which permits the interface assembly 6200 to move between an expanded orientation and a contracted orientation. The interface assembly 6200 is similar to the interface assemblies 5800 of FIGS. 58-61 in that the circumference can be enlarged to facilitate application or removal; however, preferably, the interface assembly 6200 provides the ability to enlarge the circumference via a non-elasticated folding clasp 6240 in contrast to the elasticated arrangements of FIGS. 58-61.

The illustrated interface assembly 6200 includes an interface 6202 and a headgear 6204. The illustrated interface 6202 is a nasal-oral mask but, as described herein, other types of interfaces can be used with the disclosed headgear 6204. The illustrated mask 6202 generally comprises a frame 6206 that supports a seal 6208. The mask 6202 can be connected to a supply conduit 6209, which can be used to supply breathing gases to a user. As described above, in some configurations, the mask 6202 can seal around a mouth of a user and on an underside of a nose of the user. Such a mask 6202 can provide pressurized air flow to both the nose and the mouth of the user.

The headgear 6204 can be coupled to the mask 6202 at one or more mounting locations or mounting points 6210. Preferably, a lower strap portion 6218 and an upper strap portion 6220 are provided on one or both sides of the headgear 6204 to connect the mask 6202 to a rear portion of the headgear 6204. In some configurations, the headgear 6204 can provide for adjustment in addition to the folding clasp 6240 or other elongation arrangement. With such an arrangement, the headgear 6204 can be adjusted to an appropriate or desired adjustment position separately from the action of the folding clasp 6240, such that the folding clasp 6204 can be used solely to facilitate application and, once properly adjusted, the headgear 6204 should not require readjustment with each application of the interface assembly 6200. Any suitable adjustment mechanism for the headgear 6204 can be provided, such as folding over the straps 6218, 6220 on one or both sides of the interface assembly 6200 after engagement with the mask 6202 to create adjustment loops 6222 that can be secured by any suitable fastener, such as a hook-and-loop fastener, for example.

The folding clasp 6240 can include multiple sections or segments that are foldable relative to one another between a contracted (e.g., stacked or folded) orientation and an expanded (e.g., unfolded) orientation. In the illustrated arrangement, a first segment 6242 is defined or carried by the mask 6202, such as by the mask frame 6206. A second segment 6244 is defined by or carried by a member (e.g., a clip) coupled to the headgear 6204 (e.g., one or both of the straps 6218, 6220). In some configurations, an third or intermediate segment 6246 is pivotally connected to the first segment 6242 at a first end and to the second segment 6244 at a second end. The pivot axes between the segments 6242, 6244, 6246 preferably are aligned with one another and oriented perpendicular to a circumferential direction of the headgear 6204/interface assembly 6200. Such an arrangement maintains the segments 6242, 6244, 6246 in the proper plane relative to one another and, in the illustrated arrangement, maintains the forward portion of the headgear 6204 in horizontal alignment with the mask 6202 to facilitate non-visual location of the second segment 6244 of the folding clasp 6240 in the unfolded orientation.

As illustrated in FIGS. 63 and 64, respectively, in the contracted orientation the segments 6242, 6244, 6246 are stacked relative to one another to have an increased overall thickness and reduced length and in the expanded orientation the segments 6242, 6244, 6246 are unstacked and positioned end-to-end to reduce the overall thickness and increase the length. Folding clasps 6240 can be provided on one or both sides of the interface assembly 6200. Preferably, when contracted or folded, the folding clasp 6240 is located on the mask 6202 or forward of a rearward edge of the mask 6202. Such an arrangement avoids contact between the folding clasp 6240 and the user for increased comfort. In some configurations, the a locking mechanism (e.g., snap-fit arrangement) can be provided to lock or retain the folding clasp 6240 in the closed position or contracted orientation and inhibit or prevent unintentional opening of the folding clasp 6240. A finger grip portion 6250 and corresponding recessed portion 6260 can be provided on the clip 6230 and mask frame 6206, respectively, to facilitate opening of the folding clasp 6240. Unless indicated otherwise, features of the interface assembly 6200 or portions thereof can be the same as or similar to other interfaces or portions thereof described herein, or can be of another suitable arrangement.

FIGS. 65-68 illustrate an interface assembly 6200 that is similar in many respects to the interface assembly 6200 of FIGS. 62-64. Therefore, the same reference numbers are used to refer to the same or corresponding components or features. In addition, the interface assembly 6200 of FIGS. 65-68 is described in the context of the differences relative to the interface assembly 6200 of FIGS. 62-64. Features of the interface assembly 6200 or portions thereof not specifically described can be assumed to be the same as or similar to features of the interface assembly 6200 of FIGS. 62-64, other interfaces or portions thereof described herein, or can be of another suitable arrangement.

Figure 67:
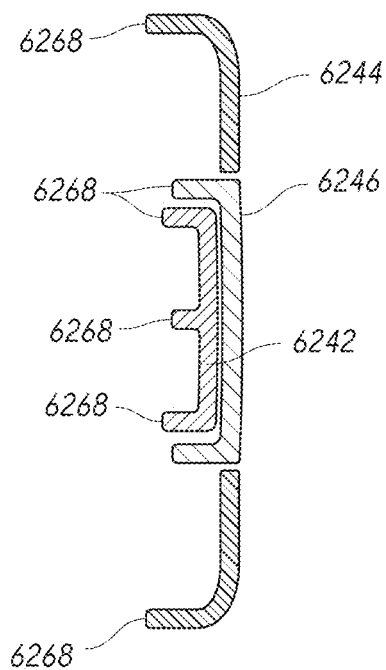
FIG. 67 is a cross-sectional view of the folding clasp quick-release mechanism of FIG. 65.
Figure 68:
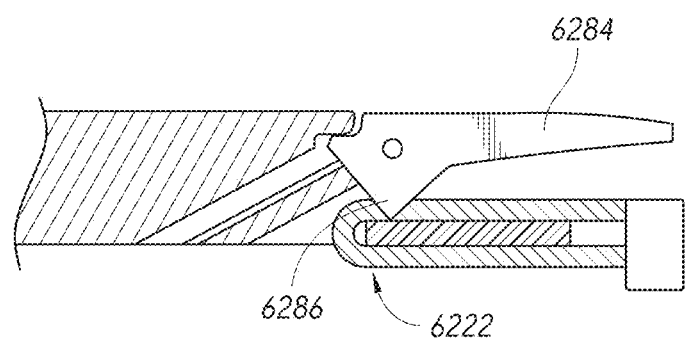
FIG. 68 is an enlarged view of a headgear strap adjustment assembly of the interface assembly of FIG. 65.

The folding clasp 6240 of FIGS. 65-68 is more space efficient in at least some respects compared to the folding clasp 6240 of FIGS. 62-64. In particular, the folding clasp 6240 of FIGS. 65-68 has an overall thickness that is substantially equal to a thickness of two of the segments 6242, 6244, 6246 in a closed or folded configuration, as illustrated in FIG. 67. Any one or all of the segments 6242, 6244, 6246 can define a height that is less than a height of the second segment 6244. In some configurations, the height of the first segment 6242 can be substantially equal to or less than a distance between the lower strap 6218 and the upper strap 6220 at a location where the straps 6218, 6220 meet the mask 6202. The height of the second segment 6244 can be substantially equal to or greater than a distance between a lower edge of the lower strap 6218 and an upper edge of the upper strap 6220 at a location where the straps 6218, 6220 meet the mask 6202. The second segment 6244 can have a generally U-shaped profile with a base 6270 and a pair of arms 6272. The arms 6272 can define a space 6270 therebetween, which can have a distance between the arms 6272 that is at least as great as a height of the first segment 6242. The intermediate segment 6246 can be connected at one end to a rearward end of the first segment 6242 and at a second end to a base 6270 of the second segment 6244. The intermediate segment 6246 can be received within the space 6270 and can overlap at least a portion of the first segment 6242 in a folded orientation of the folding clasp 6240.

The folding clasp 6240 can comprise a locking mechanism, such as a resilient latch 6280, which engages a surface surrounding an opening 6282 to secure the folding clasp 6240 in the closed position or folded orientation. In the illustrated arrangement, the opening is defined by the mask frame 6206 or first segment 6242 and the latch 6280 is carried by the second segment 6244.

Rearward or free ends of the arms 6272 of the U-shaped second segment 6244 can connect to the straps 6218, 6220 of the headgear 6204. The straps 6218, 6220 can be adjustable relative to the mask 6202 and/or folding clasp 6240. For example, the straps 6218, 6220 can be folded to define adjustment loops 6222. The adjustment loops 6222 can be secured by a locking mechanism, such as a locking lever 6284. The locking lever 6284 can include an engagement portion 6286 that engages the loops 6222 of the strap 6218, 6220 to selectively secure the strap 6218, 6220 in place.

Figure 69:
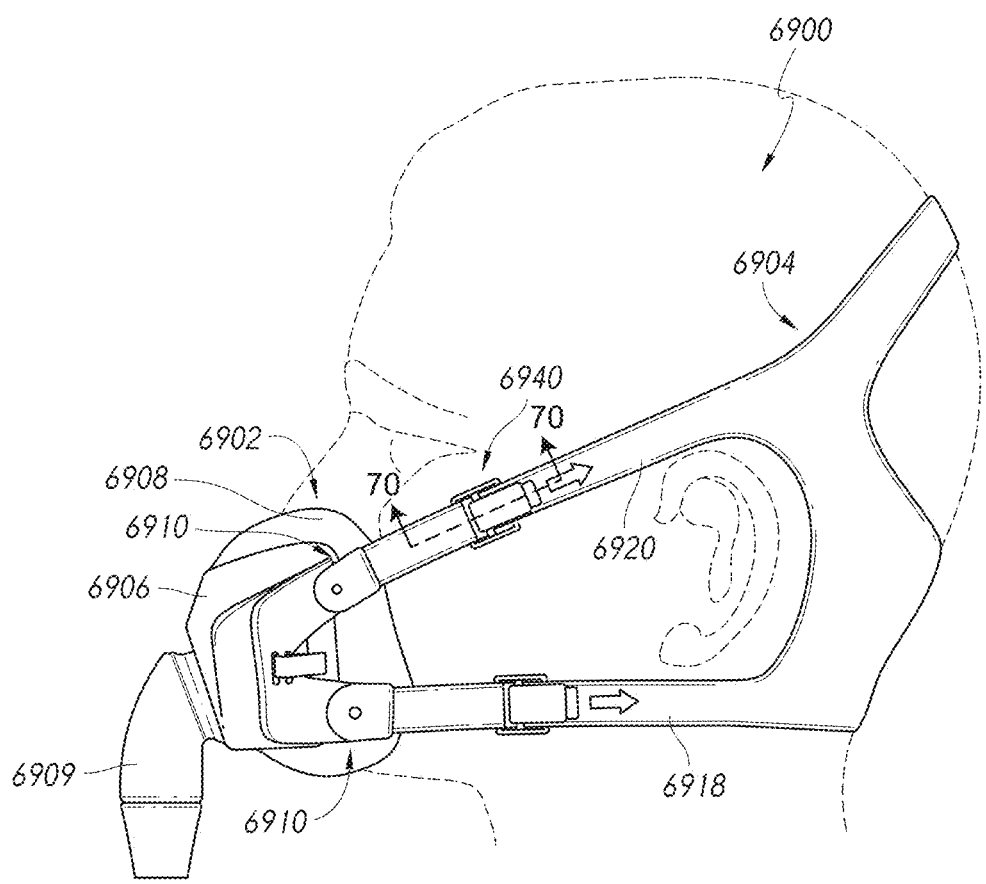
FIG. 69 is a side view of an interface assembly having an interface, such as a mask, and a headgear. A sliding buckle adjustment mechanism permits adjustment of the headgear.
Figure 70:
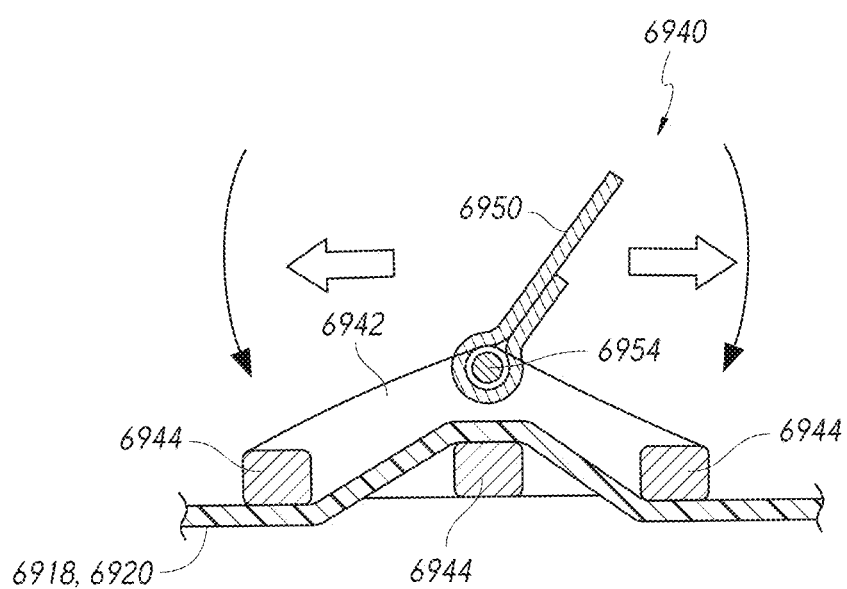
FIG. 70 is a cross-sectional view of the sliding buckle adjustment mechanism of FIG. 69.
Figure 71:
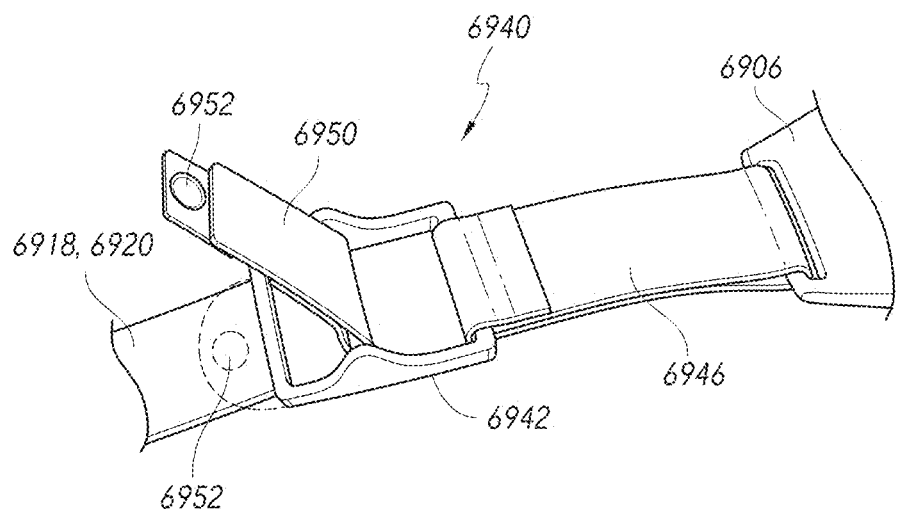
FIG. 71 is a perspective view of the sliding buckle adjustment mechanism of FIG. 69.

FIGS. 69-71 illustrates an interface assembly 6900 that is arranged and configured in accordance with certain features, aspects and advantages of the present disclosure. The illustrated interface assembly 6900 includes an alternative arrangement for providing adjustability and/or closed-loop elongation functionality. In particular, the interface assembly 6900 incorporates one or more sliding buckle arrangements 6940 that permits adjustment of a circumference of the interface assembly 6900. Sliding buckle arrangements 6940 can be provided on one or both sides of the interface assembly 6900.

Similar to other interface assemblies disclosed herein, the interface assembly 6900 includes an interface 6902 and a headgear 6904. The illustrated interface 6902 is a nasal-oral mask but, as described herein, other types of interfaces can be used with the disclosed headgear 6904. The illustrated mask 6902 generally comprises a frame 6906 that supports a seal 6908. The mask 6902 can be connected to a supply conduit 6909, which can be used to supply breathing gases to a user. As described above, in some configurations, the mask 6902 can seal around a mouth of a user and on an underside of a nose of the user. Such a mask 6902 can provide pressurized air flow to both the nose and the mouth of the user.

The headgear 6904 can be coupled to the mask 6902 at one or more mounting locations or mounting points 6910 by any suitable arrangement, such as any of those disclosed herein. Preferably, a lower strap portion 6918 and an upper strap portion 6920 are provided on each side of the headgear 6904 to connect the mask 6902 to a rear portion of the headgear 6904. In the illustrated configuration, a sliding buckle arrangement 6940 is provided within each of the lower strap 6918 and the upper strap 6920 to permit length adjustment of the straps 6918, 6920. Sliding buckle arrangements 6940 can be provided on one or both sides of the headgear 6904. FIGS. 70 and 71 illustrate a sliding buckle arrangement 6940 within one of the straps 6918, 6920; however, other sliding buckle arrangements 6940 can be of the same or a similar construction.

The illustrated sliding buckle arrangement 6940 includes a buckle 6942 having multiple posts 6944, which create a tortuous path for the strap 6918, 6920. The strap 6918, 6920 can be engaged (directly or indirectly) with the mask 6902 and folded over onto itself to create an adjustment loop 6946. An end of the adjustment loop 6946 is coupled to the buckle 6942 such that movement of the buckle 6942 along the strap 6918, 6920 varies the size of the adjustment loop 6946, or the length of the overlap of the strap 6918, 6920, to adjust an effective length of the strap 6918, 6920. The buckle 6942 can be moved in either direction along the strap 6918, 6920 to permit lengthening or shortening of the strap 6918, 6920.

Figure 72:
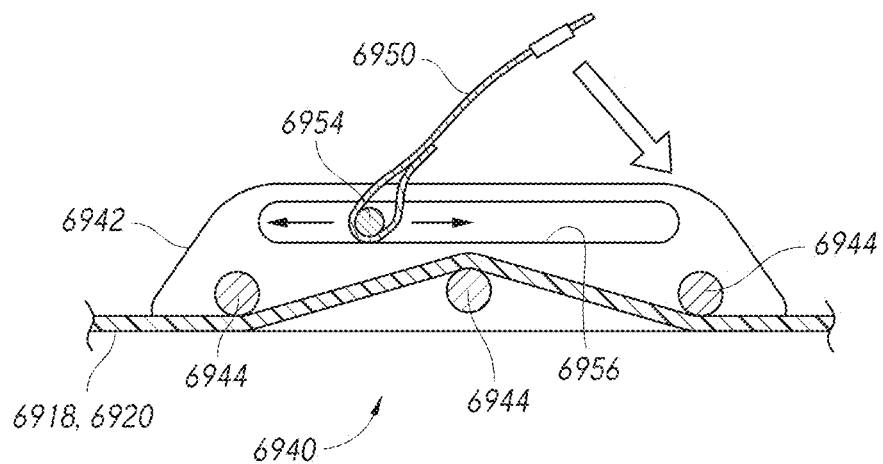
FIG. 72 is a cross-sectional view of an alternative sliding buckle adjustment mechanism having a slidable pull tab.

The buckle 6942 can include a finger grip tab or pull tab 6950 to facilitate movement of the buckle 6942. The pull tab 6950 can include a coupler 6952 to allow the pull tab 6950 to be secured to the buckle 6942 and/or strap 6918, 6920 when not in use. The illustrated coupler 6952 is a magnetic coupler; however, other suitable couplers could be used, including snaps, clips or hook-and-loop fastener, for example and without limitation. The pull tab 6950 can be generally centrally-located along a length of the buckle 6942, such as rotatably supported by a post 6954. FIG. 72 illustrates a sliding pull tab 6950 in which the post 6954 is slidably supported within a slot 6956, which permits the pull tab 6950 and post 6954 to move toward an end of the buckle 6942 in the direction of travel or intended travel of the buckle 6942.

The sliding buckle arrangement 6940 can be utilized for closed-loop elongation or can be used for headgear 6904 adjustment and other opening arrangements can be provided, such as a clip 6930 that is removable from the mask 6902. The clip 6930 can be completely separable from the mask 6902 (i.e., open loop) or can be tethered to the mask 6902 (i.e., closed loop). Unless indicated otherwise, features of the interface assembly 6900 or portions thereof can be the same as or similar to other interfaces or portions thereof described herein, or can be of another suitable arrangement.

The elongating closed-loop arrangements described herein (such as in FIGS. 58-72, for example) preferably provide sufficient elongation in an open state to permit removal and/or application of the associated interface assembly. As described, elongating arrangements can be provided on one or both sides of the interface assembly. If provided on only one side, preferably, the single elongating arrangement provides sufficient elongation in an open state to permit removal and/or application of the associated interface assembly. If provided on both sides, each elongating arrangement can provide sufficient elongation in an open state to permit removal and/or application of the associated interface assembly so that a user can elect to use one side or the other. In some configurations, however, each elongating arrangement can provide a portion of the total elongation, which preferably is sufficient to permit removal and/or application of the associated interface assembly; however, the elongation of either one of the arrangements may not be sufficient on its own to permit removal and/or application of the associated interface assembly. In some configurations, the total elongation between a closed state and an open state is at least 100 millimeters. In elastic configurations, the elongation with the elastic element(s) in an unstretched state can be less than 100 millimeters, but can increase to at least 100 millimeters upon stretching of the elastic element(s). For example, in some configurations, the initial elongation can be about 30 millimeters with the elastic element(s) unstretched and the elastic element(s) can stretch to provide at least 100 millimeters of total elongation. In some configurations, the initial elongation (without stretching) can be about one-third to about one-half of the total elongation (with stretching).

Figure 73:
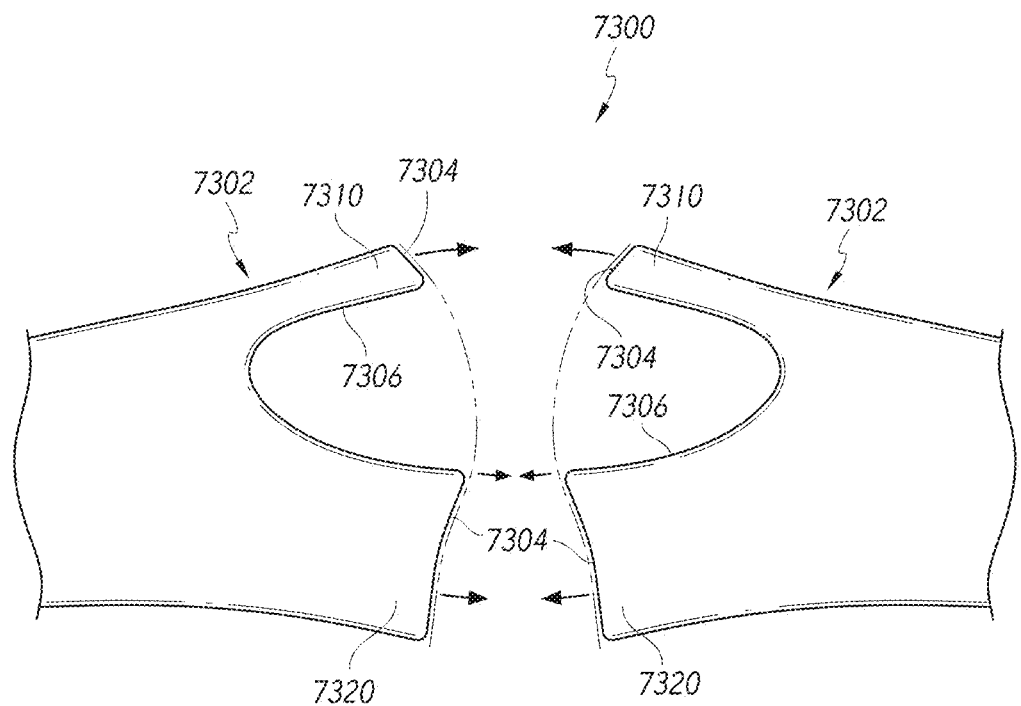
FIG. 73 illustrates portions of a contoured headgear prior to joining.
Figure 74:
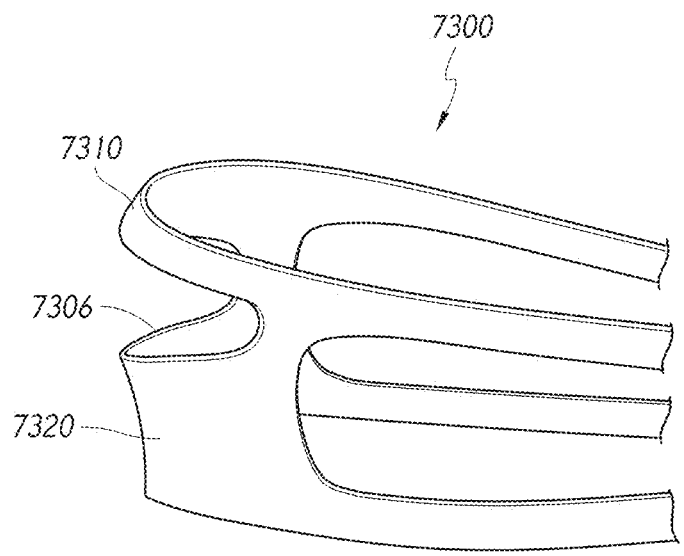
FIG. 74 illustrates the portions of FIG. 73 joined to create a contoured headgear.
Figure 75:
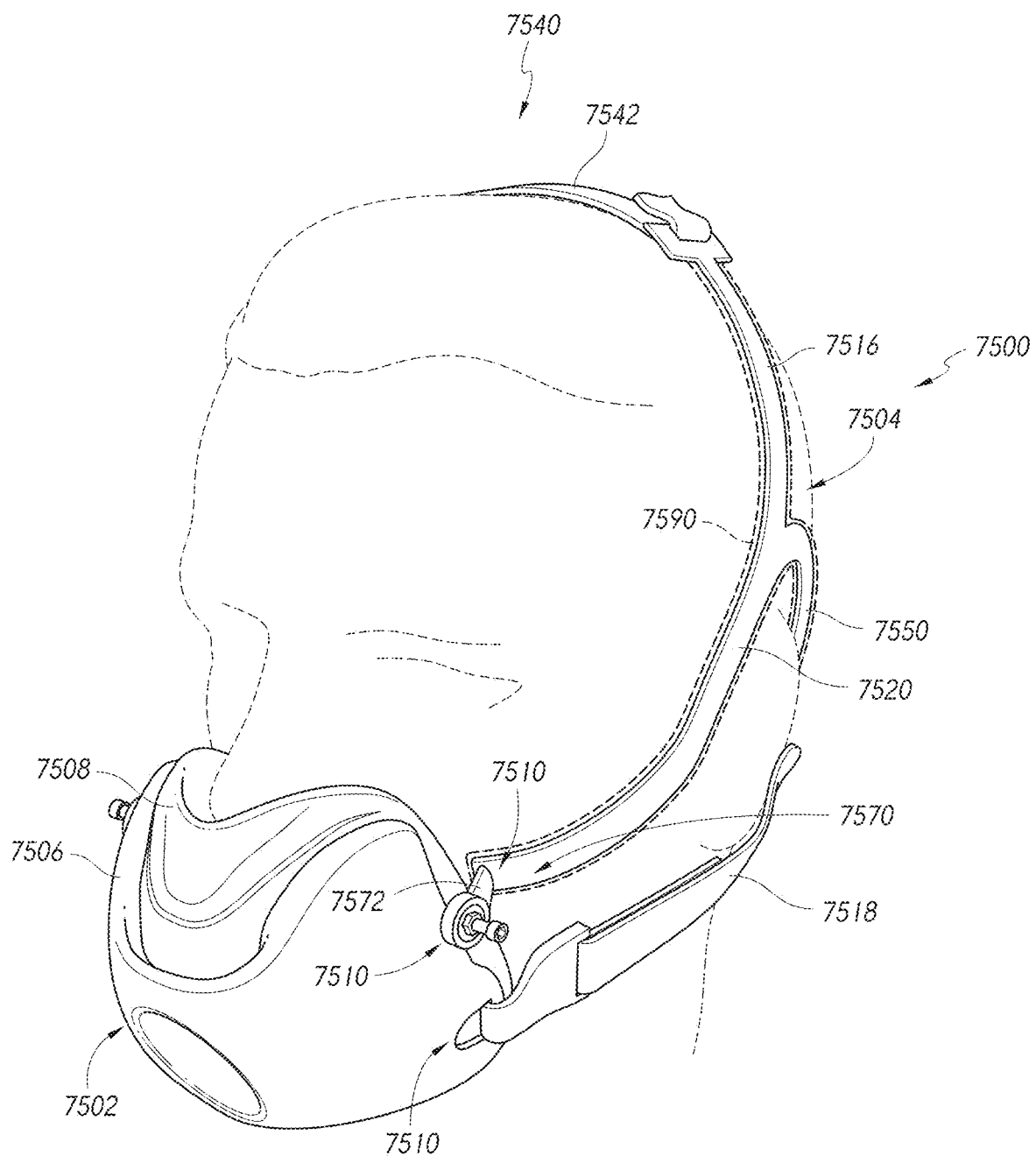
FIG. 75 is a front perspective view of an interface assembly having an interface, such as a mask, and a headgear. The headgear includes at least one relatively rigid section.
Figure 76:
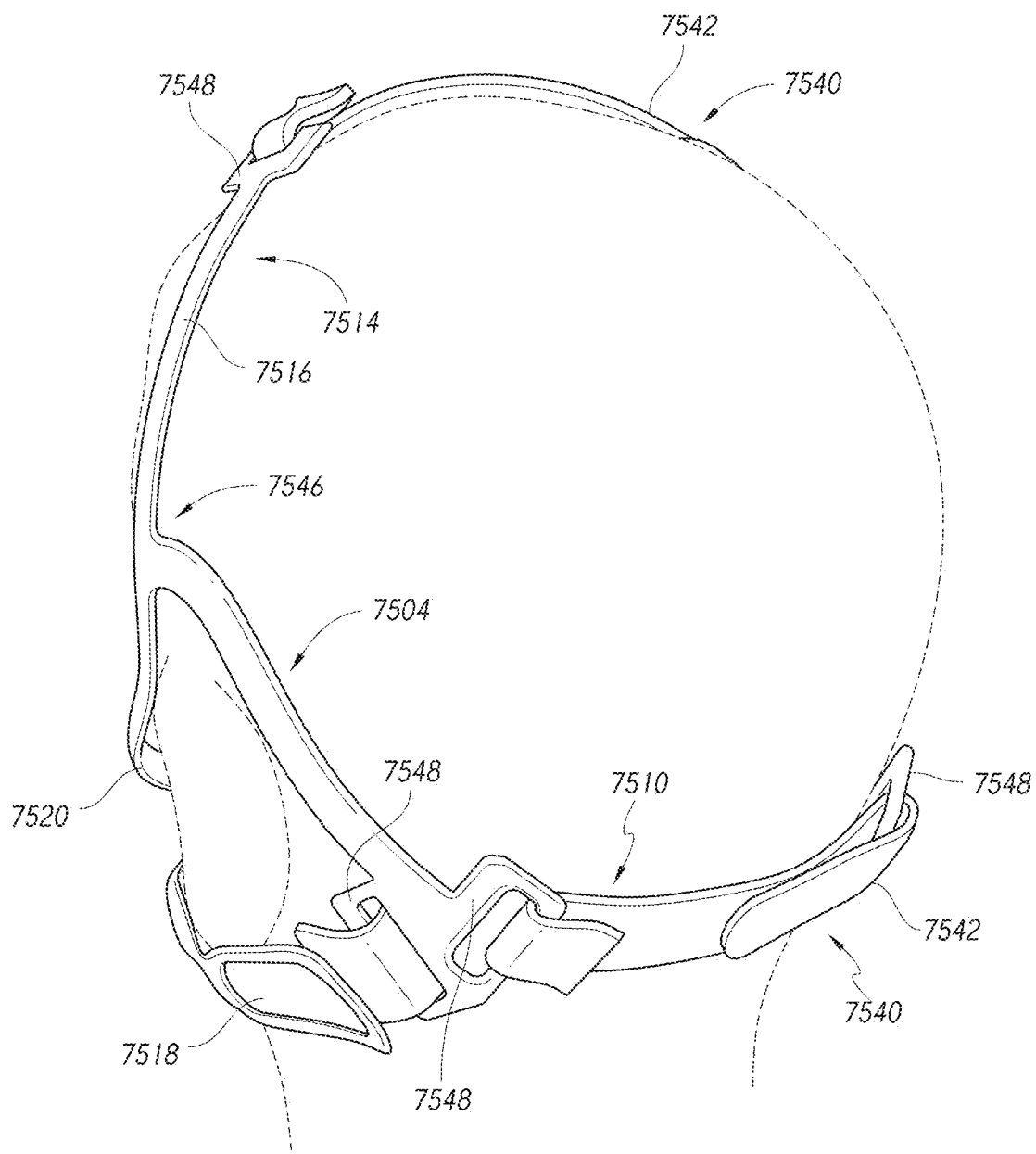
FIG. 76 is a side view of the interface assembly of FIG. 75.
Figure 77:
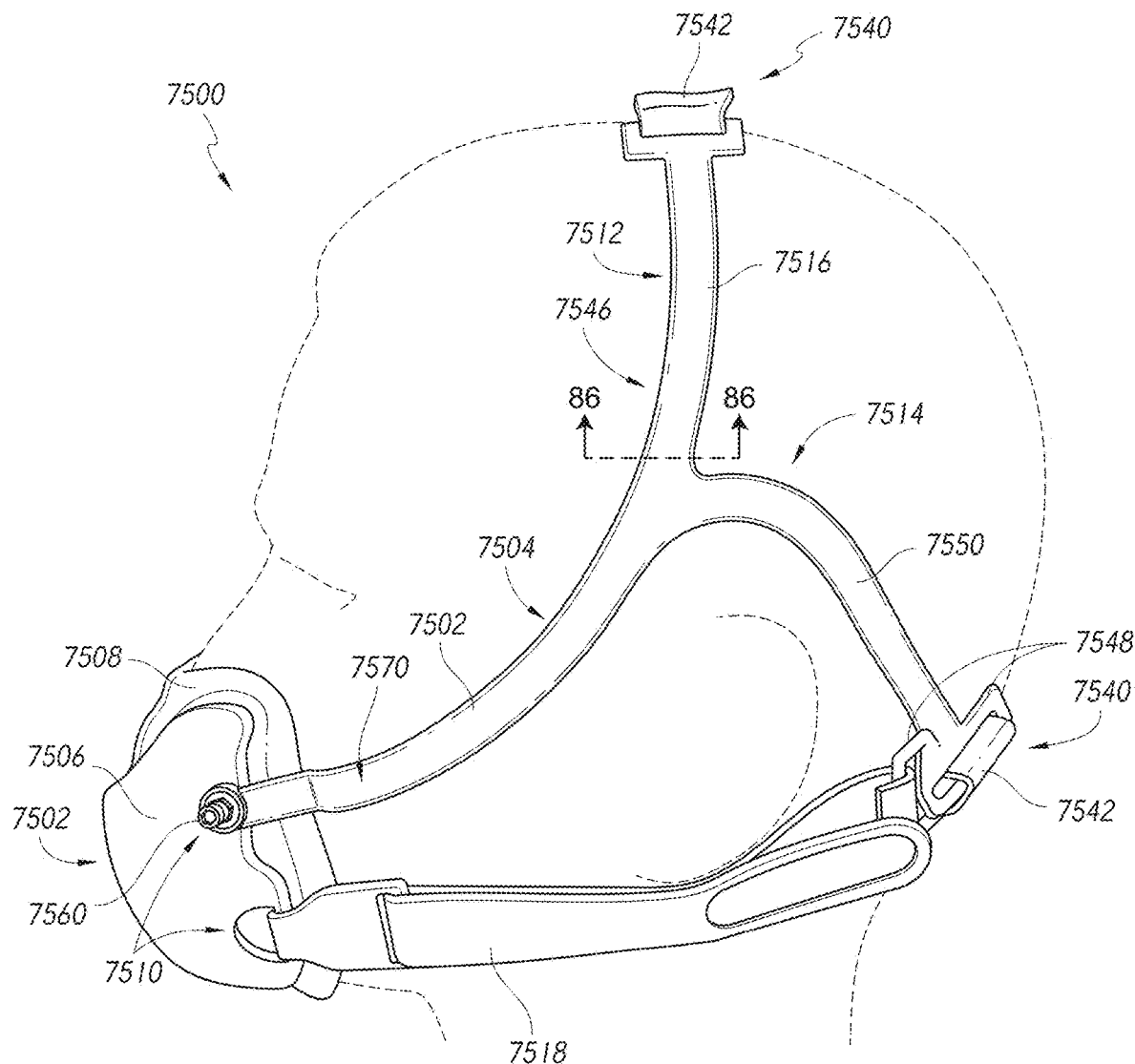
FIG. 77 is a rear perspective view of the interface assembly of FIG. 75.
Figure 78:
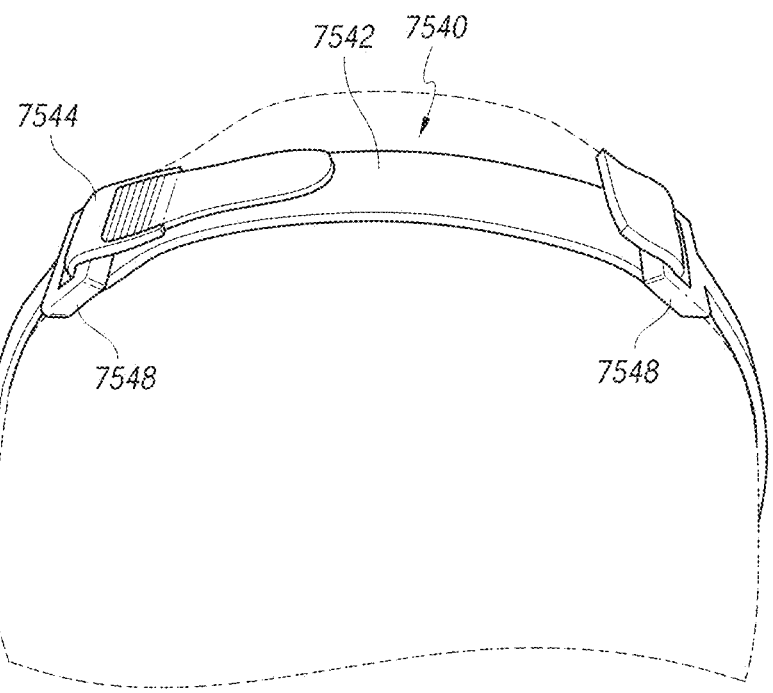
FIG. 78 is top view of an adjustment mechanism within a crown strap portion of the headgear of FIG. 75.
Figure 79:
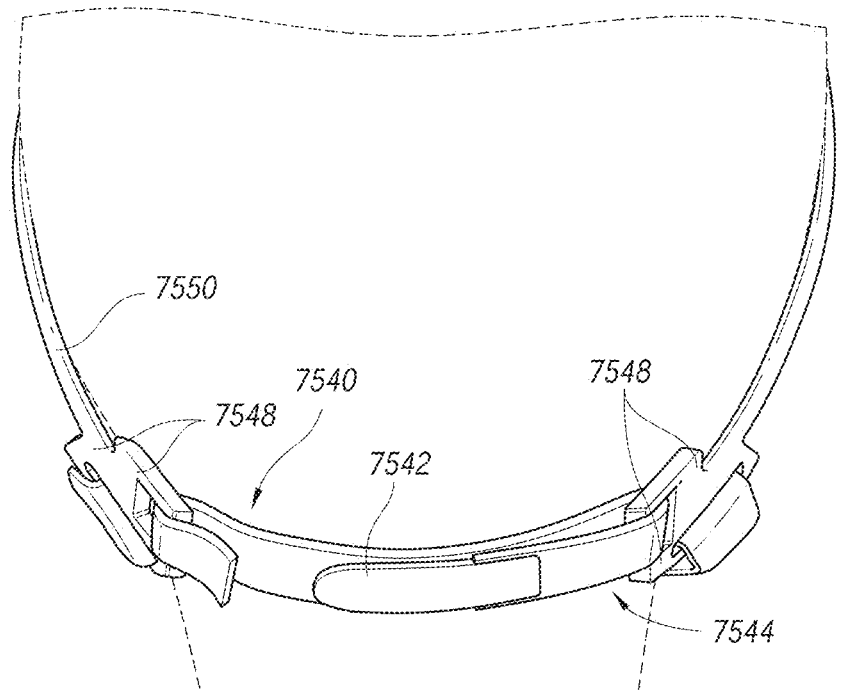
FIG. 79 is a rear view of an adjustment mechanism within a rear strap portion of the headgear of FIG. 75.

FIGS. 73 and 74 illustrate a contoured headgear arrangement 7300 in component parts (FIG. 73) and as assembled (FIG. 74). Many of the headgear assemblies disclosed herein can be constructed in whole or in part of a flexible material, such as a fabric or textile material, for example. Such flexible materials often are in the form of a flat sheet, which can result in a semi-cylindrical shape or curvature about only one axis (a vertical axis) when formed into a headgear assembly. In some configurations, the disclosed headgear arrangements, including but not limited to the headgear arrangement 7300, are curved about at least two axes (a vertical axis and one or more horizontal axes). Such an arrangement allows the headgear arrangement 7300 to better conform to the user's head shape and, preferably, spread loads relatively evenly within an area of the headgear arrangement 7300 to reduce pressure points, such as line loads along the edges, for example. Such contoured headgear arrangements 7300 can also tend to hold their shape when not fitted to a user, such as resisting gravitational forces and tangling, for example. Such partially or fully self-supporting constructions can make the headgear arrangements 7300 and associated interface assemblies easier to fit to a user.

In the illustrated arrangement, two or more components 7302 are assembled together by a suitable process (e.g., sewing, bonding, welding, etc.) to form a portion or an entirety of a headgear arrangement 7300. In some configurations, the components 7302 are in the form of flat patterns of textile material. The shape of the patterns 7302 can be adjusted to create desired tension or compression in the material when the components 7302 are assembled. By adjusting the outline shape of the flat pattern 7302, the assembled headgear arrangement 7300 can be made to fit more ergonomically to the user's head shape. Such an arrangement can spread the loading more evenly over the user's head.

In the illustrated configuration, a shape of edges 7304 that create a vertical (e.g., rear) seam of the headgear arrangement 7300 are selected to provide a desired final shape once assembled. For example, the patterns 7302 can be mirror images of one another and can include cut-outs 7306 that together form an opening in the headgear arrangement 7300 to accommodate, for example, a user's hair arranged in a ponytail. An upper portion 7310 of the patterns 7302 above the cut-out 7306 can have a curved edge 7304 that curves outwardly in a direction from a bottom to a top of the edge 7312. A lower portion 7320 of the patterns 7302 below the cut-out 7306 can have a curved edge 7304 that curves inwardly from a bottom to a top of the edge 7304. Overall, the edges 7304 can cooperate to define a generally hourglass shape, as illustrated in FIG. 73. As illustrated in FIG. 74, such an arrangement, when assembled, can result in an upper strap portion 7310 that curves inwardly from bottom to top and a lower strap portion 7320 that has a concave curvature. The lower strap portion 7320 can also generally move inwardly from top to bottom. Such an arrangement can conform to the shape of the user's head, for example, the rear of the head. The lower strap portion 7320 can conform to the portion of the head formed by the occipital bone and/or the upper neck. The upper strap portion 7310 can be positioned higher, such as on a portion of the head formed by the parietal bone or a junction between the parietal bone and the occipital bone. Although illustrated as edges 7304, portions of material can be connected along sew lines or attachment lines that are not edges of material, but one or more of the sew lines or attachment lines can be located in an intermediate portion of material.

FIGS. 75-79 illustrates an interface assembly 7500 that is arranged and configured in accordance with certain features, aspects and advantages of the present disclosure. The illustrated interface assembly 7500 includes an interface 7502 and a headgear 7504. The illustrated interface 7502 is a nasal-oral mask but, as described herein, other types of interfaces can be used with the disclosed headgear 7504. The illustrated mask 7502 generally comprises a frame 7506 that supports a seal 7508. The mask 7502 can be connected to a supply conduit (not shown), which can be used to supply breathing gases to a user. As described above, in some configurations, the mask 7502 can seal around a mouth of a user and on an underside of a nose of the user. Such a mask 7502 can provide pressurized air flow to both the nose and the mouth of the user.

The headgear 7504 can be coupled to the mask 7502 at one or more mounting locations or mounting points 7510. Preferably, at least a portion of the headgear 7504 comprises or is constructed from a relatively rigid material, such as a semi-rigid or rigid material. As described herein, preferably, the relatively rigid material resists substantial deformation in response to blow-off forces and, preferably, in response to hose pull forces and/or other expected external forces. For example and without limitation, the relatively rigid material can be polycarbonate, nylon, ABS, polypropylene or other materials having similar mechanical properties, especially with respect to rigidity. In some configurations, at least a portion of the headgear 7504 that contacts the user's face is relatively rigid. As described further below, the relatively rigid portion(s) 7570 that contact the user's face can be positioned on or near the user's cheeks, such as a portion corresponding to the zygomatic and/or maxilla bones. In some configurations, the relatively rigid portions 7570 that contact the user's face are positioned adjacent each side of an upper portion of the mask 7502, such as generally rearward of the corresponding (e.g., upper) mounting points 7510. Such an arrangement can permit the headgear 7504 to anchor onto or be supported on the user's face at the portions 7570 so that tightening of the headgear 7504 tends to cause an increase in the pressure applied to the user's face by the headgear 7504, with substantial compression of the mask seal 7508 avoided or limited. Rather, compression of the mask seal 7508 can be at least primarily controlled by the geometry of the interface assembly 7500 (and/or a seal adjustment mechanism, such as the arrangement described in connection with FIG. 92) instead of the force applied to the mask 7502 by the headgear 7504. That is, the headgear 7504 can be configured to support the mask 7502 at a desired location relative to the user's face and the contact of the rigid portions 7570 of the headgear 7504 with the user's face can avoid or limit substantial compression of the seal 7508 in response to tightening of the headgear 7504. In other words, the rigid portions 7570 of the headgear 7504 may fix the distance between the user's cheeks and the seal housing or frame 7506, thereby inhibiting or preventing possible overcompression of the seal 7508 as a result of tightening of the headgear 7504. Preferably, forces created by tightening of the headgear 7504 are resisted at least in part by the relatively rigid portion(s) 7570 and not entirely by the mask seal 7508. In some configurations, the relatively rigid portion(s) 7570 provide significantly greater resistance to tightening forces than the mask seal 7508.

In some configurations, a lower strap portion 7518 and an upper arm portion 7520 are provided on each side of the headgear 7504 to connect the mask 7502 to a rear portion of the headgear 7504. The lower strap 7518 and upper arm 7520 can connect to the mask 7502 at respective lower and upper mounting locations 7510. In some configurations, the rigid portions 7570 can be defined by, secured to or otherwise carried by the upper arm 7520. The rigid portion 7570 of the upper arm 7520 can comprise support arms 7572 that extend away from the user's face and define the mounting points 7510 between the headgear 7504 and the mask 7502.

The headgear 7504 can also comprise a crown strap portion 7516 and a rear strap portion 7550. The crown strap 7516 extends from respective rearward ends of the upper arms 7520 across the top of the user's head. The rear strap portion 7550 extends from rearward ends of the upper arms 7520 around the back of the user's head. The upper arm 7520, crown strap 7516 and rear strap 7550 can converge at a location generally above an ear of the user.

In some configurations, at least the upper arms 7520 comprise or are constructed from a relatively rigid material. In some configurations, at least portions of one or both of the crown strap 7516 and the rear strap 7550 comprise or are constructed from a relatively rigid material. In the illustrated arrangement, at least portions of both of the crown strap 7516 and the rear strap 7550 comprise or are constructed from a relatively rigid material. The upper arms 7520 and crown strap 7516 (along with the mask 7502) can define a front halo portion 7512. The rear strap 7550 and the crown strap 7516 can define a rear halo portion 7514. Preferably, the lower straps are constructed from a less rigid material, such as a flexible material.

The headgear 7504 can provide for adjustment to allow the headgear 7504 to be adjusted to fit an individual user. For example, one or more adjustment mechanisms 7540 can be provided to within portions of the headgear 7504, such as one or both of the crown strap 7516 and the rear strap 7550. In the illustrated configuration, each of the crown strap 7516 and the rear strap 7550 comprise an adjustment mechanism 7540, which permits a length of the straps 7516, 7550 to be adjusted. Thus, adjustment of a circumference of each of the front halo portion 7512 and the rear halo portion 7514 is permitted. The adjustment mechanism 7540 can comprise a flexible strap section 7542 within the straps 7516, 7550. Each flexible strap section 7542 can comprise a portion that doubles over onto itself to form an adjustment loop 7544. The adjustment loop 7544 can be secured by any suitable fastener, such as a hook-and-loop fastener, for example.

In the illustrated configuration, the headgear 7504 includes two relatively rigid sections 7546, each including one of the upper arms 7520, a portion of the crown strap 7516 and a portion of the rear strap 7550. The rigid sections 7546 can be substantial mirror images of one another and can be shaped to conform to the shape of a user's head. Thus, the rigid sections 7546 can comprise curved shapes at any or all of forward, rearward and upper end portions and can be less curved in a central portion, which can be positioned generally on the side of the user's head. Such shaping can provide feedback to the user for proper placement of the headgear 7504 on the head and/or can reduce or eliminate pressure points when the headgear 7504 is slept on.

In some configurations, portions or a substantial entirety of the rigid sections 7546 can be partially or completely covered by a pad 7590. The pad 7590 can be constructed of any suitable material for increasing comfort for the user. The pad 7590, for example and without limitation, can be constructed from silicone, thermoplastic elastomer, thermoplastic polyurethane, other materials with similar mechanical properties, cloth-type materials (cloth covered foam), rubber/foam materials or other suitable soft materials. In some applications, it may be desirable for the pad 7590 to provide increased friction with the user's skin. As described above, one suitable material for a pad 7590 is silicone, which may be overmolded or otherwise applied onto the rigid sections 7546. If desired, the silicone or other material used for the pad 7590 can be mechanically interfaced with the rigid sections 7546, such as by including openings or depressions in the rigid sections 7546 that are filled with the pad 7590 material to interlock the pad 7590 with the rigid section 7546. In some configurations, the pad 7590 is provided only on a skin-contacting side of a portion or a substantial entirety of the rigid sections 7546. However, in the illustrated arrangement, the pad 7590 completely surrounds the rigid sections 7546.

Ends of the crown strap 7516 and rear strap 7550 of each rigid section 7546 can comprise one or more connectors, such as one or more loops 7548, which can provide for coupling of the flexible strap sections 7542 to the rigid sections 7546. The ends of the rear strap 7550 include two loops 7548. One loop 7548 allows coupling of the flexible strap section 7542 to the rigid section 7546 and the second loop 7548 allows coupling of the lower strap 7518 to the rigid section 7546. The loops 7548 can be oriented to direct the flexible strap sections 7542 in a desired direction. The loops 7548 of the crown strap 7516 and the loop of the rear strap 7550 for the flexible strap section 7542 can be oriented with the slot of the loop 7548 generally perpendicular to an axial direction of the strap 7516, 7550.

In some configurations, the mask 7502 is coupled to the upper strap 7520 by a rotational coupling 7560, which can be the same as or similar to any of the rotational couplings disclosed herein, such as the rotational coupling 1900 of FIG. 19, the rotational coupling 2944 of FIGS. 29 and 30 or the rotational couplings of FIGS. 35 and 36, for example and without limitation. Other suitable rotational couplings could also be used. The rotational coupling 7560 defines a pivot axis of the mask 7502. In some configurations, the lower strap 7518 can be used to secure the mask 7502 in a desired rotational position. In other configurations, the mask 7502 can be secured in a desired rotational position by another suitable mechanism, such as the detent rotational coupling 1900 of FIG. 19 or a separate lock, and the lower strap 7518 could be omitted. Unless indicated otherwise, features of the interface assembly 7500 or portions thereof can be the same as or similar to other interfaces or portions thereof described herein, or can be of another suitable arrangement.

Figure 80:
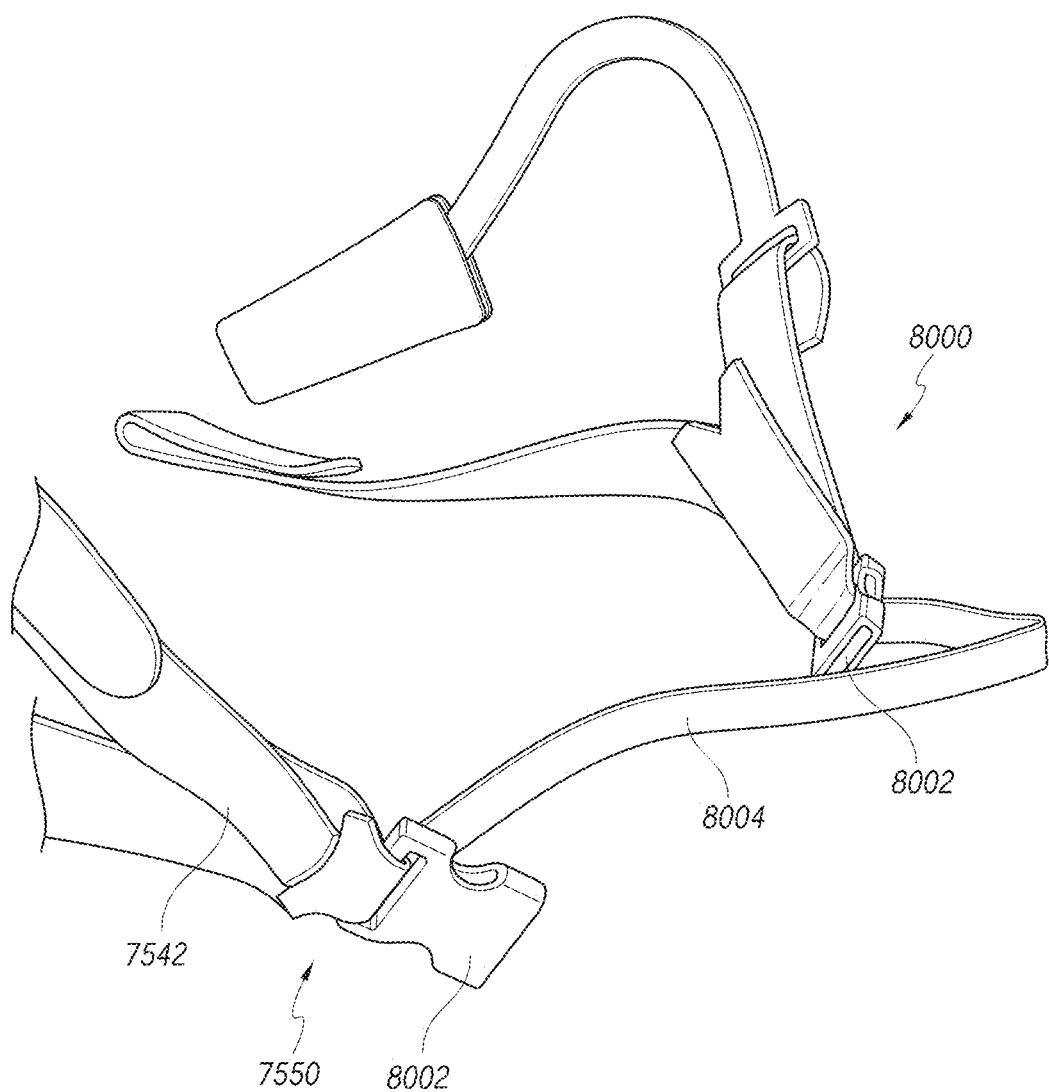
FIG. 80 is a perspective view of an alternative adjustment mechanism of FIGS. 78 and 79 having a break-fit arrangement with a tether to couple portions of the adjustment mechanism.

FIG. 80 illustrates the flexible strap section 7542 of the rear strap 7550 with a break-fit arrangement 8000 incorporated therein to permit quick transition of the rear strap 7550 between an elongated orientation and a tightened orientation. As described herein, such an arrangement can permit the rear strap 7550 to be adjusted to a desired length with the break-fit arrangement 8000 connected or in the tightened orientation. The break-fit arrangement 8000 can be disconnected or moved to the elongated orientation to permit removal or donning of the interface assembly 7500. Once donned, the break-fit arrangement 8000 can be connected to move the rear strap 7550 to the tightened orientation, which preferably results in a proper fit without requiring adjustment of the rear strap 7550 with each application of the interface assembly 7500. A break-fit arrangement 8000 can be provided in any of the flexible strap sections 7542 or within any other portion of the headgear 7504 or interface assembly 7500.

The illustrated break-fit arrangement 8000 includes a snap buckle or release buckle 8002 interposed within the rear strap 7550. The buckle 8002 can be positioned at one end of the flexible strap section 7542 or can be within the flexible strap section 7542. Preferably, a leash or tether 5804 can be provided to couple the portions of the rear strap 7550 that are separated by the break-fit arrangement 8000 to facilitate location of the separated portions of the rear strap 7550 even when the portions are not visible to the user. The tether 8004 preferably has a length that is sufficient to permit the headgear 7504/interface assembly 7500 to be applied to the user's head. In some configurations, the tether 8004 can be constructed from an elastic material, which permits elongation of the tether 8004 for application of the interface assembly 7500 and then moves the portions of the rear strap 7550 closer together to facilitate connection of the break-fit arrangement 8000. Other suitable break-fit arrangements could also be utilized, such as any of those described herein, for example and without limitation.

Figure 81:
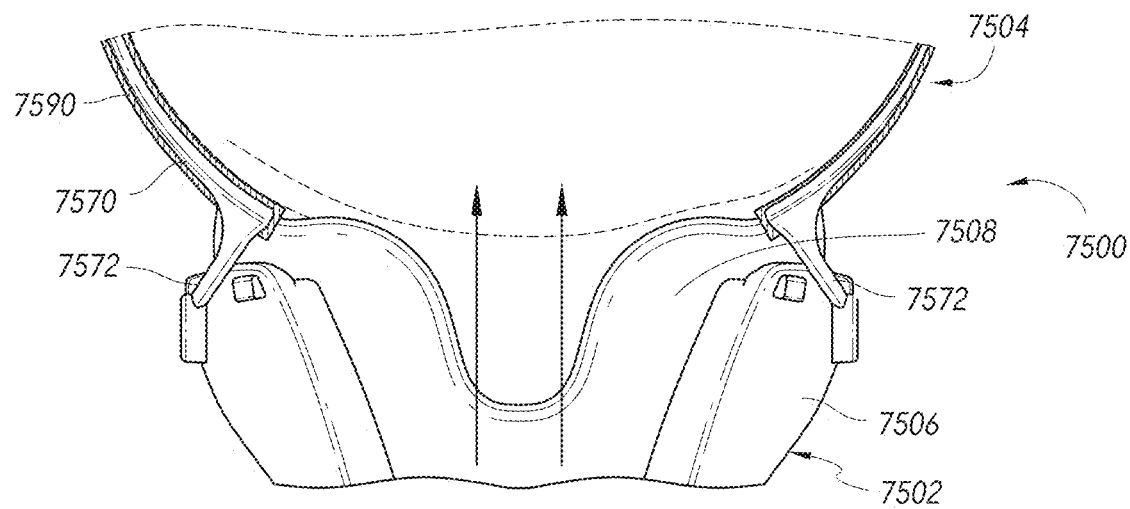
FIG. 81 is a top view of the interface assembly of FIGS. 75-79 illustrating a difference between an untightened headgear (left side) and a tightened headgear (right side).
Figure 82:
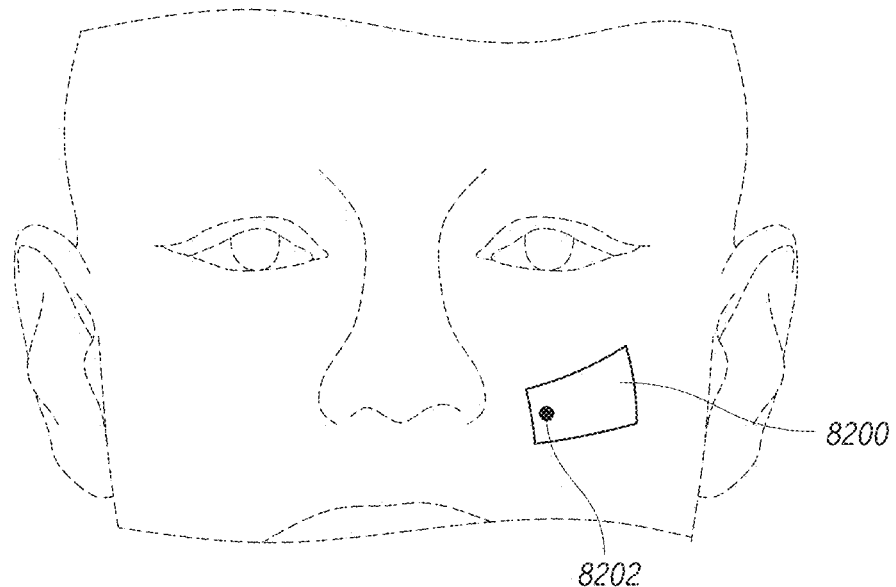
FIG. 82 is a front view illustrating a location of contact of a rigid portion of the headgear of the interface assembly of FIGS. 75-79 on a user's face.
Figure 83:
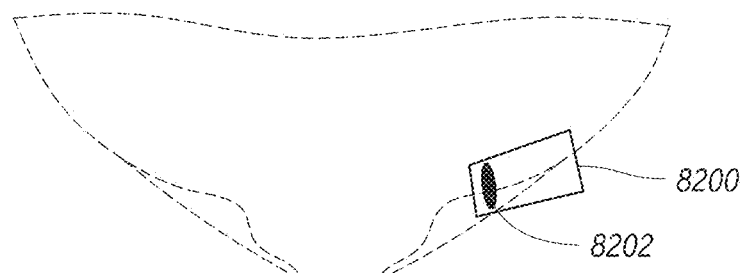
FIG. 83 is a top view illustrating the location of contact of FIG. 82.

FIGS. 81-83 illustrate an interface assembly having relatively rigid support portions which support the interface assembly relative to the user's head to provide at least some isolation of the interface from forces applied to tighten the headgear. Such an interface assembly may be the same as or substantially similar to the interface assembly 7500 and is described in that context using the same reference numbers. FIG. 81 is a top view of a portion of the user's face with the interface assembly 7500 applied. The left side of FIG. 81 (from the perspective of the viewer) illustrates the interface assembly 7500 in a less tensioned or less tightened state and the right side of FIG. 81 illustrates the interface assembly 7500 in a more tensioned or more tightened state relative to the left side to illustrate the result of an application of tensioning or tightening force to the interface assembly 7500.

With respect to the left side of FIG. 81, in a less tightened state, the rigid portion 7570 of the upper arm 7520 can lightly contact the user's face or, in some cases, may not contact the user's face. For example, under some conditions, the mask seal 7508 can hold the rigid portion 7570 away from the user's face. Preferably, at least a portion of the mask seal 7508 extends rearwardly of the forward-most edge of the rigid portion 7570 or a projection of the rigid portion 7570 to ensure that the seal 7508 contacts the user's face. The support arm 7572 holds the mask 7502 at a desired location relative to the headgear 7504 and/or the user's face.

The right side of FIG. 81 illustrates the result of a tightening force being applied to the interface assembly 7500 or headgear 7504, which is illustrated by the arrows in FIG. 81. The tightening force tends to pull the mask 7502 towards the user's face. However, unlike many interface assemblies, the rigid portion 7570 of the illustrated interface assembly 7500 contacts the user's face to limit rearward movement of the mask 7502 and, thus, limit compression of the mask seal 7508. As illustrated, the pad 7590 (if provided) can be compressed as a result of applied tightening force, but the underlying rigid portion 7570 can inhibit or prevent further rearward movement once the pad 7590 is compressed.

With reference to FIGS. 82 and 83, preferably, the rigid portions 7570 contact a portion of the user's head that can provide resistance to rearward movement of the mask 7502. In some configurations, the rigid portions 7570 contact a forward-facing portion of the user's head or face. In the illustrated arrangement, the rigid portions 7570 contact the user's cheeks. FIGS. 82 and 83 are front and top views, respectively, of a user's face illustrating one desired contact area 8200 for the rigid portions 7570, which preferably encompasses the location indicated by the dot 8202. The area 8200 can be located on the user's zygomatic and/or maxilla bone. The dot 8202 can be located on either one of the zygomatic or maxilla bone, but in at least some configurations is located on the maxilla. Placing the rigid portions 7570 close to the user's nose may be advantageous to maximize resistance to rearward movement of the rigid portions 7570 and, thus, the mask 7502. However, as is apparent from FIGS. 81-83, the shape and/or size of the mask 7502 may limit the available locations for the rigid portions 7570. Therefore, in some configurations, the rigid portions 7570 are located as close to the user's nose as possible in view of the size and shape of the particular mask 7502 or other interface that is used or with which the headgear 7504 is intended for use.

Figure 84:
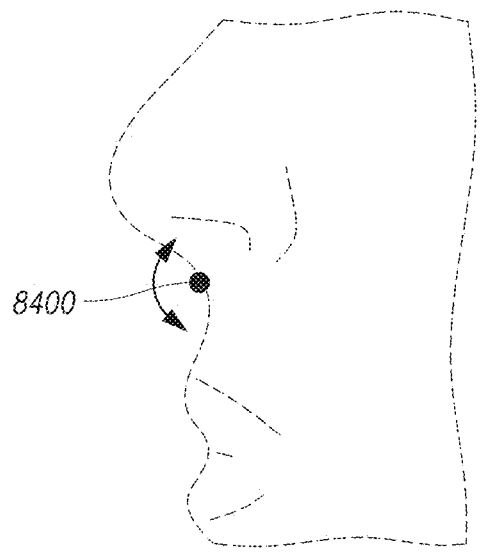
FIG. 84 is a side view illustrating a location of an axis of rotation of the mask of the interface assembly of FIGS. 75-79.
Figure 85:
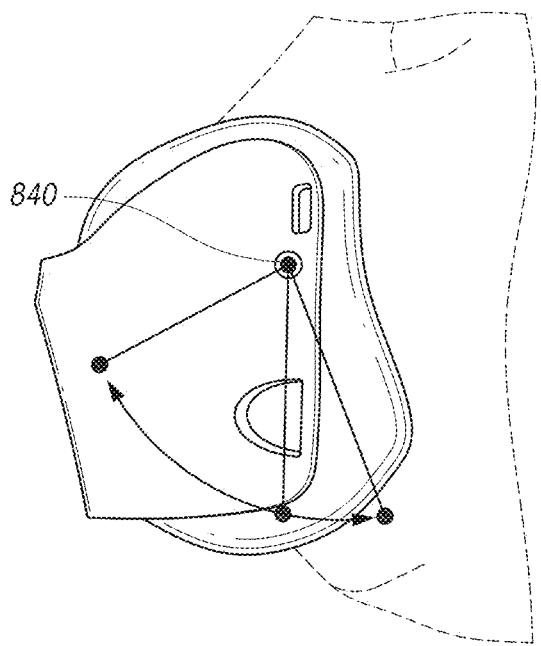
FIG. 85 is a side view of a mask of the interface assembly of FIGS. 75-79 illustrating a range of rotational adjustment of the mask.

As described above, in some configurations, the mask 7502 can be rotatably supported by the headgear 7504. Preferably, the arms 7572 of the headgear 7504 are configured to position a pivot axis of the mask 7502 at a desired location relative to the user's face and/or the rigid portions 7570 of the headgear 7504. With reference to FIGS. 84 and 85, in some configurations, the pivot axis 8400 of the mask 7502 is located below the user's nose. Preferably, the pivot axis 8400 is located below the user's nose and above the user's upper lip. In some configurations, the pivot axis 8400 can be positioned generally at a junction between the underside of the user's nose and the user's upper lip area. In practice, location of the pivot axis 8400 may vary from the preferred location due to differences in facial geometry within the overall user population. However, the location of the pivot axis 8400 will be sufficiently close to the preferred location such that the mask seal 7508 will seal against the underside of the user's nose. As described above, and illustrated in FIG. 85, the mask 7502 can rotate about the pivot axis 8400 to adjust to the user's facial geometry (e.g., chin shape) and to properly seal against the user's face. The mask 7502 can be secured in the desired rotational position relative to the pivot axis 8400 by any suitable arrangement, such as the bottom strap 7518, for example and without limitation.

Figure 86A:
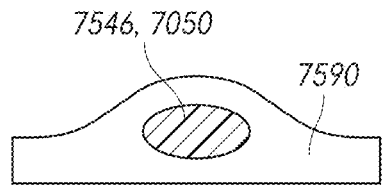
FIGS. 86A-86G are cross-sectional views of a portion of the headgear of FIGS. 75-79 illustrating several possible shapes of a rigid portion and a pad.
Figure 86E:
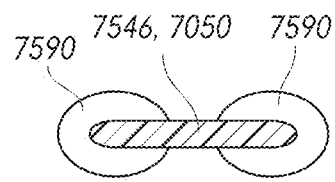
Figure 86B:
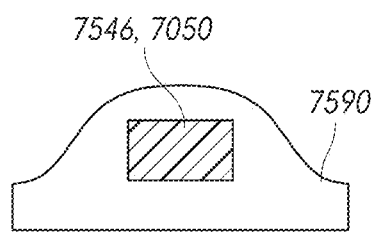

FIGS. 86a-86g illustrate several possible cross-sectional arrangements for the rigid sections 7546 and/or rigid portions 7570 of the headgear 7504 in configurations having a pad 7590, with the bottom surface being the skin contact surface. In FIG. 86a, the rigid section 7547/rigid portion 7570 is generally oval in cross-sectional shape. The pad 7590 completely surrounds the rigid section 7547/rigid portion 7570 and defines a generally or substantially flat skin contact surface. A surface opposite the skin contact surface has a convex curved shape as a result of the pad 7590 extending over the rigid section 7547/rigid portion 7570. The pad 7590 includes lateral side portions (relative to the orientation in FIG. 86a) extending outward from the rigid section 7547/rigid portion 7570. The arrangement of FIG. 86b is substantially similar to the arrangement of FIG. 86a, except the rigid section 7547/rigid portion 7570 is rectangular or square in cross-sectional shape in FIG. 86b.

Figure 86F:
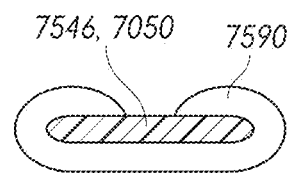
Figure 86C:
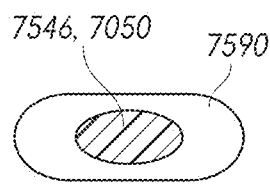

FIG. 86c illustrates an arrangement having a generally oval rigid section 7547/rigid portion 7570 covered by a generally oval pad 7590. The pad 7590 can have lateral side portions than are thicker than the portions above and below the rigid section 7547/rigid portion 7570. FIG. 86d illustrates an arrangement having a generally oval rigid section 7547/rigid portion 7570 and a pad 7590 that defines a generally flat skin contacting surface. One lateral end of the pad 7590 can be curved and generally match the shape of the rigid section 7547/rigid portion 7570 and the other lateral end of the pad 7590 can have a tapered shape.

Figure 86G:
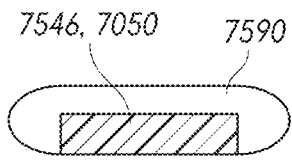
Figure 86D:
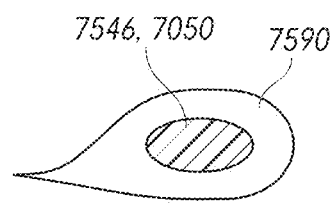

FIGS. 86e-86g illustrate arrangements having a generally flat strap or flat rectangular shaped rigid section 7547/rigid portion 7570. In FIG. 86e, the pad 7590 covers each end of the rigid section 7547/rigid portion 7570 and leaves a center portion of the rigid section 7547/rigid portion 7570 uncovered. In FIG. 86f, the pad 7590 covers both ends and a skin contact side of the rigid section 7547/rigid portion 7570, with a center portion of the side opposite the skin contact side of the rigid section 7547/rigid portion 7570 uncovered.

In FIG. 86g, the pad 7590 does not cover the skin contact surface. However, preferably, the pad 7590 covers all other surfaces of the rigid section 7547/rigid portion 7570. Such arrangements are merely examples. Other suitable arrangements can also be used.

Figure 87:
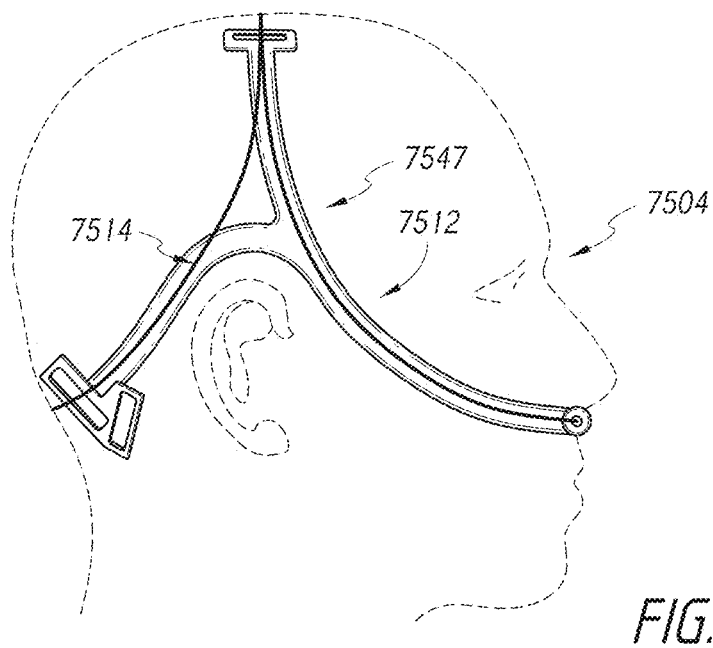
FIG. 87 is a side view of the headgear of FIGS. 75-79 illustrating a front halo portion and a rear halo portion.

FIG. 87 is a side view of a user with the rigid section 7547 of the headgear 7504 positioned on the user. As described herein, many of the interface assemblies generally define one or both of a front halo portion and a rear halo portion. The headgear 7504 defines both a front halo portion 7512 and a rear halo portion 7514, each of which define a generally halo shape. As illustrated in FIG. 87, the halo shape of the halo portions 7512, 7514 does not necessarily coincide with the physical structure of the headgear 7504 throughout the entire circumference of the halo shape. However, the physical structure of the headgear 7504 alone or in combination with the mask 7502 or other interface preferably defines a closed loop for each halo portion 7512, 7514. Many different physical shapes to accomplish the halo portions 7512, 7514 are possible.

Figure 88A:
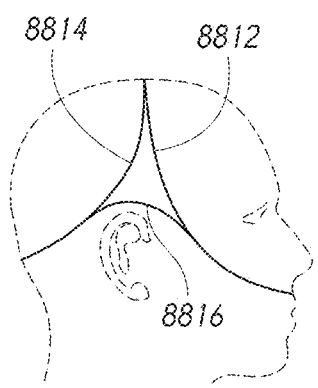
FIGS. 88A-88F illustrate alternative headgear arrangements relative to FIG. 87 each having a front halo portion and a rear halo portion.
Figure 88B:
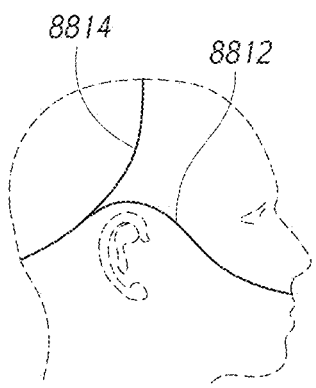

FIGS. 88a-88f illustrate approximate shapes of a headgear that can form both a front halo portion 8812 and a rear halo portion 8814. The headgear can include additional structures, as well, such as lower mask straps, for example. In FIG. 88a, the front halo portion 8812 and the rear halo portion 8814 meet at the top of the user's head. In some configurations, an ear strap portion 8816 can extend over the user's ear between the front halo portion 8812 and the rear halo portion 8814. In FIG. 88b, the rear halo portion 8814 is a generally continuous circular shape. The front halo portion 8812 curves over the user's ear to intersect with the rear halo portion 8814, in a manner similar to the ear strap portion 8816 of FIG. 88a. However, the upper part of the rear halo portion 8814 above the intersection with the lower front halo portion 8812 also defines an upper part of the front halo portion 8812.

Figure 88C:
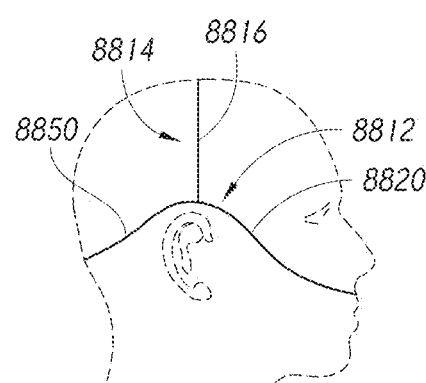
Figure 88D:
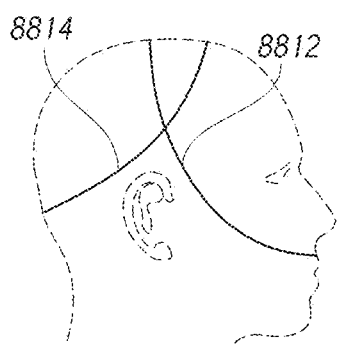

In FIG. 88c, the headgear has a front strap portion 8820, a rear strap portion 8850 and a crown strap portion 8816. The crown strap 8816 passes directly over the top of the user's head from ear to ear. The crown strap 8816 forms a portion of each of the front halo portion 8812 and the rear halo portion 8814 in combination with the front strap 8820 and the rear strap 8850, respectively. In FIG. 88d, each of the front halo portion 8812 and the rear halo portion 8814 is substantially circular in shape. The front halo portion 8812 and the rear halo portion 8814 cross over one another at a location generally above the user's ear such that an upper portion of the front halo portion 8812 is rearward of an upper portion of the rear halo portion 8814.

Figure 88E:
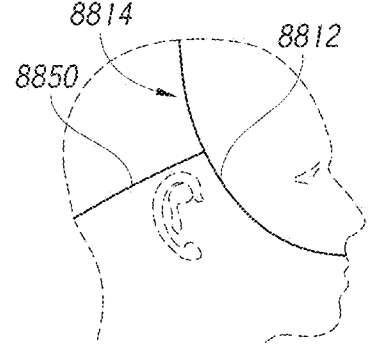
Figure 88F:
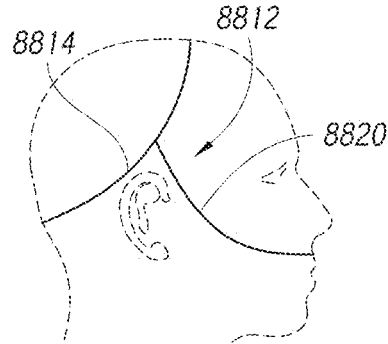

In FIG. 88e, the front halo portion 8812 is substantially circular and the rear strap 8850 extends from one side of the front halo portion 8812 to the other passing over the user's ears and around the back of the head. The rear strap 8850 and the upper part of the front halo portion 8812 form the rear halo portion 8814. In FIG. 88f, the rear halo portion 8814 is substantially circular and the front straps 8820 curved from a side of the rear halo portion 8814 passing above the user's ears and toward the underside of the nose. The upper part of the rear halo portion 8814 and the front straps 8820 cooperate to form the front halo portion 8812 (along with the mask or other interface). The headgear of FIG. 88f is substantially similar to the headgear of FIG. 88d with the upper part of the front halo portion 8812 removed. The shapes of FIGS. 88a-88f are merely examples of possible headgear having front halo portions 8812 and rear halo portions 8814. Other shapes are also possible.

Figure 89A:
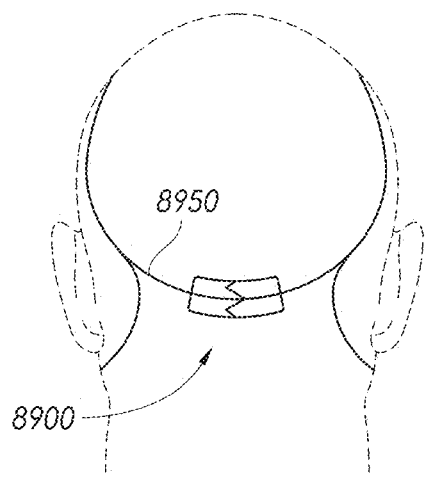
FIGS. 89A-89F illustrate several possible locations for break-fit assemblies within a headgear, such as the headgear of FIGS. 75-79.
Figure 89B:
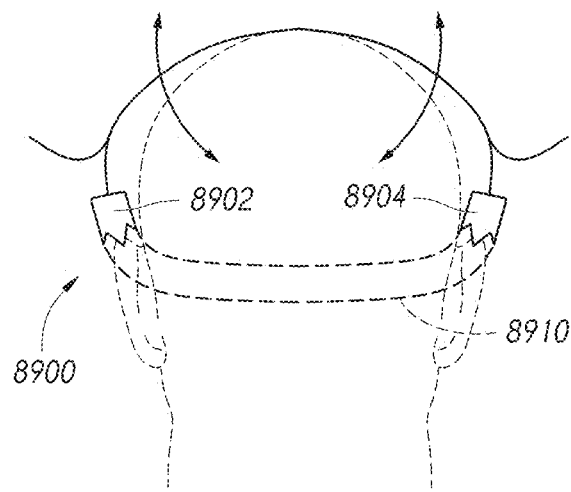

As described herein, the various interface assemblies can include break-fit assemblies that permit the interface assembly to be conveniently enlarged to facilitate application and removal. Preferably, the break-fit assemblies permit application and removal of the interface assemblies without readjustment upon each application. FIGS. 89a-89f illustrate various possible locations for the break-fit assemblies within the headgear. FIGS. 89a and 89b illustrate a break-fit assembly 8900 within a rear halo portion, such as a rear strap 8950 of the headgear, which extends around the back of the user's head. FIG. 89a illustrates the break-fit assembly 8900 in a connected state and FIG. 89b illustrates the break-fit assembly 8900 in a disconnected state. Optionally, the portions 8902, 8904 of the break-fit assembly 8900 can be coupled by a tether 8910 that limits separation of the portions 8902, 8904 and can facilitate non-visual location of the portions 8902, 8904 for reconnection. In some configurations, the tether 8910 is elasticated.

Figure 89C:
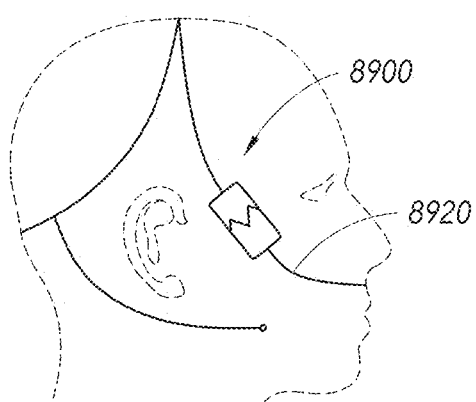
Figure 89D:
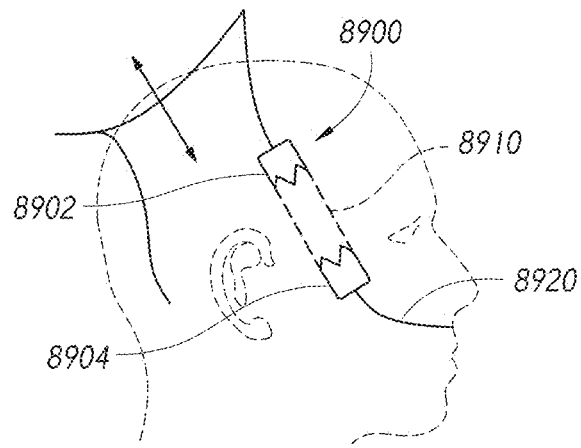

FIGS. 89c and 89d illustrate a break-fit assembly 8900 in a front halo portion, such as an upper strap 8920 of the headgear. FIG. 89c illustrates the break-fit assembly 8900 in a connected state and FIG. 89d illustrates the break-fit assembly 8900 in a disconnected state. The portions 8902, 8904 of the break-fit assembly 8900 can optionally be coupled by a tether 8910, which can be elasticated in some configurations.

Figure 89E:
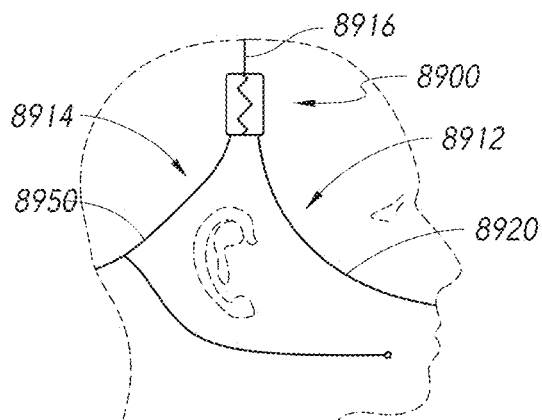
Figure 89F:
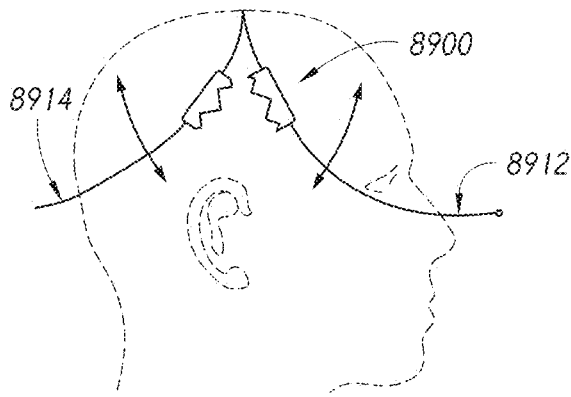

FIGS. 89e and 89f illustrate a break-fit assembly 8900 between a front halo portion 8912 and a rear halo portion 8914 of the headgear. For example, the break-fit assembly 8900 can be positioned at an intersection of a rear strap portion 8950, an upper strap portion 8920 and a crown strap portion 8916. The break-fit assembly 8900 can permit at least limited separation of the front halo portion 8912 and the rear halo portion 8914 to facilitate application or removal of the headgear. In some configurations, the front halo portion 8912 and the rear halo portion 8914 do not completely separate and, therefore, a tether is not provided. However, if desired, a tether could be provided whether or not the front halo portion 8912 and the rear halo portion 8914 completely separate.

Figure 90:
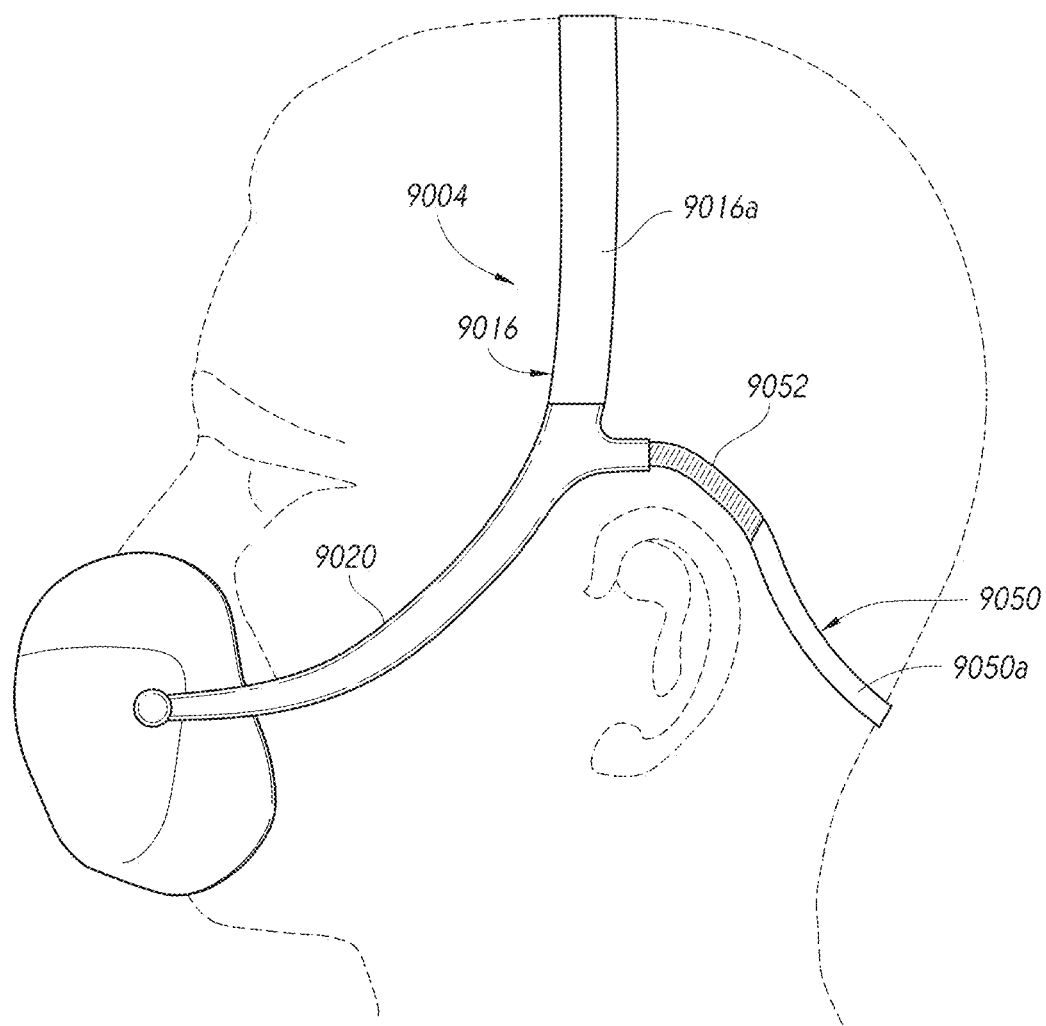
FIG. 90 is a side view of a headgear for an interface assembly illustrating optional locations for relatively rigid and relatively non-rigid portions of the headgear.

With reference to FIG. 90, a headgear 9004 is illustrated that is similar to other headgear arrangements disclosed herein. The headgear 9004 has a front or upper strap or arm portion 9020, a crown strap portion 9016 and a rear strap portion 9050. Although not illustrated, the headgear 9004 could include additional structural portions, such as a lower strap portion, for example. Similar to the headgear 7504 of the interface assembly 7500, preferably at least a portion of the headgear 9004 is relatively rigid, such as rigid or semi-rigid. In the illustrated arrangement, at least the upper arm 9020 is relatively rigid. Preferably, a rearward portion of the upper arm 9020 that is divided and forms initial portions of the crown strap 9016 and the rear strap 9050 is also relatively rigid and can be of a unitary construction with the remainder of the upper arm 9020. As illustrated, the upper arm 9020 is curved. Preferably, the upper arm 9020 is sufficiently rigid to inhibit substantial deformation of the curved shape at least in response to blow-off forces.

Preferably, at least the initial curved portions 9052 of the rear strap 9050 rearward of the user's ears (end portions of the rear strap 9050 indicated with dashed lines) are constructed from at least a semi-rigid material to resist deformation of the curved shape at least in response to blow-off forces. In some configurations, the portions 9052 are constructed from a rigid material, which can be the same material as the upper arm 9020. The portions 9052 can be unitarily formed with the upper arms 9020. The remaining portions 9016*a*, 9050*a* of the crown strap 9016 and the rear strap 9050, respectively, can be constructed from a relatively rigid material or a non-rigid material. As illustrated, the portions 9016*a* and 9050*a* are subject to primarily axial forces. Accordingly, flexible or non-rigid materials can be used if desired, such as for comfort reasons.

Figure 91:
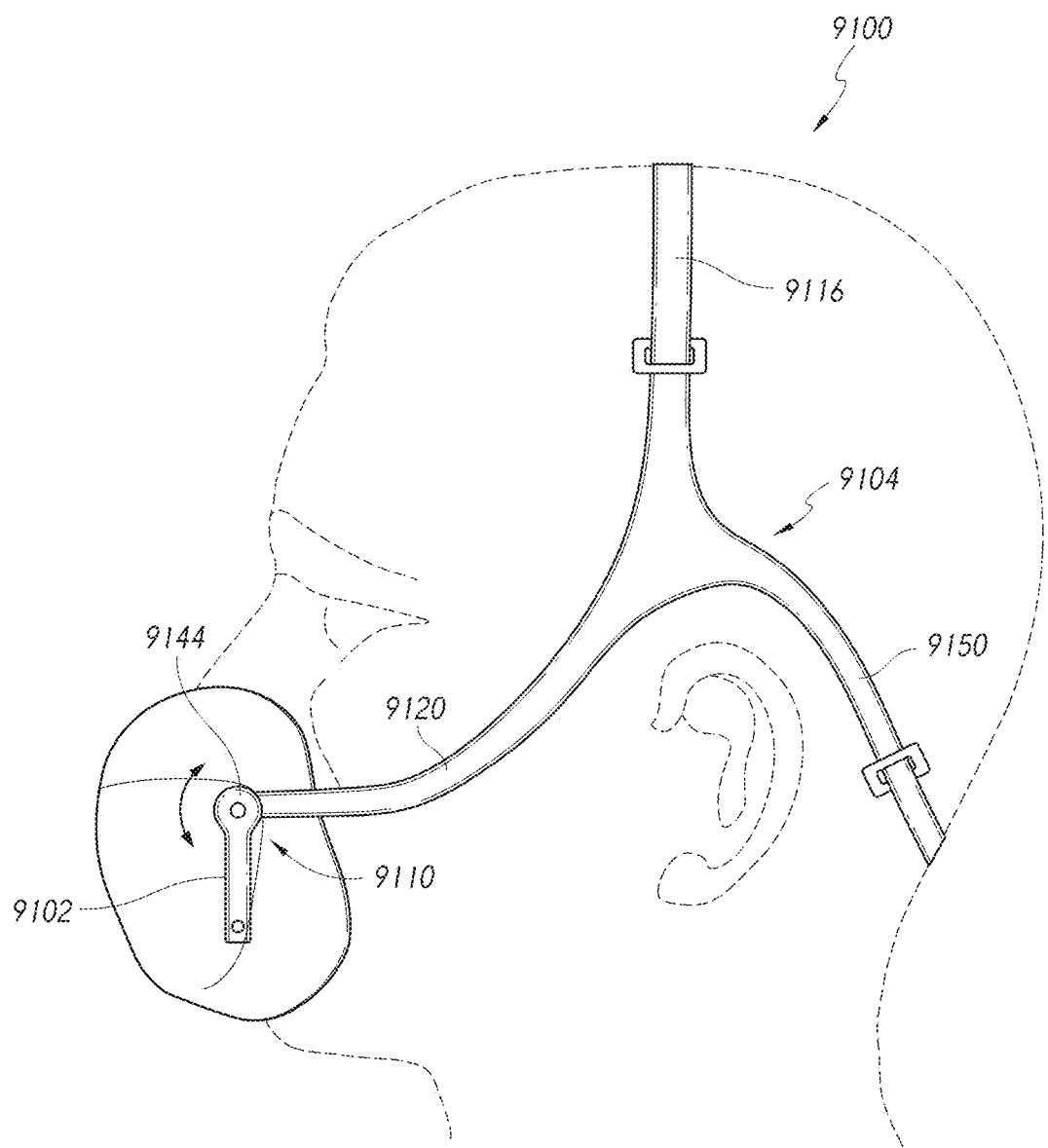
FIG. 91 is a side view of an interface assembly having an interface, such as a mask, and a headgear. The interface assembly includes a rotational coupling between the mask and the headgear.

FIG. 91 illustrates an interface assembly 9100 comprising an interface 9102 and a headgear 9104. The interface 9102 (shown schematically) can be any suitable interface 9102, such as a nasal-oral mask that can seal around a mouth of a user and on an underside of a nose of the user, for example. The mask 9102 can be similar to any of the interfaces/masks disclosed herein. However, other types of interfaces can be used with the disclosed headgear 9104. The illustrated headgear 9104 is coupled to the mask 9102 at a mounting location or mounting point 9110 on each side of the mask 9102. Preferably, the mask 9102 is coupled to the headgear 9104 by a rotational coupling 9144, which can be of any suitable arrangement, such as any of the rotational couplings herein. Preferably, the rotational coupling 9144 can be locked in a desired rotational position. For example, the rotational coupling 9144 can include a detent arrangement, such as the arrangement described with respect to FIG. 19, for example. The rotational coupling 9144 could be manually locked in the desired rotational position. Other suitable arrangements could also be used.

Preferably, the rotational coupling 9144 can be secured in place without a lower strap portion. However, if desired, the headgear 9104 can include a lower strap portion. The illustrated headgear 9104 includes an upper strap portion 9120 on each side of the headgear 9104 to connect the mask 9102 to a rear portion of the headgear 9104. The headgear 9104 can also include a crown strap 9116 and a rear strap 9150. Unless indicated otherwise, features of the interface assembly 9100 or portions thereof can be the same as or similar to other interfaces or portions thereof described herein, or can be of another suitable arrangement.

Figure 92:
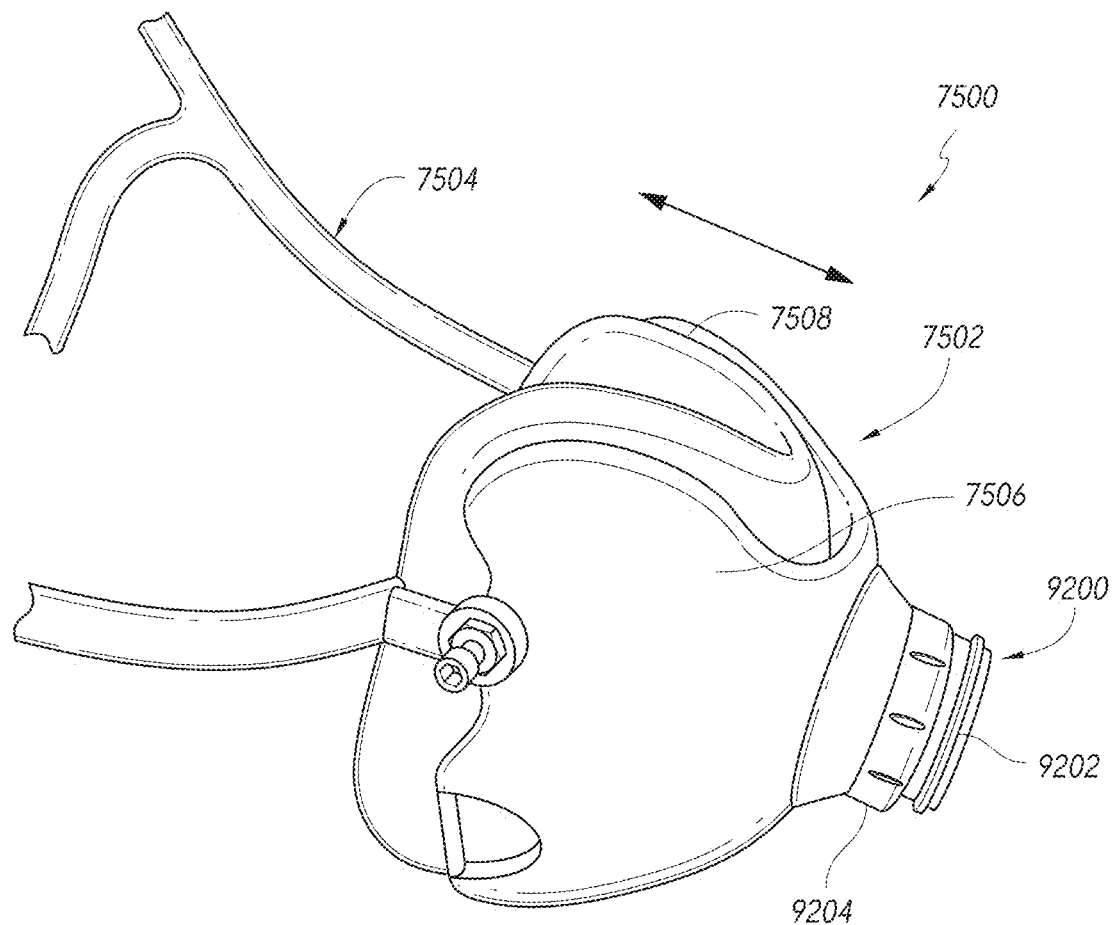
FIG. 92 is a perspective view of an interface assembly having an interface, such as a mask, and a headgear. The interface assembly includes an adjustment arrangement for a position of the mask.

FIG. 92 illustrates an interface assembly 7500 that is similar in many respects to the interface assembly 7500 of FIGS. 75-79. Therefore, the same reference numbers are used to refer to the same or corresponding components or features. In addition, the interface assembly 7500 of FIG. 92 is described in the context of the differences relative to the interface assembly 7500 of FIGS. 75-79. Features of the interface assembly 7500 or portions thereof not specifically described can be assumed to be the same as or similar to features of the interface assembly 7500 of FIGS. 75-79, other interfaces or portions thereof described herein, or can be of another suitable arrangement.

The illustrated interface assembly 7500 includes an interface 7502 and a headgear 7504. The illustrated interface 7502 is a nasal-oral mask but, as described herein, other types of interfaces can be used with the disclosed headgear 7504. The illustrated mask 7502 generally comprises a frame 7506 that supports a seal 7508. The mask 7502 can be connected to a supply conduit (not shown), which can be used to supply breathing gases to a user. As described above, in some configurations, the mask 7502 can seal around a mouth of a user and on an underside of a nose of the user. Such a mask 7502 can provide pressurized air flow to both the nose and the mouth of the user.

As described herein, the headgear 7504 preferably supports the mask 7502 at a desired location relative to the headgear 7504 and the mask 7502 is at least partially isolated from tightening of the headgear 7504. That is, tightening of the headgear 7504 does not substantially alter a position of the mask 7502 relative to the user's face. Thus, in the illustrated arrangement, the mask 7502 includes a seal adjustment arrangement 9200, which permits a position of the seal 7508 to be adjusted relative to the frame 7506. Such an arrangement permits the position of the seal 7508 to be micro-adjusted to accommodate variations in facial geometry. Preferably, rotational adjustment of the mask 7502 is also permitted.

The illustrated seal adjustment arrangement 9200 includes a threaded tube 9202 that is coupled to the mask seal 7508. The tube 9202 can be coupled to the supply conduit and can deliver breathing gases from the supply conduit to the interior of the seal 7508. A dial 9204 can be supported by the mask frame 7502 and can include internal threads that mate with the threads of the tube 9202. Rotation of the dial 9204 can cause translation or linear movement of the seal 7508 toward and away from the mask frame 7506. Other suitable adjustment mechanisms can also be used. Examples of similar adjustment arrangements are disclosed in PCT Publication No. WO2004/052,438, the entirety of which is incorporated by reference herein.

Figure 93:
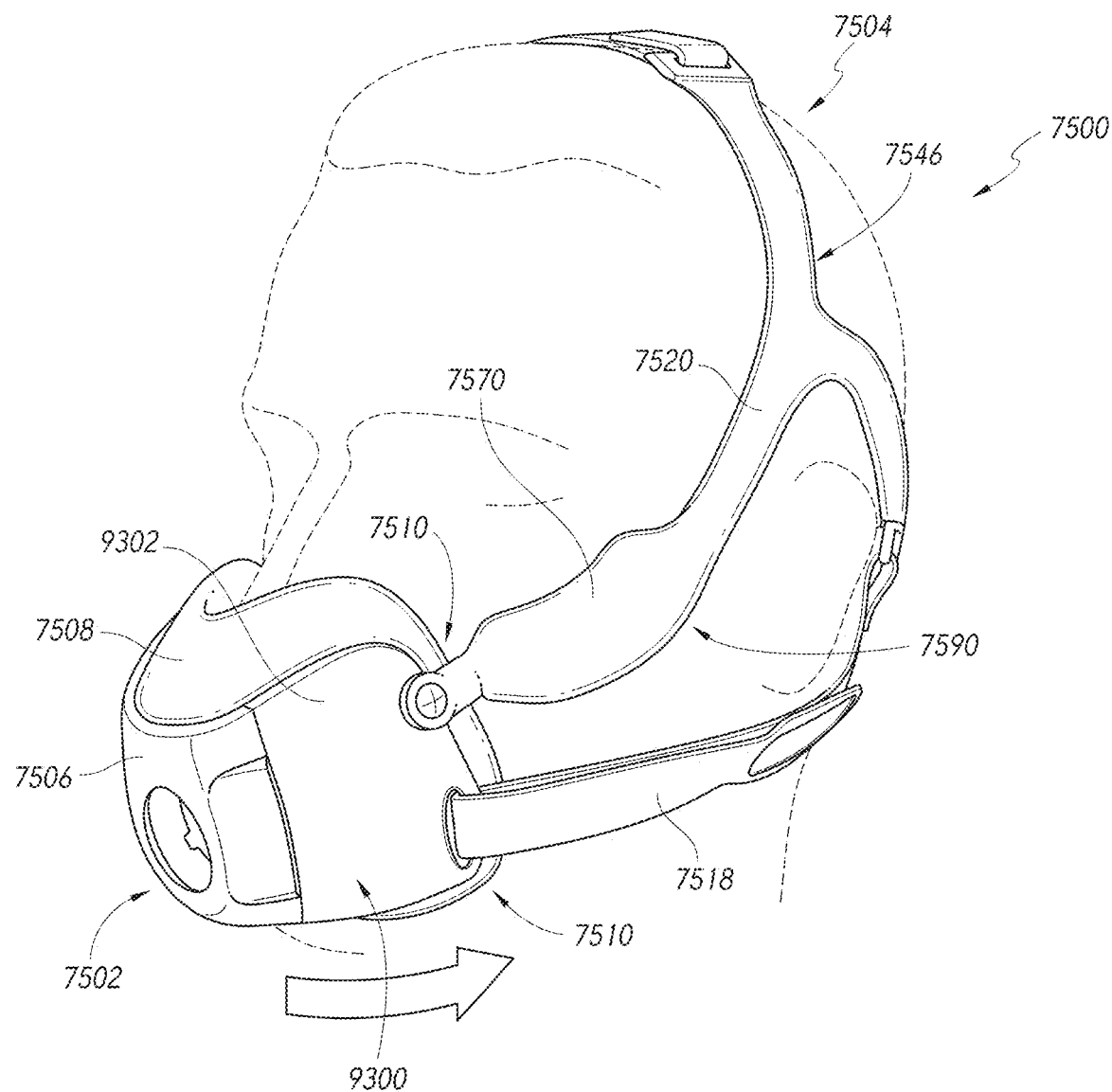
FIG. 93 is a perspective view of an interface assembly having an interface, such as a mask, and a headgear. The interface assembly includes a cheek pad in the headgear and a quick-release mechanism between the mask and the headgear.

FIG. 93 illustrates an interface assembly 7500 that is similar in many respects to the interface assembly 7500 of FIGS. 75-79. Therefore, the same reference numbers are used to refer to the same or corresponding components or features. In addition, the interface assembly 7500 of FIG. 93 is described in the context of the differences relative to the interface assembly 7500 of FIGS. 75-79. Features of the interface assembly 7500 or portions thereof not specifically described can be assumed to be the same as or similar to features of the interface assembly 7500 of FIGS. 75-79, other interfaces or portions thereof described herein, or can be of another suitable arrangement.

The illustrated interface assembly 7500 includes an interface 7502 and a headgear 7504. The illustrated interface 7502 is a nasal-oral mask but, as described herein, other types of interfaces can be used with the disclosed headgear 7504. The illustrated mask 7502 generally comprises a frame 7506 that supports a seal 7508. The mask 7502 can be connected to a supply conduit (not shown), which can be used to supply breathing gases to a user. As described above, in some configurations, the mask 7502 can seal around a mouth of a user and on an underside of a nose of the user. Such a mask 7502 can provide pressurized air flow to both the nose and the mouth of the user.

The headgear 7504 can be coupled to the mask 7502 at one or more mounting locations or mounting points 7510. Preferably, a lower strap portion 7518 and an upper arm portion 7520 are provided on each side of the headgear 7504 to connect the mask 7502 to a rear portion of the headgear 7504. The mask 7502 can be rotatably supported relative to the upper arm 7520 with the lower strap 7518 fixing a rotational position of the mask 7502. Unless indicated otherwise, features of the interface assembly 7500 or portions thereof can be the same as or similar to other interfaces or portions thereof described herein, or can be of another suitable arrangement.

The illustrated interface assembly 7500 includes an enlarged and/or contoured relatively rigid or cheek-contacting portion 7570. Such an arrangement can increase the ability of the headgear 7504 to anchor on the face of the user and at least partially isolate the mask 7502 from the adjustment of the headgear 7504. Such an arrangement can also spread the load applied to the user's face over a larger area for improved comfort. In some configurations, the portion 7570 is formed by the pad 7590 that covers the underlying rigid section 7546.

To facilitate application and removal of the interface assembly 7500, a quick-release mechanism 9300 can be provided to move the interface assembly 7500 to an enlarged circumference or open state. The quick-release mechanism 9300 can be of any suitable arrangement, such as any of the arrangements of FIGS. 50-72 or any others disclosed herein, for example and without limitation. In the illustrated arrangement, the quick-release mechanism 9300 comprises a clip 9302 that can be disconnected from the remainder of the mask 7502. In some configurations, the clip 9302 can be tethered or otherwise coupled to the remainder of the mask 7502 in the disconnected state to facilitate reconnection of the clip 9302.

Although the present invention has been described in terms of a certain embodiments, other embodiments apparent to those of ordinary skill in the art also are within the scope of this invention. Thus, various changes and modifications may be made without departing from the spirit and scope of the invention. For instance, various components may be repositioned as desired. Moreover, not all of the features, aspects and advantages are necessarily required to practice the present invention.

In addition, some portions of one assembly could be used with other portions of other assemblies to provide further assemblies not explicitly shown herein. For example, straps or portions of straps of one assembly may be used with a halo or the like from another assembly. Any of the various quick-release arrangements can be utilized with any of the headgear assemblies disclosed herein. Any of the rotational connections between the interface and the headgear can be used with any of the headgear assemblies disclosed herein. Any break-fit assemblies can be incorporated into any of the interface assemblies disclosed herein. In general, any feature from interface assembly can be incorporated into any other interface assembly to the extent possible or apparent to those skilled in the art. Such further variations should be considered expressly contained herein. Accordingly, the scope of the present invention is intended to be defined only by the claims that follow.

What is claimed is:

1. An interface assembly that omits a forehead support, comprising:
    a mask assembly comprising a mask frame and a seal configured to deliver a flow of breathing gas to a user; and
    a headgear comprising:
        a first upper strap portion configured to extend along a cheek of the user on a first side of the headgear;
        a second upper strap portion configured to extend along a cheek of the user on a second side of the headgear;
        a first lower strap portion on the first side of the headgear; and
        a second lower strap portion on the second side of the headgear, wherein the first upper strap portion and the first lower strap portion and/or the second upper strap portion and the second lower strap portion are coupled to the mask frame by a single clip on at least one of the first and/or second sides of the headgear;
    wherein the single clip comprises a first segment, a second segment, and a third segment comprising a latch, wherein the first segment is directly connected to the mask frame, the third segment is connected to the headgear, and the second segment is positioned between the first segment and the third segment, wherein the single clip is a break fit assembly that permits the headgear to move between a compacted configuration and an enlarged configuration, and a top portion of the single clip and a bottom portion of the single clip are spaced from the mask frame in the enlarged configuration to facilitate fitment or removal of the interface assembly; and
    wherein in the compacted configuration, the first segment is positioned within the second segment, the second segment is positioned within the third segment, and the latch is engaged with the first segment.

2. The interface assembly of claim 1, wherein the single clip has an overall thickness that is substantially equal to a thickness of the first segment, the second segment, and the third segment in the compacted configuration and the enlarged configuration.

3. The interface assembly of claim 1, wherein a height of the first segment is substantially less than or equal to a distance between the first upper strap portion and the first lower strap portion and/or the second upper strap portion and the second lower strap portion at a location where the first upper strap portion and the first lower strap portion and/or the second upper strap portion and the second lower strap portion meet the mask frame.

4. The interface assembly of claim 1, wherein a height of the third segment is substantially greater than or equal to a distance between a lower edge of the first lower strap portion and an upper edge of the first upper strap portion and/or a lower edge of the second lower strap portion and an upper edge of the second upper strap portion at a location whether the first lower strap portion and the first upper strap portion and/or the second lower strap portion and the second upper strap portion meet the mask frame.

5. The interface assembly of claim 1, wherein the third segment comprises a U-shaped profile.

6. The interface assembly of claim 1, wherein one or more of the first upper strap portion, the second upper strap portion, the first lower strap portion and the second lower strap portion are configured to be adjustable relative to the mask frame and/or the single clip.

7. The interface assembly of claim 1, wherein the single clip further comprises a locking mechanism.

8. An interface assembly that omits a forehead support, comprising:
    a mask assembly comprising a mask frame and a seal configured to deliver a flow of breathing gas to a user; and
    a headgear comprising:
        a first side; and
        a second side, wherein each of the first side and the second side comprises an upper strap portion configured to extend along a cheek of the user and a lower strap portion, and wherein the upper strap portion and the lower strap portion are coupled to the mask frame by a single clip on the first side of the headgear and a single clip on a second side of the headgear;
    wherein the single clip on the first side of the headgear and the single clip on the second side of the headgear each comprise a first segment, a second segment, and a third segment comprising a latch, and wherein the first segment is directly connected to the mask frame and the second segment is positioned between the first and third segment;
    wherein each of the single clip on the first side of the headgear and the single clip on the second side of the headgear are configured to move between a compacted configuration and an enlarged configuration, and wherein in the compacted configuration, the first segment is positioned within the second segment, the second segment is positioned within the third segment, and the latch is engaged with the first segment.

9. The interface assembly of claim 8, wherein each of the first clip and the second clip has an overall thickness that is substantially equal to a thickness of the first segment, the second segment, and the third segment.

10. The interface assembly of claim 8, wherein a height of the first segment is substantially less than or equal to a distance between the upper strap portion and the lower strap portion at a location where the upper strap portion and the lower strap portion meet the mask frame.

11. The interface assembly of claim 8, wherein a height of the third segment is substantially greater than or equal to a distance between a lower edge of the lower strap portion and an upper edge of the upper strap portion at a location where the lower strap portion and the upper strap portion meet the mask frame.

12. The interface assembly of claim 8, wherein the third segment comprises a U-shaped profile.

13. The interface assembly of claim 8, wherein one or more of the upper strap portion and the lower strap portion are configured to be adjustable relative to the mask assembly and/or the first and second clip.

14. The interface assembly of claim 8, wherein the first and second clip further comprise a locking mechanism.

15. An interface assembly that omits a forehead support, comprising:
 a mask assembly comprising a mask frame and a seal configured to deliver a flow of breathing gas to a user; and
 a headgear comprising:
  an upper strap portion configured to extend along a cheek of the user, and
  a lower strap portion on a first side of the headgear;
  wherein the upper strap portion and the lower strap portion are coupled to the mask frame by a single clip on the first side of the headgear; and
 wherein the single clip comprises a first segment, a second segment, and a third segment comprising a latch, wherein the first segment is directly connected to the mask frame and the second segment is positioned between the first and third segment, and wherein the single clip is a break fit assembly that permits the headgear to move between a compacted configuration and an enlarged configuration, and
 wherein in the compacted configuration, the first segment is positioned within the second segment, the second segment is positioned within the third segment, and the latch is engaged with the first segment.

16. The interface assembly of claim 15, wherein the single clip has an overall thickness that is substantially equal to a thickness of the first segment, the second segment, and the third segment.

17. The interface assembly of claim 15, wherein a height of the first segment is substantially less than or equal to a distance between the upper strap portion and the lower strap portion at a location where the upper strap portion and the lower strap portion meet the mask frame.

18. The interface assembly of claim 15, wherein a height of the third segment is substantially greater than or equal to a distance between a lower edge of the lower strap portion and an upper edge of the upper strap portion at a location where the lower strap portion and the upper strap portion meet the mask frame.

19. The interface assembly of claim 15, wherein the single clip further comprises a locking mechanism.

20. The interface assembly of claim 15, wherein one or more of the upper strap portion and the lower strap portion are configured to be adjustable relative to the mask assembly and/or the single clip.

* * * * *